US005969121A

United States Patent [19]

Allen et al.

[11] Patent Number: 5,969,121

[45] Date of Patent: Oct. 19, 1999

[54] STABLE BIOCATALYSTS FOR ESTER HYDROLYSIS

[75] Inventors: Larry Allen, Northfield; John Aikens, LaGrange Park; Michael Fonstein, Chicago; Veronika Vonstein, Chicago; David Demirjian, Chicago; Malcolm Casadaban, Chicago, all of Ill.

[73] Assignee: Thermogen, Inc., Chicago, Ill.

[21] Appl. No.: 08/781,802

[22] Filed: Jan. 10, 1997

Related U.S. Application Data

[63] Continuation-in-part of application No. 08/694,078, Aug. 7, 1996.

[60] Provisional application No. 60/019,580, Jun. 12, 1996, and provisional application No. 60/009,704, Jan. 11, 1996.

[51] Int. Cl.$^{6}$ .............................. C07H 21/04; C12N 9/16; C12N 15/55; C12Q 1/44

[52] U.S. Cl. .......................... 536/23.1; 435/19; 435/69.1; 435/196; 536/23.2

[58] Field of Search .................................. 536/23.1, 23.2; 435/19, 196, 197, 198, 69.1

[56] References Cited

PUBLICATIONS

Ozaki et al. Biosci Biotech Biochem 59(7) 1204–1207, 1995.

*Primary Examiner*—Nancy Degen
*Attorney, Agent, or Firm*—McDonnell Boehnen Hulbert & Berghoff

[57] ABSTRACT

The instant invention encompasses isolated stable esterase enzymes characterized by the ability to remain stable at certain temperatures, substrate specificities, and activity profile.

12 Claims, 47 Drawing Sheets

Figure 3. Molecular Weight calibration curve.
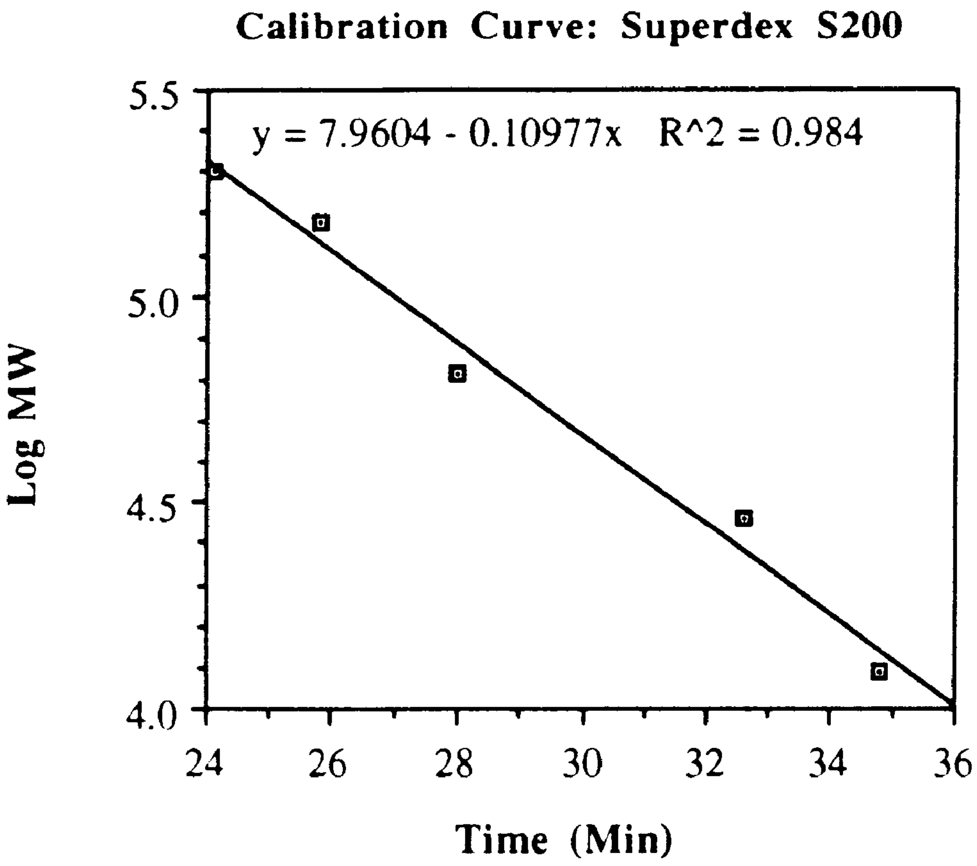

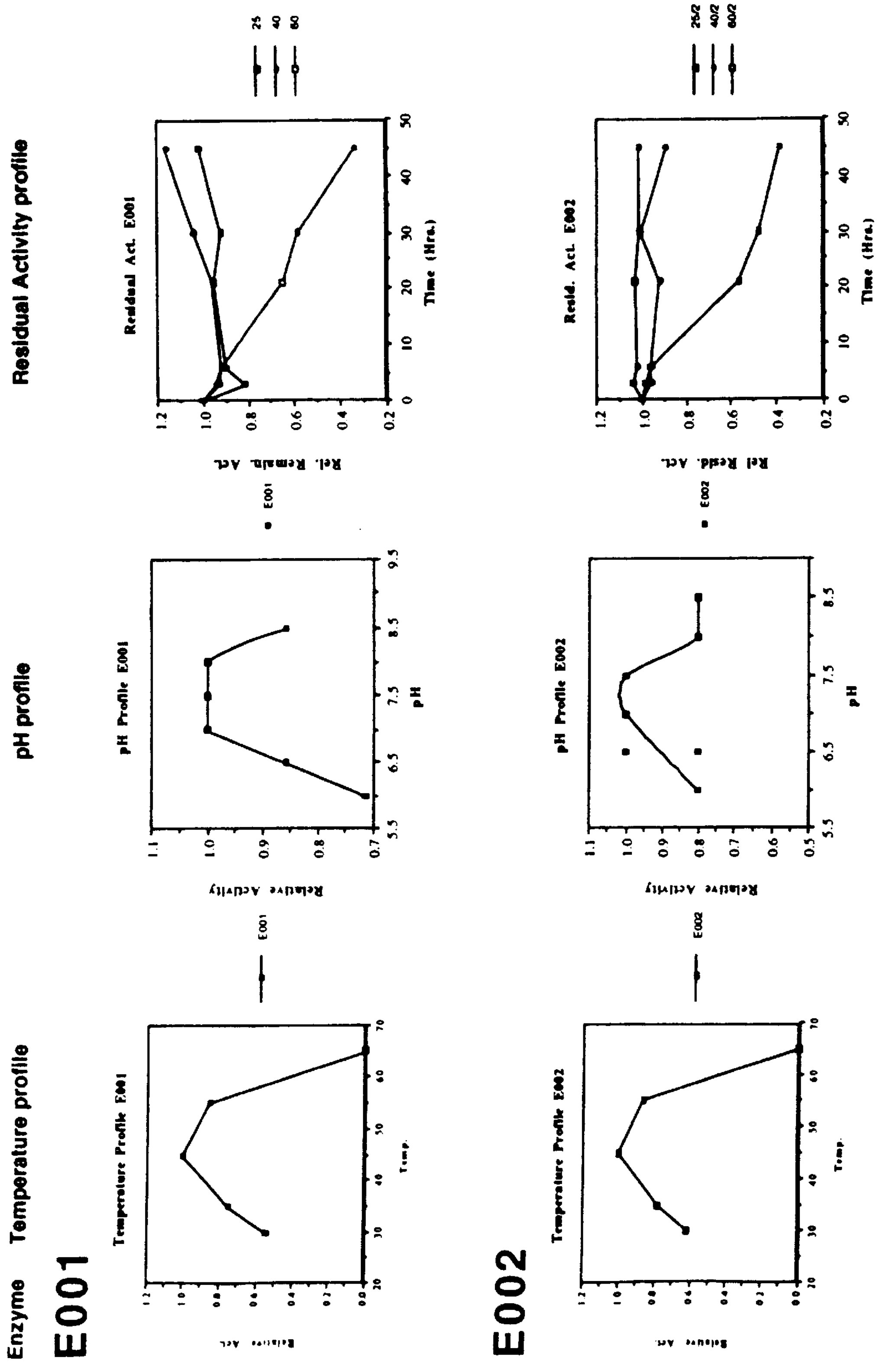
FIGURE 4 (page 1 of 11)

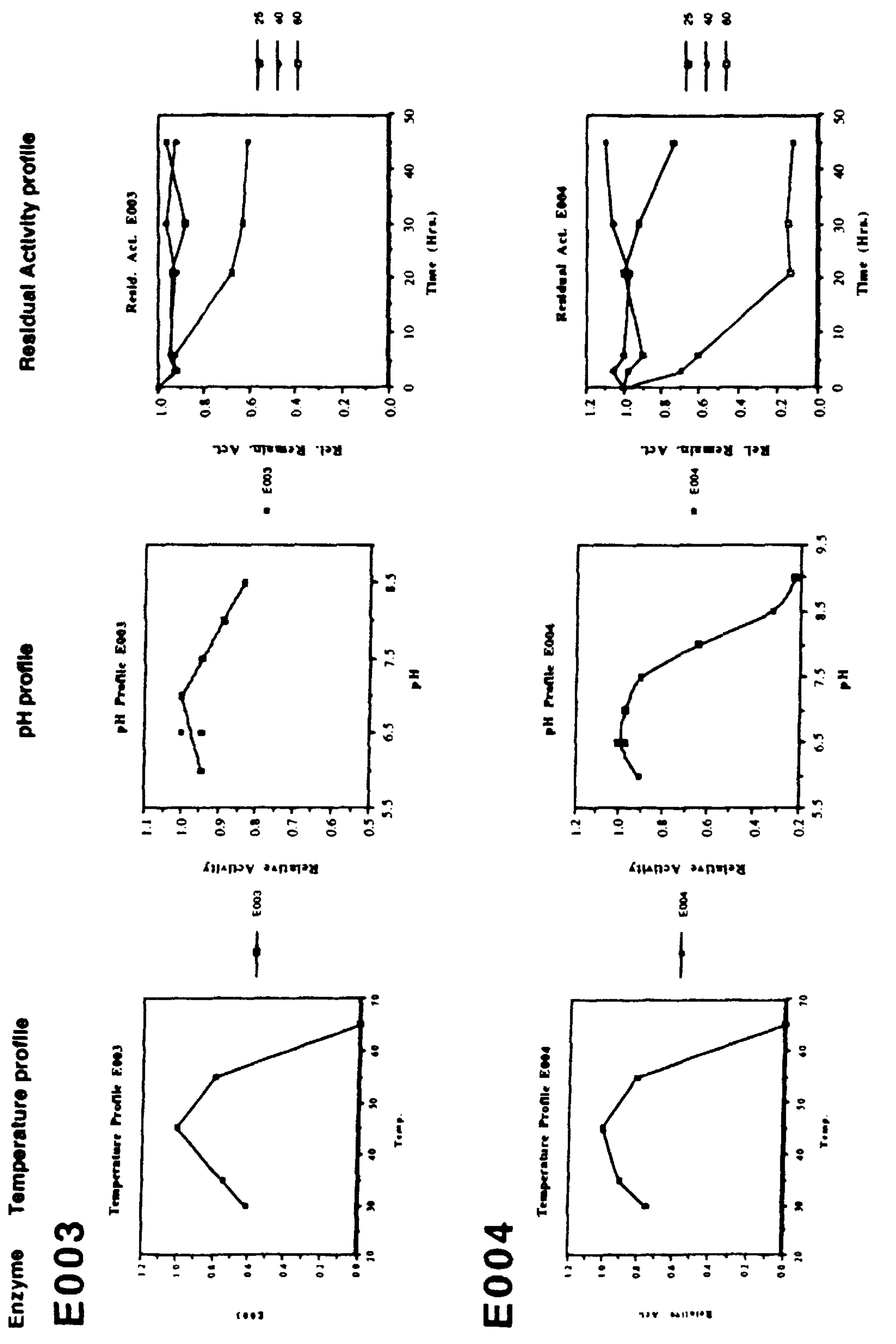
FIGURE 4 (page 2 of 11)

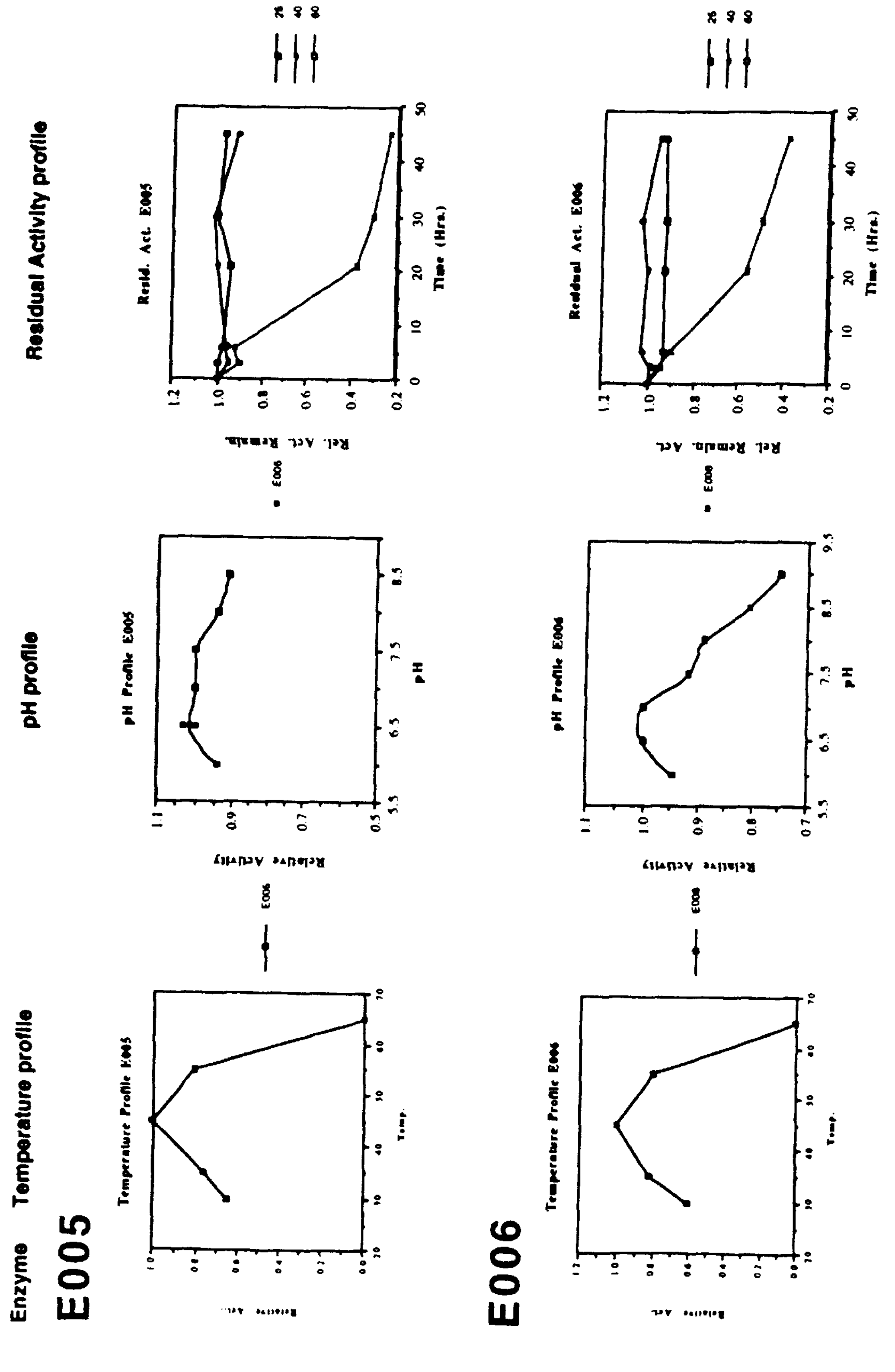
FIGURE 4 (page 3 of 11)

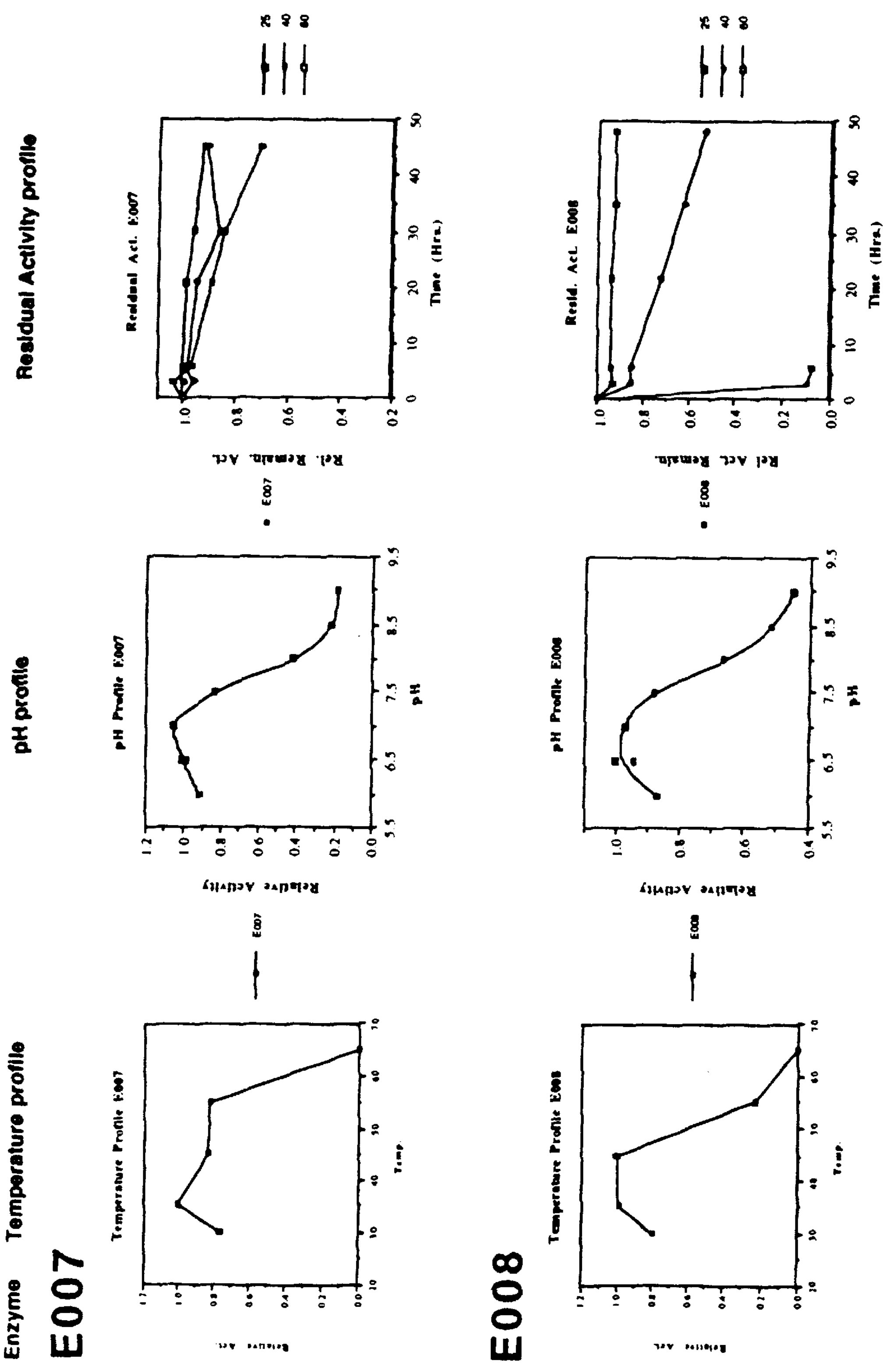
FIGURE 4 (page 4 of 11)

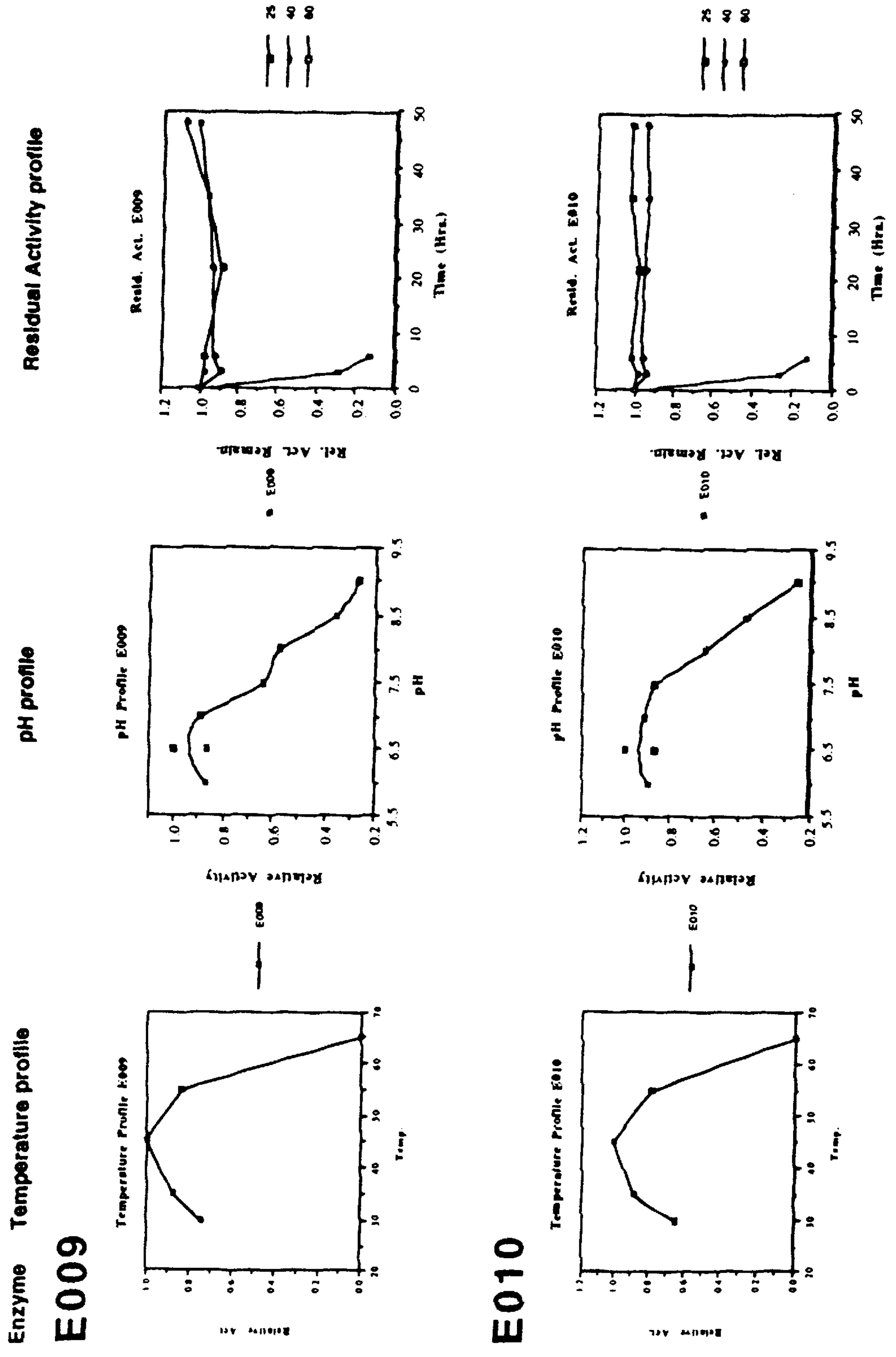
FIGURE 4 (page 5 of 11)

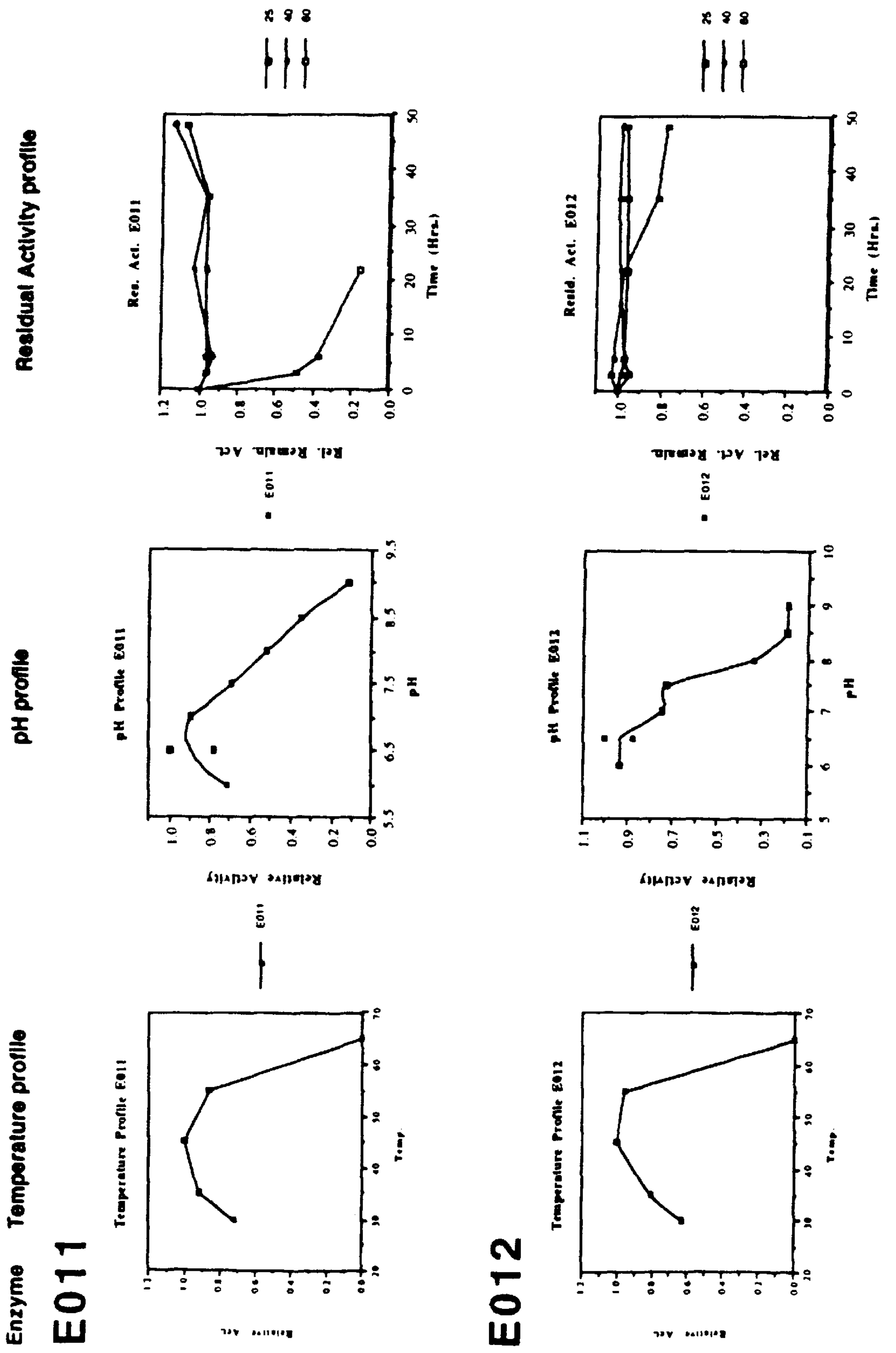
FIGURE 4 (page 6 of 11)

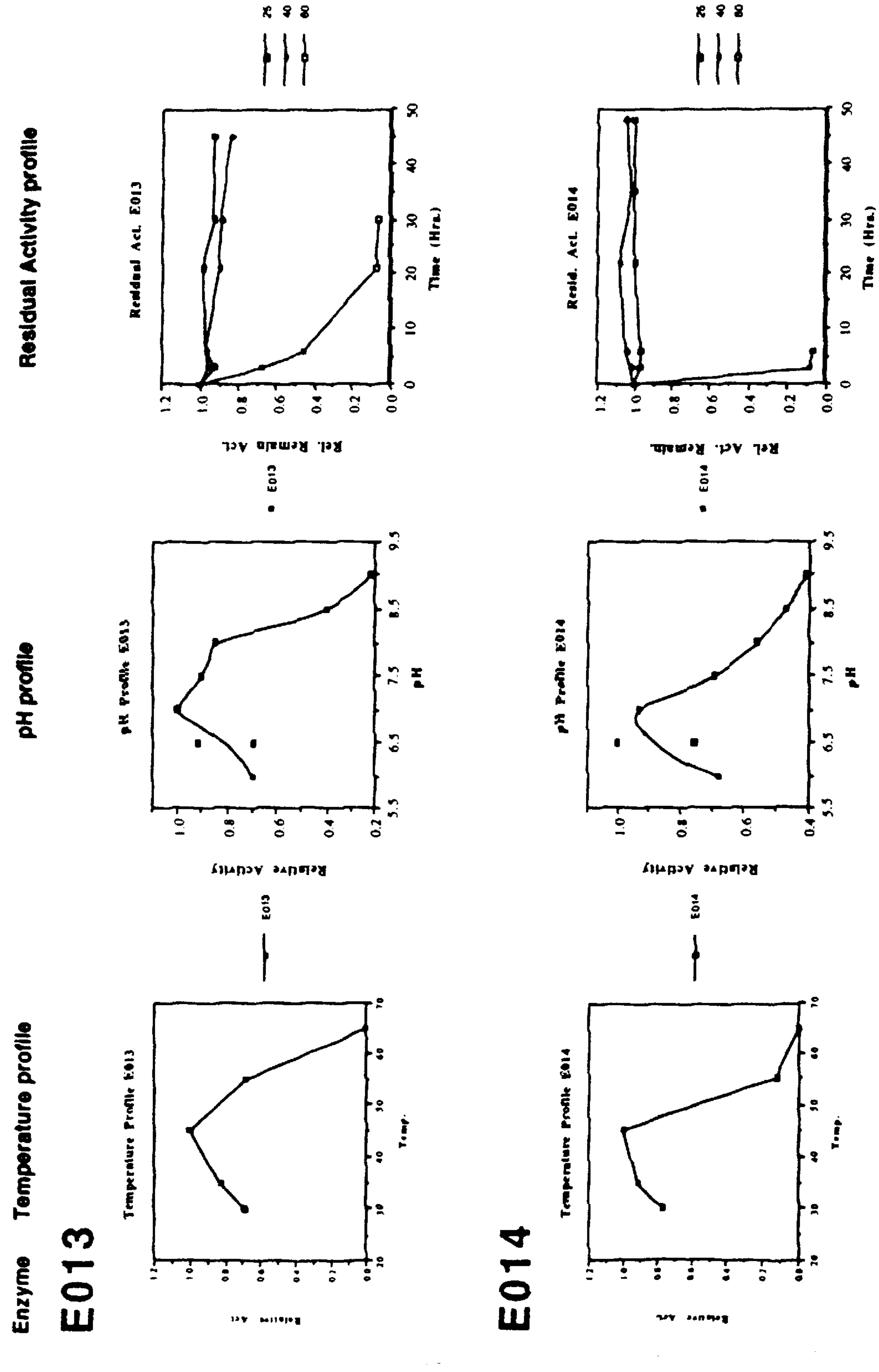
FIGURE 4 (page 7 of 11)

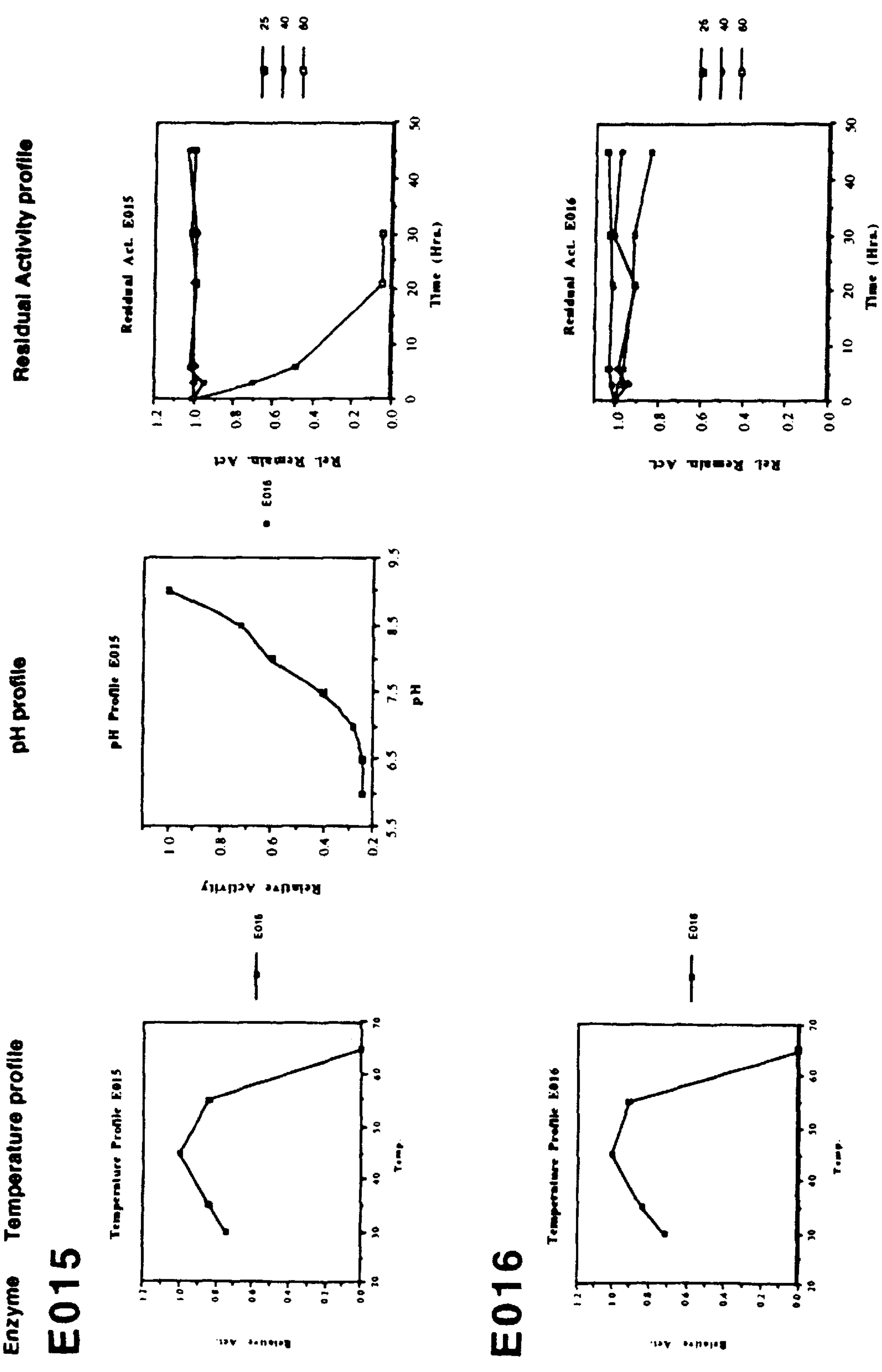
FIGURE 4 (page 8 of 11)

| Enzyme | Temperature profile | pH profile | Residual Activity profile |
|---|---|---|---|
| E017 | | | |
| E018 | | | 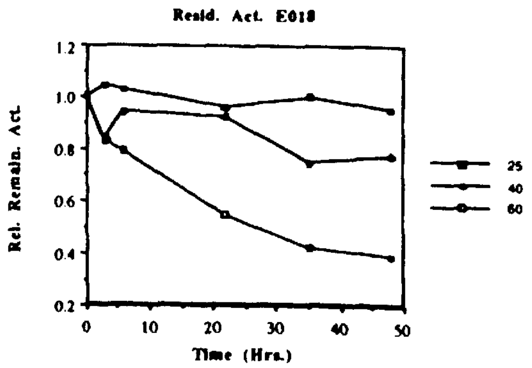 |
FIGURE 4 (page 9 of 11)

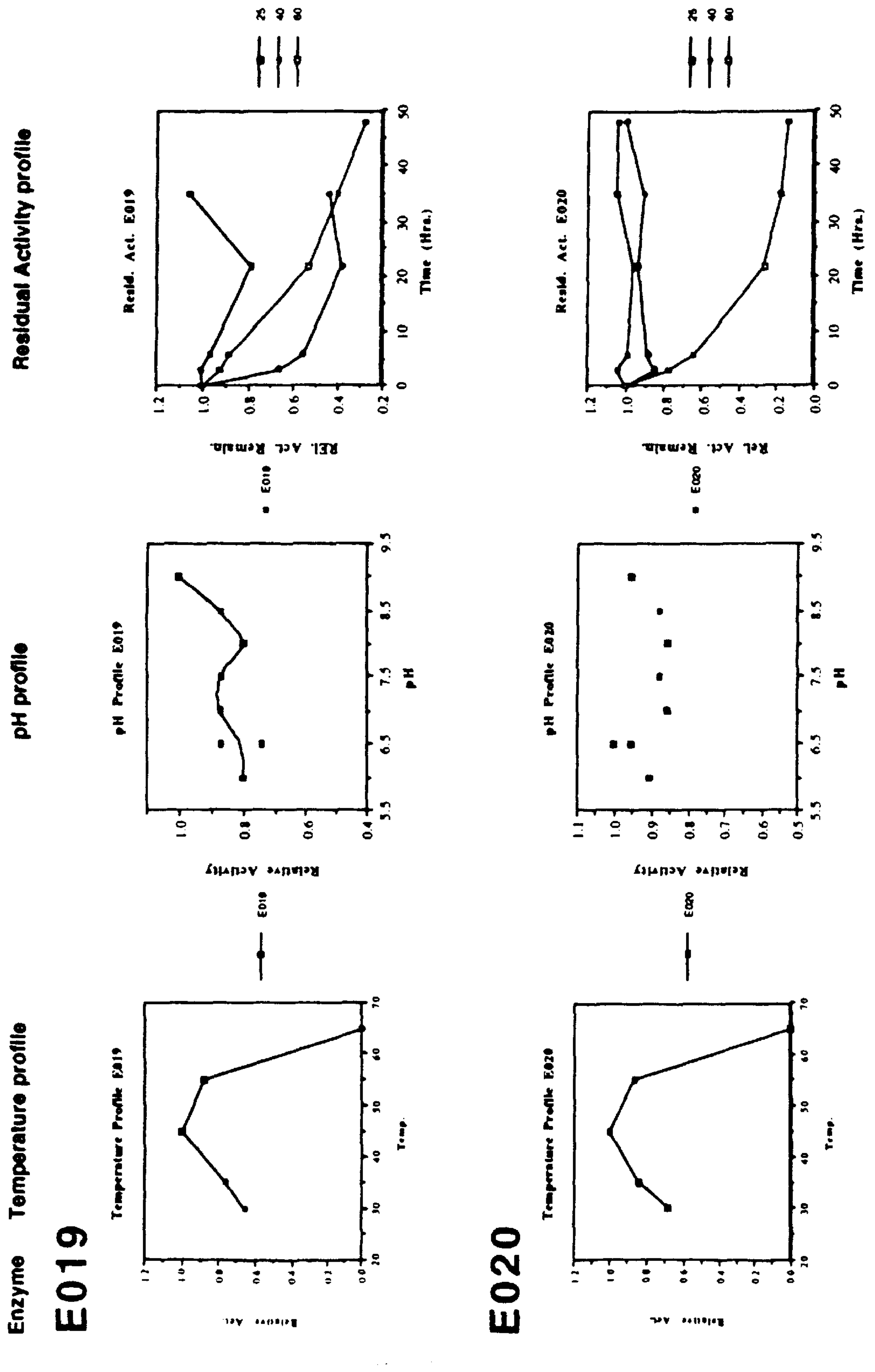
FIGURE 4 (page 10 of 11)

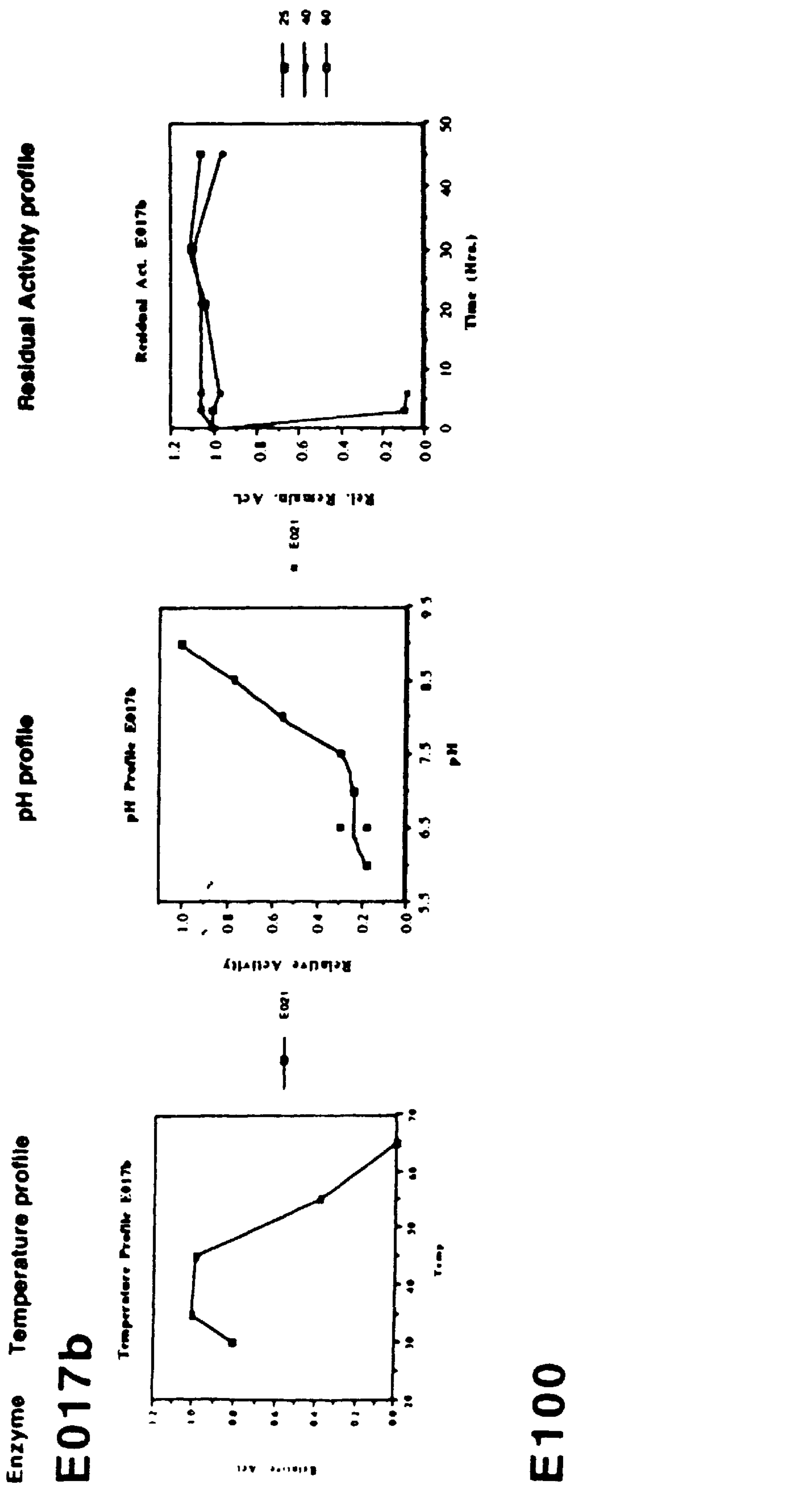
FIGURE 4 (page 11 of 11)

Figure 6. Kinetic analysis of E100
a)
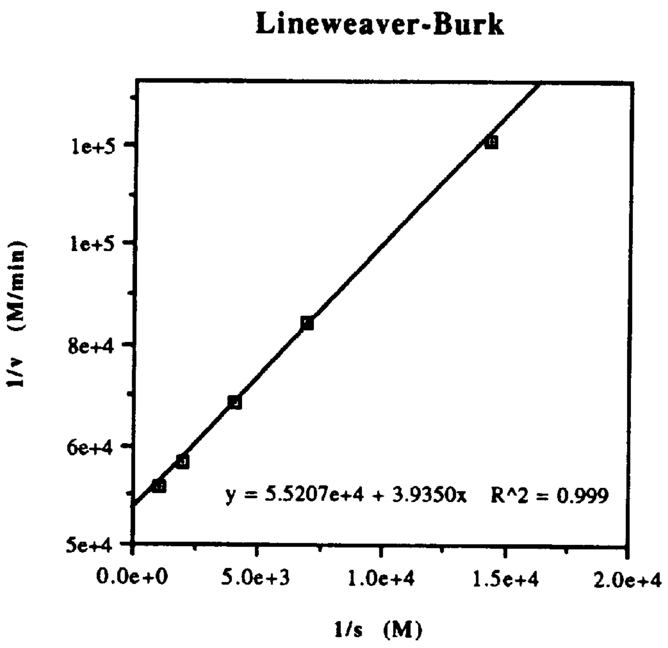
b)
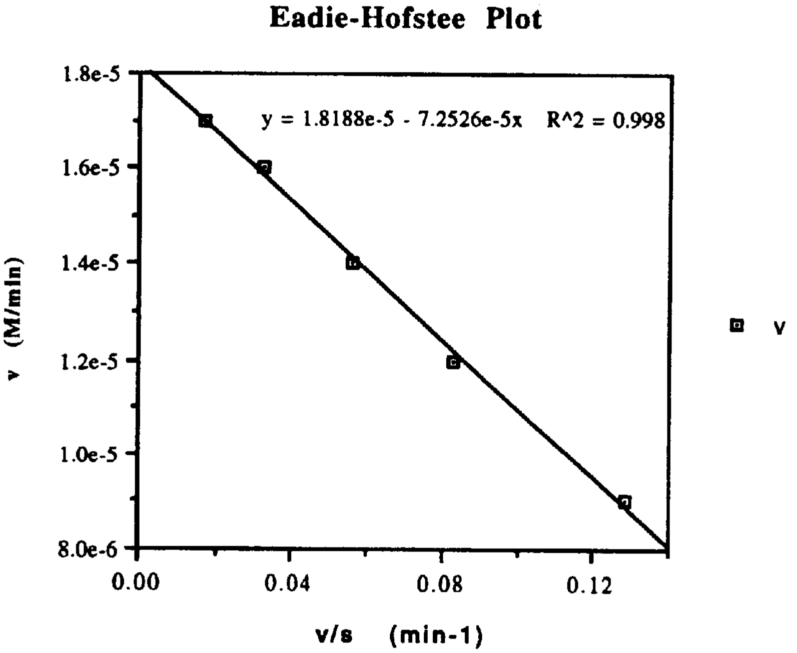

Figure 7. Temperature and pH profiles of E100
a)
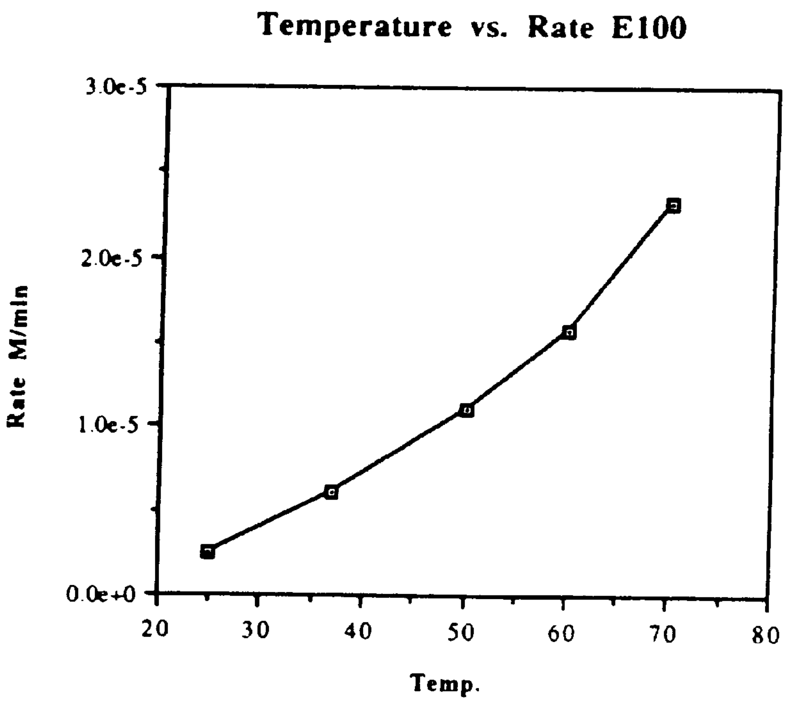
b)
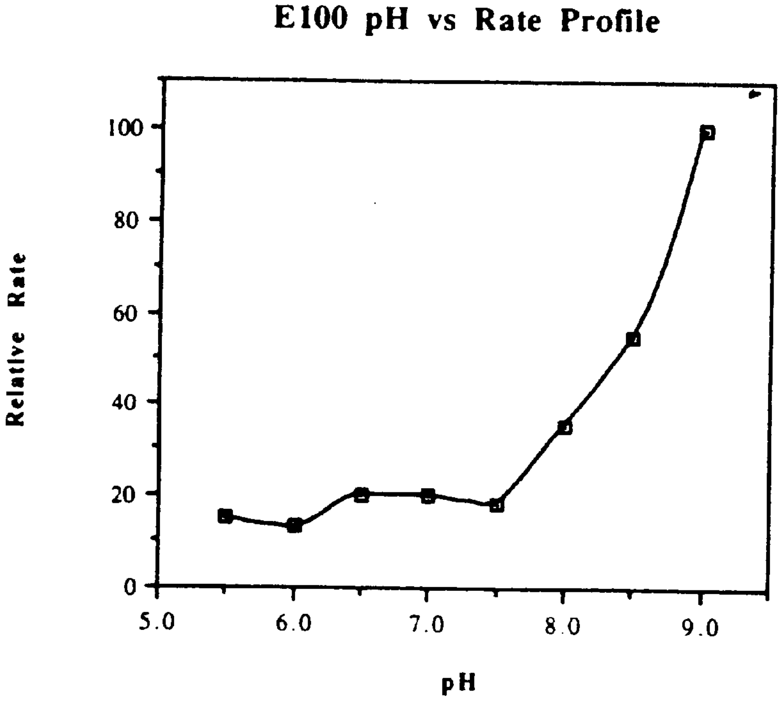

Figure 9
a)
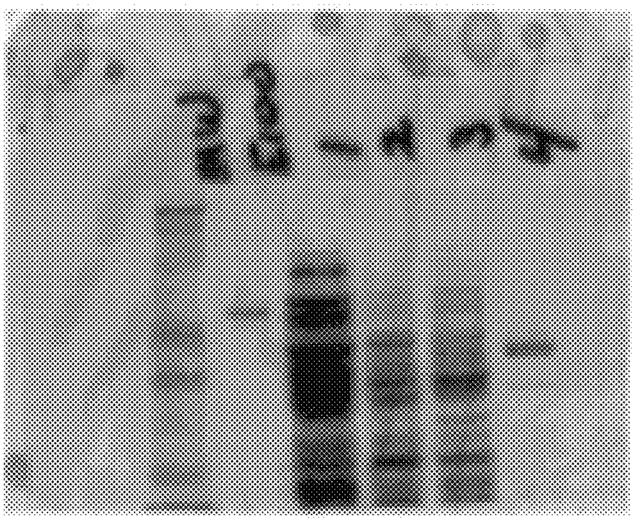
b)
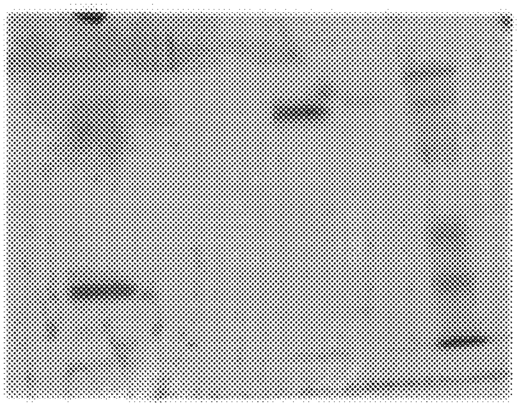

FIGURE 10A
Type I. Chirality on Carboxylate
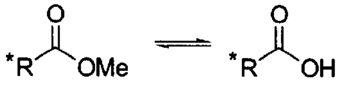
+ 1 MEOH
Reference
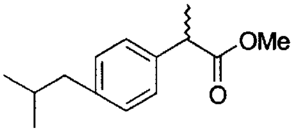
(39)
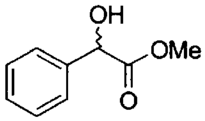
(40)
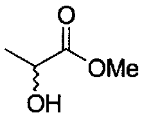
(40)
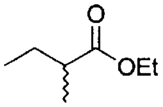
(41)
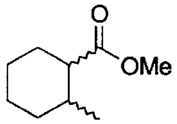
(42)
Type II. Chirality on Alcohol
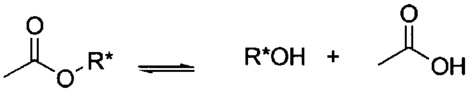
Reference
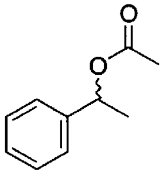
(40)
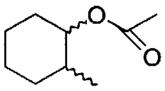
(42)
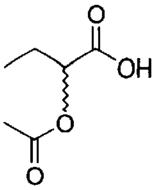
(43)
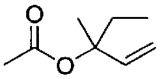
(44)

FIGURE 10B
TYPE III. Chiral Resolution of a Prochiral Center
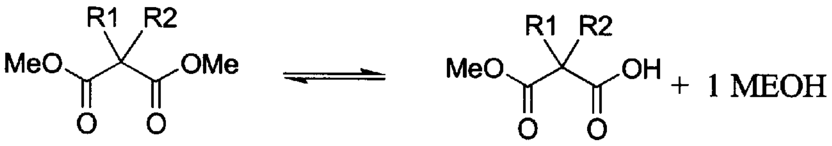
Reference
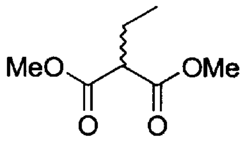
(45)
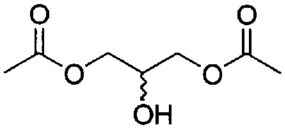
(46)
TYPE IV. Resolution of *Meso* Compounds
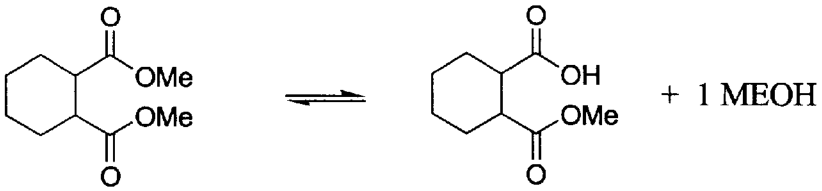
Reference
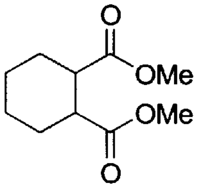
(42)
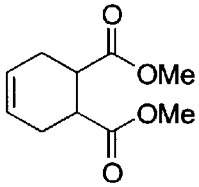
(47) (48)
Reference
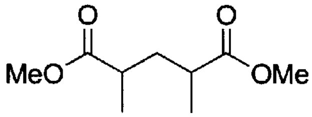
(49)
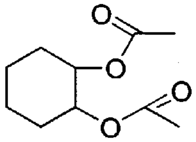
(50)
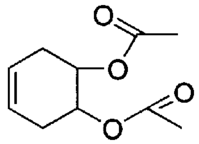
(51)

FIGURE 11
a)
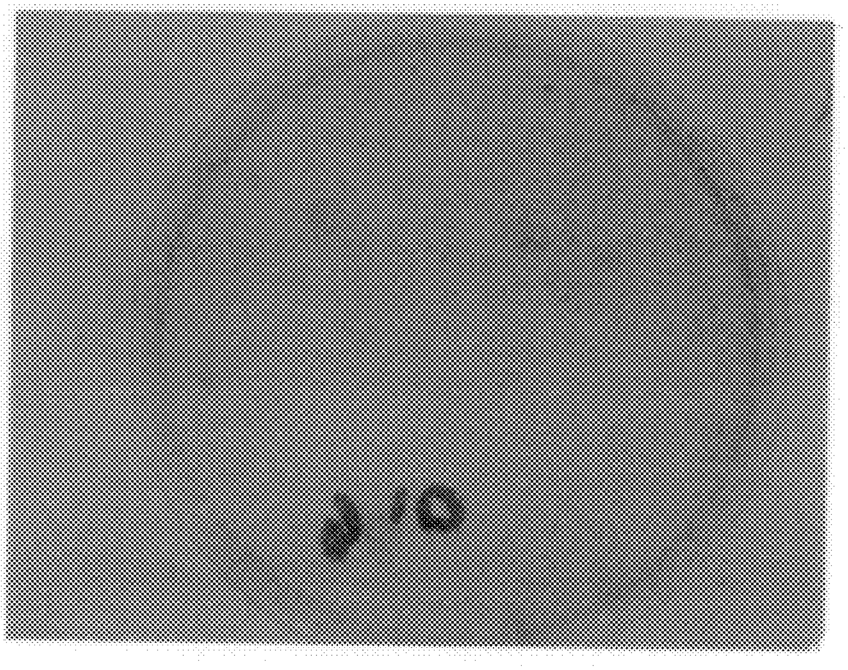
b)
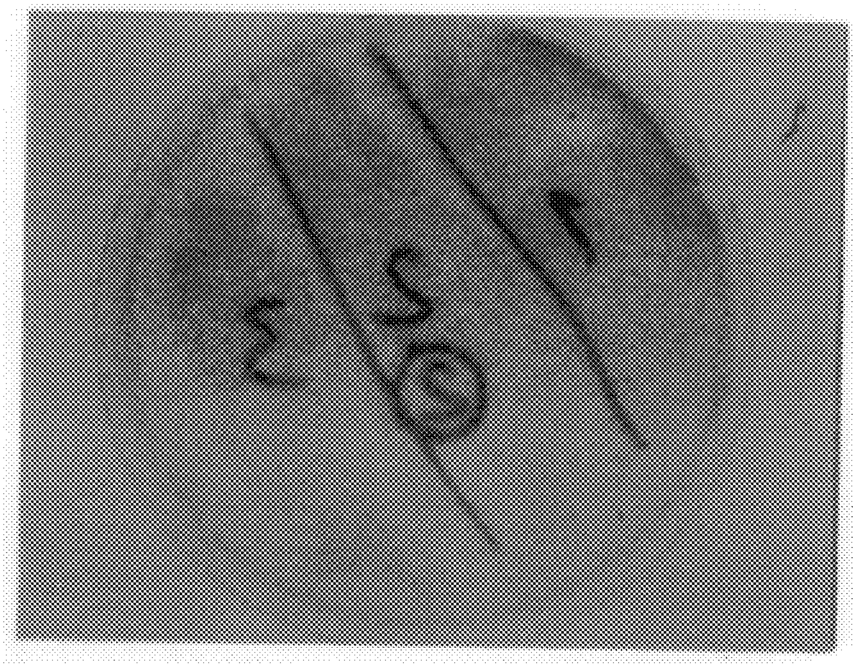

FIGURE 11
c)
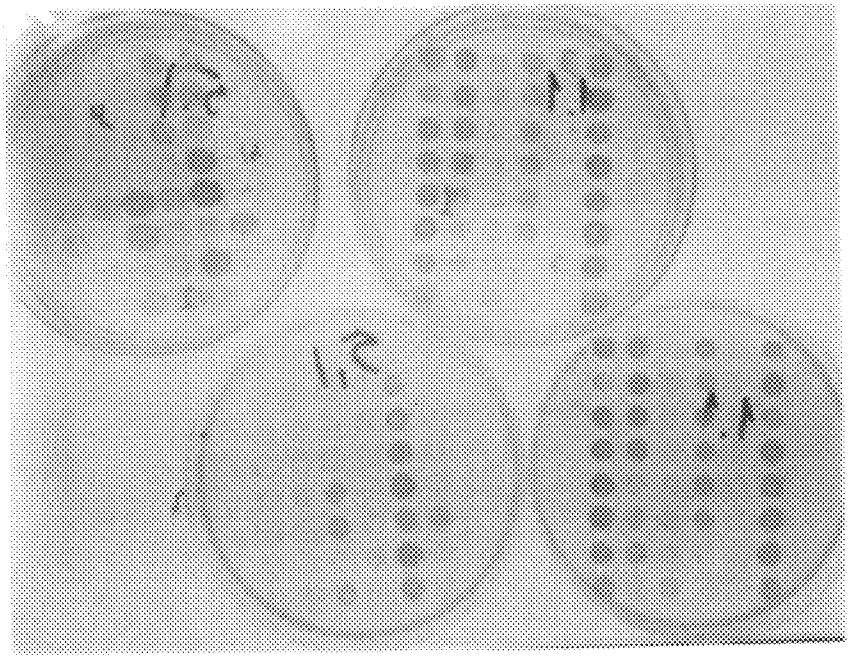
d)
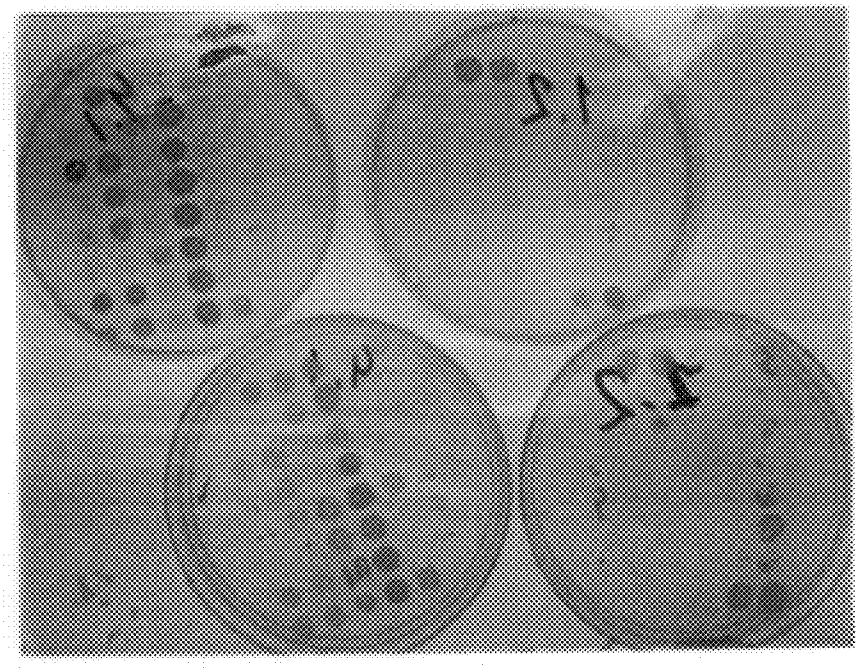

a) Screening positive lambda clones for E001 activity b) Screening positive lambda clones for E002 activity c) Screening positive lambda clones for E003 activity d) Screening positive lambda clones for E004 activity

FIGURE 12
e) Screening positive lambda clones for E005 activity
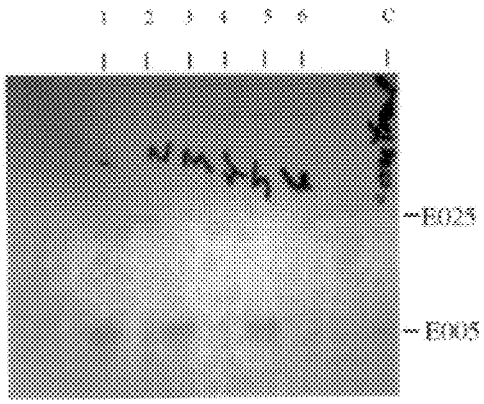
f) Screening positive lambda clones for E006 activity
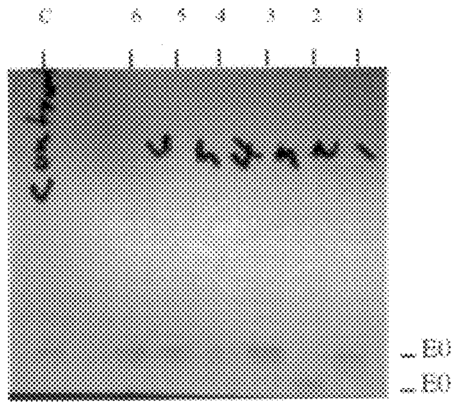
g) Screening positive lambda clones for E008 activity
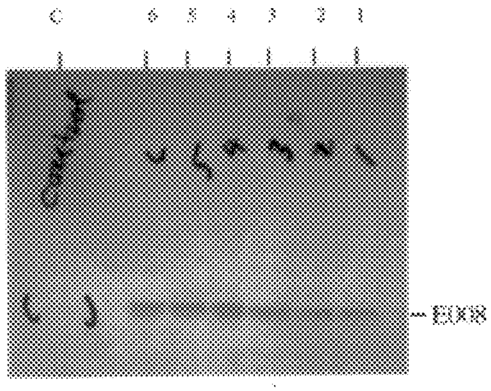
h) Screening positive lambda clones for E009 activity
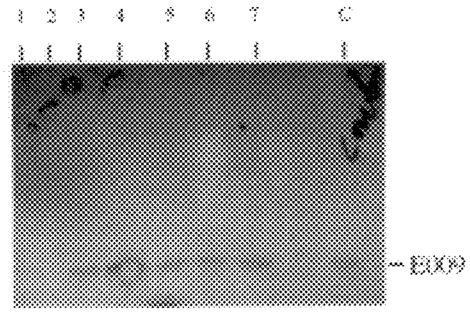

FIGURE 12
i) Screening positive lambda clones for E010 activity
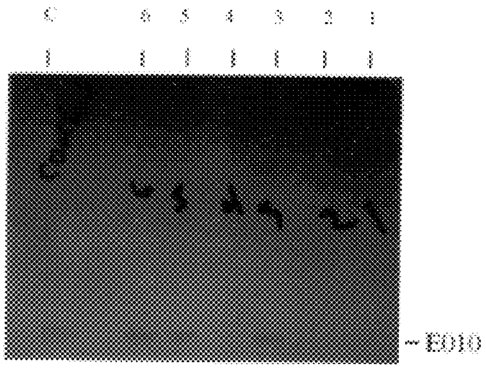
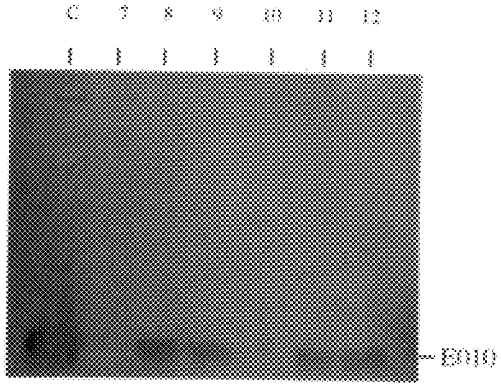
j) Screening positive lambda clones for E011 activity
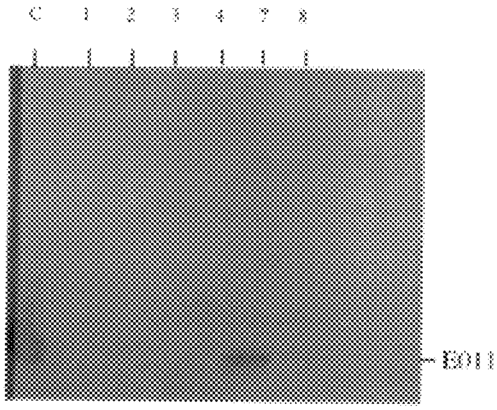
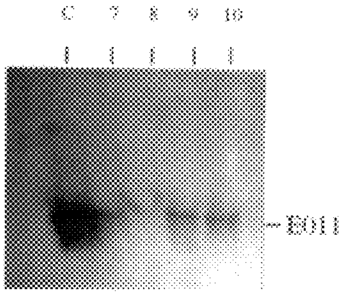

FIGURE 12
k) Screening positive lambda clones for E012 activity
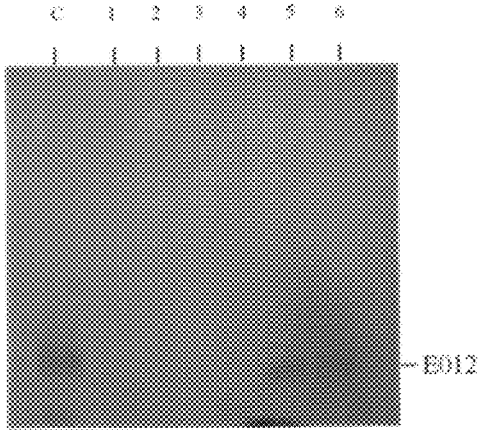
l) Screening positive lambda clones for E013 activity
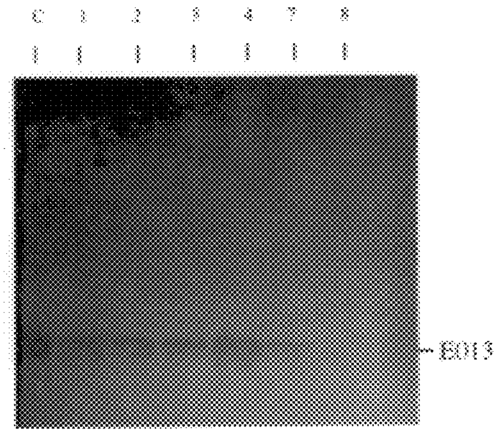
m) Screening positive lambda clones for E014 activity
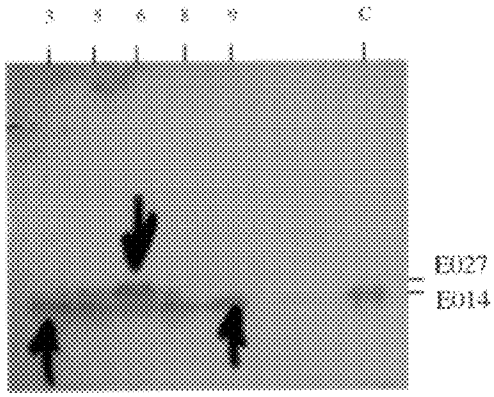
n) Screening positive lambda clones for E015 activity
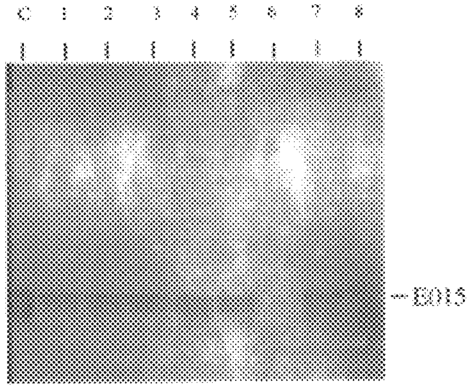

FIGURE 12
o) Screening positive lambda clones for E016 activity
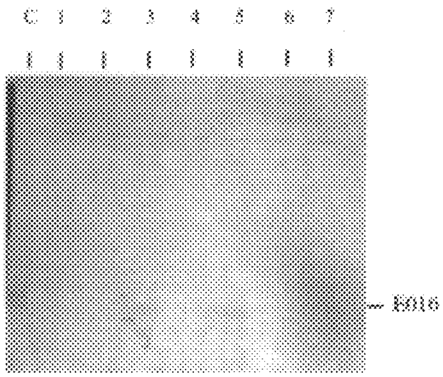
p) Screening positive lambda clones for E019 activity
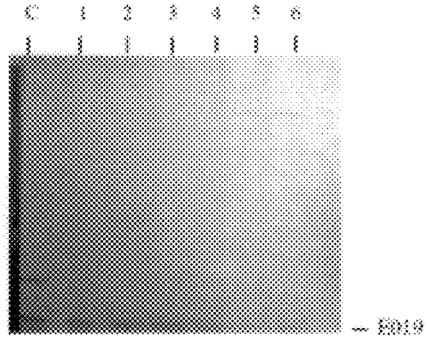
q) Screening positive lambda clones for E020 activity
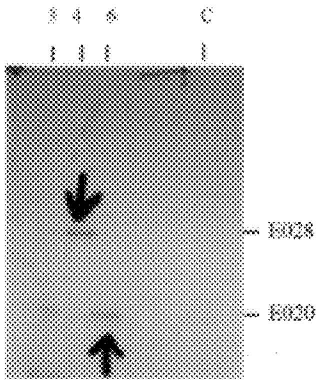
r) Screening positive lambda clones for E021 (E017b) activity
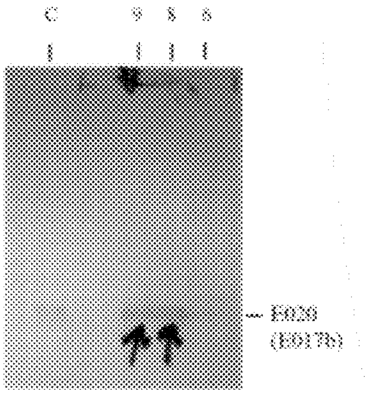

a) 28°C b) 37°C

FIGURE 15
a) EcoRI, BamHI, HindIII, and EcoRV digestions
EcoRI 1-24 BamHI 1-24
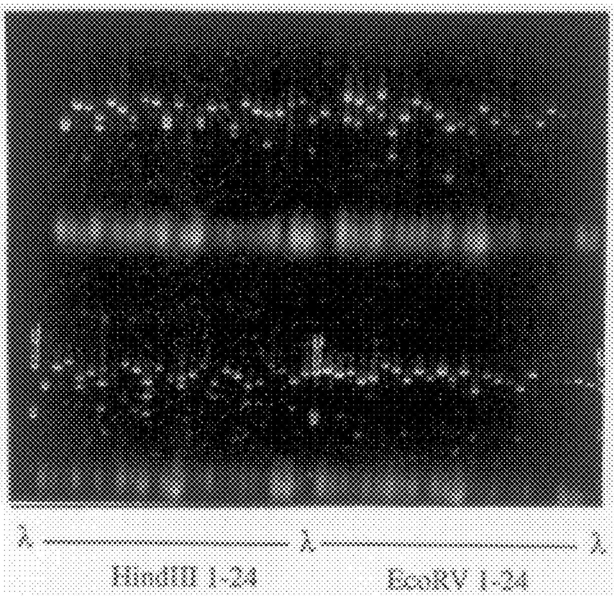
λ —— λ —— λ
HindIII 1-24 EcoRV 1-24
a) PstI 1-18
PstI 1-18
λ —— λ
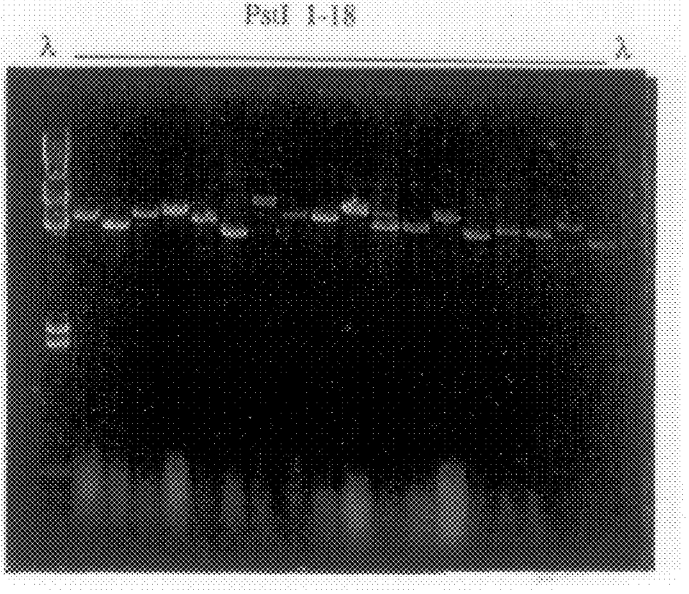

FIGURE 15
c) PstI and SbaI digestions
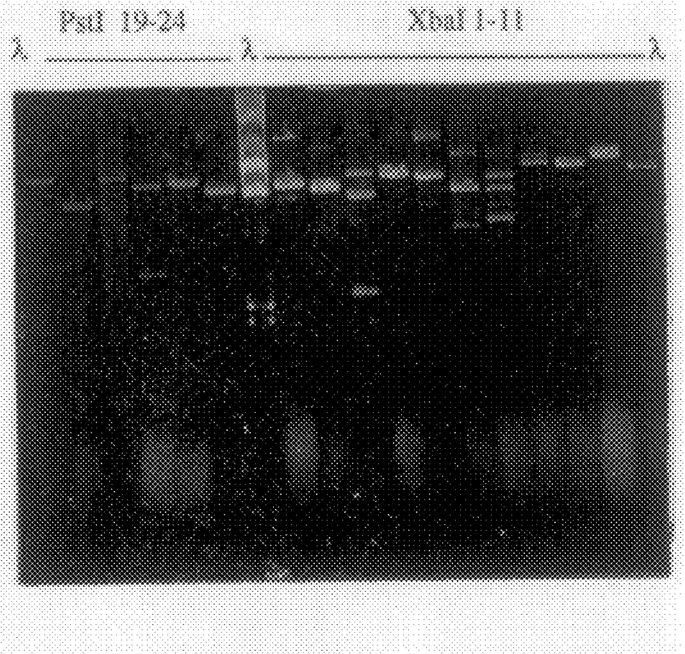
d) XbaI digestions
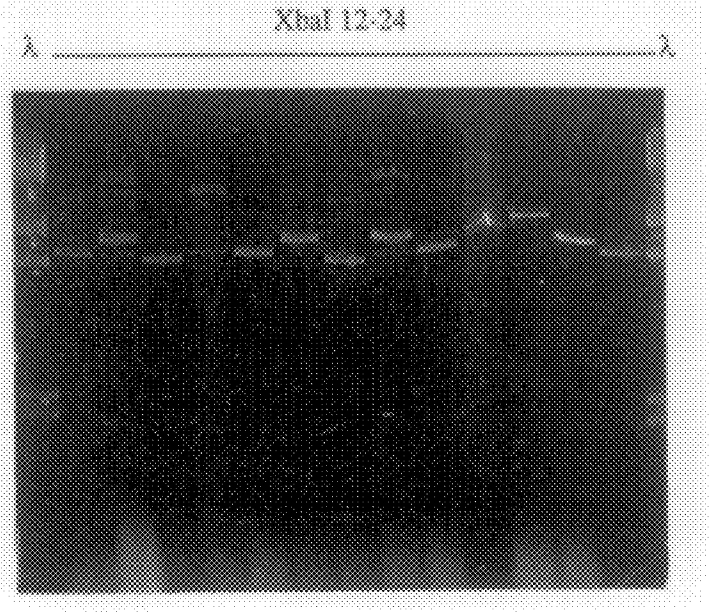

1 TTGAAAAAGG GGATGGGAAC CGTGATCGTG GAAACAAAGT ACGGTCGGTT GCGCGGGGGA ACAAATGAAG
1▸ LeuLysLysG lyMetGlyTh rValIleVal GluThrLysT yrGlyArgLe uArgGlyGly ThrAsnGluG
71 GGGTTTTCTA TTGGAAAGGG ATTCCGTACG CGAAAGCGCC GGTCGGTGAA CGCCGTTTTT TGCCGCCGGA
24▸ lyValPheTy rTrpLysGly IleProTyrA laLysAlaPr oValGlyGlu ArgArgPheL euProProGl
141 ACCGCCCGAT GCATGGGACG GAGTGCGTGA GGCGACATCG TTTGGACCGG TCGTCATGCA GCCGTCCGAT
47▸ uProProAsp AlaTrpAspG lyValArgGl uAlaThrSer PheGlyProV alValMetGl nProSerAsp
211 TCGATGTTCA GCCAGCTGCT CGGACGGATG AATGAACCAA TGAGCGAGGA TGGGTTGTAT CTGAACATTT
71▸ SerMetPheS erGlnLeuLe uGlyArgMet AsnGluProM etSerGluAs pGlyLeuTyr LeuAsnIleT
281 GGTCACCGGC GGCGGATGGG AAGAAGCGCC CGGTATTGTT TTGGATTCAT GGCGGCGCTT TTTTATTCGG
94▸ rpSerProAl aAlaAspGly LysLysArgP roValLeuPh eTrpIleHis GlyGlyAlaP heLeuPheGl
351 CTCCGGTTCA TTTCCATGGT ATGATGGAAC GGCGTTTGCC AAACACGGCG ATGTCGTTGT CGTGACGATC
117▸ ySerGlySer PheProTrpT yrAspGlyTh rAlaPheAla LysHisGlyA spValValVa lValThrIle
421 AACTACCGGA TGAGCGTGTT TGGCTTTTTG TATTTGGGAG ATGCGTTTGG CGAAACGTAT GCCCAGGCGG
141▸ AsnTyrArgM etSerValPh eGlyPheLeu TyrLeuGlyA spAlaPheGl yGluThrTyr AlaGlnAlaG
491 GAAATCTTGG CATATTGGAT CAAGTGGCGG CGCTGCGCTG GGTGAAAGAG AACATTGAGG CGTTCGGCGG
164▸ lyAsnLeuGl yIleLeuAsp GlnValAlaA laLeuArgTr pValLysGlu AsnIleGluA laPheGlyGl
561 TGATCCGGAC AACATTACGA TTTTTGGCGA ATCAGCCGGA GCGGCAAGCG TTGGCGTGCT GTTGTCGCTT
187▸ yAspProAsp AsnIleThrI lePheGlyGl uSerAlaGly AlaAlaSerV alGlyValLe uLeuSerLeu
631 CCGGAAGCAA GCGGGCTGTT TCGACGCGCT ATATTGCAAA GCGGATCGGG TTCGCTTCTT CTTCGTTCTC
211▸ ProGluAlaS erGlyLeuPh eArgArgAla IleLeuGlnS erGlySerGl ySerLeuLeu LeuArgSerP
701 CGGAGACGGC GATGGCTCTG ACTGAACGCA TTTTAGAACG TGCCGGCATC CGTCCGGGTG ACCGCGATCG
234▸ roGluThrAl aMetAlaLeu ThrGluArgI leLeuGluAr gAlaGlyIle ArgProGlyA spArgAspAr
771 GCTGCTGTCG ATTCCAGCAG CAGAGCTATT GCAGGCGGCG ATGTCGCTCG GCCCAGGAAT CACGTACGGT
257▸ gLeuLeuSer IleProAlaA laGluLeuLe uGlnAlaAla MetSerLeuG lyProGlyIl eThrTyrGly
841 CCGGTGGTTG ACGGACATGT GTTGCGACGC CATCCGATCG AAGCGCTCCA CGACGGGGCA GCAAGTGATA
281▸ ProValValA spGlyHisVa lLeuArgArg HisProIleG luAlaLeuHi sAspGlyAla AlaSerAspI
911 TTCCAATCCT AATTGGCGTG ACGAAAGACG AATACAATTT GTTTTCATTG ACTGATCCGT CATTGACAAG
304▸ leProIleLe uIleGlyVal ThrLysAspG luTyrAsnLe uPheSerLeu ThrAspProS erLeuThrAr
981 ACTCGAAGAA AAAGAACTGC TTGACCGGAT GAACCGTGAG GTCGGGCCTA TTCCGGAGGA GGCGGTACGC
327▸ gLeuGluGlu LysGluLeuL euAspArgMe tAsnArgGlu ValGlyProI leProGluGl uAlaValArg
1051 TATTACGCGG AAACAGCGGA TCGGTCGGCA CCCGCGTGGC AAACATGGCT GCGCATCATG ACGTACCTTG
351▸ TyrTyrAlaG luThrAlaAs pArgSerAla ProAlaTrpG lnThrTrpLe uArgIleMet ThrTyrLeuV
1121 TTTTTGTCGA CGGAATGTTG CGAACGGCGG ATGCCCAAGC AGCGCAAGGG GCGAATGTGT ACATGTATCG
374▸ alPheValAs pGlyMetLeu ArgThrAlaA spAlaGlnAl aAlaGlnGly AlaAsnValT yrMetTyrAr
1191 GTTTGATTAT GAAACGCCGG CGTTCGGTGG ACAACTGAAA GCGTGCCATA CGCTCGAGTT GCCGTTTGTG
397▸ gPheAspTyr GluThrProA laPheGlyGl yGlnLeuLys AlaCysHisT hrLeuGluLe uProPheVal
1261 TTTCATAACC TCCATCAGCC TGGTGTCGAG AATTTCGTCG GCAACCGACC AGAGCGTGAG GCGATTGCCA
421▸ PheHisAsnL euHisGlnPr oGlyValGlu AsnPheValG lyAsnArgPr oGluArgGlu AlaIleAlaS
1331 GCGAAATGCA TGGTGCCTGG CTTTCGTTCG CCCGCACCGG CAACCCGAAC GGCGCTCATT TACCAGAGAA
444▸ erGluMetHi sGlyAlaTrp LeuSerPheA laArgThrGl yAsnProAsn GlyAlaHisL euProGluLy
1401 GTGGCCCGTA TACACAAAAG AGCACAAACC GGTGTTTGTC TTTTCGGCTG CGAGCCATGT GGAAGACGAT
467▸ sTrpProVal TyrThrLysG luHisLysPr oValPheVal PheSerAlaA laSerHisVa lGluAspAsp
1471 CCGTTCGGTC GCGAGCGGGA AGCGTGGCAA GGACGCCTTT GA
491▸ ProPheGlyA rgGluArgGl uAlaTrpGln GlyArgLeu• • •

E001 ORF,
underlined possible
start codons.

FIGURE 16A

1 GATCAAGTGG CGATCGACCG CGCGTTGATT GAACTTGACG GCACGGAAAA CAAAGGAAAG CTTGGGGCGA
71 ATGCTATTTT AGGCGTGTCG CTCGCGGTCG CTCGCGCTGC GGCTGATGAG CTTGGCTTGC CGTTGTACCA
141 ATACTTGGGC GGCTTTAACG CTAAAACGCT GCCTGTACCG ATGATGAACA TTTTAAACGG CGGCGCGCAT
211 GCGGACAACA ACGTTGACAT TCAAGAATTC ATGATCATGC CGGTCGGTGC GGAAAGCTTC CGTGAAGCGC
281 TGCGCATGGG TGCAGAAATT TTCCATAGCT TAAAGCTGT GTTAAAAGCG AAAGGCTACA ACACGGCTGT
351 CGGTGACGAA GGCGGATTTG CTCCGAACTT AAAATCGAAC GAAGAAGCGC TGCAAACGAT CATTGAAGCG
421 ATCGAAAAAG CCGGCTACAA ACCAGGCGAA CAAGTGATGC TCGCTATGGA CGTTGCTTCG TCGGAGCTGT
491 ACAACAAAGA AGATGGCAAA TATCATTTGG AAGGCGAAGG CGTCGTCAAA ACATCAGAAG AAATGGTTGC
561 TTGGTATGAA GAGCTTGTGT CGAAATATCC GATCATCTCG ATCGAAGACG GACTTGACGA AAATGACTGG
631 GAAGGCCATA AACTGCTTAC TGAGCGCCTT GGCCACAAAG TGCAGCTCGT CGGTGACGAC TTGTTTGTAA
701 CGAACACGAA AAAACTGGCC GAAGGCATTG AAAAAGGCGT CGGCAACTCG ATTTTAATTA AAGTGAACCA
771 AATCGGTACA CTGACGGAAA CGTTCGATGC CATTGAGATG GCCAAACGCG CCGGCTACAC GGCGGTTGTG
841 TCGCACCGTT CCGGTGAAAC GGAAGACAGC ACGATTGCCG ATATCGCTGT CGCAACAAAC GCTGGCCAAA
911 TCAAAACGGG AGCACCGTCG CGTACGGACC GCGTCGCAAA ATACAACCAG CTGCTCCGCA TTGAAGACGA
981 ACTTGGCCAC ACGGCTATTT ACCAAGGCAT TCGTTCGTTT TACAATTTGA AAAAATAACG GGAATCAACA
1051 ACAAAGGGTG TCTCCAACGT TGCGAGACAC CCTCTTTAAT TACGGGAAAC AGAAATGATT TCCTATCGAT
1121 AGCAAAAAAT GGACGTGGGT AAACCATTCG TTTATAATAT CTTTTTGTAA TCGTTAGAAT ATTGAAAAAG

1▶ LeuLysLys
1191 GGGATGGGAA CCGTGATCGT GGAAACAAAG TACGGTCGGT TGCGCGGGGG AACAAATGAA GGGGTTTTCT
4▶ GlyMetGlyT hrValIleVa lGluThrLys TyrGlyArgL euArgGlyGl yThrAsnGlu GlyValPheT
1261 ATTGGAAAGG GATTCCGTAC GCGAAAGCGC CGGTCGGTGA ACGCCGTTTT TTGCCGCCGG AACCGCCCGA
27▶ yrTrpLysGl yIleProTyr AlaLysAlaP roValGlyGl uArgArgPhe LeuProProG luProProAs
1331 TGCATGGGAC GGAGTGCGTG AGGCGACATC GTTTGGACCG GTCGTCATGC AGCCGTCCGA TTCGATGTTC
50▶ pAlaTrpAsp GlyValArgG luAlaThrSe rPheGlyPro ValValMetG lnProSerAs pSerMetPhe
1401 AGCCAGCTGC TCGGACGGAT GAATGAACCA ATGAGCGAGG ATGGGTTGTA TCTGAACATT TGGTCACCGG
74▶ SerGlnLeuL euGlyArgMe tAsnGluPro MetSerGluA spGlyLeuTy rLeuAsnIle TrpSerProA
1471 CGGCGGATGG GAAGAAGCGC CCGGTATTGT TTTGGATTCA TGGCGGCGCT TTTTTATTCG GCTCCGGTTC
97▶ laAlaAspGl yLysLysArg ProValLeuP heTrpIleHi sGlyGlyAla PheLeuPheG lySerGlySe
1541 ATTTCCATGG TATGATGGAA CGGCGTTTGC CAAACACGGC GATGTCGTTG TCGTGACGAT CAACTACCGG
120▶ rPheProTrp TyrAspGlyT hrAlaPheAl aLysHisGly AspValValV alValThrIl eAsnTyrArg
1611 ATGAGCGTGT TTGGCTTTTT GTATTTGGGA GATGCGTTTG GCGAAACGTA TGCCCAGGCG GGAAATCTTG
144▶ MetSerValP heGlyPheLe uTyrLeuGly AspAlaPheG lyGluThrTy rAlaGlnAla GlyAsnLeuG
1681 GCATATTGGA TCAAGTGGCG GCGCTGCGCT GGGTGAAAGA GAACATTGAG GCGTTCGGCG GTGATCCGGA
167▶ lyIleLeuAs pGlnValAla AlaLeuArgT rpValLysGl uAsnIleGlu AlaPheGlyG lyAspProAs
1751 CAACATTACG ATTTTTGGCG AATCAGCCGG AGCGGCAAGC GTTGGCGTGC TGTTGTCGCT TCCGGAAGCA
190▶ pAsnIleThr IlePheGlyG luSerAlaGl yAlaAlaSer ValGlyValL euLeuSerLe uProGluAla
1821 AGCGGGCTGT TTCGACGCGC TATATTGCAA AGCGGATCGG GTTCGCTTCT TCTTCGTTCT CCGGAGACGG
214▶ SerGlyLeuP heArgArgAl aIleLeuGln SerGlySerG lySerLeuLe uLeuArgSer ProGluThrA
1891 CGATGGCTCT GACTGAACGC ATTTTAGAAC GTGCCGGCAT CCGTCCGGGT GACCGCGATC GGCTGCTGTC
237▶ laMetAlaLe uThrGluArg IleLeuGluA rgAlaGlyIl eArgProGly AspArgAspA rgLeuLeuSe
1961 GATTCCAGCA GCAGAGCTAT TGCAGGCGGC GATGTCGCTC GGCCCAGGAA TCACGTACGG TCCGGTGGTT
260▶ rIleProAla AlaGluLeuL euGlnAlaAl aMetSerLeu GlyProGlyI leThrTyrGl yProValVal
2031 GACGGACATG TGTTGCCGACG CCATCCGATC GAAGCGCTCC ACGACGGGGC AGCAAGTGAT ATTCCAATCC
284▶ AspGlyHisV alLeuArgAr gHisProIle GluAlaLeuH isAspGlyAl aAlaSerAsp IleProIleL
2101 TAATTGGCGT GACGAAAGAC GAATACAATT TGTTTTCATT GACTGATCCG TCATTGACAA GACTCGAAGA
307▶ euIleGlyVa lThrLysAsp GluTyrAsnL euPheSerLe uThrAspPro SerLeuThrA rgLeuGluGl
2171 AAAAGAACTG CTTGACCGGA TGAACCGTGA GGTCGGGCCT ATTCCGGAGG AGGCGGTACG CTATTACGCG
330▶ uLysGluLeu LeuAspArgM etAsnArgGl uValGlyPro IleProGluG luAlaValAr gTyrTyrAla
2241 GAAACAGCGG ATCGGTCGGC ACCCGCGTGG CAAACATGGC TGCGCATCAT GACGTACCTT GTTTTTGTCG
354▶ GluThrAlaA spArgSerAl aProAlaTrp GlnThrTrpL euArgIleMe tThrTyrLeu ValPheValA
2311 ACGGAATGTT GCGAACGGCG GATGCCCAAG CAGCGCAAGG GGCGAATGTG TACATGTATC GGTTTGATTA
377▶ spGlyMetLe uArgThrAla AspAlaGlnA laAlaGlnGl yAlaAsnVal TyrMetTyrA rgPheAspTy
2381 TGAAACGCCG GCGTTCGGTG GACAACTGAA AGCGTGCCAT ACGCTCGAGT TGCCGTTTGT GTTTCATAAC
400▶ rGluThrPro AlaPheGlyG lyGlnLeuLy sAlaCysHis ThrLeuGluL euProPheVa lPheHisAsn
2451 CTCCATCAGC CTGGTGTCGA GAATTTCGTC GGCAACCGAC CAGAGCGTGA GGCGATTGCC AGCGAAATGC
424▶ LeuHisGlnP roGlyValGl uAsnPheVal GlyAsnArgP roGluArgGl uAlaIleAla SerGluMetH
2521 ATGGTGCCTG GCTTTCGTTC GCCCGCACCG GCAACCCGAA CGGCGCTCAT TTACCAGAGA AGTGGCCCGT
447▶ isGlyAlaTr pLeuSerPhe AlaArgThrG lyAsnProAs nGlyAlaHis LeuProGluL ysTrpProVa
2591 ATACACAAAA GAGCACAAAC CGGTGTTTGT CTTTTCGGCT GCGAGCCATG TGGAAGACGA TCCGTTCGGT
470▶ lTyrThrLys GluHisLysP roValPheVa lPheSerAla AlaSerHisV alGluAspAs pProPheGly
2661 CGCGAGCGGG AAGCGTGGCA AGGACGCCTT TGACGAAAAA ATCCATAAGC AACATGTGTT CTTTGTCTGA
494▶ ArgGluArgG luAlaTrpGl nGlyArgLeu •••
2731 ACACGATCAA GGTACGCGCA TTTTCGCGGA AAAAGACCGT GGGCAAACGT TCGCCTTTAC CTCTAAAAGG

FIGURE 16B

```
2801  .GACGCAA CAT' 'GCA CTTCACAGGA AAGAGGACGA AACGGTTGGT :AGAAT.. .GAAAAGGTG
2871  TCCCGTTTTT TGG...ACCT TCTTCTATGT ATCGCTCAAT CATTTGCTTC 1GTGGCAGGA AGCCCGAATC
2941  GCTCGGCGAG TGCCGGATCA CGATCGATCG CCTCAATCAG TTTCCGCATG ACGTTCACAT CAAACGTAAA
3011  ATTCGAACCG ATTGGCGAGG TGACGAAAAT TTTCCCTTCT TTCGCCTCGC GTGCTCGTTT AAATTGATAG
3081  CCGTCAATCG CAATGACGAC TCGTTCGTCT GGCCTTGCCA TTAGGAATCC CTCCATCGCT GTTTTTTCTT
3151  TCATTGTACT TGATTTTGAG GATGAACACC AACGTTCATG ACACGCTCTT AAGGATAACG GATGGGAGAG
3221  CGTTAGAGGG CGGTGAATTT CATCAAGAAC GTAGCACAAA ACGACATTTT TTCATTATAG ACGTCTTGAT
3291  GTTTGGAATG ATCGGAAAAG GCGATTGTTA GGCGGGGATC ATGATCCACT AGCGGATGAA AGTGAAGAGC
3361  AACGAAATAG TCTCTTTGTT TCACAACAAA TGAATTGGTG CCATTCAGGG CGGAGACAGG TGAGACAGTT
3431  GCTGCAAACG ATAATGTATG GTATAGTAAA AATATTGCAA CGTAGGTCGT TGGAGGTGTC AGGCATGCAT
3501  GCCTTGCTTG TGACGTTGCT TGTCATTGTA TCGATTGCGC TGATTGCGAT TGTGTTGTTG CAGTCAGGCC
3571  GAAGCGCAGG GCTGTCGGGG GCGATTACCG GCGGTGCCGA GCAGCTGTTT GGCAAACAGA AAGCGCGCGG
3641  GCTTGATGCA GTGTTTCAGC GCGTGACGGT CGTGTTGGCC ATTTTGTTTT TTGTGTTGAC GATTCTCGTC
3711  GCATATGTCC AACCATCATA AGCGAAAAGC GGGGGGCGGT CCTAACAAAA ACGGGCTGCC TTTTCTATTT
3781  CATCTAGAGA GGAAGGAGAA CGATGATGAA AATTGTTCCG CCAAAACCGT TTTTCTTTGA AGCCGGGGAG
3851  CGTGCCGTTT TGCTTTTGCA CGGATTTACC GGAAACTCCG CTGATGTTCG GATGCTCGGA CGCTTTCTCG
3921  AATCAAAAGG CTACACGTGC CATGCGCCGA TTTACAAAGG GCATGGCGTG CCGCCGGAAG AGCTCGTCCA
3991  TACCGGTCCG GACGATTGGT GGCAAGATGT GATGAACGGT TATCAGTTTT TGAAAAACAA AGGATATGAA
4061  AAAATCGCGG TTGCTGGGTT GTCGCTTGGA GGCGTATTTT CCTTAAAATT AGGTTACACT GTACCTATAG
4131  AAGGAATTGT GACCATGTGC GCACCGATGT ACATCAAAAG CGAAGAAACG ATGTATGAAG GTGTGCTTGA
4201  GTATGCGCGC GAATATAAAA AACGGGAAGG AAAATCGGCA GAACAAATCG AACAGGAAAT GGAACGGTTC
4271  AAACAAACGC CGATGAAAAC ATTAAAAGCG CTGCAAGCGT TGATC
```

E001 sequence
with ORF

FIGURE 16B (cont.)

```
   1  TTGATTCAAA TGAATACGTT GGTGGAAACC CGTTTTGGGA AAGTGCAAGG CGGTACAGAC GGAGAGGTTT
   1▸ LeuIleGlnM etAsnThrLe uValGluThr ArgPheGlyL ysValGlnGl yGlyThrAsp GlyGluValC
  71  GTTTTTGGAA AGGGATTCCT TATGCGAAAC CTCCGGTGGG AAAACGCCGC TTTCAAAAAC CGGAACCGCC
  24▸ ysPheTrpLy sGlyIlePro TyrAlaLysP roProValGl yLysArgArg PheGlnLysP roGluProPr
 141  GGAGAAATGG GATGGCGTTT GGGAGGCCAC CCGGTTCCGG TCCATGGTGA TGCAGCCGTC CGGCACCACC
  47▸ oGluLysTrp AspGlyValT rpGluAlaTh rArgPheArg SerMetValM etGlnProSe rGlyThrThr
 211  TTCAGCACCG TGCTCGGGGA AGCGGATCTT CCTGTGAGCG AAGACGGTCT TTATCTGAAT ATCTGGTCGC
  71▸ PheSerThrV alLeuGlyGl uAlaAspLeu ProValSerG luAspGlyLe uTyrLeuAsn IleTrpSerP
 281  CGGCAGCCGA CGGAAAAAAG CGGCCGGTGC TCTTCTGGAT CCATGGCGGC GCCTACCAGT TTGGGTCCGG
  94▸ roAlaAlaAs pGlyLysLys ArgProValL euPheTrpIl eHisGlyGly AlaTyrGlnP heGlySerGl
 351  CGCTTCCCCC TGGTATGACG GGACGGAGTT TGCCAAAAAC GGAGATGTGG TGGTTGTCAC GATCAACTAC
 117▸ yAlaSerPro TrpTyrAspG lyThrGluPh eAlaLysAsn GlyAspValV alValValTh rIleAsnTyr
 421  CGGTTGAACG CGTTTGGATT TTTGTACTTG GCAGATTGGT TCGGCGACGA ATTTTCAGCG TCGGGCAACC
 141▸ ArgLeuAsnA laPheGlyPh eLeuTyrLeu AlaAspTrpP heGlyAspGl uPheSerAla SerGlyAsnL
 491  TGGGAATTTT GGACCAAGTC GCTGCACTGC GCTGGGTGAA AGAAAACATT TCGGCATTCG GCGGCGACCC
 164▸ euGlyIleLe uAspGlnVal AlaAlaLeuA rgTrpValLy sGluAsnIle SerAlaPheG lyGlyAspPr
 561  GGAGCAAATC ACCATCTTCG GGGAGTCGGC CGGAGCCGGA AGCGTCGGGG TTCTGCTTTC CCTCCCGGAA
 187▸ oGluGlnIle ThrIlePheG lyGluSerAl aGlyAlaGly SerValGlyV alLeuLeuSe rLeuProGlu
 631  ACCAAAGGGC TGTTTCAACG GGCGATCTTG CAAAGCGGAT CGGGTGCCAT TTTGCTCCGT TCCTCTCAGA
 211▸ ThrLysGlyL euPheGlnAr gAlaIleLeu GlnSerGlyS erGlyAlaIl eLeuLeuArg SerSerGlnT
 701  CAGCCTCGGG CATCGCGGAA CAAATTCTTA CGAAAGCCGG CATTCGAAAA GGAGACCGCG ACCGGTTGTT
 234▸ hrAlaSerGl yIleAlaGlu GlnIleLeuT hrLysAlaGl yIleArgLys GlyAspArgA spArgLeuLe
 771  ATCCATCCCG GCCGGTGAAC TCCTTGAAGC CGCACAATCC GTGAATCCGG GAATGGTTTT TGGTCCCGTT
 257▸ uSerIlePro AlaGlyGluL euLeuGluAl aAlaGlnSer ValAsnProG lyMetValPh eGlyProVal
 841  GTGGACGGCA CCGTATTGAA AACCCATCCG ATTGAAGCGT TGGAAACCGG AGCCGCCGGC GATATCCCGA
 281▸ ValAspGlyT hrValLeuLy sThrHisPro IleGluAlaL euGluThrGl yAlaAlaGly AspIleProI
 911  TCATCATCGG GGTGACAAAG GATGAGTACA ATTTATTTAC ACTGACTGAC CCTTCCTGGA CGACAGCGGG
 304▸ leIleIleGl yValThrLys AspGluTyrA snLeuPheTh rLeuThrAsp ProSerTrpT hrThrAlaGl
 981  AAAAGAAGAA CTGATGGACC GGATCGAACA GGAAATCGGG CCGGTTCCGG AAAAAGTTTT TCCATATTAC
 327▸ yLysGluGlu LeuMetAspA rgIleGluGl nGluIleGly ProValProG luLysValPh eProTyrTyr
1051  TTATCTTTTG GGGATCCATC GCAACCGGTA TGGCAAAAGC TGTTGCGCGC CATGACCTAC CACATCTTTA
 351▸ LeuSerPheG lyAspProSe rGlnProVal TrpGlnLysL euLeuArgAl aMetThrTyr HisIlePheT
1121  CCCGGGGCAT GTTAAAAACG GCTGACGCCC AAATCAAGCA AGGCGGGAAG GTTTGGGTTT ACCGGTTTGA
 374▸ hrArgGlyMe tLeuLysThr AlaAspAlaG lnIleLysGl nGlyGlyLys ValTrpValT yrArgPheAs
1191  TTACGAAACC CCGCTCTTTG ACGGTCGGTT GAAAGCATGT CACGCACTGG AAATCCCCTT TGTCTTTCAC
 397▸ pTyrGluThr ProLeuPheA spGlyArgLe uLysAlaCys HisAlaLeuG luIleProPh eValPheHis
1261  AACCTGCATC AACCGGGGGT CGATGTGTTC ACCGGCACAC ATCCGAAGCG GGAGCTAATT TCCCGGCAAA
 421▸ AsnLeuHisG lnProGlyVa lAspValPhe ThrGlyThrH isProLysAr gGluLeuIle SerArgGlnM
1331  TGCATGAAGC ATGGATTGCC TTTGCCCGGA CAGGGGATCC GAACGGCGAC CATCTCCCCG ATGCGTGGTT
 444▸ etHisGluAl aTrpIleAla PheAlaArgT hrGlyAspPr oAsnGlyAsp HisLeuProA spAlaTrpLe
1401  GCCCTTTGCA CAAAAAGACC GGCCGGCCAT GGTCTTTGAC ACCGAAACCA GAGCGGAAAA GCATCTGTTT
 467▸ uProPheAla GlnLysAspA rgProAlaMe tValPheAsp ThrGluThrA rgAlaGluLy sHisLeuPhe
1471  GACCGCGAGC AGGAACTGTG GGAATCAAAG GCTTGA
 491▸ AspArgGluG lnGluLeuTr pGluSerLys Ala•••
```

E009 ORF,
underlined possible
start codons.

FIGURE 16C

```
   1 GATCCAAAAA CGAAAAAAGG CTTTTGTGGA TGAATTTGTC GTCCCTTTGG TGCAAGAAGC CCACAAACTG
  71 GGGATTACGG AAAGTGAAGT GTTTGCGCTG ATCAAAAAAG AAAGGAAAGG GATTGAGGAT GAATTATAAA
 141 GTGGAATTCG ACAATGTATC GTTGCGATAC AAAGACTTTG AGGCGCTCAA AAATGTTTCC TTCCAACTGG
 211 AAAGCGGAAA GATTTACGGT TTGCTCGGCC GGAACGGAGC CGGAAAGACC TCCCTCCTTT CTCTCTTGTC
 281 ATCTTTTCGC CTGCCGACGG AAGGATCAAT CTTGATCAGC GGGGAACCGC CGTTTGAAAA CCCGAAGATC
 351 ATGCCTCATG TTGTGTTGGT TTACGAAAAA GATTACAAGG AAGAGCGGAA TAAAGTCTCC ACCTTCATTC
 421 AGGATGCAGC CAAGTTCCGC CCGTTCTTTG ACATGAATTA TGCACTTCGG CTGGCTGAGA AATTCAAGCT
 491 TCCTTTAAAC AAAGAAGTGA GAAAACTGTC AAGAGGAATG AAGTCGGCGA TGAATGTGAC CATCGGACTG
 561 GCCAGCCGGG CGCCCGTGAC CATTTTTGAC GAGGCTTATC TTGGCATGGA TGCTCCGACC CGGGAAATGT
 631 TTTATAAAGA ATTGTTGAGA GACCAAGCCA AACATCCCCG GACCATGATT TTATCCACCC ACTTGGTGTC
 701 TGAAATGGAT TATTTGTTTG AAGAAGTGCT GATTCTCGAT CGCGGAAAGC TGTTGCTCCA TGAAGACTAT
 771 GAAACCTTGA TTTCCAAGGG ACTCATCATC ACAGGAGATG CCGGGGCGGT TGATGATTTC ACCAAAGGTC
 841 GGAAGATCCT GAACGAAGAG CAGCTCGGAA ATACAAAATC GGTAATTGTG TTCGGGGATT TCAATGAAGA
 911 TCTCCGGTTG GAAGCCGAAG AACAAGGATT GGAAACCGGG ACCTGCTCTT TGCAAGATCT GTTTATTCAT
 981 TTAACAGGCA AGGAGGATGC ATATGAAACC AACAGCCGTA TTTCCTAAAG TGGCCAAAGA CATGTACTTG
1051 GAACAAATGA AATGGACGGT TTGGTTTCTG GTTTTTGTGT TGGTTACCCA AATCGTACAT CTTTATTCCA
1121 GTTATTTTAC AATCGATGAT AACACCGCGG TGAAAGGGAT TTTGGTGCAT CTTTTTCCAT CGGCAAAGGT
1191 TTATATGATC GTGATCGCAA TTATTTCCGT CAACGGATTC CTGTCTTATT ATGTCGGGCA GGGAGTCACC
1261 CGGAGAGATT TTTGGGCCGG CTCGATGCTT GCCGCGCTCG GGCTGACGGC CACGATCACT TTCTCCGCTG
1331 TGATTCTCAC TTATTTGGAA TACGGGATTT TGGAGATGTT CCAGCTATCT CATTTGCTGT CTGACGAATT
1401 TTTGAACGGA AACGGGTGGC TGGTGATTCA ATATCTGCTT AATATCTTTT TCTATTACTT GGCAGGTTAC
1471 CTGATCGGAG TCGGTTTTTA CCGGTTCCAC TGGATCGTCG GAATCGGATT TGTTGCCTTT TTCCTTCTTT
1541 CTGTTTCAGC GCTGGAATGG AGCGAAAAAT ATTCGCTCGG GCTGAATATA TTGAGTTCTG CGGCGGCCAT
1611 TGTCCTCTTT CTCACCTTAT TGCGCCAGTT AACAAAGAAT ATCGCCGTGA AGTTGTAAAT GGATCCGGGA
1681 GACTCAGGTC CGCATGTTGC CTGAGTCTCT TTGCCTTTTC ATGGCGTCTG GGATTCATCC CTTTTTTGCT
1751 TTGCCAAGCG TTTTTTTTGA ATCCAGACCA GCAATTTAAG GATCAGGAAC AACAGAAAGA TGGCTCCTGA
1821 TACAAGAATA ATGGCTCCTG ATATGATGGA CACAACCTTC CAAAAACCAA AAAAGTTCGC GGCCCGCAAA
1891 ATGATGAGCA GGATGGCAAA AGGAATGAGA AAGCCGATGA CATCCTTCCC TTTCACTAAC CCCTCTTCCT
1961 CCTTTTTTGT TGGAATATCG TTCAGGTTAA CGGGCTTGTC CCTCAGTGTC AATAAGGTGT AAGTGACAAC
2031 ATCCCAAACA AAATTCAGTG CGAAAAAACA AAGCGGACGG GATTGGCCGG AGGTTGATCA AAAGGGCACC
2101 CCCTCTAATT CACGCTGGAT CTTTCCTTTG TGTTTTAAAA CTTAAAGCAC CGGATTGCCG GCTGTATGGT
2171 CCGGTTGGAT ATTGTCATCA CATCGTGGAT ATCAGTGGAT CCGGTGCGAT GGATTGCTTC AGGGGAACTT
2241 TTAAACACTT GAGTTTGACA ACCACTCCTT AATCATTTAA GATTTAAATG AAAATTAAAA TAAATCAAAA
2311 AGATTGATTC AAATGAATAC GTTGGTGGAA ACCCGTTTTG GGAAAGTGCA AGGCGGTACA GACGGAGAGG
   1▶LeuIleG InMetAsnTh rLeuValGlu ThrArgPheG lyLysValGl nGlyGlyThr AspGlyGluV
2381 TTTGTTTTTG GAAAGGGATT CCTTATGCGA AACCTCCGGT GGGAAAACGC CGCTTTCAAA AACCGGAACC
  23▶alCysPheTr pLysGlyIle ProTyrAlaL ysProProVa lGlyLysArg ArgPheGlnL ysProGluPr
2451 GCCGGAGAAA TGGGATGGCG TTTGGGAGGC CACCCGGTTC CGGTCCATGG TGATGCAGCC GTCCGGCACC
  46▶oProGluLys TrpAspGlyV alTrpGluAl aThrArgPhe ArgSerMetV alMetGlnPr oSerGlyThr
2521 ACCTTCAGCA CCGTGCTCGG GGAAGCGGAT CTTCCTGTGA GCGAAGACGG TCTTTATCTG AATATCTGGT
  70▶ThrPheSerT hrValLeuGl yGluAlaAsp LeuProValS erGluAspGl yLeuTyrLeu AsnIleTrpS
2591 CGCCGGCAGC CGACGGAAAA AAGCGGCCGG TGCTCTTCTG GATCCATGGC GGCGCCTACC AGTTTGGGTC
  93▶erProAlaAl aAspGlyLys LysArgProV alLeuPheTr pIleHisGly GlyAlaTyrG lnPheGlySe
2661 CGGCGCTTCC CCCTGGTATG ACGGGACGGA GTTTGCCAAA AACGGAGATG TGGTGGTTGT CACGATCAAC
 116▶rGlyAlaSer ProTrpTyrA spGlyThrGl uPheAlaLys AsnGlyAspV alValValVa lThrIleAsn
2731 TACCGGTTGA ACGCGTTTGG ATTTTTGTAC TTGGCAGATT GGTTCGGCGA CGAATTTTCA GCGTCGGGCA
 140▶TyrArgLeuA snAlaPheGl yPheLeuTyr LeuAlaAspT rpPheGlyAs pGluPheSer AlaSerGlyA
2801 ACCTGGGAAT TTTGGACCAA GTCGCTGCAC TGCGCTGGGT GAAAGAAAAC ATTTCGGCAT TCGGCGGCGA
 163▶snLeuGlyIl eLeuAspGln ValAlaAlaL euArgTrpVa lLysGluAsn IleSerAlaP heGlyGlyAs
2871 CCCGGAGCAA ATCACCATCT TCGGGGAGTC GGCCGGAGCC GGAAGCGTCG GGGTTCTGCT TTCCCTCCCG
 186▶pProGluGln IleThrIleP heGlyGluSe rAlaGlyAla GlySerValG lyValLeuLe uSerLeuPro
2941 GAAACCAAAG GGCTGTTTCA ACGGGCGATC TTGCAAAGCG GATCGGGTGC CATTTTGCTC CGTTCCTCTC
 210▶GluThrLysG lyLeuPheGl nArgAlaIle LeuGlnSerG lySerGlyAl aIleLeuLeu ArgSerSerG
3011 AGACAGCCTC GGGCATCGCG GAACAAATTC TTACGAAAGC CGGCATTCGA AAAGGAGACC GCGACCGGTT
 233▶lnThrAlaSe rGlyIleAla GluGlnIleL euThrLysAl aGlyIleArg LysGlyAspA rgAspArgLe
3081 GTTATCCATC CCGGCCGGTG AACTCCTTGA AGCCGCACAA TCCGTGAATC CGGGAATGGT TTTTGGTCCC
 256▶uLeuSerIle ProAlaGlyG luLeuLeuGl uAlaAlaGln SerValAsnP roGlyMetVa lPheGlyPro
3151 GTTGTGGACG GCACCGTATT GAAAACCCAT CCGATTGAAG CGTTGGAAAC CGGAGCCGCC GGCGATATCC
 280▶ValValAspG lyThrValLe uLysThrHis ProIleGluA laLeuGluTh rGlyAlaAla GlyAspIleP
3221 CGATCATCAT CGGGGTGACA AAGGATGAGT ACAATTTATT TACACTGACT GACCCTTCCT GGACGACAGC
 303▶roIleIleIl eGlyValThr LysAspGluT yrAsnLeuPh eThrLeuThr AspProSerT rpThrThrAl
3291 GGGAAAAGAA GAACTGATGG ACCGGATCGA ACAGGAAATC GGGCCGGTTC CGGAAAAAGT TTTTCCATAT
 326▶aGlyLysGlu GluLeuMetA spArgIleGl uGlnGluIle GlyProValP roGluLysVa lPheProTyr
3361 TACTTATCTT TTGGGGATCC ATCGCAACCG GTATGGCAAA AGCTGTTGCG CGCCATGACC TACCACATCT
 350▶TyrLeuSerP heGlyAspPr oSerGlnPro ValTrpGlnL ysLeuLeuAr gAlaMetThr TyrHisIleP
3431 TTACCCGGGG CATGTTAAAA ACGGCTGACG CCCAAATCAA GCAAGGCGGG AAGGTTTGGG TTTACCGGTT
 373▶heThrArgGl yMetLeuLys ThrAlaAspA laGlnIleLy sGlnGlyGly LysValTrpV alTyrArgPh
3501 TGATTACGAA ACCCCGCTCT TTGACGGTCG GTTGAAAGCA TGTCACGCAC TGGAAATCCC CTTTGTCTTT
 396▶eAspTyrGlu ThrProLeuP heAspGlyAr gLeuLysAla CysHisAlaL euGluIlePr oPheValPhe
```

FIGURE 16D

```
3571  CA[illegible]AACCTGC ATCA[illegible]G GGTCGATGTG TTCACCGGCA CACATCCGAA GCGGG[illegible]A ATTTCC[illegible]GC
 420▶ HisAsnLeuH isGln[illegible]oGl yValAspVal PheThrGlyT hrHisProLy sArgGluLeu IleSerArgG
3641  AAATGCATGA AGCATGGATT GCCTTTGCCC GGACAGGGGA TCCGAACGGC GACCATCTCC CCGATGCGTG
 443▶ lnMetHisGl uAlaTrpIle AlaPheAlaA rgThrGlyAs pProAsnGly AspHisLeuP roAspAlaTr
3711  GTTGCCCTTT GCACAAAAAG ACCGGCCGGC CATGGTCTTT GACACCGAAA CCAGAGCGGA AAAGCATCTG
 466▶ pLeuProPhe AlaGlnLysA spArgProAl aMetValPhe AspThrGluT hrArgAlaGl uLysHisLeu
3781  TTTGACCGCG AGCAGGAACT GTGGGAATCA AAGGCTTGAG TGATTTGCTC AAGCCTTTTT TGCATTTCAC
 490▶ PheAspArgG luGlnGluLe uTrpGluSer LysAla•••
3851  GTATGTATTC GGATTTGGAA TTAAACAATG GTGCTTTTAT CGAAATGGGG AGTGTTTGCT TATAATGAAC
3921  GGGTTTACAA AGCTTGTTTT GGTACCGGAT TACTGAAATG ATCCGTGTTT ATCATTTGGA TGCTTTCTAT
3991  TGGAAACCGG GCTGGGTGGA GTCTTCCCCG GAGGAGTTCG TTGCAGCTCA GCAAGAAATT GTGAACCAAT
4061  GCCAATGGAT TGTGGAAGGG AATTACAGTA GAGAGAAATA AATAAGAACG CCGAAGAAAG GTCGAACCGT
4131  TATTATAAGA AAACATGAGA TTTTGGGGAT TAGTTCCAGC GAATAAGTGG GGGGTATTAT GAAATGGAGA
4201  AAAAGCAAGG TACCTGCTGA TAAGCAATCA ATTGATCAGG TAAAAAATTT TGGGATTCAA TTTCCTTCCG
4271  ATTTCCGACA AATTGCAATT ACTTCTCATG GAACCCAACC AAGTCCTGAT ACGATTGACT TTGGAGTTCT
4341  AAAAAATCAT CTTCTTCAAA CCAAACAGAA AAACGAACCT CACGAATCGT TTTATTCAAA ATTTCTCACT
4411  CTGTTAAAGT GGGATGTCAG TAAACGTTAT AAAAATATCT TTTGATGATT GTATCATCAG CAATGAAAGA
4481  AAGACAAAAG AGGACTATGA GATATTTCTT TACAACAAAA GATGGATTAT CCTGAGGATA GTATATATAT
4551  TCCTAATCCT TTGAATATCA TCCGGATTGG ATAGAGGGGT CGTTATGCAA TGGTATCATC ATGTTAGTGA
4621  AGATGCAAAG GCGGCTTTTT ATTTATCTTT AACAGAAAAA GTATTGGATA AAATCAGTCA TTATGAATGG
4691  TTTCCTCATG TAAAAGAAAC CATGAACATG TGTTGGGATT GGATTGAGGA AAAAGGATGG AGTGGACATG
4761  ATCTTTATGA AAGGCTTGAT GATGAAGAAT CAGAAACAGG GTTATTTTCA ATTCACATGA ATGAAGTCGA
4831  TGCTGGTTTA GATGACGATG AAGATGAACT TGCTTTTTTC TGTGTAATTG ATGCAGTGGC CTACACGGTT
4901  TGGCAAGCCT GTAAGTATGA AGAGAAAGGC TATGTTCCGC AAGCAATTGA AGTTGTAAAT GATGAATTTA
4971  CAGACGGCGA ATTTATGAGA AAAATTTGCC AGATTCATGA TTACCAAGAA GAATGGATTG AGCGATTAAA
5041  ACAACACCTG ATAAAAAACC ACCCGGCAGG CAGTGACAAG AAGATCCAAA GAGAAGAATT GTTGAGCTTG
5111  ATTGCGTAAA AATTGGTTTC ATGGATTTCT TTGAAAGCCC GCCGGTCAAA AGGTGCGGGT TTTGTTTTTG
5181  TTAAAGGTGA AAGAAAAGTA ACGTGTTTCC ATAGGTTATC ATTGAATGAT TCGATTTCAT ATTTTGGGAG
5251  GTGATCAGAG CAATGAGCGA CTTTTCTTTT TTGAAAAAAT ATGTCCTTCC ATCCGTAAAC GTTCAAGCAC
5321  CACCAGAGTA TAAACATGTA TTTTATCCGC TGGATATATG TGAAGTGGAA GAAGCGGAAC ATAGACTCAA
5391  TCGAACGTTT CCAAAAGAGT TAAGGGAATT TTATTTGCAA ATTGGATATG GCTTTATGTG TATTCATCAG
5461  AAGACTTTTG ATAACCGTAT CATGGATCCC GATTCCCTTG CAGATTTGAT CTTGGGTGAA GACATTTGGG
5531  AAGATTATGA TCTGATGGAA GAGATCGGAG AACCACATTT ATTCCCGTTT TTTTTCTTGG GTAATGATGA
5601  CTTGATTTTT TTCGATTTGA GTCAAGAGAC AAGAGAAGGA ATTCATCCGG TTGACTATGG AAGGGTGATC
5671  ATTGCGGAAT CCCTTGAAGA TTTTTTACGT AAGTTAGATG CTAAAGAAAA TTATTATATC AATGTTGTTG
5741  ATGATAAATC GGGTTTTTGA AAGATTTTCC CCCATTATAA AAAATATAGT GGCACCTGAT TGAACGATAG
5811  AATATCAAAT GCTGAAAAGT TGATTCCGAT TTTGCGGCCG ATATTATGGA ACAATGTAAC GAACTTGGGA
5881  GGCAATAGAG TGTGGAGTGG TACAAAAAGG TAAATATGGA TGCGAGAGCG GCTTATTTTT TAGCTTTATC
5951  TGAGAAAGTT TTAGATAAAT TAACTAAATT TGATTGGTTT CCGGCAATAA GAAAGTCCAT GGATTTGTGT
6021  TGGAAATGGA TCACGGCGAC GCAAATGCTG GATTCCATGC AACGCAATCC AAGGCCCACC CGGGCGGAAG
6091  CCAGCGACGT GGCCAATGCG ATTTTGGACG GAACTGATGC CATCATGTTG TCCGGGGAAA CGGCGGCCGG
6161  GAAATATCCG GTGGAATCCG TCAGTACCAT GGCGCGGATT GCCATTCGCA CGGAATCATC GCTTCGGTAT
6231  CAGGAACGTT TTCAACAAAA AATCAGAGAG ATC
```

E009 sequence
with ORF

FIGURE 16D (cont.)

```
   1  GTGATTCAAA TGAATACGTT GGTGGAAACC CGTTTTGGGA AAGTGCAAGG CGGTACAGAC GGAGAGGTTT
   1▶ValIleGlnM etAsnThrLe uValGluThr ArgPheGlyL ysValGlnGl yGlyThrAsp GlyGluValC
  71  GTTTTTGGAA AGGGATTCCT TATGCGAAAC CTCCGGTGGG AAAACGCCGC TTTCAAAAAC CGGAACCGCC
  24▶ysPheTrpLy sGlyIlePro TyrAlaLysP roProValGl yLysArgArg PheGlnLysP roGluProPr
 141  GGAGAAATGG GATGGCGTTT GGGAGGCCAC CCGGTTCCGG TCCATGGTGA TGCAGCCGTC CGGCACCACC
  47▶oGluLysTrp AspGlyValT rpGluAlaTh rArgPheArg SerMetValM etGlnProSe rGlyThrThr
 211  TTCAGCACCG TGCTCGGGGA AGCGGATCTT CCTGTGAGCG AAGACGGTCT TTATCTGAAT ATCTGGTCGC
  71▶PheSerThrV alLeuGlyGl uAlaAspLeu ProValSerG luAspGlyLe uTyrLeuAsn IleTrpSerP
 281  CGGCAGCCGA CGGAAAAAAG CGGCCGGTGC TCTTCTGGAT CCATGGCGGC GCCTACCAGT TTGGGTCCGG
  94▶roAlaAlaAs pGlyLysLys ArgProValL euPheTrpIl eHisGlyGly AlaTyrGlnP heGlySerGl
 351  CGCTTCCCCC TGGTATGACG GGACGGAGTT TGCCAAAAAC GGAGATGTGG TGGTTGTCAC GATCAACTAC
 117▶yAlaSerPro TrpTyrAspG lyThrGluPh eAlaLysAsn GlyAspValV alValValTh rIleAsnTyr
 421  CGGTTGAACG CGTTTGGATT TTTGTACTTG GCAGATTGGT TCGGCGACGA ATTTTCAGCG TCGGGCAACC
 141▶ArgLeuAsnA laPheGlyPh eLeuTyrLeu AlaAspTrpP heGlyAspGl uPheSerAla SerGlyAsnL
 491  TGGGAATTTT GGACCAAGTC GCTGCACTGC GCTGGGTGAA AGAAAACATT TCGGCATTCG GCGGCGACCC
 164▶euGlyIleLe uAspGlnVal AlaAlaLeuA rgTrpValLy sGluAsnIle SerAlaPheG lyGlyAspPr
 561  GGAGCAAATC ACCATCTTCG GGGAGTCGGC CGGAGCCGGA AGCGTCGGGG TTCTGCTTTC CCTCCCGGAA
 187▶oGluGlnIle ThrIlePheG lyGluSerAl aGlyAlaGly SerValGlyV alLeuLeuSe rLeuProGlu
 631  ACCAAAGGGC TGTTTCAACG GGCGATCTTG CAAAGCGGAT CGGGTGCCAT TTTGCTCCGT TCCTCTCAGA
 211▶ThrLysGlyL euPheGlnAr gAlaIleLeu GlnSerGlyS erGlyAlaIl eLeuLeuArg SerSerGlnT
 701  CAGCCTCGGG CATCGCGGAA CAAATTCTTA CGAAAGCCGG CATTCGAAAA GGAGACCGCG ACCGGTTGTT
 234▶hrAlaSerGl yIleAlaGlu GlnIleLeuT hrLysAlaGl yIleArgLys GlyAspArgA spArgLeuLe
 771  ATCCATCCCG GCCGGTGAAC TCCTTGAAGC CGCACAATCC GTGAATCCGG GAATGGTTTT TGGTCCCGTT
 257▶uSerIlePro AlaGlyGluL euLeuGluAl aAlaGlnSer ValAsnProG lyMetValPh eGlyProVal
 841  GTGGACGGCA CCGTATTGAA AACCCATCCG ATTGAAGCGT TGGAAACCGG AGCCGCCGGC GATATCCCGA
 281▶ValAspGlyT hrValLeuLy sThrHisPro IleGluAlaL euGluThrGl yAlaAlaGly AspIleProI
 911  TCATCATCGG GGTGACAAAG GATGAGTACA ATTTATTTAC ACTGACTGAC CCTTCCTGGA CGACAGCGGG
 304▶leIleIleGl yValThrLys AspGluTyrA snLeuPheTh rLeuThrAsp ProSerTrpT hrThrAlaGl
 981  AAAAGAAGAA CTGATGGACC GGATCGAACA GGAAATCGGG CCGGTTCCGG AAAAAGTTTT TCCATATTAC
 327▶yLysGluGlu LeuMetAspA rgIleGluGl nGluIleGly ProValProG luLysValPh eProTyrTyr
1051  TTATCTTTTG GGGATCCATC GCAACCGGTA TGGCAAAAGC TGTTGCGCGC CATGACCTAC CACATCTTTA
 351▶LeuSerPheG lyAspProSe rGlnProVal TrpGlnLysL euLeuArgAl aMetThrTyr HisIlePheT
1121  CCCGGGGCAT GTTAAAAACG GCTGACGCCC AAATCAAGCA AGGCGGGAAG GTTTGGGTTT ACCGGTTTGA
 374▶hrArgGlyMe tLeuLysThr AlaAspAlaG lnIleLysGl nGlyGlyLys ValTrpValT yrArgPheAs
1191  TTACGAAACC CCGCTCTTTG ACGGTCGGTT GAAAGCATGT CACGCACTGG AAATCCCCTT TGTCTTTCAC
 397▶pTyrGluThr ProLeuPheA spGlyArgLe uLysAlaCys HisAlaLeuG luIleProPh eValPheHis
1261  AACCTGCATC AACCGGGGGT CGATGTGTTC ACCGGCACAC ATCCGAAGCG GGAGCTAATT TCCCGGCAAA
 421▶AsnLeuHisG lnProGlyVa lAspValPhe ThrGlyThrH isProLysAr gGluLeuIle SerArgGlnM
1331  TGCATGAAGC ATGGATTGCC TTTGCCCGGA CAGGGGATCC GAACGGCGAC CATCTCCCCG ATGCGTGGTT
 444▶etHisGluAl aTrpIleAla PheAlaArgT hrGlyAspPr oAsnGlyAsp HisLeuProA spAlaTrpLe
1401  GCCCTTTGCA CAAAAAGACC GGCCGGCCAT GGTCTTTGAC ACCGAAACCA GAGCGGAAAA GCATCTGTTT
 467▶uProPheAla GlnLysAspA rgProAlaMe tValPheAsp ThrGluThrA rgAlaGluLy sHisLeuPhe
1471  GACCGCGAGC AGGAACTGTG GGAATCAAAG GCTTGA
 491▶AspArgGluG lnGluLeuTr pGluSerLys Ala•••
```

E011 ORF,
underlined possible
start codons.

FIGURE 16E

1 GATCTTTCCT TTGTGTTTTA AAACTTAAAG CACCGGATTG CCGGCTGTAT GGTCCGGTTG GATATTGTCA
71 TCACATCGTG GATATCAGTG GATCCGGTGC GATGGATTGC TTCAGGGGAA CTTTTAAACA CTTGAGTTTG
141 ACAACCACTC CTTAATCATT TAAGATTTAA ATGAAAATTA AAATAAATCA AAAAGAGTGA TTCAAATGAA
1▶Val IleGlnMetAs
211 TACGTTGGTG GAAACCCGTT TTGGGAAAGT GCAAGGCGGT ACAGACGGAG AGGTTTGTTT TTGGAAAGGG
5▶nThrLeuVal GluThrArgP heGlyLysVa lGlnGlyGly ThrAspGlyG luValCysPh eTrpLysGly
281 ATTCCTTATG CGAAACCTCC GGTGGGAAAA CGCCGCTTTC AAAAACCGGA ACCGCCGGAG AAATGGGATG
29▶IleProTyrA laLysProPr oValGlyLys ArgArgPheG lnLysProGl uProProGlu LysTrpAspG
351 GCGTTTGGGA GGCCACCCGG TTCCGGTCCA TGGTGATGCA GCCGTCCGGC ACCACCTTCA GCACCGTGCT
52▶lyValTrpGl uAlaThrArg PheArgSerM etValMetGl nProSerGly ThrThrPheS erThrValLe
421 CGGGGAAGCG GATCTTCCTG TGAGCGAAGA CGGTCTTTAT CTGAATATCT GGTCGCCGGC AGCCGACGGA
75▶uGlyGluAla AspLeuProV alSerGluAs pGlyLeuTyr LeuAsnIleT rpSerProAl aAlaAspGly
491 AAAAAGCGGC CGGTGCTCTT CTGGATCCAT GGCGGCGCCT ACCAGTTTGG GTCCGGCGCT TCCCCCTGGT
99▶LysLysArgP roValLeuPh eTrpIleHis GlyGlyAlaT yrGlnPheGl ySerGlyAla SerProTrpT
561 ATGACGGGAC GGAGTTTGCC AAAAACGGAG ATGTGGTGGT TGTCACGATC AACTACCGGT TGAACGCGTT
122▶yrAspGlyTh rGluPheAla LysAsnGlyA spValValVa lValThrIle AsnTyrArgL euAsnAlaPh
631 TGGATTTTTG TACTTGGCAG ATTGGTTCGG CGACGAATTT TCAGCGTCGG GCAACCTGGG AATTTTGGAC
145▶eGlyPheLeu TyrLeuAlaA spTrpPheGl yAspGluPhe SerAlaSerG lyAsnLeuGl yIleLeuAsp
701 CAAGTCGCTG CACTGCGCTG GGTGAAAGAA AACATTTCGG CATTCGGCGG CGACCCGGAG CAAATCACCA
169▶GlnValAlaA laLeuArgTr pValLysGlu AsnIleSerA laPheGlyGl yAspProGlu GlnIleThrI
771 TCTTCGGGGA GTCGGCCGGA GCCGGAAGCG TCGGGGTTCT GCTTTCCCTC CCGGAAACCA AAGGGCTGTT
192▶lePheGlyGl uSerAlaGly AlaGlySerV alGlyValLe uLeuSerLeu ProGluThrL ysGlyLeuPh
841 TCAACGGGCG ATCTTGCAAA GCGGATCGGG TGCCATTTTG CTCCGTTCCT CTCAGACAGC CTCGGGCATC
215▶eGlnArgAla IleLeuGlnS erGlySerGl yAlaIleLeu LeuArgSerS erGlnThrAl aSerGlyIle
911 GCGGAACAAA TTCTTACGAA AGCCGGCATT CGAAAAGGAG ACCGCGACCG GTTGTTATCC ATCCCGGCCG
239▶AlaGluGlnI leLeuThrLy sAlaGlyIle ArgLysGlyA spArgAspAr gLeuLeuSer IleProAlaG
981 GTGAACTCCT TGAAGCCGCA CAATCCGTGA ATCCGGGAAT GGTTTTTGGT CCCGTTGTGG ACGGCACCGT
262▶lyGluLeuLe uGluAlaAla GlnSerValA snProGlyMe tValPheGly ProValValA spGlyThrVa
1051 ATTGAAAACC CATCCGATTG AAGCGTTGGA AACCGGAGCC GCCGGCGATA TCCCGATCAT CATCGGGGTG
285▶lLeuLysThr HisProIleG luAlaLeuGl uThrGlyAla AlaGlyAspI leProIleIl eIleGlyVal
1121 ACAAAGGATG AGTACAATTT ATTTACACTG ACTGACCCTT CCTGGACGAC AGCGGGAAAA GAAGAACTGA
309▶ThrLysAspG luTyrAsnLe uPheThrLeu ThrAspProS erTrpThrTh rAlaGlyLys GluGluLeuM
1191 TGGACCGGAT CGAACAGGAA ATCGGGCCGG TTCCGGAAAA AGTTTTTCCA TATTACTTAT CTTTTGGGGA
332▶etAspArgIl eGluGlnGlu IleGlyProV alProGluLy sValPhePro TyrTyrLeuS erPheGlyAs
1261 TCCATCGCAA CCGGTATGGC AAAAGCTGTT GCGCGCCATG ACCTACCACA TCTTTACCCG GGGCATGTTA
355▶pProSerGln ProValTrpG lnLysLeuLe uArgAlaMet ThrTyrHisI lePheThrAr gGlyMetLeu
1331 AAAACGGCTG ACGCCCAAAT CAAGCAAGGC GGGAAGGTTT GGGTTTACCG GTTTGATTAC GAAACCCCGC
379▶LysThrAlaA spAlaGlnIl eLysGlnGly GlyLysValT rpValTyrAr gPheAspTyr GluThrProL
1401 TCTTTGACGG TCGGTTGAAA GCATGTCACG CACTGGAAAT CCCCTTTGTC TTTCACAACC TGCATCAACC
402▶euPheAspGl yArgLeuLys AlaCysHisA laLeuGluIl eProPheVal PheHisAsnL euHisGlnPr
1471 GGGGGTCGAT GTGTTCACCG GCACACATCC GAAGCGGGAG CTAATTTCCC GGCAAATGCA TGAAGCATGG
425▶oGlyValAsp ValPheThrG lyThrHisPr oLysArgGlu LeuIleSerA rgGlnMetHi sGluAlaTrp
1541 ATTGCCTTTG CCCGGACAGG GGATCCGAAC GGCGACCATC TCCCCGATGC GTGGTTGCCC TTTGCACAAA
449▶IleAlaPheA laArgThrGl yAspProAsn GlyAspHisL euProAspAl aTrpLeuPro PheAlaGlnL
1611 AAGACCGGCC GGCCATGGTC TTTGACACCG AAACCAGAGC GGAAAAGCAT CTGTTTGACC GCGAGCAGGA
472▶ysAspArgPr oAlaMetVal PheAspThrG luThrArgAl aGluLysHis LeuPheAspA rgGluGlnGl
1681 ACTGTGGGAA TCAAAGGCTT GAGTGATTTG CTCAAGCCTT TTTTGCATTT CACGTATGTA TTCGGATTTG
495▶uLeuTrpGlu SerLysAla• • •
1751 GAATTAAACA ATGGTGCTTT TATCGAAATG GGGAGTGTTT GCTTATAATG AACGGGTTTA CAAAGCTTGT
1821 TTTGGTACCG GATTACTGAA ATGATCAGAA GGAAATATCA TGACGTAATA ATCAGGGGAT CTTGAGAAAG
1891 AAATACATGG AGTGTTATGT CCCTTGAAAA ACAGAGACGC CGGTGGCATC ACCATCACAG GGTCTTTCTT
1961 TTCAAATCAT GGTTTGTAGT TTATAATGCA AACTAGTTAA TCATACATAT GGAGTGTGGT TCCATTGATG
2031 CCCTTTAAGG AAATGGCAAA ACTGAATAAA TTGATTCACG AACCGGCCCG ACTTGCCATT ATGAGCGCGC
2101 TGGACGCCTG CACGATGGCT GAATTTTTGT TTTTGCAAGA ATTGACAGGC TTGACGAAAG GAAACCTTTC
2171 TTCCCATTTA TCCAAATTAG AAAAGGCGGA ATATATCCAA ATCCAGAAAC AATTCGTACG CAAAAAAATC
2241 CCGCATACCA CCATACGAAT CACACATGAA GGCCGGGCTG CGCTTCACAA TTATTGGGAA CAACTGGATC
2311 GCATCCGCGA GGTAACCAAA AAATGGAATA ATAGTTAGGA AGCGGATTCT CTCAACCTCT TCCCCTCTGT
2381 TTTTCAGAGG GTTTTTCTTC CTTAAAATCC CAACACAAAG AGAGCGATTC CAAGGCCCCT TACATCTTTT
2451 CACCCCCTTT TTCGACCTGT TCCTCTCAAA AAGAAATAAA CCGCCCTTAA ATCGAAAATC AGAAGGCCGT
2521 TTTTTCTGAA ACGAAATTTT TGATTCCATT TATTGGAATG TATTTTTCTC CATCCGGCTG CTTATCTCTT
2591 GATTATTTTG TTTGTTCTGA TTAACAAGAA TATTTGTGGC GCGAAACAGC CGCGGGTTTC CTTCTCCTCC
2661 CTCTTGATCC ACTCTATTTA TGCCCTCTAC AGGGTTACAA AACAATTCTT TTGTAACTAT ATAAAGATAA
2731 AATGCCGAAA CCCCTTTATT TACAAGGGGT TTGGCGATCG GATATTTCCC ACACATTTTT CCATCTGTCT
2801 GAGAGTCAAA TGGTCGTCTC ACCAAGTTAA CTTGTTAATG AGATATCAAT CTGCTGCTAT TTTCTTCACC
2871 ATATGGACGT TATTCAAAAA CATGTGAAAT CCTTCCTCCT CCAGCAAGCC CGTCACCATT TTCTTCTTTG
2941 CGGGGCAGTA TAAAAACTGG TATCGGGATG CTTCCGCGGA AGCCATCACA TGTCGCAACA ACTGACGGGC
3011 CAGTTCTTCC GCTTCAGGAT GCTCCGGGGC TGTCTCCAAT TGCAACAAAG TCAAATCTTG CACTCGTCCT
3081 AGGTCATCGG TTGTCCGCCT CACCAACGCA TATCCGGCTT CCTTTCCGGA AGAATCGGAA ATGATCCATG
3151 CTTCATCTCC TTGAAACCAA TGGGTTTGCC ACGGAGCCGG ATCGGGATAA AAAGAAAAAG CGGCAACGGT
3221 TACCGGATGG GCGCTGCGGA TGTTGTATCC GGGAGCCGCT GGTTGTTTCC GGCTGAAGTT TTCTGTCTGG

FIGURE 16F

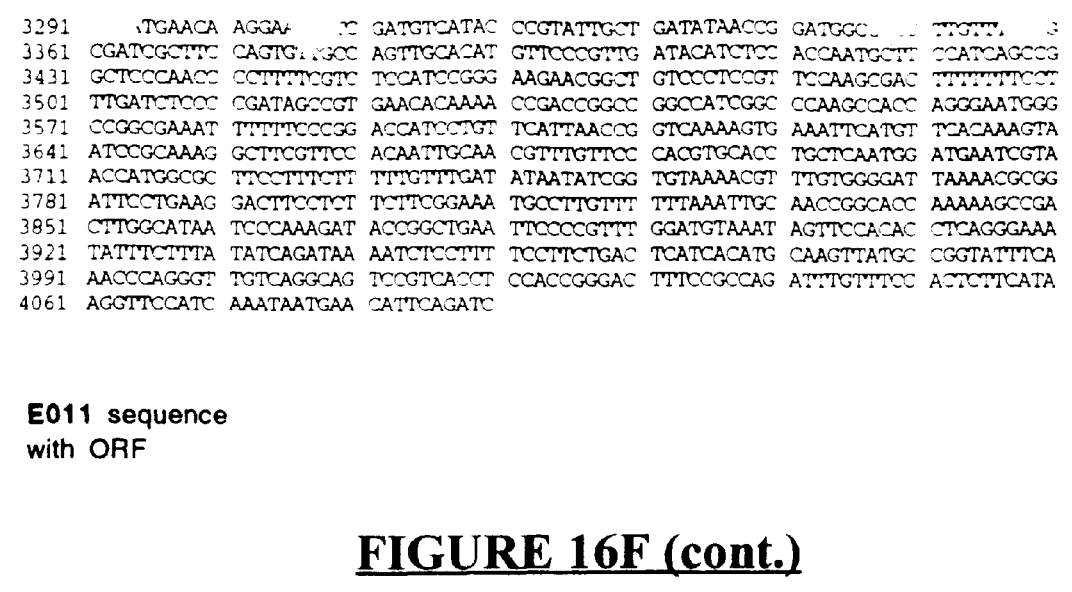

```
3291    TGAACA AGGA    C GATGTCATAC CCGTATTGCT GATATAACCG GATGGC     TTGTT     G
3361 CGATCGCTTC CAGTG  GCC AGTTGCACAT GTTCCCGTTG ATACATCTCC ACCAATGCTT CCATCAGCCG
3431 GCTCCCAACC CCTTTTCGTC TCCATCCGGG AAGAACGGCT GTCCCTCCGT TCCAAGCGAC TTTTTTTCCT
3501 TTGATCTCCC CGATAGCCGT GAACACAAAA CCGACCGGCC GGCCATCGGC CCAAGCCACC AGGGAATGGG
3571 CCGGCGAAAT TTTTTCCCGG ACCATCCTGT TCATTAACCG GTCAAAAGTG AAATTCATGT TCACAAAGTA
3641 ATCCGCAAAG GCTTCGTTCC ACAATTGCAA CGTTTGTTCC CACGTGCACC TGCTCAATGG ATGAATCGTA
3711 ACCATGGCGC TTCCTTTCTT TTTGTTTGAT ATAATATCGG TGTAAAACGT TTGTGGGGAT TAAAACGCGG
3781 ATTCCTGAAG GACTTCCTCT TCTTCGGAAA TGCCTTGTTT TTTAAATTGC AACCGGCACC AAAAAGCCGA
3851 CTTGGCATAA TCCCAAAGAT ACCGGCTGAA TTCCCCGTTT GGATGTAAAT AGTTCCACAC CTCAGGGAAA
3921 TATTTCTTTA TATCAGATAA AATCTCCTTT TCCTTCTGAC TCATCACATG CAAGTTATGC CGGTATTTCA
3991 AACCCAGGGT TGTCAGGCAG TCCGTCACCT CCACCGGGAC TTTCCGCCAG ATTTGTTTCC ACTCTTCATA
4061 AGGTTCCATC AAATAATGAA CATTCAGATC
```

E011 sequence
with ORF

FIGURE 16F (cont.)

```
  1  ATGAGGCGGC TTTTGGGGCT CCTTTTGTTC CTGGCCTTGG CCTTGGCGCA AGGCCTTGGC CCTTACTGGC
  1▶ MetArgArgL euLeuGlyLe uLeuLeuPhe LeuAlaLeuA laLeuAlaGl nGlyLeuGly ProTyrTrpG
 71  AGGAGGTTCA GGCCCAGGGT ACGGTCTGCT CGGACGGCTC CCCCTGGCGG TTCTACGTGA GCCCGGGGGA
 24▶ lnGluValGl nAlaGlnGly ThrValCysS erAspGlySe rProTrpArg PheTyrValS erProGlyAs
141  CCCCAAGAAG GTCCTTCTGG ACTTCCAGGG GGGCGGGGCC TGCTGGGACG CCCAGACCTG CGGTCCCCAG
 47▶ pProLysLys ValLeuLeuA spPheGlnGl yGlyGlyAla CysTrpAspA laGlnThrCy sGlyProGln
211  AGCCAGACCT ACCGGAAGCG GGTGGACGTG CAGGAACTCC TCCTGGCCCA GGGGATCTAC AACCGGGCGA
 71▶ SerGlnThrT yrArgLysAr gValAspVal GlnGluLeuL euLeuAlaGl nGlyIleTyr AsnArgAlaS
281  GCATCGCCAA CCCCTTCTTC GGCTGGACCC ACGTCTTCAT CCCCTACTGC ACGGGGGACC TGCACGTGGG
 94▶ erIleAlaAs nProPhePhe GlyTrpThrH isValPheIl eProTyrCys ThrGlyAspL euHisValGl
351  CCGGGCCACG GTGGACTACG GCGGCTTTAA GGTCCACCAC CAGGGGGCGC GAAACGCCCT GGCCGCCTTG
117▶ yArgAlaThr ValAspTyrG lyGlyPheLy sValHisHis GlnGlyAlaA rgAsnAlaLe uAlaAlaLeu
421  GAGTACGTCT TCAAGAACTA CCCCAAGGCA GAGCGGGTCT TCGTCACCGG GTGCAGCGCC GGGGGGTACG
141▶ GluTyrValP heLysAsnTy rProLysAla GluArgValP heValThrGl yCysSerAla GlyGlyTyrG
491  GGGCGGTCTT CTGGGCGGAC AAGGTCCTTG CCACCTACAA AAGCGCCCAG ATCGCCGTTT GCGGGGACGC
164▶ lyAlaValPh eTrpAlaAsp LysValLeuA laThrTyrLy sSerAlaGln IleAlaValC ysGlyAspAl
561  CGCCTTGGGC GTGAGCACAT CGGACTTCCC CGGGAGCCGG GTTTGGAACG CCCGCCTGCC CGAGCTTCCC
187▶ aAlaLeuGly ValSerThrS erAspPhePr oGlySerArg ValTrpAsnA laArgLeuPr oGluLeuPro
631  GGCCTGGGCC CGAACCCCAG CGTGGAGGAG ATCTACCGGG CCCTGGCCCG GGCCTACCCC GGCGCGGCCT
211▶ GlyLeuGlyP roAsnProSe rValGluGlu IleTyrArgA laLeuAlaAr gAlaTyrPro GlyAlaAlaP
701  TCGCCCAGTA CACCACCCAG CTGGACGGGA CCCAGATCTA CTTCTACGCC CTCATGAAGA AGGAGGTACC
234▶ heAlaGlnTy rThrThrGln LeuAspGlyT hrGlnIleTy rPheTyrAla LeuMetLysL ysGluValPr
771  CCCCTCCGAG GCCACCGCCC GGGAGTGGGC CGTCCGGGCC CAGACCAGCC TCCAGAGCCT GGCCCAGGAG
257▶ oProSerGlu AlaThrAlaA rgGluTrpAl aValArgAla GlnThrSerL euGlnSerLe uAlaGlnGlu
841  TCCAACTTCA CCTACTACCT GGCCCCGGGG AGCCAACACT GCATCCTGCC CCGGCCCGAG CTCTACACCC
281▶ SerAsnPheT hrTyrTyrLe uAlaProGly SerGlnHisC ysIleLeuPr oArgProGlu LeuTyrThrL
911  TGAAGGTGGG GGAGGTGAGC GTTCTGGACT GGCTCAGGAG CCTGGCGGAG AAGGGGCAGG CCCCCCGCGT
304▶ euLysValGl yGluValSer ValLeuAspT rpLeuArgSe rLeuAlaGlu LysGlyGlnA laProArgVa
981  AGGTCCGTGA
327▶ lGlyPro•••
```

TspA E101 ORF,
underlined possible
start codons.

FIGURE 16G

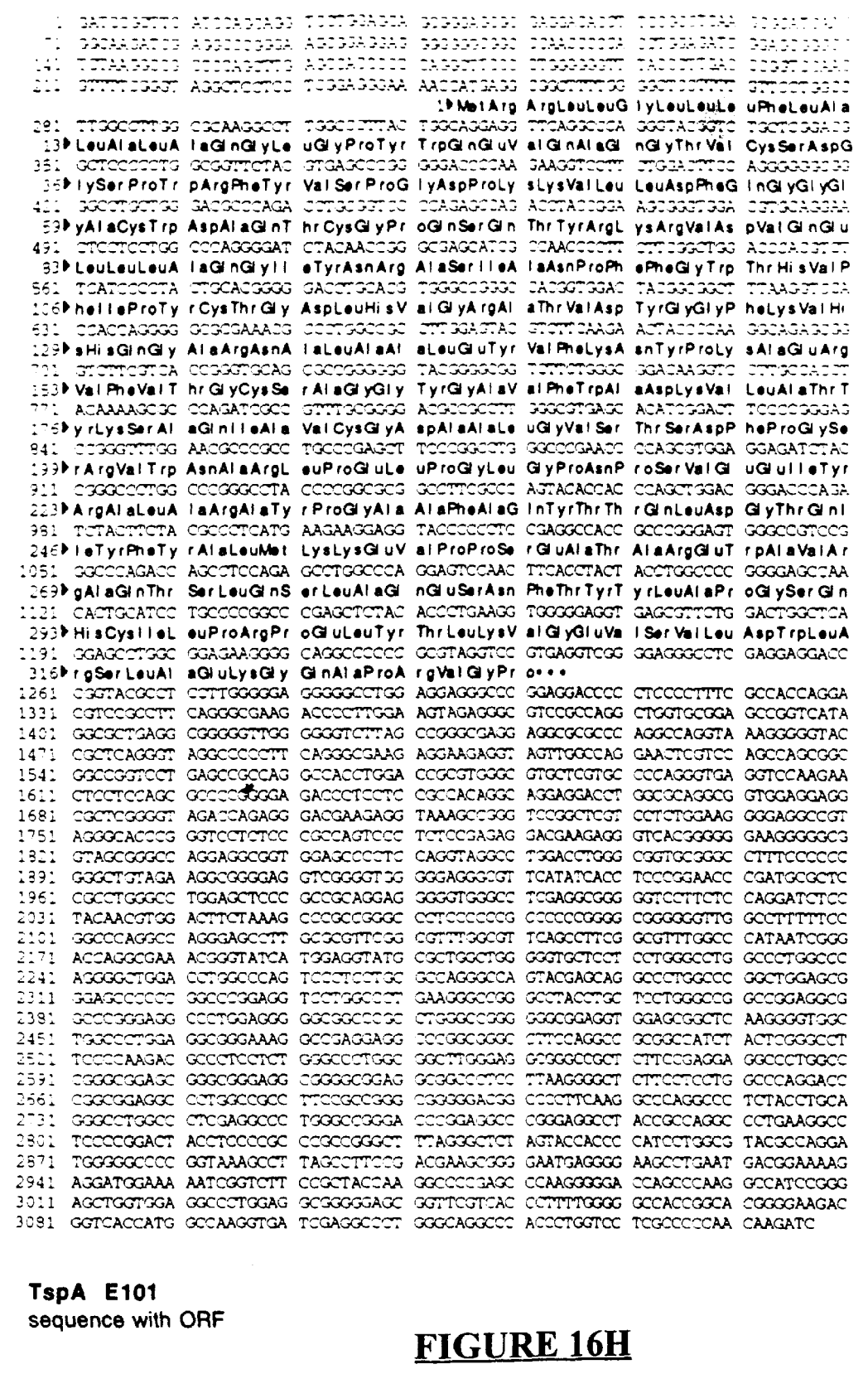

```
   1 GATCCGCTTC ATCCAGCAGG TCCTGGAGCA GCGGGAGCGC GAGGAGACCT TCCGCCTCAA CCGCATCGC
  71 GGCAAGATCG AGGCCCGGGA AGCGGAGGAG GGCGCCCGGC CCAACCCCCA CCTGGAGATC GGAGCCGCC
 141 TCTAAGGCCG CCCCAGCTTG AGCCACCCCC CAGGCTTCCC CTGGGGGCTT TACCCTTGAC CCGGTCCAAC
 211 GTTTTCGGGT AGGCTCCTCC TCGGAGGGAA AACCATGAGG CGGCTTTTGG GGCTCCTTTT GTTCCTGGCC
                                       1▶MetArg ArgLeuLeuG lyLeuLeuLe uPheLeuAla
 281 TTGGCCTTGG CGCAAGGCCT TGGCCCTTAC TGGCAGGAGG TTCAGGCCCA GGGTACGGTC TGCTCGGACG
  13▶LeuAlaLeuA laGlnGlyLe uGlyProTyr TrpGlnGluV alGlnAlaGl nGlyThrVal CysSerAspG
 351 GCTCCCCCTG GCGGTTCTAC GTGAGCCCGG GGGACCCCAA GAAGGTCCTT CTGGACTTCC AGGGGGGCGG
  36▶lySerProTr pArgPheTyr ValSerProG lyAspProLy sLysValLeu LeuAspPheG lnGlyGlyGl
 421 GGCCTGCTGG GACGCCCAGA CCTGCGGTCC CCAGAGCCAG ACCTACCGGA AGCGGGTGGA CGTGCAGGAA
  59▶yAlaCysTrp AspAlaGlnT hrCysGlyPr oGlnSerGln ThrTyrArgL ysArgValAs pValGlnGlu
 491 CTCCTCCTGG CCCAGGGGAT CTACAACCGG GCGAGCATCG CCAACCCCTT CTTCGGCTGG ACCCACGTCT
  83▶LeuLeuLeuA laGlnGlyIl eTyrAsnArg AlaSerIleA laAsnProPh ePheGlyTrp ThrHisValP
 561 TCATCCCCTA CTGCACGGGG GACCTGCACG TGGGCCGGGC CACGGTGGAC TACGGCGGCT TTAAGGTCCA
 106▶heIleProTy rCysThrGly AspLeuHisV alGlyArgAl aThrValAsp TyrGlyGlyP heLysValHi
 631 CCACCAGGGG GCGCGAAACG CCCTGGCCGC CCTGGAGTAC GTCTTCAAGA ACTACCCCAA GGCAGAGCGG
 129▶sHisGlnGly AlaArgAsnA laLeuAlaAl aLeuGluTyr ValPheLysA snTyrProLy sAlaGluArg
 701 GTCTTCGTCA CCGGGTGCAG CGCCGGGGGG TACGGGGCGG TCTTCTGGGC GGACAAGGTC CTTGCCACCT
 153▶ValPheValT hrGlyCysSe rAlaGlyGly TyrGlyAlaV alPheTrpAl aAspLysVal LeuAlaThrT
 771 ACAAAAGCGC CCAGATCGCC GTTTGCGGGG ACGCCGCCTT GGGCGTGAGC ACATCGGACT TCCCCGGGAG
 176▶yrLysSerAl aGlnIleAla ValCysGlyA spAlaAlaLe uGlyValSer ThrSerAspP heProGlySe
 841 CCGGGTTTGG AACGCCCGCC TGCCCGAGCT TCCCGGCCTG GGCCCGAACC CCAGCGTGGA GGAGATCTAC
 199▶rArgValTrp AsnAlaArgL euProGluLe uProGlyLeu GlyProAsnP roSerValGl uGluIleTyr
 911 CGGGCCCTGG CCCGGGCCTA CCCCGGCGCG GCCTTCGCCC AGTACACCAC CCAGCTGGAC GGGACCCAGA
 223▶ArgAlaLeuA laArgAlaTy rProGlyAla AlaPheAlaG lnTyrThrTh rGlnLeuAsp GlyThrGlnI
 981 TCTACTTCTA CGCCCTCATG AAGAAGGAGG TACCCCCCTC CGAGGCCACC GCCCGGGAGT GGGCCGTCCG
 246▶leTyrPheTy rAlaLeuMet LysLysGluV alProProSe rGluAlaThr AlaArgGluT rpAlaValAr
1051 GGCCCAGACC AGCCTCCAGA GCCTGGCCCA GGAGTCCAAC TTCACCTACT ACCTGGCCCC GGGGAGCCAA
 269▶gAlaGlnThr SerLeuGlnS erLeuAlaGl nGluSerAsn PheThrTyrT yrLeuAlaPr oGlySerGln
1121 CACTGCATCC TGCCCCGGCC CGAGCTCTAC ACCCTGAAGG TGGGGGAGGT GAGCGTTCTG GACTGGCTCA
 293▶HisCysIleL euProArgPr oGluLeuTyr ThrLeuLysV alGlyGluVa lSerValLeu AspTrpLeuA
1191 GGAGCCTGGC GGAGAAGGGG CAGGCCCCCC GCGTAGGTCC GTGAGGTCGG GGAGGGCCTC GAGGAGGACC
 316▶rgSerLeuAl aGluLysGly GlnAlaProA rgValGlyPr o•••
1261 CGGTACGCCT CCTTGGGGGA GGGGGCCTGG AGGAGGGCCC GGAGGACCCC CTCCCCTTTC GCCACCAGGA
1331 CGTCCGCCTT CAGGGCGAAG ACCCCTTGGA AGTAGAGGGC GTCCGCCAGG CTGGTGCGGA GCCGGTCATA
1401 GGCGCTGAGG CGGGGGTTGG GGGGTCTTAG CCGGGCGAGG AGGCGCGCCC AGGCCAGGTA AAGGGGGTAC
1471 CGCTCAGGGT AGGCCCCCTT CAGGGCGAAG AGGAAGAGGT AGTTGGCCAG GAACTCGTCC AGCCAGCGGC
1541 GGCCGGTCCT GAGCCGCCAG GCCACCTGGA CCGCGTGGGC GTGCTCGTGC CCCAGGGTGA GGTCCAAGAA
1611 CTCCTCCAGC GCCCCGGGGA GACCCTCCTC CGCCACAGGC AGGAGGACCT GGCGCAGGCG GTGGAGGAGG
1681 CGCTCGGGGT AGACCAGAGG GACGAAGAGG TAAAGCCGGG TCCGGCTCGT CCTCTGGAAG GGGAGGCCGT
1751 AGGGCACCCG GGTCCTCTCC CGCCAGTCCC TCTCCGAGAG GACGAAGAGG GTCACGGGGG GAAGGGGGCG
1821 GTAGCGGGCC AGGAGGCGGT GGAGCCCCTC CAGGTAGGCC TGGACCTGGG CGGTGCGGGC CTTTCCCCCC
1891 GGGCTGTAGA AGGCGGGGAG GTCGGGGTGG GGGAGGGCGT TCATATCACC TCCCGGAACC CGATGCGCTC
1961 CGCCTGGGCC TGGAGCTCCC GCCGCAGGAG GGGGTGGGCC TCGAGGCGGG GGTCCTTCTC CAGGATCTCC
2031 TACAACGTGG ACTTCTAAAG CCCGCCGGGC CCTCCCCCCG CCCCCCGGGG CGGGGGGTTG GCCTTTTTCC
2101 GGCCCAGGCC AGGGAGCCTT GCGCGTTCGG CGTTTGGCGT TCAGCCTTCG GCGTTTGGCC CATAATCGGG
2171 ACCAGGCGAA ACGGGTATCA TGGAGGTATG CGCTGGCTGG GGGTGCTCCT CCTGGGCCTG GCCCTGGCCC
2241 AGGGGCTGGA CCTGGCCCAG TCCCTCCTGC GCCAGGGCCA GTACGAGCAG GCCCTGGCCC GGCTGGAGCG
2311 GGAGCCCCCC GGCCCGGAGG TCCTGGCCCT GAAGGGCCGG GCCTACCTGC TCCTGGGCCG GCCGGAGGCG
2381 GCCCGGGAGG CCCTGGAGGG GGCGGCCCGC CTGGGCCGGG GGGCGGAGGT GGAGCGGCTC AAGGGGTGGC
2451 TGGCCCTGGA GGCGGGAAAG GCCGAGGAGG CCCGGCGGGC CTTCCAGGCC GCGGCCATCT ACTCGGGCCT
2521 TCCCCAAGAC GCCCTCCTCT GGGCCCTGGC GGCTTGGGAG GCCGGCCGCT CTTCCGAGGA GGCCCTGGCC
2591 CGGGCGGAGC GGGCGGGAGG CGGGGCGGAG GCGGCCCTCC TTAAGGGGCT CTTCCTCCTG GCCCAGGACC
2661 CGGCGGAGGC CCTGGCCGCC TTCCGCCGGG CGGGGGACGG CCCCTTCAAG GCCCAGGCCC TCTACCTGCA
2731 GGGCCTGGCC CTCGAGGCCC TGGGCCGGGA CCCGGAGGCC CGGGAGGCCT ACCGCCAGGC CCTGAAGGCC
2801 TCCCCGGACT ACCTCCCCGC CCGCCGGGCT TTAGGGCTCT AGTACCACCC CATCCTGGCG TACGCCAGGA
2871 TGGGGGCCCC GGTAAAGCCT TAGCCTTCCG ACGAAGCGGG GAATGAGGGG AAGCCTGAAT GACGGAAAAG
2941 AGGATGGAAA AATCGGTCTT CCGCTACCAA GGCCCCGAGC CCAAGGGGGA CCAGCCCAAG GCCATCCGGG
3011 AGCTGGTGGA GGCCCTGGAG GCGGGGGAGC GGTTCGTCAC CCTTTTGGGG GCCACCGGCA CGGGGAAGAC
3081 GGTCACCATG GCCAAGGTGA TCGAGGCCCT GGGCAGGCCC ACCCTGGTCC TCGCCCCCAA CAAGATC
```

TspA E101 sequence with ORF

FIGURE 16H

```
      TTGAAAAAGGGGATGGGAACCGTGATCGTGGAAACAAAGTACGGTCGGT
   1▶ LeuLysLysGlyMetGlyThrValIleValGluThrLysTyrGlyArgL
1446  TGCGCGGGGGAACAAATGAAGGGGTTTTCTATTGGAAAGGGATTCCGTACGCGAAAGCGCCGGTCGGTGAACGCCGTTTTTTGCC
  17▶ euArgGlyGlyThrAsnGluGlyValPheTyrTrpLysGlyIleProTyrAlaLysAlaProValGlyGluArgArgPheLeuPr
1531  GCCGGAACCGCCCGATGCATGGGACGGAGTGCGTGAGGCGACATCGTTTGGACCGGTCGTCATGCAGCCGTCCGATTCGATGTTC
  45▶ oProGluProProAspAlaTrpAspGlyValArgGluAlaThrSerPheGlyProValValMetGlnProSerAspSerMetPhe
1616  AGCCAGCTGCTCGGACGGATGAATGAACCAATGAGCGAGGATGGGTTGTATCTGAACATTTGGTCACCGGCGGCGGATGGGAAGA
  74▶ SerGlnLeuLeuGlyArgMetAsnGluProMetSerGluAspGlyLeuTyrLeuAsnIleTrpSerProAlaAlaAspGlyLysL
1701  AGCGCCCGGTATTGTTTTGGATTCATGGCGGCGCTTTTTTATTCGGCTCCGGTTCATTTCCATGGTATGATGGAACGGCGTTTGC
 102▶ ysArgProValLeuPheTrpIleHisGlyGlyAlaPheLeuPheGlySerGlySerPheProTrpTyrAspGlyThrAlaPheAl
1786  CAAACACGGCGATGTCGTTGTCGTGACGATCAACTACCGGATGAGCGTGTTTGGCTTTTTGTATTTGGGAGATGCGTTTGGCGAA
 130▶ aLysHisGlyAspValValValValThrIleAsnTyrArgMetSerValPheGlyPheLeuTyrLeuGlyAspAlaPheGlyGlu
1871  ACGTATGCCCAGGCGGGAAATCTTGGCATATTGGATCAAGTGGCGGCGCTGCGCTGGGTGAAAGAGAACATTGAGGCGTTCGGCG
 159▶ ThrTyrAlaGlnAlaGlyAsnLeuGlyIleLeuAspGlnValAlaAlaLeuArgTrpValLysGluAsnIleGluAlaPheGlyG
1956  GTGATCCGGACAACATTACGATTTTTGGCGAATCAGCCGGAGCGGCAAGCGTTGGCGTGCTGTTGTCGCTTCCGGAAGCAAGCGG
 187▶ lyAspProAspAsnIleThrIlePheGlyGluSerAlaGlyAlaAlaSerValGlyValLeuLeuSerLeuProGluAlaSerGl
2041  GCTGTTTCGACGCGCTATATTGCAAAGCGGATCGGGTTCGCTTCTTCTTCGTTCTCCGGAGACGGCGATGGCTCTGACTGAACGC
 215▶ yLeuPheArgArgAlaIleLeuGlnSerGlySerGlySerLeuLeuLeuArgSerProGluThrAlaMetAlaLeuThrGluArg
2126  ATTTTAGAACGTGCCGGCATCCGTCCGGGTGACCGCGATCGGCTGCTGTCGATTCCAGCAGCAGAGCTATTGCAGGCGGCGATGT
 244▶ IleLeuGluArgAlaGlyIleArgProGlyAspArgAspArgLeuLeuSerIleProAlaAlaGluLeuLeuGlnAlaAlaMetS
2211  CGCTCGGCCCAGGAATCACGTACGGTCCGGTGGTTGACGGACATGTGTTGCGACGCCATCCGATCGAAGCGCTCCACGACGGGGC
 272▶ erLeuGlyProGlyIleThrTyrGlyProValValAspGlyHisValLeuArgArgHisProIleGluAlaLeuHisAspGlyAl
2296  AGCAAGTGATATTCCAATCCTAATTGGCGTGACGAAAGACGAATACAATTTGTTTTCATTGACTGATCCGTCATTGACAAGACTC
 300▶ aAlaSerAspIleProIleLeuIleGlyValThrLysAspGluTyrAsnLeuPheSerLeuThrAspProSerLeuThrArgLeu
2381  GAAGAAAAAGAACTGCTTGACCGGATGAACCGTGAGGTCGGGCCTATTCCGGAGGAGGCGGTACGCTATTACGCGGAAACAGCGG
 329▶ GluGluLysGluLeuLeuAspArgMetAsnArgGluValGlyProIleProGluGluAlaValArgTyrTyrAlaGluThrAlaA
2466  ATCGGTCGGCACCCGCGTGGCAAACATGGCTGCGCATCATGACGTACCTTGTTTTTGTCGACGGAATGTTGCGAACGGCGGATGC
 357▶ spArgSerAlaProAlaTrpGlnThrTrpLeuArgIleMetThrTyrLeuValPheValAspGlyMetLeuArgThrAlaAspAl
2551  CCAAGCAGCGCAAGGGGCGAATGTGTACATGTATCGGTTTGATTATGAAACGCCGGCGTTTGGTGGACAACTGAAAGCGTGCCAT
 385▶ aGlnAlaAlaGlnGlyAlaAsnValTyrMetTyrArgPheAspTyrGluThrProAlaPheGlyGlyGlnLeuLysAlaCysHis
2636  ACGCTCGAGTTGCCGTTTGTGTTTCATAACCTCCATCAGCCTGGTGTCGAGAATTTCGTCGGCAACCGACCAGAGCGTGAGGCGA
 414▶ ThrLeuGluLeuProPheValPheHisAsnLeuHisGlnProGlyValGluAsnPheValGlyAsnArgProGluArgGluAlaI
2721  TTGCCAGCGAAATGCATGGTGCCTGGCTTTCGTTCGCCCACACCGGCAACCCGAACGGCGCTCATTTACCAGAGAAGTGGCCCGT
 442▶ leAlaSerGluMetHisGlyAlaTrpLeuSerPheAlaHisThrGlyAsnProAsnGlyAlaHisLeuProGluLysTrpProVa
2806  ATACACAAAAGAGCACAAACCGGTGTTTGTCTTTTCGGCTGCGAGCCATGTGGAAGACGATCCGTTCGGTCGCGAGCGGGAAGCG
 470▶ lTyrThrLysGluHisLysProValPheValPheSerAlaAlaSerHisValGluAspAspProPheGlyArgGluArgGluAla
2891  TGGCAAGGACGCCTT
 499▶ TrpGlnGlyArgLeu
```

E019ORF

FIG. 17A

```
   1 TCGGCGCGNCATTCNACCCG?AGANGTGGAAGTAAACACGGGAAGAAGGCGGTTTCGCCCGTGCGTTAGTGCCAAGCGGCGTTTC
  86 GACGGGCGAATATGAAGCGGTTGAATTGCGTGACGGCGACAAAAACCGCTACTTCGGCAAAGGGGTGTTCAAAGCGGTTGAGAAC
 171 GTCAACGAAGTGATTGCTCCGGAAATCATCGGCTTAGAAGTGACTGATCAAGTGGCGATCGACCGCGCGTTGATTGAACTTGACG
 256 GCACGGAAAACAAAGGAAAGCTTGGGGCGAATGCTATTTTAGGCGTGTCGCTCGCGGTCGCTCGCGCTGCGGCTGATGAGCTTGG
 341 CTTGCCGTTGTACCAATACTTGGGCGGCTTTAACGCTAAAACGCTGCCTGTACCGATGATGAACATTTTAAACGGCGGCGCGCAT
 426 GCGGACAACAACGTTGACATTCAAGAATTCATGATCATGCCGGTCGGTGCGGAAAGCTTCCGTGAAGCGCTGCGCATGGGTGCAG
 511 AAATTTTCCATAGCTTAAAAGCTGTGTTAAAAGCGAAAGGCTACAACACGGCTGTCGGTGACGAAGGCGGATTTGCTCCGAACTT
 596 AAAATCGAACGAAGAAGCGCTGCAAACGATCATTGAAGCGATCGAAAAAGCCGGCTACAAACCAGGCGAACAAGTGATGCTCGCT
 681 ATGGACGTTGCTTCGTCGGAGCTGTACAACAAAGAAGATGGCAAATATCATTTGGAAGGCGAAGGCGTCGTCAAAACATCAGAAG
 766 AAATGGTTGCTTGGTATGAAGAGCTTGTGTCGAAATATCCGATCATCTCGATCGAAGACGGACTTGACGAAAATGACTGGGAAGG
 851 CCATAAACTGCTTACTGAGCGCCTTGGCCACAAAGTGCAGCTCGTCGGTGACGACTTGTTTGTAACGAACACGAAAAAACTGGCC
 936 GAAGGCATTGAAAAAGGCGTCGGCAACTCGATTTTAATTAAAGTGAACCAAATCGGTACACTGACGGAAACGTTCGATGCCATTG
1021 AGATGGCCAAACGCGCCGGCTACACGGCGGTTGTGTCGCACCGTTCCGGTGAAACGGAAGACAGCACGATTGCCGATATCGCTGT
1106 CGCAACAAACGCTGGCCAAATCAAAACGGGAGCACCGTCGCGTACGGACCGCGTCGCAAAATACAACCAGTTGCTCCGCATTGAA
1191 GACGAACTTGGCCACACGGCTATTTACCAAGGCATTCGTTCGTTTTACAATTTGAAAAAATAACGGGAATCAACAACAAAGGGTG
1276 TCTCCAACGTTGCGAGACACCCTCTTTAATTACGGGAAACAGAAATGATTTCCTATCGATAGCAAAAAATGGACGTGGGTAAACC
1361 ATTCGTTTATAATATCTTTTTGTAATCGTTAGAATATTGAAAAAGGGGATGGGAACCGTGATCGTGGAAACAAAGTACGGTCGGT
                                                  1▶ LeuLysLysGlyMetGlyThrValIleValGluThrLysTyrGlyArgL
1446 TGCGCGGGGGAACAAATGAAGGGGTTTTCTATTGGAAAGGGATTCCGTACGCGAAAGCGCCGGTCGGTGAACGCCGTTTTTTGCC
  17▶ euArgGlyGlyThrAsnGluGlyValPheTyrTrpLysGlyIleProTyrAlaLysAlaProValGlyGluArgArgPheLeuPr
1531 GCCGGAACCGCCCGATGCATGGGACGGAGTGCGTGAGGCGACATCGTTTGGACCGGTCGTCATGCAGCCGTCCGATTCGATGTTC
  45▶ oProGluProProAspAlaTrpAspGlyValArgGluAlaThrSerPheGlyProValValMetGlnProSerAspSerMetPhe
1616 AGCCAGCTGCTCGGACGGATGAATGAACCAATGAGCGAGGATGGGTTGTATCTGAACATTTGGTCACCGGCGGCGGATGGGAAGA
  74▶ SerGlnLeuLeuGlyArgMetAsnGluProMetSerGluAspGlyLeuTyrLeuAsnIleTrpSerProAlaAlaAspGlyLysL
1701 AGCGCCCGGTATTGTTTTGGATTCATGGCGGCGCTTTTTTATTCGGCTCCGGTTCATTTCCATGGTATGATGGAACGGCGTTTGC
 102▶ ysArgProValLeuPheTrpIleHisGlyGlyAlaPheLeuPheGlySerGlySerPheProTrpTyrAspGlyThrAlaPheAl
1786 CAAACACGGCGATGTCGTTGTCGTGACGATCAACTACCGGATGAGCGTGTTTGGCTTTTTGTATTTGGGAGATGCGTTTGGCGAA
 130▶ aLysHisGlyAspValValValValThrIleAsnTyrArgMetSerValPheGlyPheLeuTyrLeuGlyAspAlaPheGlyGlu
1871 ACGTATGCCCAGGCGGGAAATCTTGGCATATTGGATCAAGTGGCGGCGCTGCGCTGGGTGAAAGAGAACATTGAGGCGTTCGGCG
 159▶ ThrTyrAlaGlnAlaGlyAsnLeuGlyIleLeuAspGlnValAlaAlaLeuArgTrpValLysGluAsnIleGluAlaPheGlyG
1956 GTGATCCGGACAACATTACGATTTTTGGCGAATCAGCCGGAGCGGCAAGCGTTGGCGTGCTGTTGTCGCTTCCGGAAGCAAGCGG
 187▶ lyAspProAspAsnIleThrIlePheGlyGluSerAlaGlyAlaAlaSerValGlyValLeuLeuSerLeuProGluAlaSerGl
2041 GCTGTTTCGACGCGCTATATTGCAAAGCGGATCGGGTTCGCTTCTTCTTCGTTCTCCGGAGACGGCGATGGCTCTGACTGAACGC
 215▶ yLeuPheArgArgAlaIleLeuGlnSerGlySerGlySerLeuLeuLeuArgSerProGluThrAlaMetAlaLeuThrGluArg
2126 ATTTTAGAACGTGCCGGCATCCGTCCGGGTGACCGCGATCGGCTGCTGTCGATTCCAGCAGCAGAGCTATTGCAGGCGGCGATGT
 244▶ IleLeuGluArgAlaGlyIleArgProGlyAspArgAspArgLeuLeuSerIleProAlaAlaGluLeuLeuGlnAlaAlaMetS
2211 CGCTCGGCCCAGGAATCACGTACGGTCCGGTGGTTGACGGACATGTGTTGCGACGCCATCCGATCGAAGCGCTCCACGACGGGGC
 272▶ erLeuGlyProGlyIleThrTyrGlyProValValAspGlyHisValLeuArgArgHisProIleGluAlaLeuHisAspGlyAl
2296 AGCAAGTGATATTCCAATCCTAATTGGCGTGACGAAAGACGAATACAATTTGTTTTCATTGACTGATCCGTCATTGACAAGACTC
 300▶ aAlaSerAspIleProIleLeuIleGlyValThrLysAspGluTyrAsnLeuPheSerLeuThrAspProSerLeuThrArgLeu
2381 GAAGAAAAAGAACTGCTTGACCGGATGAACCGTGAGGTCGGGCCTATTCCGGAGGAGGCGGTACGCTATTACGCGGAAACAGCGG
 329▶ GluGluLysGluLeuLeuAspArgMetAsnArgGluValGlyProIleProGluGluAlaValArgTyrTyrAlaGluThrAlaA
2466 ATCGGTCGGCACCCGCGTGGCAAACATGGCTGCGCATCATGACGTACCTTGTTTTTGTCGACGGAATGTTGCGAACGGCGGATGC
 357▶ spArgSerAlaProAlaTrpGlnThrTrpLeuArgIleMetThrTyrLeuValPheValAspGlyMetLeuArgThrAlaAspAl
2551 CCAAGCAGCGCAAGGGGCGAATGTGTACATGTATCGGTTTGATTATGAAACGCCGGCGTTTGGTGGACAACTGAAAGCGTGCCAT
 385▶ aGlnAlaAlaGlnGlyAlaAsnValTyrMetTyrArgPheAspTyrGluThrProAlaPheGlyGlyGlnLeuLysAlaCysHis
2636 ACGCTCGAGTTGCCGTTTGTGTTTCATAACCTCCATCAGCCTGGTGTCGAGAATTTCGTCGGCAACCGACCAGAGCGTGAGGCGA
 414▶ ThrLeuGluLeuProPheValPheHisAsnLeuHisGlnProGlyValGluAsnPheValGlyAsnArgProGluArgGluAlaI
2721 TTGCCAGCGAAATGCATGGTGCCTGGCTTTCGTTCGCCCACACCGGCAACCCGAACGGCGCTCATTTACCAGAGAAGTGGCCCGT
 442▶ leAlaSerGluMetHisGlyAlaTrpLeuSerPheAlaHisThrGlyAsnProAsnGlyAlaHisLeuProGluLysTrpProVa
2806 ATACACAAAAGAGCACAAACCGGTGTTTGTCTTTTCGGCTGCGAGCCATGTGGAAGACGATCCGTTCGGTCGCGAGCGGGAAGCG
 470▶ lTyrThrLysGluHisLysProValPheValPheSerAlaAlaSerHisValGluAspAspProPheGlyArgGluArgGluAla
2891 TGGCAAGGACGCCTTTGACGAAAAAATCCATAAGCAACATGTGTTCTTTGTCTGAACACGATCAAGGTACGCGCATTTTCGCGGA
 499▶ TrpGlnGlyArgLeu
2976 AAAAGACCGTGGGCAAACGTTCGCCTTTACCTCTAAAAGGAATGACGCAACATGTCTGCACTTCACAGGAAAGAGGACGAAACGG
3061 TTGGTTTTCAGAATAGGAAAAGGTGTCCCGTTTTTTGGGACACCTTCTTCTATGTATCGCTCAATCATTTGCTTCTGTGGCAGGA
3146 AGCCCGAATCGCTCGGCGAGTGCCGGATCACGATCGATCGCCTCAATCAGTTTCCGCATGACGTTCACATCAAACGTAAAATTCG
3231 AACCGATTGGCGAGGTGACGAAAATTTTCCCTTCTTTCGCCTCGCGTGCTCGTTTAAATTGATAGCCGTCAATCGCAATGACGAC
3316 TCGTTCGTCTGGCCTTGCCATTAGGAATCCCTCCATCGCTGTTTTTTCTTTCATTGTACTTGATTTTGAGGATGAACACCAACGT
3401 TCATGACACGCTCTTAAGGATAACGGATGGGAGAGCGTTAGAGGGCGGTGAATTTCATCAAGAACGTGGCACAAAACGACATTTT
3486 TTCATTATAGACGTCTTGATGTTTGGAATGATCGGAAAAGGCGATTGTTAGGCGGGGATC
```

FIG. 17B

```
     IIGAAAAAGGGGATGGGAACCGTGATCGTGGAAACAAAGTACGGTCGGTT
   1▶LeuLysLysGlyMetGlyThrValIleValGluThrLysTyrGlyArgLe
1137 GCGCGGGGGAACAAATGAAGGGGTTTTCTATTGGAAAGGGATTCCGTACGCGAAAGCGCCGGTCGGTGAAC
  17▶uArgGlyGlyThrAsnGluGlyValPheTyrTrpLysGlyIleProTyrAlaLysAlaProValGlyGluA
1208 GCCGTTTTTTGCCGCCGGAACCGCCCGATGCATGGGACGGAGTGCGTGAGGCGACATCGTTTGGACCGGTC
  41▶rgArgPheLeuProProGluProProAspAlaTrpAspGlyValArgGluAlaThrSerPheGlyProVal
1279 GTCATGCAGCCGTCCGATTCGATGTTCAGCCAGCTGCTCGGACGGATGAATGAACCAATGAGCGAGGATGG
  65▶ValMetGlnProSerAspSerMetPheSerGlnLeuLeuGlyArgMetAsnGluProMetSerGluAspGl
1350 GTTGTATCTGAACATTTGGTCACCGGCGGCGGATGGGAAGAAGCGCCCGGTATTGTTTTGGATTCATGGCG
  88▶yLeuTyrLeuAsnIleTrpSerProAlaAlaAspGlyLysLysArgProValLeuPheTrpIleHisGlyG
1421 GCGCTTTTTTATTCGGCTCCGGTTCATTTCCATGGTATGATGGAACGGCGTTTGCCAAACACGGCGATGTC
 112▶lyAlaPheLeuPheGlySerGlySerPheProTrpTyrAspGlyThrAlaPheAlaLysHisGlyAspVal
1492 GTTGTCGTGACGATCAACTACCGGATGAGCGTGTTTGGCTTTTTGTATTTGGGAGATGCGTTTGGCGAAAC
 136▶ValValValThrIleAsnTyrArgMetSerValPheGlyPheLeuTyrLeuGlyAspAlaPheGlyGluTh
1563 GTATGCCCAGGCGGGAAATCTTGGCATATTGGATCAAGTGGCGGCGCTGCGCTGGGTGAAAGAGAACATTG
 159▶rTyrAlaGlnAlaGlyAsnLeuGlyIleLeuAspGlnValAlaAlaLeuArgTrpValLysGluAsnIleG
1634 AGGCGTTCGGCGGTGATCCGGACAACATTACGATTTTTGGCGAATCAGCCGGAGCGGCAAGCGTTGGCGTG
 183▶luAlaPheGlyGlyAspProAspAsnIleThrIlePheGlyGluSerAlaGlyAlaAlaSerValGlyVal
1705 CTGTTGTCGCTTCCGGAAGCAAGCGGGCTGTTTCGACGCGCTATATTGCAAAGCGGATCGGGTTCGCTTCT
 207▶LeuLeuSerLeuProGluAlaSerGlyLeuPheArgArgAlaIleLeuGlnSerGlySerGlySerLeuLe
1776 TCTTCGTTCTCCGGAGACGGCGATGGCTCTGACTGAACGCATTTTAGAACGTGCCGGCATCCGTCCGGGTG
 230▶uLeuArgSerProGluThrAlaMetAlaLeuThrGluArgIleLeuGluArgAlaGlyIleArgProGlyA
1847 ACCGCGATCGGCTGCTGTCGATTCCAGCAGCAGAGCTATTGCAGGCGGCGATGTCGCTCGGCCCAGGAATC
 254▶spArgAspArgLeuLeuSerIleProAlaAlaGluLeuLeuGlnAlaAlaMetSerLeuGlyProGlyIle
1918 ACGTACGGTCCGGTGGTTGACGGACATGTGTTGCGACGCCATCCGATCGAAGCGCTCCACGACGGGGCAGC
 278▶ThrTyrGlyProValValAspGlyHisValLeuArgArgHisProIleGluAlaLeuHisAspGlyAlaAl
1989 AAGTGATATTCCAATCCTAATTGGCGTGACGAAAGACGAATACAATTTGTTTTCATTGACTGATCCGTCAT
 301▶aSerAspIleProIleLeuIleGlyValThrLysAspGluTyrAsnLeuPheSerLeuThrAspProSerL
2060 TGACAAGACTCGAAGAAAAAGAACTGCTTGACCGGATGAACCGTGAGGTCGGGCCTATTCCGGAGGAGGCG
 325▶euThrArgLeuGluGluLysGluLeuLeuAspArgMetAsnArgGluValGlyProIleProGluGluAla
2131 GTACGCTATTACGCGGAAACAGCGGATCGGTCGGCACCCGCGTGGCAAACATGGCTGCGCATCATGACGTA
 349▶ValArgTyrTyrAlaGluThrAlaAspArgSerAlaProAlaTrpGlnThrTrpLeuArgIleMetThrTy
2202 CCTTGTTTTTGTCGACGGAATGTTGCGAACGGCGGATGCCCAAGCAGCGCAAGGGGCGAATGTGTACATGT
 372▶rLeuValPheValAspGlyMetLeuArgThrAlaAspAlaGlnAlaAlaGlnGlyAlaAsnValTyrMetT
2273 ATCGGTTTGATTATGAAACGCCGGCGTTCGGTGGACAACTGAAAGCGTGCCATACGCTCGAGTTGCCGTTT
 396▶yrArgPheAspTyrGluThrProAlaPheGlyGlyGlnLeuLysAlaCysHisThrLeuGluLeuProPhe
2344 GTGTTTCATAACCTCCATCAGCCTGGTGTCGAGAATTTCGTCGGCAACCGACCAGAGCGTGAGGCGATTGC
 420▶ValPheHisAsnLeuHisGlnProGlyValGluAsnPheValGlyAsnArgProGluArgGluAlaIleAl
2415 CAGCGAAATGCATGGTGCCTGGCTTTCGTTCGCCCACACCGGCAACCCGAACGGCGCTCATTTACCAGAGA
 443▶aSerGluMetHisGlyAlaTrpLeuSerPheAlaHisThrGlyAsnProAsnGlyAlaHisLeuProGluL
2486 AGTGGCCCGTATACACAAAAGAGCACAAACCGGTGTTTGTCTTTTCGGCTGCGAGCCATGTGGAAGACGAT
 467▶ysTrpProValTyrThrLysGluHisLysProValPheValPheSerAlaAlaSerHisValGluAspAsp
2557 CCGTTCGGTCGCGAGCGGGAAGCGTGGCAAGGACGCCTT
 491▶ProPheGlyArgGluArgGluAlaTrpGlnGlyArgLeu
```

E005ORF

FIG. 17C

```
   1 TTGAYRCCAAGCTCGAAATTAACCCTCACTAAAGGGAACAAAAGCTGGAGCTCGCGCGCCTGCAGGTCGAC
  72 ACTAGTGGATCCCCTTTCATTTATGATTTTGCAGCGGTCGAGCTGCTTTTATGTTGTTGAATGAACTGTTC
 143 AATTTGATCATGCCGGTCGGTGCGGAAAGCTTCCGTGAAGCGCTGCGCATGGGTGCAGAAATTTTCCATAG
 214 CTTAAAAGCTGTGTTAAAAGCGAAAGGCTACAACACGGCTGTCGGTGACGAAGGCGGATTTGCTCCGAACT
 285 TAAAATCGAACGAAGAAGCGCTGCAAACGATCATTGAAGCGATCGAAAAAGCCGGCTACAAACCAGGCGAA
 356 CAAGTGATGCTCGCTATGGACGTTGCTTCGTCGGAGCTGTACAACAAAGAAGATGGCAAATATCATTTGGA
 427 AGGCGAAGGCGTCGTCAAAACATCAGAAGAAATGGTTGCTTGGTATGAAGAGCTTGTGTCGAAATATCCGA
 498 TCATCTCGATCGAAGACGGACTTGACGAAAATGACTGGGAAGGCCATAAACTGCTTACTGAGCGCCTTGGC
 569 CACAAAGTGCAGCTCGTCGGTGACGACTTGTTTGTAACGAACACGAAAAAACTGGCCGAAGGCATTGAAAA
 640 AGGCGTCGGCAACTCGATTTTAATTAAAGTGAACCAAATCGGTACACTGACGGAAACGTTCGATGCCATTG
 711 AGATGGCCAAACGCGCCGGCTACACGGCGGTTGTGTCGCACCGTTCCGGTGAAACGGAAGACAGCACGATT
 782 GCCGATATCGCTGTCGCAACAAACGCTGGCCAAATCAAAACGGGAGCACCGTCGCGTACGGACCGCGTCGC
 853 AAAATACAACCAGCTGCTCCGCATTGAAGACGAACTTGGCCACACGGCTATTTACCAAGGCATTCGTTCGT
 924 TTTACAATTTGAAAAAATAACGGGAATCAACAACAAAGGGTGTCTCCAACGTTGCGAGACACCCTCTTTAA
 995 TTACGGGAAACAGAAATGATTTCCTATCGATAGCAAAAAATGGACGTGGGTAAACCATTCGTTTATAATAT
1066 CTTTTTGTAATCGTTAGAATATTGAAAAAGGGGATGGGAACCGTGATCGTGGAAACAAAGTACGGTCGGTT
                                  1▶ LeuLysLysGlyMetGlyThrValIleValGluThrLysTyrGlyArgLe
1137 GCGCGGGGGAACAAATGAAGGGGTTTTCTATTGGAAAGGGATTCCGTACGCGAAAGCGCCGGTCGGTGAAC
  17▶ uArgGlyGlyThrAsnGluGlyValPheTyrTrpLysGlyIleProTyrAlaLysAlaProValGlyGluA
1208 GCCGTTTTTTGCCGCCGGAACCGCCCGATGCATGGGACGGAGTGCGTGAGGCGACATCGTTTGGACCGGTC
  41▶ rgArgPheLeuProProGluProProAspAlaTrpAspGlyValArgGluAlaThrSerPheGlyProVal
1279 GTCATGCAGCCGTCCGATTCGATGTTCAGCCAGCTGCTCGGACGGATGAATGAACCAATGAGCGAGGATGG
  65▶ ValMetGlnProSerAspSerMetPheSerGlnLeuLeuGlyArgMetAsnGluProMetSerGluAspGl
1350 GTTGTATCTGAACATTTGGTCACCGGCGGCGGATGGGAAGAAGCGCCCGGTATTGTTTTGGATTCATGGCG
  88▶ yLeuTyrLeuAsnIleTrpSerProAlaAlaAspGlyLysLysArgProValLeuPheTrpIleHisGlyG
1421 GCGCTTTTTTATTCGGCTCCGGTTCATTTCCATGGTATGATGGAACGGCGTTTGCCAAACACGGCGATGTC
 112▶ lyAlaPheLeuPheGlySerGlySerPheProTrpTyrAspGlyThrAlaPheAlaLysHisGlyAspVal
1492 GTTGTCGTGACGATCAACTACCGGATGAGCGTGTTTGGCTTTTTGTATTTGGGAGATGCGTTTGGCGAAAC
 136▶ ValValValThrIleAsnTyrArgMetSerValPheGlyPheLeuTyrLeuGlyAspAlaPheGlyGluTh
1563 GTATGCCCAGGCGGGAAATCTTGGCATATTGGATCAAGTGGCGGCGCTGCGCTGGGTGAAAGAGAACATTG
 159▶ rTyrAlaGlnAlaGlyAsnLeuGlyIleLeuAspGlnValAlaAlaLeuArgTrpValLysGluAsnIleG
1634 AGGCGTTCGGCGGTGATCCGGACAACATTACGATTTTTGGCGAATCAGCCGGAGCGGCAAGCGTTGGCGTG
 183▶ luAlaPheGlyGlyAspProAspAsnIleThrIlePheGlyGluSerAlaGlyAlaAlaSerValGlyVal
1705 CTGTTGTCGCTTCCGGAAGCAAGCGGGCTGTTTCGACGCGCTATATTGCAAAGCGGATCGGGTTCGCTTCT
 207▶ LeuLeuSerLeuProGluAlaSerGlyLeuPheArgArgAlaIleLeuGlnSerGlySerGlySerLeuLe
1776 TCTTCGTTCTCCGGAGACGGCGATGGCTCTGACTGAACGCATTTTAGAACGTGCCGGCATCCGTCCGGGTG
 230▶ uLeuArgSerProGluThrAlaMetAlaLeuThrGluArgIleLeuGluArgAlaGlyIleArgProGlyA
1847 ACCGCGATCGGCTGCTGTCGATTCCAGCAGCAGAGCTATTGCAGGCGGCGATGTCGCTCGGCCCAGGAATC
 254▶ spArgAspArgLeuLeuSerIleProAlaAlaGluLeuLeuGlnAlaAlaMetSerLeuGlyProGlyIle
1918 ACGTACGGTCCGGTGGTTGACGGACATGTGTTGCGACGCCATCCGATCGAAGCGCTCCACGACGGGGCAGC
 278▶ ThrTyrGlyProValValAspGlyHisValLeuArgArgHisProIleGluAlaLeuHisAspGlyAlaAl
1989 AAGTGATATTCCAATCCTAATTGGCGTGACGAAAGACGAATACAATTTGTTTTCATTGACTGATCCGTCAT
 301▶ aSerAspIleProIleLeuIleGlyValThrLysAspGluTyrAsnLeuPheSerLeuThrAspProSerL
2060 TGACAAGACTCGAAGAAAAAGAACTGCTTGACCGGATGAACCGTGAGGTCGGGCCTATTCCGGAGGAGGCG
 325▶ euThrArgLeuGluGluLysGluLeuLeuAspArgMetAsnArgGluValGlyProIleProGluGluAla
2131 GTACGCTATTACGCGGAAACAGCGGATCGGTCGGCACCCGCGTGGCAAACATGGCTGCGCATCATGACGTA
 349▶ ValArgTyrTyrAlaGluThrAlaAspArgSerAlaProAlaTrpGlnThrTrpLeuArgIleMetThrTy
2202 CCTTGTTTTTGTCGACGGAATGTTGCGAACGGCGGATGCCCAAGCAGCGCAAGGGGCGAATGTGTACATGT
 372▶ rLeuValPheValAspGlyMetLeuArgThrAlaAspAlaGlnAlaAlaGlnGlyAlaAsnValTyrMetT
2273 ATCGGTTTGATTATGAAACGCCGGCGTTCGGTGGACAACTGAAAGCGTGCCATACGCTCGAGTTGCCGTTT
 396▶ yrArgPheAspTyrGluThrProAlaPheGlyGlyGlnLeuLysAlaCysHisThrLeuGluLeuProPhe
2344 GTGTTTCATAACCTCCATCAGCCTGGTGTCGAGAATTTCGTCGGCAACCGACCAGAGCGTGAGGCGATTGC
 420▶ ValPheHisAsnLeuHisGlnProGlyValGluAsnPheValGlyAsnArgProGluArgGluAlaIleAl
2415 CAGCGAAATGCATGGTGCCTGGCTTTCGTTCGCCCACACCGGCAACCCGAACGGCGCTCATTTACCAGAGA
 443▶ aSerGluMetHisGlyAlaTrpLeuSerPheAlaHisThrGlyAsnProAsnGlyAlaHisLeuProGluL
2486 AGTGGCCCGTATACACAAAAGAGCACAAACCGGTGTTTGTCTTTTCGGCTGCGAGCCATGTGGAAGACGAT
 467▶ ysTrpProValTyrThrLysGluHisLysProValPheValPheSerAlaAlaSerHisValGluAspAsp
2557 CCGTTCGGTCGCGAGCGGGAAGCGTGGCAAGGACGCCTTTGACGAAAAAATCCATAAGCAACATGTGTTCT
 491▶ ProPheGlyArgGluArgGluAlaTrpGlnGlyArgLeu
2628 TTGTCTGAACACGATC
```

FIG. 17D

STABLE BIOCATALYSTS FOR ESTER HYDROLYSIS

This application claims priority to U.S. Provisional Application for patent Ser. No. 60/019,580, filed Jun. 12, 1996; Ser. No. 60/009,704, filed Jan. 11, 1996; and is a continuation-in-part of U.S. patent application Ser. No. 08/694,078, filed Aug. 7, 1996, all of which are hereby incorporated by reference in their entirety.

STATEMENT OF GOVERNMENT RIGHTS

The work disclosed in this application was supported in part by Grant Number: NCI 1-R43-CA63876-01 from the NIH-SBIR to ThermoGen Inc., therefore, the U.S. Government may have some rights in the present invention.

FIELD OF THE INVENTION

The instant disclosure is directed to the field of isolated stable biocatalysts that are suitable for enzymatic application in commercial pharmaceutical and chemical synthesis, DNA vectors for the production of recombinant ester hydrolyzing proteins, host cells transformed by such vectors, and recombinant ester hydrolyzing proteins produced by such vectors and transformed cells.

BACKGROUND OF THE INVENTION

Esterases and Lipases. Esterases and lipases catalyze the hydrolysis of ester bonds to produce alcohols and carboxylic acids as shown below.

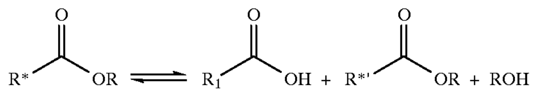

Esterases and lipases can be characterized by different substrate specificities, R group or chain length preference, and unique inhibitors (1, 2). The many esterases and lipases range from hydrolases such as the broad carboxyl esterases which preferentially hydrolyze esters with long carbon chain R groups, to choline esterases, and to acetyl esterases which act on very specific substrates. In many cases, these hydrolases are also known to show stereo- and regio-selective preferences resulting from the chiral nature inherent in protein active sites. This preferential hydrolytic activity make them useful for reactions requiring different regioselectivity and stereoselectivity or for kinetic resolution methods on racemic mixtures. For enzymes that demonstrate stereoselectivity, if R* is a racemic mixture, the product of enzyme catalyzed hydrolysis, $R_1$, would be the most rapidly hydrolyzed stereoisomer while the remaining ester designated R*' would be the enriched antipode mixed with any remaining $R_1$. The products can then be separated by chromatography to provide pure $R_1$. The availability of a large pool of esterases and lipases with varying specificities would be useful for screening the enzymes for specific reactions, and developing optimal protocols for specific chemical synthesis. The expedience of this process would facilitate the production scale-up of many useful pharmaceutical products.

In aqueous solvent systems, esterases and lipases carry out their natural reactions: the hydrolysis of ester bonds. In vitro, these enzymes can be used to carry out reactions on a wide variety of substrates, including esters containing cyclic and acyclic alcohols, mono- and di-esters, and lactams (3). By carrying out the reactions in organic solvents (4, 5) where water is excluded, the reactions of esterases and lipases can be reversed. These enzymes can catalyze esterification or acylation reactions to form ester bonds (3, 6, 7). This process can also be used in the transestenrfication of esters and in ring closure or opening reactions.

Optically pure chiral pharmaceuticals. Currently, the majority of synthetic chiral pharmaceuticals are sold as racemic mixtures. However, due to advances in the synthesis of optically pure (single isomer) chiral compounds, this situation is changing (7). Racemic drugs often contain one isomer which is therapeutically active and the other enantiomer which is at best inactive and at worst a major cause of potentially harmful side effects. The non-useful isomer in a racemic drug is increasingly being viewed as a contaminant. Indeed; the FDA's Policy Statement for the Development of New Drugs recommends "that the pharmacokinetic profile of each isomer should be characterized in animals and later compared to the clinical pharmacokinetic profile obtained in Phase I" drug testing (8). Thus, pharmaceutical companies will need to develop a synthesis or separation route to produce each pure isomer of each new synthetic drug.

Enzymatic synthesis of optically pure pharmaceuticals and intermediates. Since it is often very difficult to generate optically pure solutions of certain chiral molecules by classical chemical synthesis, new enzymatic biocatalysts will play a major role in this endeavor. In some cases, enzymes may be able to replace hazardous chemical synthesis procedures with more environmentally-friendly biological synthesis processes. It can also be much more cost effective to produce a pharmaceutical intermediate enzymatically if an enzyme can eliminate several chemical protection and deprotection steps at once (7). All six major classes of enzymes (oxidoreductases, transferases, hydrolases, lyases, isomerases, and ligases) have been useful in the synthesis of optically pure compounds as described in several detailed reviews (3, 7). The hydrolases have proven to be the most useful group of enzymes, due to the abundance of hydrolases, the information about them, their independence from cofactors, and the wide variety of substrates they can accept.

A survey of the literature shows many examples of mesophilic hydrolases particularly esterases and lipases used in chemical synthesis or chiral resolution. These include esterases from pig (9, 10) and horse (3) livers and a wide variety of lipases from Aspergillus sp, (11) Candida sp. (12–16), Pseudomonas sp., (17–19), Rhizopus sp. (20) and others. Several lipases have been used in the synthesis of propranolol (7), a beta-adrenergic blocking agent used in the treatment of angina and hypertension. Ibuprofen, a nonsteaoidal antiinflammatory agent has been synthesized via stereo selective hydrolysis of its methyl ester using carboxyesterase (7). While these enzymes have begun to demonstrate the utility of biocatalysts in chemical synthesis, there is still a profound need for a wider variety of esterases and lipases which have varying substrate specificities, regioselectivities, and steroselectivities. In addition, since these enzymes need to be employed in a large-scale industrial setting, there is a need for them to have increased stability, higher thermotolerance and a longer "shelf life".

Thermostable enzymes. Thermophilic organisms have already provided a rich source of useful proteins that catalyze reactions at higher temperatures and are stable for much longer periods of time (21, 22). One example is the DNA Polymerase I from *Thermus aquaticus* and its use in polymerase chain reaction (PCR) (23, 24). Thermophilic enzymes have become the most commercially successful enzymes in industry because of their long-term stability and ease of use. The most successful enzyme to date, alpha-amylase, is used in corn processing and comes from the moderate thermophile *B. stearothermophilus* (25). Another commercially successful industrial enzyme is subtilisin, a serine protease also found in various strains of Bacillus, has been widely used in laundry detergents and other cleaning solutions.

The commercial success of these enzymes can be attributed to their ease of use. In addition to functioning at high temperatures, thermostable enzymes generally posses an increased shelf life which markedly improves handling conditions, especially by those not trained in biochemistry to work with the specific range of conditions used for mesophilic enzymes. If enzymes are to play a significant role in large scale processing of chemicals, they must be able to endure the harsh conditions associated with these processes. Thermostable enzymes are easier to handle, last longer, and given the proper immobilization support should be reusable for multiple applications.

Finally, the hydrophobic and electrostatic forces that allow these enzymes to survive high temperatures also allow them to generally function better in organic solvents (26–31). While most enzymes lose a significant portion of their activity in organic solvents, thermostable enzymes may prove more tolerant to the denaturing conditions of many organic solvents. Highly thermostable esterases and lipases are necessary to expand the application of these biocatalysts in large scale industrial reactions.

Thermostable esterases and lipases. To date, only one esterase and a few lipases have been reported with moderately thermostable characteristics. Tulin et al. (32) reported a *Bacillus stearorhermophilus* esterase cloned into *Bacillus brevis* which was stable up to 10 minutes at 70° C. Sugihara et al.(33, 34) have isolated novel thermostable lipases from two microorganisms, A Bacillus soil isolate and a *Pseudomonas cepacia* soil isolate. The former lipase is stable up to 30 minutes at 65° C. but rapidly inactivated above this temperature. The lipase from *Pseudomonas cepacia* was stable when heated for 30 minutes at 75° C. and pH 6.5 but had only 10% of its activity when assayed at this temperature. A thermoalcalophilic lipase (35) was identified from a Bacillus species MC7 isolated by continuous culture and had a half-life of 3 hours at 70° C. Finally, Sigurgisladottir et al. (6) have reported the isolation of one Thermus and two Bacillus strains which posses lipases active on olive oil up to 80° C., although there was no report on enzyme stability in this study.

These enzymes offer only limited variations in substrate specificities and only moderate thermostability profiles. They do not address the need for different substrate specificities, the need to produce large scale quantities which can be economically commercialized, and many of them have only limited overall stability. In this patent application we have identified a series of esterases and lipases which offer a range of substrate specificities (including regioselectivity, stereoselectivity), enhanced enzyme stability, and can be produced in large quantities for commercial use.

SUMMARY OF THE INVENTION

The instant invention provides for the isolation and characterization of commercial grade enzyme preparations characterized by esterase activity, and corresponding to the data as disclosed in FIGS. 1–4 and Table 1. In a preferred embodiment, the instant invention provides for the isolation, and characterization of specifically purified esterase which is characterized by esterase activity, and corresponding to the data as disclosed in Table 1 and FIGS. 5–9. In a most preferred embodiment, the instant invention provides for proteins generated by recombinant DNA technology which have esterase activity. The enzymes of the instant disclosure can be isolated from thermophilic organisms from various sources including soil, water and refuse sites from across the United States and elsewhere in the world. These organisms generally grow in the temperature range of 45° C. to 90° C. which classifies them as moderate to extreme thermophiles. Proteins isolated from this group of organisms are similar in function to those isolated from species that grow at lower temperatures 25° C. to 37° C., but are lacking in thermostable characteristics. The enzymes of the instant disclosure encompass proteins produced by thermophilic organisms including the esterase enzymes which are responsible for the hydrolysis of ester bonds to yield carboxylic acids and alcohols. The proteins of the instant disclosure possess activity lifetimes considerably longer than found for unmodified mesophilic enzymes: retain activity even after exposure to elevated temperatures for extended periods of time, and resist inactivation in the presence of organic cosolvents. The proteins encompassed by the instant disclosure can be isolated by standard purification methods, specifically, and by ion exchange chromatography. The enzymes of the instant disclosure are all intracellular proteins that can be recovered by cell disruption and loaded on to DEAE cellulose. Purified esterases of the instant disclosure are eluted by NaCl gradients; fractions containing single activities are pooled and concentrated prior to lyophilization for storage. Specific activity is determined by measuring the total concentration of protein either by the Pierce BCA method or by measuring the UV absorbance at 280 nm followed by an activity assay based on the initial hydrolysis rate of p-nitrophenylproprionate. The proteins of the instant disclosure can be characterized by the strain of bacteria from which they were isolated, the growth in TT media at 55° C. and 65° C., and by esterase hydrolytic activity. The proteins of the instant disclosure can be characterized by esterase activity in selection microtiter plate assay. The proteins of the instant disclosure can also be characterized by the temperature profile, protein stability profile, and pH profile of the protein. The proteins of the instant disclosure can be characterized by apparent molecular weight corresponding to esterase activity stain on native gradient PAGE gels. Specific molecular weight can be further characterized by chromatography, and specific activity can be further determined under standard conditions, where Table 10 contains a summary of many of these characteristics for selected proteins. Thus the proteins of the instant invention can be characterized by inherent properties as well as by their amino acid protein sequence, or by a nucleic acid sequence which will encode for the amino acid protein sequence of the protein.

Thus, the instant disclosure encompasses a library of stable esterases isolated from a bank of thermophilic organisms, which are useful in the selective preparation of chiral pharmaceutical intermediates and other fine chemicals. The library consists of at least 23 purified enzymes that can be used either in various combinations as a screening kit, or as individual protein preparations to carry out chemical reactions or prepare chiral products using kinetic resolution techniques. Under these conditions, racemic esters will have different rates of hydrolysis catalyzed by the enzymes depending on which stereoisomer best fits the structural parameters of the enzyme active site. The products carrying the chiral center(s) may be on either the carboxylic acid or the alcohol. In addition, many of the esterases described herein may be used to prepare chiral esters from carboxylic acids and alcohols if the reaction is run in the synthetic direction under transesterification conditions in which water is limited in solvent.

The instant disclosure encompasses lambda phage expression vectors which contain an insert that can be used for the production of recombinant ester hydrolyzing proteins of the instant invention, from a transformed cell host. The insert contained on the lambda phage expression vector may be used in, for example, a phage-plasmid hybrid expression vector or other suitable expression vector such as, but not limited to, plasmids, YACs, cosmids, phagemids, etc. In a preferred embodiment, a lambda expression vector is one of the vectors named in Table 7, or one which contains an insert which encodes for a substantially similar recombinant protein. The instant disclosure also provides for vectors which are capable of transforming a host cell, and which encode for recombinant ester hydrolyzing proteins, the transformed host cells, and the recombinant ester hydrolyzing protein. Appropriate host cells include but are not limited to: *E. coli*, Bacilli, Thermus sp., etc. The recombinant ester hydrolyzing protein encoded by the vector is capable of hydrolyzing 5-bromo-4-chloro-3-indolyl-acetate (X-acetate). The recombinant ester hydrolyzing protein produced by the vector can be further characterized by a half-life stability comparable to that of a corresponding protein purified from the isolates. The recombinant ester hydrolyzing protein is also characterized by the ability to remain stable at temperatures comparable to, or better than that of the corresponding protein from the original isolates. Recombinant ester hydrolyzing protein encoded for by the vector can also be characterized by certain substrate specificities as discussed below, which are comparable to those of the corresponding purified protein from the isolates. In a preferred embodiment the vector is a vector named in Table 7 or 8, or one which contains an insert which encodes for a substantially similar recombinant protein. In a preferred embodiment of the instant invention, a vector which encodes specific recombinant ester hydrolyzing protein is one of the vectors named and listed in Table 8, and deposited with the American Type Culture Collection (ATCC, Rockville, Md., USA) under the terms and conditions of the Budapest Treaty for the Deposit of Microorganisms, and given a specific designation number by the ATCC, to be amended to the specification upon receipt of such numbers.

BRIEF DESCRIPTION OF THE DRAWINGS

FIG. 3. Molecular Weight calibration curve. FIG. 3 depicts a standard molecular weight calibration curve.

FIGS. 4A–T. Enzyme Characteristics. FIGS. 4A–T depict the activity profiles which characterize enzymes of the instant disclosure. For each enzyme listed, Graph 1 depicts the Temperature Profile of the enzyme plotting relative esterase activity versus temperature. Graph 2 depicts the Residual Esterase Activity of the listed enzyme plotting relative remaining activity versus time in hours, at 25° C., 40° C., and 65° C. Graph 3 depicts the pH profile for the listed enzyme plotting Relative Esterase Activity versus pH.

FIG. 6. Kinetic analysis of E100. The enzyme displays normal Michaelis kinetics yielding linear data with both a) Lineweaver-Burke and b) Eadie-Hofstee analysis to give a $Km=7.2\times10^{-5}M$ and $Vmax=1.8\times10^{-5}Mmin^{-1}$ using p-NP as the substrate.

FIG. 7. Temperature and pH profiles of E100. a) Temperature profile of E100. Plot of E100 catalyzed hydrolysis of p-nitrophenyl proprionate as a function of temperature. Enzyme activity was determined upon exposure to different temperatures. Initial rates of nitrophenylproprionate hydrolysis were determined in 50 mM borate Buffer pH 8.5 equilibrated to the desired temperature to which 0.25 mM substrate dissolved in $CH_3CN$ was added followed by enzyme. Rates were determined by monitoring the change in absorbance at 405 nm and corrected for the spontaneous hydrolysis of substrate substituting bovine serum albumin for enzyme. b) pH profile of E100. The effect of pH on the hydrolysis of p-nitrophenyl proprionate catalyzed by E100. The pH profile of the enzyme was determined by preparing different buffers appropriate for the desired pH's at 10 mM concentration; Reactions were performed by addition of the substrate (0.25 mM) dissolved in CH3CN to the buffer solution followed by the enzyme. Reactions were incubated for 5 minutes after which the reaction was terminated by addition of 0.1 mM PMSF dissolved in $CH_3CN$. The pH of the mixture is adjusted to 8.5 by addition of 0.1 M Tris-HCl. Absorbances are recorded at 405 nm and concentrations calculated based on the $\epsilon=17\ mM^{-1}\ cm^{-1}$ for the product nitrophenol. Formation of products is corrected for the spontaneous hydrolysis of the substrate.

FIG. 9. Purification of E101. a) Steps in the purification of E101 as shown by 10% SDS-PAGE. Lane 1. Molecular weight markers. Lane 2. purified E100 (included as standard). Lane 3. dialyzed protein after $NH_4SO_4$ fractionation. Lane 4. DEAE load/wash. Lane 5. SP Sepharose load/wash. Lane 6. Purified E101 eluted from S200 gel column. b) 10% SDS-PAGE of E101. Lane 1. Boiled E101. Lane 2. Nonboiled E101. Lane 3. Molecular weight markers.

FIG. 10. Substrates used to screen stereo- and regioselectivity. Esterases are versatile biocatalysts in the sense that stereo- and regio-selectivity can be mediated by substrate structure which fall into four types. The compounds listed represent a range of different structural features encountered in common substrates with potential importance for the chemical intermediate industry. Several of the substrates are commercially available in entantio- or diastereomerically pure form and can be used in qualitative screening procedures described in the text. Four classes of substrates most commonly associated with hydrolytic biocatalysts for chiral centers resolution are considered. A) Type I substrates position the desired product on the carboxylic acid side of the product, while Type II compounds the alcohol contains the requisite functionality. B) Type III and Type IV substrates can be considered subsets of Types I and II, but their unique properties dictate that they be classified separately. Type III molecules require that the enzyme differentiates a prochiral substrate while Type IV compounds are meso structures. These last two substrate types demonstrate the synthetic importance of biocatalyst based resolution methods as these types of compounds are very difficult to selectively operate upon by other chemical means.

FIG. 11. Selection process for Recombinant Esterases. a). Screening of the phage library from strain isolate 28 (E009) using an X-Acetate gel overlay. Blue halos surround single phage plaques expressing esterase. b) Purification of hybrid phages produced from the 54 (E002) strain. Halos of the hydrolyzed X-Acetate chromogenic substrate surround each phage plaque of the three phage stocks. c) and d) A Spot-test for the hydrolyzing activity of the plasmid-carrying strains derived from phages λTGE1.1; λTGE1.2; λTGE1.3; λTGE2.1; λTGE2.2; λTGE2.3; λTGE2.4; λTGE2.8; λTGE3.2; λTGE3.3; λTGE3.4; λTGE4.1; λTGE4.2; λTGE4.3; λTGE11.1; λTGE11.3; λTGE11.4; TGE11.7; λTGE11.9; λTGE11.10; λTGE15.1; λTGE15.3; λTGE15.5; λTGE15.8; λTGE15.9. Higher activity detected by X-Acetate is strongly associated with weaker growth.

FIG. 15. Digestion patterns for 24 recombinant esterases. The restriction endonuclease digestion patterns for the set of 24 plasmid listed in Table 8 is shown. (a) The 24 plasmids are cut by EcoRI (1–24), BamHI (25–48), HindIII (49–72) and EcoRV(73–96). (b). A gel showing the PstI digestion pattern for plasmids 1–18. (c). A gel showing the PstI digestion patterns for plasmids 19–24 and the XbaI digestion patterns for plasmids 1–11. (d). A gel showing the XbaI digestion patterns for plasmids 12–24. For all gels, lanes 1–24 refer to the following plasmids in the following order: pTGE1.1, pTGE2.1, pTGE2.2, pTGE3.2, pTGE4.6, pTGE5.3, pTGE6.3, pTGE7.1, pTGE8.5, pTGE9.4, pTGE10.3, pTGE11.10, pTGE12.2, pTGE13.2, pTGE14.3, pTGE14.6, pTGE15.9, pTGE16.1, pTGE19.4, pTGE20.4, pTGE21.8, pTGE21.8x, pTGE20.3, pTGE16.3. Plasmid pTGE21.8x is a variant of pTGE21.8 which was isolated that had a loss in activity.

FIG. 16. Nucleic acid sequence and translated protein amino acid sequence. The isolation and cloning of the genes encoding for the enzymes of the instant invention will result in DNA segments in which an open reading frame (ORF) may be found which corresponds to the translated protein amino acid sequence. Alternative start codons are recognized in the art, however the encoded protein will comprise at minimum a core protein ORF. FIG. 16A (coding portion of SEQ. ID NO.: 1) is an isolated nucleic acid sequence, and translated amino acid sequence which correspond to E001 enzyme ORF, alternative start codons are underlined. FIG. 16B (SEQ. ID NO.: 1) is the cloned isolated nucleic acid sequence which contains the E001 ORF. FIG. 16C (coding portion of SEQ ID NO.: 3) is an isolated nucleic acid sequence, and translated amino acid sequence which correspond to E009 enzyme ORF, alternative start codons are underlined. FIG. 16D (SEQ ID NO.: 3) is the cloned isolated nucleic acid sequence which contains the E009 ORF. FIG. 16E (coding portion of SEQ ID NO.: 5) is an isolated nucleic acid sequence, and translated amino acid sequence which correspond to E011 enzyme O alternative start codons are underlined. FIG. 16F (SEQ ID NO.: 5) is the cloned isolated nucleic acid sequence which contains the E011 ORF. FIG. 16G (coding portion of SEQ ID NO.: 7) is an isolated nucleic acid sequence, and translated amino acid sequence which corresponds to E101 enzyme ORF, alternative start codons are underlined. FIG. 16H (SEQ ID NO.: 7) is the cloned isolated nucleic acid sequence which contains the E101 ORF.

FIG. 17. Nucleic acid sequence and translated protein amino acid sequence.

FIG. 17A (coding portion of SEQ ID NO.: 9) is an isolated nucleic acid sequence, and translated amino acid sequence which corresponds to E019 enzyme. FIG. 17B (SEQ ID NO.: 9) is the cloned isolated nucleic acid sequence which contains the E019 ORF. FIG. 17C (coding portion of SEQ ID NO.: 11) is an isolated nucleic acid sequence, and translated amino acid sequence which corresponds to E005 enzyme ORF. FIG. 17D (SEQ ID NO.: 11) is the cloned isolated nucleic acid sequence which contains the E005 ORF.

DETAILED DESCRIPTION OF THE INVENTION

Figure 1:
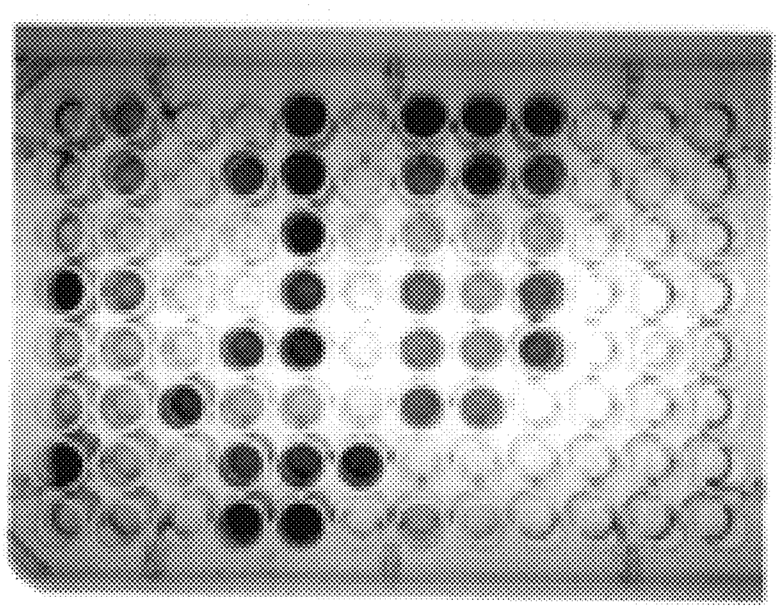
FIG. 1. Esterase Screening plate. Fifty microliters of cell extract is transferred to a well on a microtiter plate consisting of 0.1 mg/ml of either 5-bromo-4-chloro-3-indolyl acetate or butyrate (for esterase activities) suspended in 0.7% agarose and 0.1M Tris-HCl pH 8.0. Control wells consist of addition of either buffer, 20 U of Pig Liver Esterase (PLE), or 20 U of Porcine Pancreatic Lipase (PPL). Plates are incubated for sufficient time to allow full color development in control wells, usually about twenty minutes at 37° C. Dark wells represent positive activity. This photograph demonstrates the screening of 65 candidate isolates, and the resulting positives.

The instant invention provides for isolated commercially useful protein preparations from themostable bacteria which are selected for enzymatic activity, and characterized by apparent molecular weight, pH, and temperature stability. The isolated protein of the instant disclosure can be used as molecular weight markers for finding similar enzymes, as well as functionally as enzymes for carrying out biocatalysis. Commercial chemical synthesis of specific racemic products often require the use of such isolated enzyme preparations.

The results of characterization assays demonstrate that the esterase enzymes described have a range of optimal parameters. For instance, E100 and E101 have optimal operating temperatures above 70° C. as would be consistent with enzymes isolated from an extreme thermophile, and E001–E021 have optimal commercial temperatures in the range of 40–50° C. as would be consistent with enzymes isolated from the more moderate thermophilic organisms. Both groups, however, provide added stability and functionality as compared to other known esterases from thermophilic bacteria. E001–E021 provide an optimal temperature environment for chemists who wish to work in less extreme temperature ranges, and also function well at room temperature. The results also demonstrate that the enzymes described posses a variety of pH optima including some with no apparent preference under the conditions of the experiment, however the trend for most of the proteins is to have pH optima near or slightly below neutral.

The following examples are meant by way of illustration, and not limitation, as to the specific embodiments of the instant invention. One of ordinary skill in the art would understand that many equivalents to the instant inventions can be made with no more than routine experimentation.

EXAMPLE 1

Isolation and Propagation of Thermophilic Organisms

Strains—Thermus sp. T351 (ATCC 31674) is available from the American Type Culture Collection (ATCC). All isolated strains and cultures are grown on TT medium (36). This medium consists of (per liter): BBL Polypeptone (8 gm), Difco Yeast Extract (4 gm), and NaCl (2 gm). Small scale cultures for screening are grown at 65° C. at 250–300 rpm with 1 liter of medium in a 2 liter flask. Larger scale production of cells for enzyme purification are grown in 17 liter fermentors (LH Fermentation, Model 2000 series 1). The fermentors have a working volume of 15 liters and cultures were grown in TT broth, 250 rpm, 0.3 to 0.5 vvm (volumes air/volume media per minute) at 65° C. Temperature is maintained by circulating 65° C. water from a 28 liter 65° C. water reservoir through hollow baffles within the stirred jars. *E. coli* strains are grown as described in (37).

Enrichment Procedures for Newly Isolated Thermophiles Multiple Strain sediments, composting organic materials, and soil samples are used to isolate new strains. These samples are collected from numerous geographic sites ranging from the Midwest to the Southeast. Samples (~1 gm) are resuspended in 2 ml of TT broth and 50–100 μl of these samples were plated onto TT agar plates containing twice the usual amount of agar (3%). Agar is usually added to a final concentration of 1.5% for solid media This prevents highly motile microorganisms from overcrowding the plate at the expense of other microbes. Plates are incubated at 55°

C. or 65° C. for one to two days and isolates then purified by numerous restreaks onto fresh plates for single colony isolation. The initial basis for differentiation is color, colony morphology, microscopic examination, temperature of growth, and lipase and esterase activities. Several hundred strains were initially isolated. 65 different microorganisms were chosen for further study.

EXAMPLE 2

Methods for Esterase Identification and Assay

Esterase Plate assay—Organisms are grown in liquid cultures on TT media at either 55° C. or 65° C. Cells are pelleted by centrifugation (3,000 RPM for 20 minutes) and the supernatants saved to be tested. Pellets are washed with 2 volumes of 10 mM Tris HCl pH 8.0 three times after which the cell pellets are resuspended in fresh Tris buffer and disrupted by sonication. Cell debris is removed by centrifugation and the crude extracts were tested for esterase activity as are shown in FIG. 1. Both cell extracts and culture supernatants are tested for esterase activity by this method. Only cell extracts showed significant esterase activity.

Esterase Liquid assay and determination of specific activity—Protein concentrations are determined by the Pierce BCA assay using defined concentrations of bovine serum albumin as the standard. Protein concentrations are obtained from the calibrated absorbance of the sample solutions at 562 nm and are expressed as milligrams of protein. Esterase activities are routinely measured by determining the rate of hydrolysis of p-nitrophenylproprionate (0.5 mM from a 10 mM stock dissolved in CH3CN) in 50 mM sodium phosphate buffer pH 7.0 equilibrated at 40° C. and monitored at 346 nm (isosbestic point for the acid/carboxylate couple $\epsilon$=4800). The specific activity is defined as the amount of p-nitrophenol produced in micromoles per minute per milligram of total protein.

Identification of extremely stable esterases.—Native (non denaturing) 10% polyacrylamide gels are run on crude extracts. These gels can then be stained with an esterase activity stain containing either 5-bromo-4-chloro-3-indolyl acetate (X-acetate), 5-bromo-4-chloro-3-indolyl butyrate (X-butyrate) or 5-bromo-4-chloro-3-indolyl caprylate (X-caprylate) and produced indigo precipitates. Two major bands were apparent in the lanes with Thermus crude extracts. A single small band of activity is seen in the *E. coli* control lanes. Esterases can be identified from Thermus sp. T351 and from several of the new isolates. Table 1 summarizes the activities which are found from these organisms.

TABLE 1

Summary of New Esterases and Strains Identified

| Isolate[1] | Esterase | Source | Growth Temp (° C.) 37 | 55 | 65 | Isolation Temp (° C.) | mw (kD)[2] | Specific Activity[3] |
|---|---|---|---|---|---|---|---|---|
| S1 | E001 | soil | nd | nd | + | 65 | 22 | 0.011 |
| 54 | E002 | compost | − | + | + | 65 | 28 | 0.87 |
| 50 | E003 | compost | − | + | + | 65 | 28 | 2.2 |
| GP1 | E004 | soil | nd | nd | + | 65 | 36 | 0.3 |
| C-1 | E005 | compost | nd | nd | + | 65 | 28 | 2.3 |
| 55 | E006 | compost | − | + | + | 65 | 36 | 2.1 |
| 46 | E007 | compost | − | + | + | 65 | 28 | 0.3 |
| 30 | E008 | soil | − | + | + | 55 | 28 | 2.1 |
| 28 | E009 | soil | − | + | + | 55 | 36 | 2.0 |
| 29 | E010 | soil | − | + | − | 55 | 46.5 | 2.3 |
| 31 | E011 | soil | − | + | − | 55 | 36 | 3.6 |
| 26b | E012 | soil | − | + | − | 55 | 28 | 5.2 |
| 27 | E013 | soil | − | + | + | 55 | 36 | 2.7 |
| 34 | E014 | soil | − | + | +/− | 55 | 36 | 0.8 |
| 62 | E015 | compost | − | + | + | 55 | 36 | 3.4 |
| 47 | E016 | compost | − | + | + | 65 | 28 | 0.8 |
| 49 | E017 | soil | − | + | + | 65 | 36 | 0.03 |
| C-3 | E018 | compost | nd | nd | + | 65 | 36 | 0.077 |
| 4 | E019 | compost | − | + | + | 55 | 30 | 0.4 |
| 7 | E020 | compost | − | + | + | 55 | 28 | 1.6 |
| 32 | E021/17b[4] | soil | − | + | +/− | 55 | 36 | 0.3 |
| Thermus sp. T351 | E100 | ATCC# 31674 | nd | + | + | 65 | 45 | 0.0032 |
| Thermus sp. T351 | E101 | ATCC# 31674 | nd | + | + | 65 | 135 | 0.032 |

[1]Isolates GP1, 27, 28, 29, 30, 31, 32, 34, 62 appear to be thermophilic Actinomyces.
[2]Approximate molecular weight as determined by chromatography for E001–E021 or SDS-PAGE for E100 and E101.
[3]Specific activity is the amount of p-nitrophenol produced in micromoles per minute per milligram of total protein at 40° C. after purification to homogeneity (for E100 and E101) or semi-purification (for E001–E021) as described in the Examples.
[4]E021 is also referred to as E017b.

EXAMPLE 3

Procedure for Purification of Esterase Activity to Homogeneity

Protein Isolation—A large batch cell culture is grown according to the methods described in Example 1 and the cell paste is collected by centrifugation and stored at −80° C. 100 g of cell paste is thawed in 200 ml of a stirred solution composed of 50 mM phosphate buffer at pH 7.5 containing 200 mM KCl and 0.1 mM EDTA. Once dissolved, the suspension is allowed to warm to room temperature and then treated with lysozyme (0.1 mg/ml) for 2 hours. The solution is then sonicated to completely disrupt the cells. Settings used on a 375 watt Sonics & Materials Vibra Cell sonicator with a standard ¼" horn were 5 minutes of power setting 8 disruption with a 50% pulse rate. Alternative methods for cell disruption can include processing the cells through a device such as a french press, Gaullen homogenizer, microfluidizer or other homogenizer. Cell debris is removed by centrifugation and proteins can be precipitated by $NH_4SO_4$ fractionation to 60% saturation. Precipitated protein is centrifuged and resuspended in minimal volume of 50 mM phosphate pH 6.5 containing 1 mM β-mercaptoethanol (BME).

DEAE Purification—The protein solution is dialyzed against the resuspension buffer 3 times using 10 Kd pore size dialysis tubing. The resulting protein solution is diluted two fold in the buffer and applied to a 100 ml bed volume DEAE column equilibrated in the same buffer. The column is washed with 200 ml equilibration buffer and then eluted with a linear gradient from 0 to 0.5 M NaCl.

Q Resin purification—Active fractions isolated from DEAE purification are pooled and dialyzed against three changes of equilibration buffer and dialysate was applied to a 50 ml bed volume of sepharose Q resin equilibrated with the buffer above. The column is washed with 100 ml of 50 mM phosphate pH 6.5 containing 0.1M KCl and 1 mM BME and then eluted with 150 ml of a KCl gradient from 0.1 M to 0.6M added to the above buffer.

Ultrafiltration Concentration—Active fractions are pooled and concentrated using an Amicon Ultrafiltration system fitted with a 30 Kd cut off membrane.

Preparative SDS PAGE—Concentrated protein solutions are loaded to a preparative 10% SDS-PAGE gel using the standard SDS loading buffer without boiling the sample. After development, the gel is treated with 0.7% agarose containing 0.1M phosphate pH 7.5 and 0.1 mg/ml 5-bromo-4-chloro-indoylacetate. The resulting blue band was excised from the gel, placed in dialysis tubing and the protein is recovered by electroelution in 0.05M Tris buffer pH 8.5 for 1 hour. At this stage the protein is purified to homogeneity as observed by both native- and SDS-PAGE stained with either coomassie or silver stain. Protein can be stored at 4° C. for future use.

Gel filtration—A gel filtration column can also be used as a further or substituted purification step.

EXAMPLE 4

Method for Commercial Grade Preparation of Isolated Esterase

For many industrial applications, a completely purified preparation of enzyme is neither required nor desired due to production cost considerations. A rapid, inexpensive protocol to produce a protein of interest in a form which is isolated to contain protein with significant esterase activity is desired. One such semi-purification procedure is described here. 50 g of cell paste is thawed in 100 ml of 50 mM Tris HCl buffer at pH 7.5 containing 0.1M NaCl and 0.01 mM EDTA. Cells are disrupted by sonication and the cell debris is removed by centrifugation. The crude cell lysate is diluted by three fold with 50 mM Tris-HCl pH 7.5 and the material is loaded to a DEAE cellulose column (bed volume 60 ml) equilibrated with the dilution buffer. The column is washed with three column volumes of dilution buffer followed by a salt gradient of 0–0.5M NaCl over 4 column volumes. Active fractions eluted from the ion exchange resin in the salt gradient window of 0.25–0.35 M. Fractions were assayed for activity as described under determination of specific activity and those showing the highest activity were pooled and concentrated by ultrafiltration with 10 Kd molecular weight cut off membrane. Concentrated enzyme samples are stored at 4° C. for further use. In some instances, more than one ester hydrolysis activity may still be detected under long term exposure to substrate agarose overlays of proteins separated on native PAGE, indicating very small quantities of a second esterase activity which should not interfere with most industrial applications. A further purification (such as an Ammonium sulfate salt precipitation, gel filtration, or other methods as described in Example 3) can be applied if necessary. The process can be scaled up or down as desired.

EXAMPLE 5

Method for Determination of Temperature Profile

Optimal temperature profiles for an esterase protein is performed by measuring the activity of the esterase diluted into 0.1M sodium phosphate buffer pH 7.0 equilibrated at 30° C., 35° C., 45° C., 55° C. and 65° C. respectively for five minutes. The temperature profile is then determined by measuring the rate of hydrolysis of p-nitrophenylproprionate added to the equilibrated solution under reaction conditions described for determination of specific activity in Example 2 (modified by the various temperatures used in this experiment). Control reactions that substitute bovine serum albumin for esterase enzymes are used to allow correction for temperature dependent autohydrolysis of the substrate. The data is then plotted as relative activity versus the temperature of the reaction.

EXAMPLE 6

Method for Determination of Enzyme Stability

The long term catalytic stability the esterase enzyme is evaluated by testing the activity remaining after exposure to various temperatures. The enzyme stock solution is diluted into 0.1 M sodium phosphate buffer pH 7.0 and placed in a temperature bath equilibrated to 25° C., 40° C. or 60° C. respectively under sealed conditions to avoid concentration effects due to evaporation. Residual activity is then determined by removing aliquots at regular intervals and measuring the rate of hydrolysis of p-nitrophenyl-proprionate as described above. Results are plotted as relative activity vs. time. The results (see FIG. 4) indicate that all enzymes retain most of the initial activity for at least 48 hours when exposed to temperatures up to and including 40° C. Activity does decrease at 60° C. particularly for enzymes isolated from organisms with optimal growth temperatures near 55° C.

EXAMPLE 7

Method for Determination of pH Profile

The pH profile of an esterase is determined as follows. The rate of p-nitrophenylproprionate hydrolysis is determined under reaction conditions similar to those described for determination of specific activity in Example 2 with buffers of wide useful pH windows that overlap with at least one data point. For the purposes of these experiments two buffers were selected that met the above criteria, Mes (useful range of 6–6.5) and Bis-tris propane (useful buffer range 6.5–9). All pH tests were corrected for spontaneous autohydrolysis by subtraction of experimental runs from controls substituting bovine serum albumen for esterase. This control data treatment becomes especially important for pH's greater than 7.5.

EXAMPLE 8

Solvent Effects on Esterase Activity

Industrial applications for biocatalysts often require that enzymes function under non-native and harsh conditions.

Exposure to elevated temperatures and pH fluctuations are possible challenges to enzyme activity, however the lack aqueous solubility of many compounds that may serve as substrate targets for biocatalysts is a significant challenge to the industrial organic chemist. Organic cosolvents are commonly used in reactions and isolated enzymes must be able to survive under conditions of relatively high concentrations of cosolvent. Experiments are run in the presence of various organic solvents such as ethanol, acetonitrile, dimethylformamide, dioxane, toluene, hexane and detergents like SDS, triton X100 and Tween 20. Additional experiments are also performed to test the activity of isolated catalysts in nearly anhydrous solvent conditions in which the enzymes will be lyophilized from buffers and pH's of optimal activity.

EXAMPLE 9

Method for Protein Characterization by Migration on Native PAGE

Figure 2:
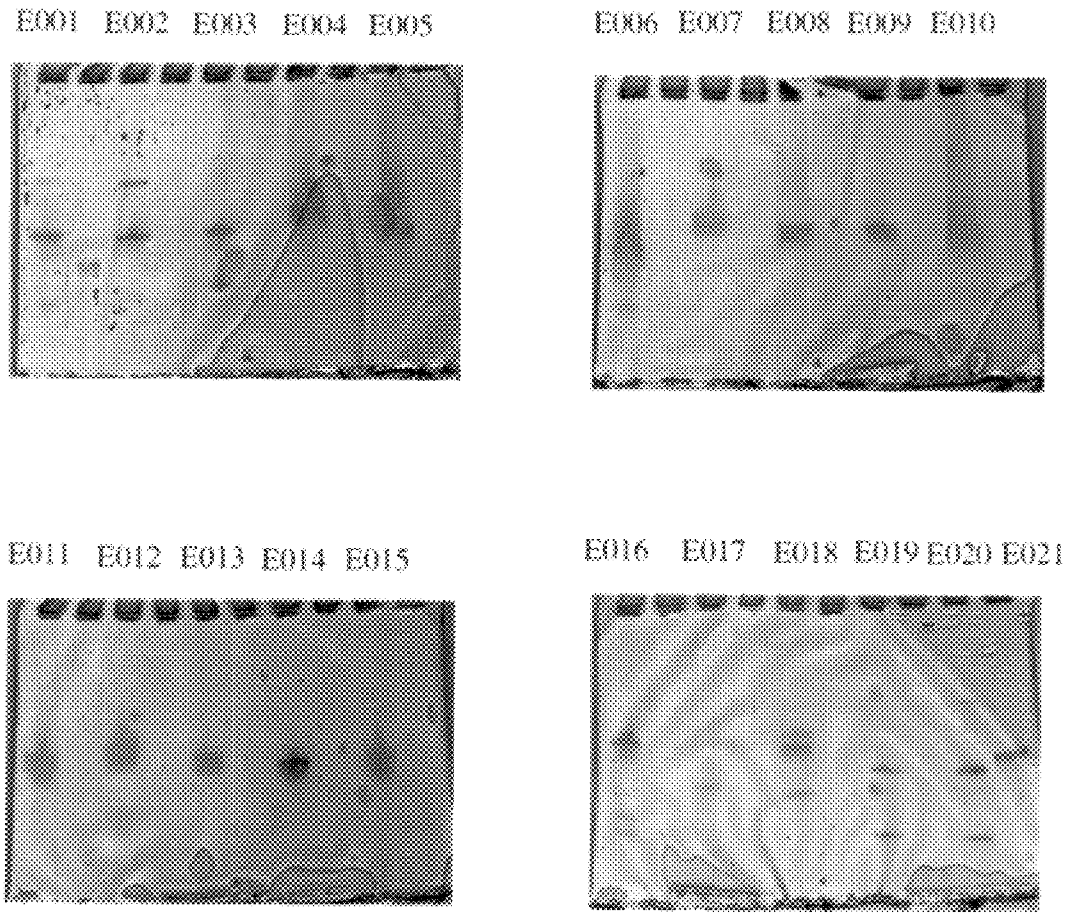
FIG. 2. Esterase activity stain of crude extracts from thermophiles. After electrophoresis, the gels are equilibrated in pH 7.6 Trizma buffer and then stained for activity in either 0.15% X-acetate. The gels are then incubated at 55° C. for up to 30 minutes.

The number of esterase enzymes in each semi-pure sample is determined from native gel PAGE using 4–15% acrylamide gradient (precast gels purchased from Bio-Rad laboratories) separating proteins based on their charge to size ratio. The gel shows trace contamination with other enzymes capable of indoylacetate hydrolysis that could not be detected easily with the HPLC because of column dilution effects. What is clear from the gel experiments is that most of the samples have a single major activity that have similar migration characteristics as shown in FIG. 2.

EXAMPLE 10

Determination of Relative Molecular Weight by Chromatography

The estimated native molecular weights for the protein of interest is determined by separation on a Pharmacia Superdex S200 FPLC column fitted to a Hitachi HPLC 6200 system. Proteins were separated by isocratic elution in 0.05 M sodium phosphate buffer at pH 7.0 containing 0.1 M NaCl. The solvent flow rate was maintained at 0.5 ml/min and protein was detected by UV at 280 nm. Esterase active fractions were detected initially by 5-bromo-3-chloro-3-indolyl-acetate plate assay with follow-up assay of most active fractions by p-nitrophenyl-proprionate hydrolysis (both methods are described in Example 2). Molecular weights are estimated by comparison to standard elution profiles (plotted as the log of molecular weight vs. time in minutes) generated by use of the following proteins: β-amylase 200 Kd, alcohol dehydrogenase 150 Kd, bovine serum albumin 66 Kd, carbonic anhydrase 29 Kd, cytochrome c 12.3 Kd.

EXAMPLE 11

Characterization of Substrate Specificities

Substrate preference of esterases for hydrolytic activity on various esters can be determined as follows. A grid of molecules is prepared on microtiter plates by dissolving each substrate (0.1 mM final concentration) in $CH_3CN$ and mixing with 0.1M phosphate buffer pH 7.5. Partially purified enzymes is then added to the wells and the reaction mixture is incubated for 30 minutes. Crude lysates can also be tested this way. Plates are checked after 10, 20 and 30 minutes to determine relative activities. For experiments with noncolored substrates, reactions are run in test tubes under the same conditions as described for the colored substrates except that the reactions are extracted three times with dichloromethane. The organic layers are combined, dried with $MgSO_4$ and concentrated to 0.1 ml in a nitrogen stream. The concentrates are then spotted to silica gel TLC plates and developed in a solvent mixture of 80:20:0.01 hexane:ethyl ether:acetic acid. TLC plates are visualized with UV and $I_2$.

EXAMPLE 12

Rapid Screen Assay for Quick Substrate Specificity Characterization

A new method was developed to rapidly screen for esterase activity based on the mechanism of the enzyme catalyzed hydrolysis reaction wherein the pH of the system is reduced by the release of protons upon ester hydrolysis. The proton flux in the reaction can be monitored by use of indicator dyes that have pH-dependent color transitions in the desired pH range of enzyme activity. The best indicators tested are phenol red for enzymes that function optimally at slightly elevated pHs (starting point pH 8.5) or bromothymol blue (starting point pH 7.2) for enzymes that operate well at more neutral conditions.

The indicator reactions are monitored by one of two methods. Spectroscopic studies are performed by measuring the UV/Vis maxima of a 0.001% solution of either phenol red or bromothymol blue dissolved in different pH buffers at 5 mM concentration. Hydrolytic reactions are then performed by adding the substrate (0.1 mM final concentration) to a 5 mM buffer solution (sodium phosphate pH 7.2 for bromothymol blue indicator and sodium borate pH 8.5 for phenol red indicator) and equilibrating the temperature at 25° C. for five minutes followed by initiation of the reaction by addition of 0.1 U target enzyme.

An alternative method for monitoring the hydrolytic reactions is useful for broad screening applications. 5 mM buffer containing 0.001% indicator dye and substrates dissolved in $CH_3CN$, DMF or DMSO to an organic solvent composition of no more than 10% is added to a stirred 24 well microtiter tray. The temperature is allowed to equilibrate for five minutes at 25° C. after which the reaction is initiated by addition of 0.1 U of the esterase. Reaction progress is monitored by solution color changes upon which, aliquots of NaOH are added to return the reaction color to the starting point. Reactions are determined to be complete when no further color change is detected after prolonged incubation. Product formation is verified by TLC analysis of reactions acidified with 0.1 M HCl, extracted with ethyl acetate, dried with $Na_2SO4$ and concentrated under a stream of $N_2$. For testing substrates in which enzyme-based chiral resolution is being screened, products are separated and isolated by chiral phase HPLC and enantiomeric purity is determined by integration of peak areas for each isomer.

Rapid assay of a variety of hydrolytic activities, in this cases esterases, is determined in a microtiter plate experiment using several different enzymes and substrates. Accurate comparison of commercially available enzymes can be insured by using the same specific activity for each enzyme determined from the total protein and the initial rate of hydrolysis of the common substrate p-nitrophenylproprionate. The data are recorded as the time required to visualize a pH dependent color change for the given indicator dye. Control experiments using BSA as the protein source cause no change in indicator color and establish that pH changes in solution are the result of an enzyme catalyzed hydrolysis. Control tests of reaction solutions containing enzymes and indicators without substrates established that color changes in the solutions are not the result of buffer salts or the enzymes alone.

Studies performed to determine whether the microtiter plate format was amenable to small scale preparative chemistry are performed as follows. Using racemic phenethylacetate and pig liver esterase, reactions are run and titrated with aliquots of 0.1N NaOH to maintain original solution color until no further color changes occurred at which point the reactions are stopped. Products are isolated and tested by TLC and compared to total amount of base added to verify the extent of the reaction. Phenethyl alcohol is separated from starting acetyl ester by flash column chromatography followed by analysis by chiral phase HPLC. The enantiomeric excess of the hydrolysis products is determined from the peak integration and compared to an identical reaction run in the absence of indicator dye. The results from these experiments suggest that inclusion of indicator dye has no effect on the stereoselectivity of esterase catalyzed resolution of phenethylacetate.

In order to test the assay for usefulness in a broad-based enzyme screening method, seven organisms isolated from various sources in the environment were tested for their ability to produce enzymes that would catalyze the hydrolysis of a group of structurally diverse compounds. Table 2 shows the results of these studies.

TABLE 2

Substrate Specificity.

| | Lysate Hydrolytic Rate (min) | | | | | | | | |
|---|---|---|---|---|---|---|---|---|---|
| Substrate | N/E | E001 | E003 | E004 | E005 | E006 | E016 | E017 | E018 |
| 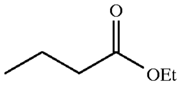 | — | 60 | 240 | 20 | <5 | <5 | — | — | 15 |
| 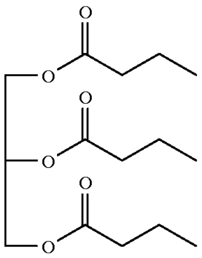 | — | 60 | 20 | <5 | <5 | <5 | <5 | 120 | 60 |
| 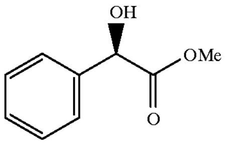 | — | — | 240 | — | 120 | 240 | — | 300 | — |
| 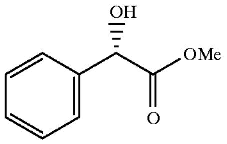 | — | — | 300 | 240 | 240 | 240 | — | — | 240 |
| 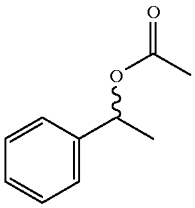 | — | 240 | 240 | 20 | 60 | 60 | 120 | 900 | 60 |
| Solvent Control | — | — | — | — | — | — | — | — | — |

Results are reported as the amount of time required to change indicator color. The data is indicative of variable substrate specificity between different environmental isolates. Of particular note is the suggestion of stereoselectivity as determined from the relative rates of hydrolysis for substrate enantiomers. Control reactions are similar to those described above in the substrate specificity studies with commercially available enzymes.

EXAMPLE 13

Further Characterization of Substrate Specificities

Depicted in FIG. 10 are examples of the substrates that can be tested with each enzyme activity. These molecules have been chosen specifically because of their importance as intermediates in the synthetic literature with the potential for industrial application. Experiments can be performed with crude lysates or proteins isolated from media broth in cases where the activities are known to rapidly assess the likely reaction chemistry including substrate preference and stereochemistry. All structure activity tests are compared to standard mesophile biocatalysts such as pig liver esterase. The reactions are monitored by TLC analysis to compare the products to standards purchased from commercial sources or prepared by chemical means (for example, base-catalyzed hydrolysis of esters).

Investigations of stereochemical preference by each esterase can be evaluated by one of two methods. In the first method, standard single stereoisomers of commercially available entantiomerically pure substrate esters are hydrolyzed by each enzyme and the relative rates of hydrolysis for each antipode are used as diagnostic qualitative determinants of potential chiral selectivity. In the second method, those molecules not commercially available as single stereoisomers are hydrolyzed as racemates using kinetic resolution methods (running the reaction generally less than 50% completion). The products of the reaction are isolated and analyzed for their enantiomeric excess (ee) by chiral phase HPLC (Diacel Chiralcel OD or OB) or $^1$H NMR of the corresponding diasteriomers prepared by derivatizing products to Mosher derivatives (alcohol products) or menthyl derivatives (carboxylate products). Diastereomeric ratios determined from the NMR spectra are based on corresponding peak integrations and compared to either literature values or standards obtained from commercial sources using of chiral shift reagents when necessary. Optical rotations and absolute configurations of the products are then determined by polarimetric analysis and compared to values found in the literature or determined from standards obtained from commercial suppliers.

EXAMPLE 14

Characterization of Proteins E001–E021/17b

Strains from the identified sources as listed in Table 1 were isolated by growth in TT media at 65° C. as described in Example 1 (ie. S1 from soil, etc.). Specific esterase hydrolytic activity was identified by the methods described in Example 2 and the isolated esterase protein assigned the identifier as listed in Table 1 (ie. E001 etc.) To prepare enzyme, a 15 liter culture of isolate is grown and the cells are spun down and collected as described in Example 1. The cells are lysed and a isolated preparation of was purified according to the procedures outlined in Example 4. The protein was characterized using the methods described in Example 5 to determine the temperature profile, Example 6 to determine protein stability, and Example 7 to determine the pH profile, and the results are shown in FIG. 4. The protein was characterized by migration on Native gradient PAGE as described in Example 9 and the data is shown in FIG. 2. The specific activity was determined as described in Example 2 and the molecular weight was determined by chromatography as described in Example 10 and are presented in Table 1. Substrate specificity for several proteins has been demonstrated and are shown in Table 2. Thus the identified and characterized esterases have been demonstrated to be useful, and to posesses unique activity at commercially useful purity. Certain results are summarized in Table 10.

EXAMPLE 15

Characterization of E100

Figure 5:
FIG. 5. Migration profile of E100 on 8% SDS-PAGE. Lane 1. Boiled E100 following DEAE and Q Sepharose chromatography. Lane 2. Nonboiled purified E100. Lane 3. Boiled E100. Lane 4. Molecular weight markers.

Purification of E100–E100 is purified from Thermus sp. T351 over 300 fold by a series of four steps described in Example 3: DEAE purification, Q Resin purification, Ultrafiltration concentration, and preparative SDS PAGE. The specific activity could not be measured in the crude lysate since there was a secondary esterase activity present (E101). The secondary activity could be completely removed from the target esterase during the first chromatographic step in which the secondary esterase passed through the DEAE column unbound. For purification of various technical grades of E100, DEAE purification alone is sufficient to yield E100 enzyme substantially purified away from any other contaminating activity. Q Resin purification and ultrafiltration allow for higher purity product to be produced as required by specific applications. A final SDS PAGE purification step allows the protein to be purified to homogeneity for determination of molecular characteristics. Protein Characterization—The active band is collected by electroelution on a preparative SDS-PAGE gel and rerun on 10% SDS-PAGE under denaturing conditions. This shows a single band with a relative molecular mass of about ~45 Kd (FIG. 5). Unboiled samples run on the same SDS-PAGE gels show multiple bands in approximate increments of the proposed monomeric molecular mass. Additionally, the non-boiled sample can be stained for activity, however only bands corresponding to multimeric forms of the enzyme are found to retain activity beginning with dimeric species. The specific activity of the purified protein is approximately $3.2\times10^{-6}$ $Mmin^{-1}$ $mg^{-1}$ using 4-methyl-umbelliferyl-butyrate (MUB) as the substrate.

Measurement of E100 Enzyme Activity—Esterase activity is measured by monitoring the hydrolysis of p-nitrophenylproprionate (pNP), or in some cases MUB. Each substrate is dissolved in acetonitrile and added to the reaction mixture (100 $\mu$M final concentration) which contain 50 mM Tris HCl pH 8.5 adjusted for temperature dependent pH variation. Reactions are thermally equilibrated at 37° C. for 5 minutes prior to initiation of the reaction by addition of 10 $\mu$L of enzyme sample, while control reactions substituted equivalent amounts of BSA. The reaction is monitored spectrophotometrically at 405 nm $\epsilon$=17 $mM^{-1}$ $cm^{-1}$ for pNP and 360 nm $\epsilon$=7.9 $mM^{-1}$ $cm^{-1}$ for MUB.

The rates of enzyme catalyzed hydrolysis are corrected for the spontaneous hydrolysis of the substrate. Protein concentrations are determined by either the absorbance at 280 nm or by Lowery assay. Crude activity is determined by a calorimetric assay based on the hydrolysis of 5-bromo-4-chloro-3-indoyl esters suspended in a 0.7% agar matrix on microtiter plates. A 0.1 mg/ml solution of the indolyl derivative is dissolved in a minimal volume of acetonitrile and added to a warm solution of 0.7% agar containing 0.1 M phosphate buffer pH 7.5. 10 $\mu$L of this solution is distributed to microtiter plates which, when cooled, could be used with as much as 100 $\mu$L of enzyme sample and incubated at temperatures from ambient to >65° C.

E100 was effectively inhibited when exposed to tosyl fluoride but was unaffected by the presence of either metal ions, chelating agents or reducing molecules Table 3.

TABLE 3

| Inhibition by reaction components on the hydrolysis of p-nitrophenylprorionate by E100. | |
|---|---|
| Additive (concentration) | Relative Rate[a] (%) |
| None | 100 |
| PMSF(0.1 mM) | 0 |
| BME(10 mM) | 99 |
| DTT(1 mM) | 101 |
| $CaCl_2$(10 mM) | 108 |
| $MgCl_2$(10 mM) | 95 |
| $ZnCl_2$(10 mM) | 90 |
| EDTA(1 mM) | 96 |

Reaction conditions are those described in the general experimental above except for the addition of specified components. Relative rates are corrected for the spontaneous rate of hydrolysis of the uncatalyzed reaction.

Substrate specificity of E100—The substrate specificity was tested as outlined as according to Example 1, and the results from the structure activity experiments for E100 are shown in summary Table 4. E100 displays a broad substrate specificity catalyzing the hydrolysis of a number of nitrophenyl, coumaryl and alkyl esters. The enzyme displays hydrolytic activity towards both straight chain and aromatic moieties on the carboxylate side of substrates however, carboxylate R groups of long alkyl chains >C8 or those containing naphthyl leaving groups are not substrates. The enzyme displays no significant activity towards either casein or milk as assayed by clearing zones on agar plates.

TABLE 4

| Substrate Activity of E100 | | |
|---|---|---|
| Substrate | E100 | Control |
| I-acetate[a] | ++ | − |
| I-butyrate[a] | ++ | −− |
| I-caprylate[a] | + | −− |
| N-acetate[a] | −− | −− |
| U-acetate[a] | ++ | +/− |
| U-stearate[a] | −− | −− |
| pN-acetate[a] | ++ | −− |
| pN-proprionate[a] | ++ | −− |
| oN-proprionate[a] | ++ | −− |
| oN-caprylate[a] | + | − |
| oN-palmitate[a] | +− | − |
| oN-stearate[a] | − | −− |
| Me-PA[b] | + | −− |
| Et-PA[b] | + | −− |
| isoProp-PA[b] | + | −− |

Structure activity assay of partially purified esterase E100 from Thermus species. (++) highest activity as determined by (a) color formation in less then 10 min or significant product formation on (b)TLC. The remaining activity measurements follow the order: +>+/−>−>−−. Structure abbreviations are as follows: I, chloro-bromo-indoyl, N, a-napthyl, U, methylumbelliferyl, pN, p-nitrophenyl, oN, o-nitrophenyl, PA, phenylacetate.

Determination of Kinetic Characteristics—Kinetic characteristics are determined by measuring the concentration dependent initial rates of enzyme catalyzed hydrolysis of nitrophenyl proprionate. Reactions are run at pH 8.5 in 50 mM Tris-HCl buffer equilibrated to 37° C. and initiated by addition of enzyme. Rates are determined from the absorbance changes due to formation of product nitrophenol at 405 nm. Rates are corrected for the spontaneous hydrolysis of substrate during the course of the reaction. Concentration vs. rate data are analyzed by both double reciprocal plots and by Hanes Wolff plots to determine Km, Vmax and Vmax/Km. The kinetic characteristics of E100 determined from plots of the initial rates of hydrolytic reactions are shown in FIG. 6.

Determination of Temperature Profile and Optimal pH for E100—The temperature profile of the enzyme is determined as shown in FIG. 7*a*. Enzyme activity is observed to steadily increase to the limit of the assay, over 70° C., (where the background signal from autohydrolysis of the substrate became too high and is no longer correctable) as the temperature of the reaction is elevated and suggests that the low end for optimal activity for E100 is greater than 70° C. E100 displays a basic pH profile with a low end optimal activity observed to be approximately 9.0, the limit of substrate stability at 37° C. (FIG. 7*b*).

Figure 8:
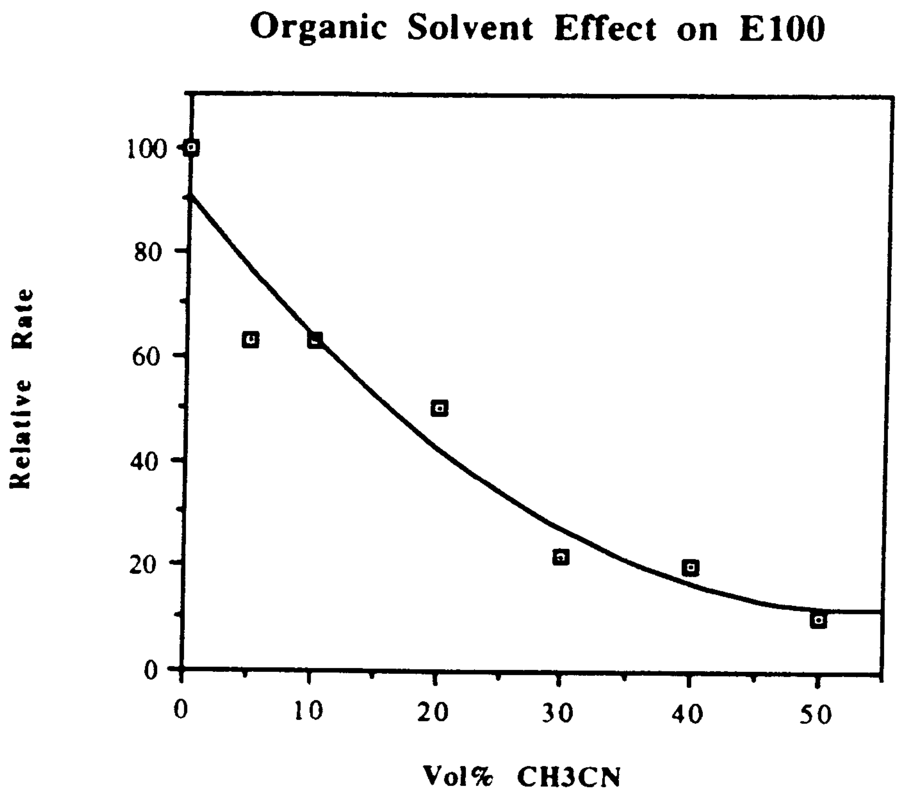
FIG. 8. The tolerance of E100 to the presence of organic cosolvents on the hydrolysis of p-nitrophenyl proprionate as determined by relative rates. Residual activity of the enzyme is determined in the presence of organic solvent by measuring the initial rate of enzyme catalyzed hydrolysis of pNP in the presence of various concentrations of $CH_3CN$. Reactions are run in 50 mM Tris-HCl pH 8.5 at 37° C. as described in determination of activity. Changes in absorbance are corrected for spontaneous hydrolysis of the substrate and the changes in extinction coefficient of the product in the presence of organic cosolvent.

Determination of Enzyme Stability in the Presence of Organic Solvents—E100 is tested for tolerance to organic solvent composition using the polar aprotic cosolvent acetonitrile as a preliminary system. the enzyme retained 50% of its activity in a solvent mixture of 20 vol % organic cosolvent (FIG. 8).

N-Terminal Sequencing of E100—Purified proteins are run on 10% SDS-PAGE gels and then transferred to PVDF membranes by electroblotting. Membranes are washed with several changes of doubly distilled water to remove any remaining SDS or other contaminants and then stained with coomassie blue. Membranes were then destained with several changes of 50:40:10 MeOH:$H_20$:AcOH followed by one wash of 10% MeOH. Membranes are then air dried and then submitted for sequencing. The N-terminal sequence of E100 was determined at the University of Illinois Urbana Champaign genetic engineering facility.

The N-terminus of E100 was determined by automated sequencing of the polypeptide purified by 10% SDS-PAGE and transferred to a PVDF support. The sequence obtained was: MKLLEWLK?EV, where the letters refer to the standard amino acid single letter code and the "?" refers to an indeterminate amino acid. Thus, E100 has been demonstrated to be a useful esterase with unique activity at commercially useful purity.

EXAMPLE 16

Characterization of E101

E101 is one of two esterase activities that are isolated from Thermus sp T351. E101 can be purified away from a second esterase, E100, in an early purification step. Purification of E101—A Thermus sp. T351 supernatant prepared as described in Examples 1 and 2 is fractionated with $NH_4SO_4$ and the precipitated proteins are collected between 20–60% saturation. Pellets are redissolved in 30 ml of buffer (50 mM Tris-HCl pH 8.0, 1 mM BME) and dialyzed against the same buffer using 30 Kd cutoff dialysis tubing. Dialysate is loaded to 100 ml bed volume of DEAE resin equilibrated with the buffer above and the column was washed with 150 ml of the equilibration buffer. Active protein is observed in the load and wash fractions, pooled, and concentrated with the use of an Amicon concentrator fitted with a YM30 membrane. Concentrated proteins are then loaded directly to a 25 ml bed volume of sepharose SP resin equilibrated with the above buffer. Active fractions appear in the load and wash fractions which are pooled and concentrated as above. Concentrate is then loaded to a Sephracryl HR200 gel filtration column (1×40 cm) and 0.5 ml fractions are collected at a flow rate of 2 ml/hr. Active fractions are collected and analyzed by SDS-PAGE. In order to perform N-terminal sequencing, fractions considered to be homogeneous are concentrated and submitted to a protein sequencing service center. The enzyme is stored at 4° C. for future use.

E101 can be purified over 35 fold by these methods and possesses characteristics dramatically different from E100, the other esterase which is isolated from this strain. Attempts to use ion exchange chromatography result in subtractive purification since in no instance was the protein retained. Resins investigated include DEAE, Q sepharose, CM cellulose, SP sepharose and hydroxyappatite under conditions that varied from pH 6.0 to 9.0, and buffers from phosphate to borate including Tris and Hepes. After two ion exchange steps the protein is purified to homogeneity by gel filtration chromatography however, the protein appears to have an interaction with the column as retention is considerably longer than the molecular weight would suggest. The molecular weight of the protein appears to be approximately 135 Kd with a monomer mass of ~35 Kd as determined from native and denaturing SDS-PAGE respectively (FIG. 9).

E101 Characteristics—The specific activity of the enzyme is ten fold greater than observed for E100 with 4-methyl-umbelliferyl butyrate (MUB) as the substrate. E101 is inhibited by PMSF but is insensitive to metal ions or metal ion chelators. The specific activity of the purified protein was found to be $3.2\times10^{-5}$ mol $min^{-1}$ $mg^{-1}$ and was determined from initial rates of hydrolysis using methyl umbelliferyl butyrate as a substrate. Table 5 outlines the inhibitory effect of various substances on E101 activity.

TABLE 5

The inhibitory effect of reaction components on the hydrolysis of p-nitrophenylprorionate by E101.

| Additive (concentration) | Relative Rate[a] |
|---|---|
| None | 100% |
| PMSF(0.1 mM) | 0 |
| BME(10 mM) | 96 |
| DTT(1 mM) | 98 |
| $CaCl_2$(10 mM) | 102 |
| $MgCl_2$(10 mM) | 97 |
| $ZnCl_2$(10 mM) | 100 |
| EDTA(1 mM) | 93 |

Reaction conditions are those described in the general experimental above except for the addition of specified components. Relative rates are corrected for the spontaneous rate of hydrolysis of the uncatalyzed reaction.

Substrate specificity of E101—The substrate specificity of E101 was determined as described in Example 11. The results from the structure activity experiments for E101 are shown in Table 6. The hydrolytic activity of the enzyme is similar to that observed for E100 and has no observable protease activity toward milk or casein.

TABLE 6

Substrate Activity of E101

| Substrate | E101 | Control |
|---|---|---|
| I-acetate[a] | ++ | – |
| I-butyrate[a] | ++ | –– |
| I-caprylate[a] | + | –– |
| N-acetate[a] | –– | –– |
| U-acetate[a] | ++ | +/– |
| U-stearate[a] | +/– | –– |
| pN-acetate[a] | + | –– |
| pN-proprionate[a] | + | –– |
| oN-proprionate[a] | ++ | –– |
| oN-caprylate[a] | +/– | – |
| oN-palmitate[a] | +/– | – |
| oN-stearate[a] | – | –– |
| Me-PA[b] | ++ | –– |
| Et-PA[b] | ++ | –– |
| isoProp-PA[b] | + | –– |

Structure activity assay of partially purified esterase E101 from Thermus species. (++) highest activity as determined by (a) color formation in less then 10 min or significant product formation on (b)TLC. The remaining activity measurements follow the order: +>+/–>–>––. Structure abbreviations are as follows: I, chloro-bromo-indoyl, N, a-napthyl, U, methylunmbelliferyl, pN, p-nitrophenyl, oN, o-nitrophenyl, PA, phenylacetate.

Thus, E101 has been demonstrated to be a useful esterase with unique activity at commercially useful purity.

EXAMPLE 17

Cloning of Esterase

General Cloning Strategy—The λ ZAP cloning system from Stratagene™ can be used for the library constructions and detection of esterase activity. Other cloning systems can also be used to yield similar results. The usual efficiency of cloning in λ vectors vary from $10^5$ to $10^7$ hybrid clones per mg of cloned DNA and is sufficient to produce a representative gene library from a convenient amount of size-selected chromosomal DNA fragments. We have found that detection of esterase activity in phage plaques, as opposed to bacterial colonies, is more efficient due to the easier access of substrate to the enzyme. Phages are generally less sensitive to the toxic action of cloned proteins and are also able to survive at the temperatures up to 70° C. The ability of the cloning system to tolerate elevated temperatures and potential toxicity of the cloned proteins is necessary for the detection of the activity of thermophilic proteins, such as the esterases described here.

Isolation of DNA for Construction of gene banks—Genomic DNA is prepared from a culture of the appropriate strain containing the esterase of interest as described in Example 1. Cells of different strains are grown to late log phase in 100 ml TT broth (8 g Polypeptone (BBL 11910), 4 g yeast extract, 2 g NaCl, per liter) at 55° C. or 65° C. overnight shaking at 250 RPM. Cells are recovered by centrifugation and the pellet is resuspended in 5 ml of lysis buffer (10 mM Tris-HCL, pH 7.0, 1 mM EDTA, and 10 mM NaCl). Lysozyme is added to a final concentration of 2 mg/ml. Cells are incubated at 37° C. for 15 minutes followed by the addition of SDS to 1%. The lysate is gently extracted three times with phenol/chloroform/iso-amyl alcohol (25/24/1) and the DNA spooled from a 95% ethanol overlay of the aqueous phase.

One of ordinary skill would find other methods for preparation of DNA which are well known in the art (37). For example, fresh colonies of a strain containing the esterase of interest are inoculated in 50 ml of TT media in 250 ml Erlenmeyer flask and incubated at 55° C. for 24 hours at 200 rpm in a New Brunswick Environmental Shaker. The cells are harvested by centrifugation at 3000 g for 15 min., resuspended in 5 ml of GTE buffer (50 mM Glucose, 25 mM Tris-HCl pH 8, 10 mM EDTA) and treated with 2 mg/ml of lysozyme at 37° C. for 10 min. Lysozyme-generated spheroplasts are lysed by the addition of 1% SDS and partially deproteinased by addition of 100 μg/ml of proteinase K at 24° C. for 10 min. Chromosomal DNA is further purified by three phenol/chloroform extractions, precipitated with 2.5 volumes of ethanol and resuspended in 1 ml of TE (10 mM Tris pH 8.0; 1 mM EDTA), after washing in 20 ml of 75% ethanol. The extracted fraction consists of DNA fragments larger than 50 kb, with a concentration of about 0.5 ng/μl, as detected by gel electrophoresis using a 0.7% agarose gel run at 10 V/cm for 4 hours.

Construction of Gene Libraries—Genomic DNA is partially digested with the restriction enzyme Sau3A and then ligated to predigested Lambda ZAP Express (Stratagene Cloning Systems). Products of ligation reactions are packed in vitro using λ packaging extracts which are purchased from Promega. This vector accommodates DNA up to 12 kb in length and allows identification of clones both by expression off the T3 and T7 promoters and by probe hybridization to plaques. The library is retained and screened for esterase activity. Other methods for generating genomic DNA libraries are also well known in the art.

Five samples of 10 μg of chromosomal DNA of each of the strains prepared as described above, are treated with different concentrations of Sau3A restriction endonuclease (New England BioLabs) according to the manufacturer's instructions for 30 min at 37° C. in a volume of 50 μl each. The concentration of Sau3A is varied from 0.1 u to 0.002 u/μg of the digested DNA in separate tubes. The reactions are stopped by heat inactivation of the endonuclease at 70° C. for 10 minutes and analyzed by gel electrophoresis on a 0.7% agarose gel run at 10 V/cm for 4 hours (a typical digestion pattern is obtained, data not shown). Fractions with an average fragment size of 5 kb are chosen for cloning. For native strains containing E001, E002, E003, E006, E007, E008, E009, E010, E012, E016, E020 these the second of the five samples of digested chromosomal DNA with the concentration of Sau3A of about 0.02 u/μg of the DNA. For the rest of the strains, the proper degree of partial digestion is achieved in the first test tube with 0.1 u of Sau3A /μg of the DNA. Fifty ng of chromosomal DNA fragments are ligated with equimolar amounts of dephosphorilatyed BarnHI-arrns of the lambda ZAP phage vector (Stratagene) in 5 μl with 1 unit of ligase (New England Biolabs). Ligation reactions are performed at 18° C. for 8 hours and stopped by heat inactivation at 70° C. for 10 min. One μl of the ligation reaction, containing approximately 10 ng of DNA insert, is used for in vitro packaging with 10 μl of lambda proheads (produced by Promega Corp). The packaging reaction is performed at 28° C. for 90 min, combined with 100 μl of an overnight culture of *E. coli* XL1 Blue and plated using 2 ml of 0.7% top agar (0.8% NaCl, 10 mM MgSO4) per plate onto five 90-mm Petri plates containing LB media. Serial dilutions of the packaging mixture are produced in order to determine the cloning efficiency which is generally about $1.0\times10^7$ hybrid phages/μg of cloned DNA. Cloning efficiencies for each individual strain varied, the size of the library generated fell within a range of 0.5 to $2.5\times10^5$ from which two to twelve positive clones were analyzed (data not shown). Hybrid phages from one plate are harvested to collect the amplified library, which is stored in 3 ml of LB media with 25% glycerol. The four other primary plates are treated with indicator agar containing 5-bromo-4-chloro-3-indolyl-acetate (X-Acetate) as described below, to find hybrid plaques carrying esterase genes.

Screening of gene banks for esterase activity—The products of the above packaging reactions are infected into *E. coli* XL1 blue MRF' (Stratagene). Primary plaques of an unamplified gene library are screened for enzyme activity by overlaying the plates with top agar containing X-Acetate for 30 minutes at 65° C. The concentration of substrate in the indicator overlay is diluted from a 4% stock in ethanol or N,N-dimethyl formamide to a concentration generally between 0.1 and 1% (usually about 0.4% is used) in the final solution. Other suitable substrates may be substituted in this procedure including, but not limited to, 5-bromo-4-chloro-3-indolyl-butyrate (X-butyrate), 5-bromo-4-chloro-3-indolyl-proprionate (X-proprionate), 5-bromo-4-chloro-3-indolyl-stearate (X-stearate), 4-methylumbelliferyl-acetate (MUA), 4-methylumbelliferyl-butyrate (MUB), 4-methylumbelliferyl-proprionate (MUP), or other 5-bromo-4-chloro-3-indolyl- or 4-methylumbelliferyl-esters which may be either synthesized or purchased from a commercial vendor such as Sigma Chemical. In order to inactivate background endogenous esterase activity from *E. coli*, the plates are preheated at 65° C. for 20 minutes. Hybrid phages surviving this procedure are picked and re-screened three times. The extracts are then analyzed for the presence of a protein band with the same mobility as the native protein as described below. The lambda ZAP cloning system permits an excision of smaller plasmid vector to simplify the insert characterization. While other methods may be employed for screening gene banks for esterase activity, i.e. isolation, purification, and N-terminal sequencing of protein; creation of degenerate nucleotide probes from N-terminal sequence; screening of gene bank with degenerate probes, the instant method is efficient and uniquely suited for the purpose of isolation of promising clones.

In particular, the four primary plates with phage colonies generated during the cloning described above, are incubated at 65° C. for 30 min. in order to inactivate some of the potential *E. coli* esterase activities. Approximately two ml of 0.7% top agar (0.8% NaCl, 10 mM $MgSO_4$) containing about 1 mg/ml of the colorimetric esterase substrate X-Acetate or other substrate (including but not limited to X-butyrate, X-proprionate, X-stearate, and 4-methylumbelliferyl based substrates) is overlaid onto each plate. Expression of cloned esterases can be detected by blue halos around phage colonies (or fluorescent halos in the case of the 4-methylumbelliferyl substates). As an example, the expression pattern observed for the gene library from strain isolate 28 (E009) is depicted in FIG. 11*a*. A typical result for this process can yield a ratio of 1: 3000 positive colonies to hybrid phages.

Between two and twelve primary positive phage plaques are generally picked up from each set of plates, resuspended in 50 μl of LB medium, and streaked onto a lawn of *E. coli* XL1 Blue using sterile paper strips. These purified phage plaques are then overlaid by indicator agar containing X-Acetate as before, and positive plaques were selected as in primary screening experiment. An example of this restreaking is shown in FIG. 11*b*. Three rounds of such purification are generally sufficient to produce a pure hybrid phage clone expressing esterase activity. All these clone candidates demonstrate significant esterase activity in the X-Acetate plate assay. Several clone candidates from each strain are chosen for further analysis, each representing the progeny of single primary phage plaque.

Testing Protein Profiles Produced by Phage Clones—Production and analysis of protein from the phage clones is perfonmed as follows, but alternative methods are possible: A single plaque from each clone is resuspended in 20 μl of an overnight culture of *E. coli* XL1 Blue (grown in LB medium with the presence of 10 mM of $MgSO_4$), incubated for 20 min at 24° C. in one well of a 96-well microtiter plate to allow adsorption, transferred into 15-ml test tube containing 2 ml of LB, and grown overnight at 37° C. in a New Brunswick Environmental Shaking incubator set at approximately 300 rpm. Cell debris can be removed by centrifugation at 12,000 g for 10 min. Phage lysates from the clones are then subjected to 4–15% gradient Native polyacrylamide gel electrophoresis (PAGE) for comparison to the native proteins purified from the original organisms. Precast gradient gels are purchased from BioRad Laboratories (catalog number 161-0902) and used according to the manufacturer's instructions for native gels to generate the gels shown in FIG. 12*a–m*. An esterase preparation from the original strain, purified by HPLC to a single protein band is used as a control on the same gel. Alternatively, a native protein preparation which has not been purified to homogeneity but is purified to a single esterase activity can be used as a control. Protein bands possessing an esterase activity can be detected by applying an X-Acetate overlay and incubating at room temperature for 5–20 min. The relative mobility of the clone candidates can be compared to the native esterase protein.

FIGS. 12*a–z* shows the results of the typical comparison of the esterase activities detected in lambda clones compared to the host strain. The data generated for 107 hybrid phage clone candidates from 20 strains are summarized in Table 7. For each gene library screened, there is at least one clone candidate expressing an esterase protein with the mobility of the protein purified from the original strain. Several of the λ clone candidates express esterase activities which have mobilities that are different from the major component of the esterase specimens purified from the original strains. Similar sized bands possessing esterase activity are observed in the native organism as minor components (data not shown). These cloned ester hydrolyzing activities are given names depicted in Table 7.

Excision of the Plasmid Vector from the Phage—The lambda ZAP vector allows the phage clone to be conveniently converted into a plasmid vector to allow better physical characterization of the DNA insert and regulated expression of cloned genes. Induction of M13-specific replication by co-infection with the helper phage results in excision of a multi-copy plasmid carrying the cloned insert. 10 μl phage stocks of the lambda hybrids (with about $10^7$ Colony Forming Units (CFU)) and 1 μl of Exassist M13 helper phage (about $10^{10}$ CFU) are used to infect 20 μl of an overnight culture of the *E. coli* XL1 Blue grown in LB. After 20 min at 24° C., the cell suspension is transferred from one of the wells of a 96-well microtiter plate into a 15-ml culture tube, diluted with 2 ml of LB, grown overnight at 37° C. and 300 rpm, heated at 65° C. for 10 min, and cleared by centrifugation at 3000 g for 20 min. Excised plasmids packed in M13 particles are transduced into a lambda resistant strain, XLOLR, that does not permit the development of the M13 helper phage. Ten μl of excised phage lysate are mixed with 30 μl of the overnight culture of the *E. coli* XLOLR strain in one well of 96-well microtiter plate, incubated for 20 min at 37° C. to allow adsorption, diluted with 100 μl of LB, and incubated at 37° C. for 40 min to express the kanamycin (Km) resistance marker (neo) of the plasmid. Cells are plated onto two LB plates supplemented with 40 mg/ml Km. One of the plates also contains 50 μl of a 4% X-Acetate stock solution.

Preliminary experiments are performed by growing plates at 37° C. to demonstrate that a significant phenotypic segregation occurs with the transductant *E. coli* colonies expressing cloned thernnophilic esterases. In an extreme case of the CE020 strain, very few colonies not expressing any esterase activity could be re-streaked from primary transductant colonies, which actively expressed esterase activity. Because of this segregation and apparent instability of plasmids containing the active clones, protocols for manipulation of most of the esterase clones needed to be modified as compared with the standard protocol of plasmid excision recommended by Stratagene. It was possible that the instability was due to the function of the cloned protein expressed in the cell, thus it was hypothesized that lowering the growth temperature might overcome the segregation problem, since the esterases were from thermophilic organisms and may not be as active at the lower temperatures.

Figure 13:
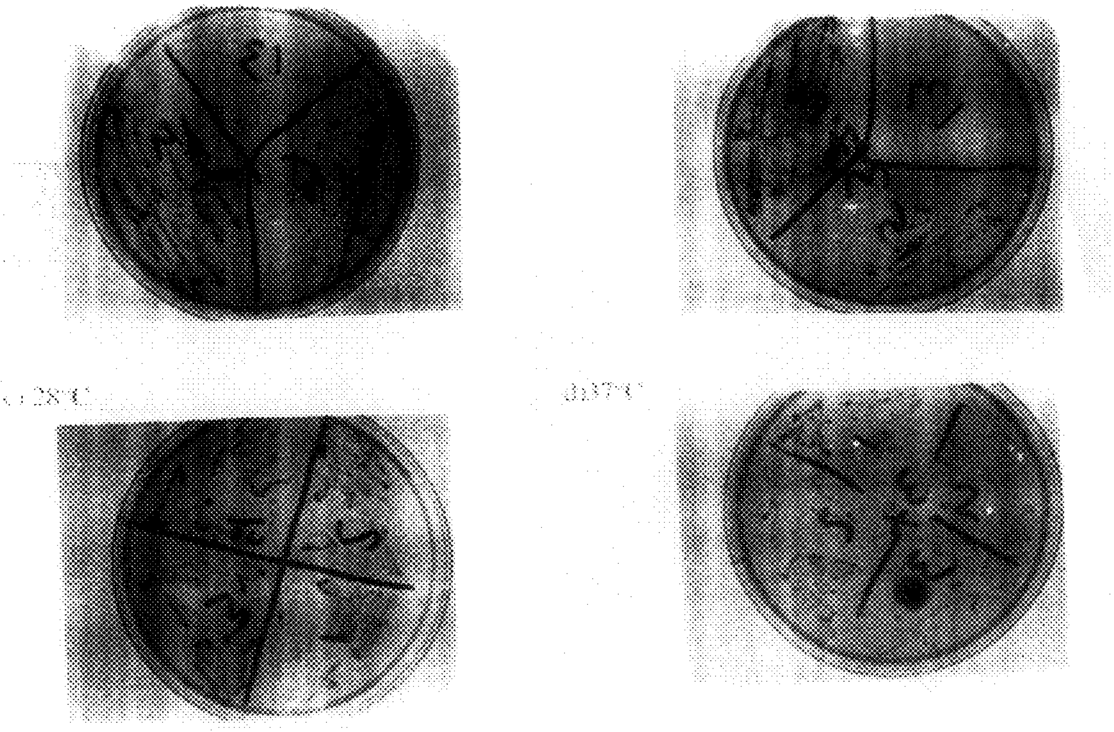
FIG. 13. The effect of temperature on stability of clones. The recombinant strains harboing plasmids with active esterase proteins often exhibited a phenotypic segregation of the esterase activity on X-acetate plates. This segregation could be due to plasmid or insert loss if the esterase activity had toxic properties to the cell. To overcome this cells could be grown at lower temperatures (presumably reducing the activity of the cloned thermophilic esterases). Shown in this figure, strains TGE15.2 (15) and TGE 15.9 (14) are plated with X-Acetate at 28° C. (a) and 37° C. (b). Yellow colonies of faster growing segregants are visible at both temperatures, but contra-selection at 37° C. is much stronger. The same phenomenon is shown in (c) and (d) for strains TGE2.1 (1); TGE2.2 (2) and TGE3.2 (3) grown at 28° C. and 37° C. respectively.
Figure 14:
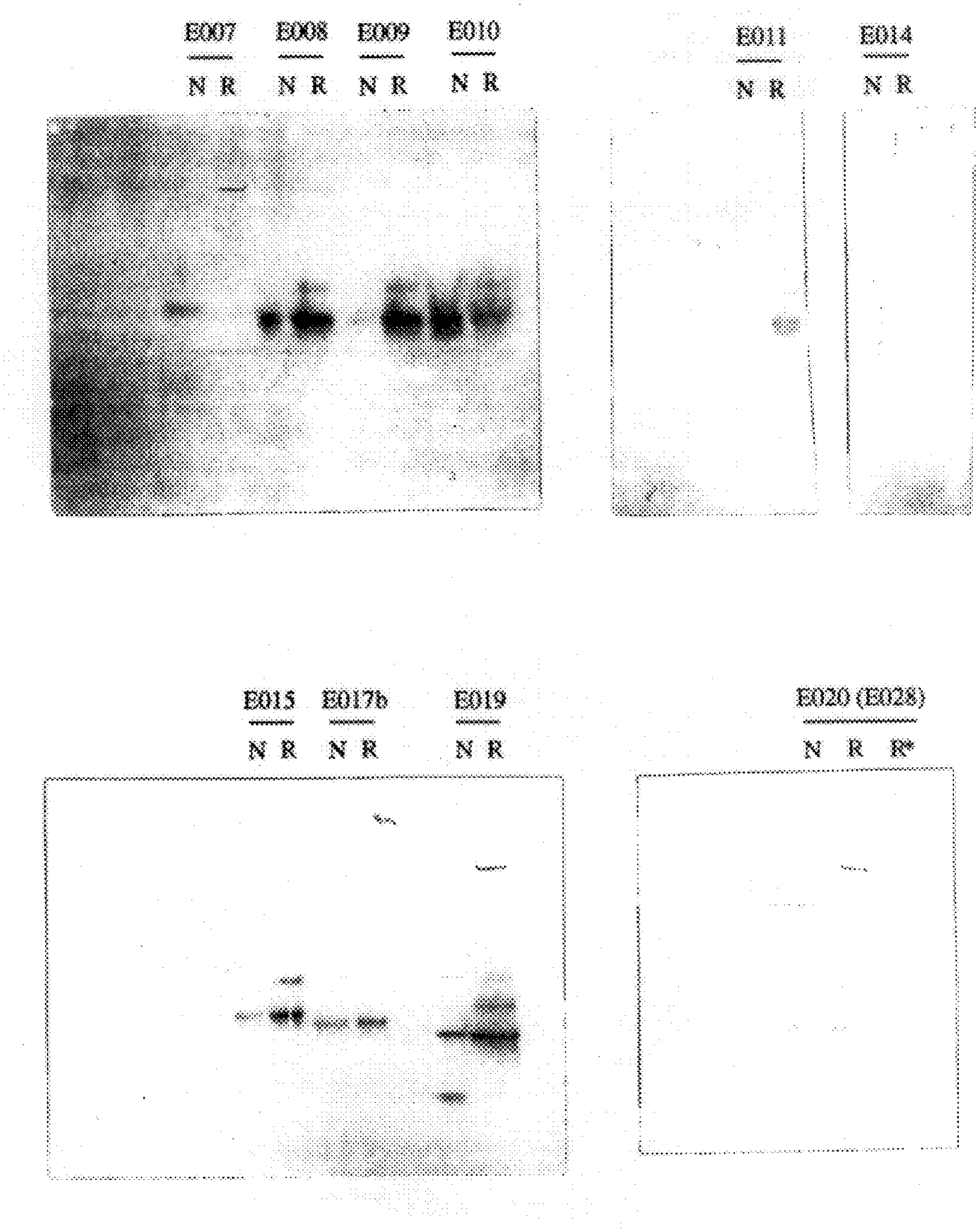
FIGS. 14. Examples of esterase stain of recombinant protein from plasmids. Protein extracts from both the native organism (single column purified) and a recombinant production strain are compared. Protein extracts are run on a 4–15% Gradient BioRad Ready Gel. After electrophoresis, the gels are equilibrated in pH 7.6 Trizma buffer and then stained for activity in either 0.4% X-acetate using an X-Acetate overlay. The gels are then incubated at room temperature for up to 30 minutes. In these examples: E007 from the native organism (E007 N) and a protein extract from strain CE007 with no visible activity on this stained gel; E008 from the native strain and recE008 from CE008; E009 fronti the native organism and recE009 from strain CE009; E010 from the native organism and recE010 from strain CE010; E011 from the native organism and recE011 from strain CE011; E014 from the native organism and recE014 from strain CE014; E015 from the native organism and recE015 from strain CE015; E017b from the native organism and recE017b from strain CE017b; E019 from the native organism and recE019 from strain CE019; E021 from the native organism, recE020 from strain CE009 (R) and recE028 from strain CE028—both isolated from the same gene bank. recE028 can be seen in the background of the native protein prep as a low level secondary activity; N=Native protein; R=Recombinant protein; R*=alternate recombinant protein with a different migration pattern (in this case E028, cloned from the same strain as E020).

Therefore, to overcome the problem of instability due to the activity of the esterase containing plasmids, cultivation of E. coli cells harboring thermophilic esterases is performed at 28° C. and 30° C., with the result that the effective phenotypic segregation is reduced. Thus, in the event that a cloned thermophilic esterase activity is lethal or partially lethal to the host cell, the growth temperature of the strain should be lowered to 30° C. or even room temperature. This is demonstrated in FIG. 13. After determining that temperature makes a large difference in stability of the clone phenotype, further experiments are carried out by plating all plasmid based clones at 26° C., generally for 48 hours. *E. coli* cells are plated in a medium containing X-Acetate to detect expression of cloned esterase by the plasmid, and a degree of segregation in or between primary colonies. Thus, growth of the transformed cells at a temperature which reduces the activity of the cloned esterase is important to the effective isolation of productive plasmids.

In the specific case, eight bacterial colonies derived from each of the phage clones are picked from the plates without X-Acetate, transferred into 100 ml of LB supplemented with 40 mg/ml Km in a 96-well plate and grown overnight. Progeny of these colonies are analyzed by a spot-test using X-Acetate containing agar. Several plasmid clones derived from each phage are chosen for further study by picking ones producing brightest blue halos and least amount of the esterase- segregants.

Selection for the Stable Plasmid Variants—Since it is determined that the plasmid-based vectors carrying esterase genes are often unstable, stable variants of the plasmids are isolated. One method for such isolation is as follows. *E. coli* cells carrying excised plasmids are purified using LB plates supplemented with Km and a limited amount of X-Acetate to reduce any potential negative growth impacts from production of the somewhat lethal indole product of the colorimetric reaction. Colonies are selected by their phenotype (in general giving a modest growth rate and intensive blue color) and grown in 2 ml of LB with Km in 15 ml test tube for 48 hours to reach $OD_{600}$ of about 1.0 and harvested by centrifugation at 12,000 g for 1 min. Cell pellets are resuspended in 500 ml of 0.1 M Phosphate buffer pH 7.0 and sonicated using a Sonics & Materials Vibra Cell 375 Watt sonicator at 4° C. Sonication is performed using a microtip, 40% max capacity, 50% time pulse for 45 sec. Lysates are centrifuged at 12,000 g for 5 min and tested for its relative esterase activity. Variants with the highest activity are selected for the next round of growth and analysis. Three rounds of plating followed by growth in liquid medium and activity assays are performed to verify the stability of the clones.

Deviations in specific esterase activity among variants from the same plasmid lineage can be reduced to a factor of three from over a factor of 100 by this procedure. Stabilization of the activity generally occurs at the level corresponding to the highest activity values detected in the first round of stabilization. This could indicate that *E. coli* host mutations are being selected which allow higher tolerance of the cloned protein, rather than simply suppressed activity of cloned toxic gene.

Physical Characterization of Plasmid Clones—Plasmid DNA is extracted from *E. coli* cells using a standard alkali lysis procedure, or other procedures known in the art (37). The DNA is digested with a series of restriction endonucleases such as EcoRI, BamHI, HindIII, PstI, EcoRV, and XbaI to establish digestion pattern of the clone and to determine a size of the cloned DNA fragment. The physical map patterns for the 24 selected production clones are depicted in FIG. 15. The insert sizes for each clone are calculated from this data and is summarized in Table 8.

TABLE 7

Cloned Esterase Candidates and Analysis

| # | Native Strain | Activity in phage lysate? | Recomb. Esterases Identified in Phage Lysate | Primary Clone Name | Derivative Plasmid Name | Active Plasmid Derivative | Specific Activity in Stabilized clone U/mg |
|---|---|---|---|---|---|---|---|
| 1 | S1 | + | E001 | lambdaTGE 1.1 | pTGE1.1 | + | 1536 |
| 2 | S1 | + | E001, E022 | lambdaTGE 1.2 | pTGE1.2 | + | |
| 3 | S1 | + | E001, E022 | lambdaTGE 1.3 | pTGE1.3 | + | |
| 4 | S1 | + | E001 | lambdaTGE 1.4 | pTGE1.4 | + | |
| 5 | S1 | + | E001 | lambdaTGE 1.5 | pTGE1.5 | + | 1489 |
| 6 | S1 | nt | nt | lambdaTGE 1.6 | pTGE1.6 | + | |
| 7 | S1 | nt | nt | lambdaTGE 1.7 | pTGE1.7 | + | |
| 8 | S1 | + | E022 | lambdaTGE 1.8 | pTGE1.8 | − | |
| 9 | 54 | + | E002 | lambdaTGE 2.1 | pTGE2.1 | + | 8300 |
| 10 | 54 | + | E023 | lambdaTGE 2.2 | pTGE2.2 | nt | 550 |
| 11 | 54 | + | E023 | lambdaTGE 2.3 | pTGE2.3 | + | |
| 12 | 54 | + | E002 | lambdaTGE 2.4 | pTGE2.4 | + | 2530 |
| 13 | 54 | + | E002 | lambdaTGE 2.8 | pTGE2.8 | − | |
| 14 | 50 | + | E003 | lambdaTGE 3.1 | pTGE3.1 | − | |
| 15 | 50 | + | E003 | lambdaTGE 3.2 | pTGE3.2 | + | 2610 |
| 16 | 50 | + | E003 | lambdaTGE 3.3 | pTGE3.3 | + | |
| 17 | 50 | + | E003 | lambdaTGE 3.4 | pTGE3.4 | + | |
| 18 | GP1 | + | E004 | lambdaTGE 4.1 | pTGE4.1 | − | |
| 19 | GP1 | + | E024 | lambdaTGE 4.2 | pTGE4.2 | + | |
| 20 | GP1 | + | E004 | lambdaTGE 4.3 | pTGE4.3 | + | 320 |
| 21 | GP1 | + | E004 | lambdaTGE 4.4 | pTGE4.4 | − | |
| 22 | GP1 | + | E004 | lambdaTGE 4.5 | pTGE4.5 | nt | |
| 23 | GP1 | + | E004 | lambdaTGE 4.6 | pTGE4.6 | + | 490 |
| 24 | C-1 | + | E005 | lambdaTGE 5.1 | pTGE5.1 | − | |
| 25 | C-1 | + | E025 | lambdaTGE 5.2 | pTGE5.2 | + | |
| 26 | C-1 | + | E005 | lambdaTGE 5.3 | pTGE5.3 | + | 984 |
| 27 | C-1 | − | | lambdaTGE 5.4 | pTGE5.4 | nt | |
| 28 | C-1 | + | E005 | lambdaTGE 5.5 | pTGE5.5 | nt | |
| 29 | 55 | + | E006 | lambdaTGE 6.1 | pTGE6.1 | − | |
| 30 | 55 | +/− | E026 | lambdaTGE 6.2 | pTGE6.2 | − | |
| 31 | 55 | + | E006 | lambdaTGE 6.3 | pTGE6.3 | + | 230 |
| 32 | 55 | + | E006 | lambdaTGE 6.4 | pTGE6.4 | − | |
| 33 | 55 | + | E006 | lambdaTGE 6.5 | pTGE6.5 | − | |
| 34 | 55 | + | E006 | lambdaTGE 6.6 | pTGE6.6 | − | |
| 35 | 46 | +− | *** | lambdaTGE 7.1 | pTGE7.1 | + | 210 |
| 36 | 46 | +− | *** | lambdaTGE 7.2 | pTGE7.2 | + | |
| 37 | 30 | + | E008 | lambdaTGE 8.1 | pTGE8.1 | − | |
| 38 | 30 | + | E008 | lambdaTGE 8.2 | pTGE8.2 | − | |
| 39 | 30 | + | E008 | lambdaTGE 8.3 | pTGE8.3 | + | |
| 40 | 30 | + | E008 | lambdaTGE 8.4 | pTGE8.4 | + | |
| 41 | 30 | + | E008 | lambdaTGE 8.5 | pTGE8.5 | + | 330 |
| 42 | 28 | − | | lambdaTGE 9.1 | pTGE9.1 | + | |
| 43 | 28 | − | | lambdaTGE 9.2 | pTGE9.2 | − | |
| 44 | 28 | + | E009 | lambdaTGE 9.3 | pTGE9.3 | + | 512 |
| 45 | 28 | + | E009 | lambdaTGE 9.4 | pTGE9.4 | + | >270 |
| 46 | 28 | + | E009 | lambdaTGE 9.5 | pTGE9.5 | − | |
| 47 | 28 | + | E009 | lambdaTGE 9.6 | pTGE9.6 | + | |
| 48 | 28 | + | E009 | lambdaTGE 9.7 | pTGE9.7 | + | |
| 49 | 29 | − | | lambdaTGE 10.1 | pTGE10.1 | − | |
| 50 | 29 | − | | lambdaTGE 10.2 | pTGE10.2 | − | |
| 51 | 29 | + | E010 | lambdaTGE 10.3 | pTGE10.3 | + | 546 |
| 52 | 29 | − | | lambdaTGE 10.4 | pTGE10.4 | + | >600 |
| 53 | 29 | + | E010 | lambdaTGE 10.5 | pTGE10.5 | + | |
| 54 | 29 | + | E010 | lambdaTGE 10.6 | pTGE10.6 | − | |
| 55 | 29 | − | | lambdaTGE 10.7 | pTGE10.7 | − | |
| 56 | 29 | + | E010 | lambdaTGE 10.8 | pTGE10.8 | + | |
| 57 | 31 | − | | lambdaTGE 11.1 | pTGE11.1 | + | |
| 58 | 31 | − | | lambdaTGE 11.2 | pTGE11.2 | − | |
| 59 | 31 | + | E011 | lambdaTGE 11.4 | pTGE11.4 | + | |
| 60 | 31 | + | E011 | lambdaTGE 11.9 | pTGE11.9 | + | |
| 61 | 31 | + | E011 | lambdaTGE 11.10 | pTGE11.10 | + | 1052 |

TABLE 7-continued

Cloned Esterase Candidates and Analysis

| # | Native Strain | Activity in phage lysate? | Recomb. Esterases Identified in Phage Lysate | Primary Clone Name | Derivative Plasmid Name | Active Plasmid Derivative | Specific Activity in Stabilized clone U/mg |
|---|---|---|---|---|---|---|---|
| 62 | 31 | − | | lambdaTGE 11.7 | pTGE11.7 | + | |
| 63 | 26b | + | | lambdaTGE 12.1 | pTGE12.1 | + | |
| 64 | 26b | + | | lambdaTGE 12.2 | pTGE12.2 | + | >600 |
| 65 | 26b | + | | lambdaTGE 12.3 | pTGE12.3 | + | |
| 66 | 26b | + | | lambdaTGE 12.4 | pTGE12.4 | + | |
| 67 | 26b | + | E029 | lambdaTGE 12.5 | pTGE12.5 | − | |
| 68 | 26b | + | E029 | lambdaTGE 12.6 | pTGE12.6 | − | |
| 69 | 27 | + | E013 | lambdaTGE 13.1 | pTGE13.1 | + | |
| 70 | 27 | + | E013 | lambdaTGE 13.2 | pTGE13.2 | + | 428 |
| 71 | 27 | + | E013 | lambdaTGE 13.3 | pTGE13.3 | + | 33 |
| 72 | 27 | + | E013 | lambdaTGE 13.4 | pTGE13.4 | + | |
| 73 | 34 | − | | lambdaTGE 14.2 | pTGE14.2 | − | |
| 74 | 34 | + | E014 | lambdaTGE 14.3 | pTGE14.3 | + | 460 |
| 75 | 34 | − | | lambdaTGE 14.4 | pTGE14.4 | − | |
| 76 | 34 | + | E014 | lambdaTGE 14.5 | pTGE14.5 | + | >1200 |
| 77 | 34 | + | E027 | lambdaTGE 14.6 | pTGE14.6 | + | >900 |
| 78 | 34 | − | | lambdaTGE 14.7 | pTGE14.7 | + | |
| 79 | 34 | + | E014 | lambdaTGE 14.8 | pTGE14.8 | − | |
| 80 | 34 | + | E014 | lambdaTGE 14.9 | pTGE14.9 | + | |
| 81 | 62 | + | E015 | lambdaTGE 15.1 | pTGE15.1 | + | |
| 82 | 62 | + | E015 | lambdaTGE 15.2 | pTGE15.2 | + | |
| 83 | 62 | + | E015 | lambdaTGE 15.3 | pTGE15.3 | + | |
| 84 | 62 | + | E015 | lambdaTGE 15.4 | pTGE15.4 | + | |
| 85 | 62 | + | E015 | lambdaTGE 15.5 | pTGE15.5 | + | |
| 86 | 62 | + | E015 | lambdaTGE 15.6 | pTGE15.6 | + | |
| 87 | 62 | + | E015 | lambdaTGE 15.7 | pTGE15.7 | + | |
| 89 | 62 | + | E015 | lambdaTGE 15.9 | pTGE15.9 | + | 4700 |
| 90 | 47 | + | E016 | lambdaTGE 16.1 | pTGE16.1 | + | 600 |
| 91 | 47 | + | | lambdaTGE 16.2 | pTGE16.2 | + | |
| 92 | 47 | + | E016 | lambdaTGE 16.3 | pTGE16.3 | + | >1200 |
| 93 | 47 | + | | lambdaTGE 16.4 | pTGE16.4 | + | |
| 94 | 47 | + | E016 | lambdaTGE 16.5 | pTGE16.5 | + | |
| 95 | 47 | + | | lambdaTGE 16.6 | pTGE16.6 | + | |
| 96 | 47 | + | | lambdaTGE 16.7 | pTGE16.7 | + | |
| 97 | C-3 | + | | lambdaTGE 18.1 | pTGE18.1 | + | nt |
| 98 | C-3 | + | | lambdaTGE 18.2 | pTGE18.2 | − | |
| 99 | 4 | + | E019 | lambdaTGE 19.1 | pTGE19.1 | + | >120 |
| 100 | 4 | + | E019 | lambdaTGE 19.2 | pTGE19.2 | + | |
| 101 | 4 | + | E019 | lambdaTGE 19.3 | pTGE19.3 | + | |
| 102 | 4 | + | E019 | lambdaTGE 19.4 | pTGE19.4 | + | 1960 |
| 103 | 4 | + | E019 | lambdaTGE 19.5 | pTGE19.5 | − | |
| 104 | 4 | + | E019 | lambdaTGE 19.6 | pTGE19.6 | + | |
| 105 | 7 | − | | lambdaTGE 20.1 | pTGE20.1 | + | |
| 105 | 7 | − | | lambdaTGE 20.2 | pTGE20.2 | + | |
| 106 | 7 | + | E020 | lambdaTGE 20.3 | pTGE20.3 | + | 2470 |
| 107 | 7 | + | E028 | lambdaTGE 20.4 | pTGE20.4 | + | |
| 108 | 7 | − | | lambdaTGE 20.5 | pTGE20.5 | + | |
| 109 | 7 | + | E020 | lambdaTGE 20.6 | pTGE20.6 | + | |
| 110-104 | 32 | − | | lambdaTGE 21.1–21.5 | pTGE21.1–21.5 | + | |
| 105 | 32 | + | E017b | lambdaTGE 21.6 | pTGE21.6 | + | |
| 106 | 32 | + | E017b | lambdaTGE 21.8 | pTGE21.8 | + | 930 |
| 107 | 32 | + | E017b | lambdaTGE 21.9 | pTGE21.9 | + | |

***No protein detected by activity stain.

TABLE 8

Production Clone Data

| Production Enzyme | Selected Production plasmid | Re-combinant Strain Name | Approx. DNA Insert Size[1] (kb) | Lane # on gels in FIG. 15 | Specific Activity in Typical Recombinant Crude Extract[2] (U/mg) |
|---|---|---|---|---|---|
| recE001 | pTGE1.1 | CE001 | 3.5 | 1 | 1,536 |
| recE001.5 | pTGE1.5 | CE001.5 | nt | nt | nt |

TABLE 8-continued

Production Clone Data

| Production Enzyme | Selected Production plasmid | Re-combinant Strain Name | Approx. DNA Insert Size[1] (kb) | Lane # on gels in FIG. 15 | Specific Activity in Typical Recombinant Crude Extract[2] (U/mg) |
|---|---|---|---|---|---|
| recE002 | pTGE2.1 | CE002 | 2.5 | 2 | 8,300 |
| recE003 | pTGE3.2 | CE003 | 4.1 | 4 | 2,610 |

TABLE 8-continued

Production Clone Data

| Production Enzyme | Selected Production plasmid | Re-combinant Strain Name | Approx. DNA Insert Size[1] (kb) | Lane # on gels in FIG. 15 | Specific Activity in Typical Recombinant Crude Extract[2] (U/mg) |
|---|---|---|---|---|---|
| recE004 | pTGE4.6 | CE004 | 3.4 | 5 | 490 |
| recE005 | pTGE5.3 | CE005 | 1.9 | 6 | 984 |
| recE006 | pTGE6.3 | CE006 | 6 | 7 | 230 |
| recE007 | pTGE7.1 | CE007 | 3.7 | 8 | 210 |
| recE008 | pTGE8.5 | CE008 | 3.2 | 9 | 330 |
| recE009 | pTGE9.4 | CE009 | 4.5 | 10 | 270 |
| recE010 | pTGE10.3 | CE010 | 2.5 | 11 | 546 |
| recE011 | pTGE11.10 | CE011 | 2.4 | 12 | 1,052 |
| recE029 | pTGE12.2 | CE029 | 4.2 | 13 | 600 |
| recE013 | pTGE13.2 | CE013 | 2.2 | 14 | 428 |
| recE014 | pTGE14.3 | CE014 | 2.5 | 15 | 460 |
| recE015 | pTGE15.9 | CE015 | 3.5 | 17 | 4,700 |
| recE016 | pTGE16.1 | CE016 | 2 | 18 | 600 |
| recE016.3 | pTGE16.3 | CE016.3 | 1.8 | 24 | 1,200 |
| recE017b | pTGE21.8 | CE017b | 3.8 | 21 | 930 |
| recE019 | pTGE19.4 | CE019 | 3.7 | 19 | 1,960 |
| recE020 | pTGE20.3 | CE020 | 2.7 | 23 | 2,470 |
| recE022 | pTGE1.8 | CE022 | nt | nt | nt |
| recE023 | pTGE2.2 | CE023 | 3.7 | 3 | 550 |
| recE024 | pTGE4.2 | CE024 | nt | nt | nt |
| recE025 | pTGE5.2 | CE025 | nt | nt | nt |
| recE027 | pTGE14.6 | CE027 | 2.6 | 16 | 900 |
| recE028 | pTGE20.4 | CE028 | 2.5 | 20 | nt |

[1]Insert sizes are estimated from the agarose gel. The estimated insert size is based on a vector size of 4.5 kb and the accuracy which could be achieved analyzing each of the six digestion patterns.
[2]Specific activity is calculated as the amount of p-nitrophenol produced in micromoles per minute per milligram of total protein as described in Example 2. The numbers reported here are from a typical production batch and may vary.

Generation of the tag sequences for PCR identification of esterase containing inserts The DNA sequences of the ends of the insert fragment carrying esterase genes can be determined by sequencing the ends of the inserts using standard T7 and S6 primers to produce unique tags of the cloned DNA. Sequence analysis can be carried out to design PCR primers which can uniquely amplify the DNA inserts from both the clones and the host organisms. These tags can be potentially used to generate this DNA fragment from the chromosome of the studied organisms using PCR technique.

Screening of the Cosmid library with an oligonucleotide probe—For cloning of enzymes which cannot be cloned by activity, other methods are used. A degenerative probe is prepared to the N-terminal sequence of the protein and hybridized to plaques from the recombinant phage bank. Alternatively, degenerate PCR amplification probes can be made using the N-terminal sequence or sequences obtained from the n-termini of internal protein fragments which have been obtained after proteolytic digestion of the enzyme. Using these sequences, a probe can be made from an amplified region between the N-terminus and an internal fragment or between two internal fragment sequences to identify a clone carrying the DNA encoding for the enzyme of interest.

EXAMPLE 18

Overproduction and Overexpression of Esterases

Production of recombinant esterase—The production strains used are listed in Table 8. Cloned enzymes are produced from *E. coli*. strain XLOLR. Alternatively, any suitable *E. coli* host may be used, including but not limited to HB101, C600, TG1 and XL1-Blue.

Several media can be used to produce cloned esterases. LB (10 gm/l tryptone, 5 gm/l yeast extract and 10 gm/l NaCl) and Terrific Broth (12 gm/l tryptone, 24 gm/l yeast extract and 4ml/l glycerol supplemented with 100 ml of a sterile solution of 0.17 M $KH_2PO_4$, 0.72 M $K_2HPO_4$ after autoclaving) have been tested and the results from optimal growth conditions for the production strains listed in Table 9 below. Each media is supplemented with 10–50 $\mu$g/ml kanamycin.

Optimal production media depends on a number of factors, including media cost and specific activity of the produced proteins. TB media is a richer media and therefore more expensive. For instance, in the case of CE009, while more total units are produced in a single fermentation run, not enough is produced to justify the higher cost of the media. In addition, the specific activity is higher for the LB media preparation.

Fermentation production is run in 17 L Fermentors (15 L working volume/LH Fermentation) at 30° C., 600 RPM, and 0.5 vvm air flow. The seed train is established as follows. A loopful of a frozen production culture is used to inoculate 50 ml of production media in a 250 ml Erlenmeyer flask. The flask is incubated at 30° C. for two days (250 RPM) and then used to inoculate a 1 liter flask with 250 ml of production media. This flask is incubated 1 day at 30° C. and 250 RPM. The 1 liter flask is used to inoculate the fermentor.

Production of substantially purified preparations from a cell paste of strains producing the recombinant enzymes are carried out similar to the methods described in Example 4 and the specific protocols described in Examples 14–34 for the native proteins.

TABLE 9

Preferred media for Strains CE001–CE010.

| | LB | | | TB | | | |
|---|---|---|---|---|---|---|---|
| Strain | Specific Activity (U/mg) | Total Cell mass (g) | Total Units | Specific Activity (U/mg) | Total Cell mass (g) | Total Units | Current Growth media of choice* |
| CE001 | 213 | 0.41 | 4500 | 138 | 0.84 | 6725 | TB |
| CE002 | 98 | 0.52 | 1625 | 101 | 0.93 | 4575 | TB |
| CE003 | 272 | 0.42 | 4200 | 22 | 0.87 | 1025 | LB |
| CE004 | 208 | 0.47 | 3650 | 28 | 0.90 | 1350 | LB |
| CE005 | 123 | 0.40 | 3675 | 125 | 1.00 | 7600 | TB |
| CE006 | 85 | 0.42 | 2125 | 71 | 0.62 | 2175 | LB |
| CE007 | 9 | 0.39 | 225 | 19 | 0.75 | 500 | TB |
| CE008 | 71 | 0.51 | 2775 | 45 | 0.80 | 2350 | LB |
| CE009 | 109 | 0.42 | 2650 | 74 | 0.81 | 3050 | LB |
| CE010 | 418 | 0.42 | 2200 | 225 | 0.95 | 8375 | TB |

*Given current media costs

Optimization of esterase production—Further optimization of esterase production is performed by media studies in shake flasks followed by further optimization at the 1 liter to 20 liter scale. Depending on the enzyme, final fermentation conditions can involve either a fed-batch or continuous fermentation process. Since the esterase activity being analyzed is intracellular, the use of a clear or defined media such as TT media is necessary. Organisms of interest are grown and cell pellets are collected by centrifugation. Pellets are disrupted by sonication and enzymes can be purified using the standard techniques of ion exchange and gel permeation chromatography described in Examples 3 and 4. Growth conditions including media composition, pH, and temperature are optimized at the small scale (ie. shake flasks, and 1 liter fermentors) to give the highest cell density while retaining the highest amount of enzyme.

Isolation of High-production mutants—Several simple mutagenesis schemes are used to try and isolate high-producing mutants of the different activities of interest. These include mutagenesis with uv-light or chemical mutagens such as ethylmethane sulfanoate (EMS) or N-methyl-N'-nitro-N-nitrosoguanidine (MNNG). The cells are treated with varying concentrations of the mutagen (or varying exposure times with uv light) according to methods described in Miller (38). Optimal concentrations of the different mutagens with different organisms vary. In general, killing concentrations allowing 80% survival for EMS, approximately 50% survival for MNNG, or 10–50% survival for uv light are desired. Mutagenized cultures are then grown up, allowing the mutagen to wash out and plated onto solid media.

Mutants are identified by applying an esterase plate screen to the cells. For example with an esterase screen, an agar overlay containing a colorimetric or fluorogenic substrate such as 5-bromo-4-chloro-3-indolyl-acetate or 4-methyulumbelliferyl acetate will be applied. Colonies which show a significant increase in activity by hydrolysis of the substrate will be identified.

Candidate mutants are then analyzed by native polyacrylamide gel electrophoresis and compared to the parental strain. Standard assay methods described in Example 2 or the rapid esterase/lipase screen described in Example 12 can then be applied to identify any differences in amounts of enzyme activity. If a production level increase is large an increased band on either a Native or SDS polyacrylamide gel after coomassie staining may be seen. Strains with multiple activities can also be differentiated in this way, verifying that the increase is in the enzyme of interest. It is then confirmed that the mutants have unaltered kinetic and substrate properties as the parental enzyme. The majority of mutations identified by this approach are expression mutations which can be isolated in either a promoter region, repressor molecule, or other controlling element. Most mutations in the enzyme structural genes will likely inactivate the enzyme, however, an enhanced activity may also be isolated. If it is apparent that the mutation increases the activity of the desired protein band but not the intensity of the band on a coomassie stained gel, the mutant is recharacterized to determine if it is a more efficient biocatalyst.

EXAMPLE 19

Esterase Screening Kit

A large subset of enzymes can be packaged into an easy to use screening kit to rapidly analyze a large number of enzymes at once. The kits are formulated to eliminate as many potential errors as possible and each enzyme is provided in a lyophilized form if possible near its optimal buffer and reaction conditions.

Many different formats for the kit are possible, from a series of glass vials, to varying size microtiter plates constructed of different plastic materials. The microtiter plate is favored because of its ease of handling and manipulating. Most microtiter plates are made of polystyrene however, which will not stand up to most organic solvents. For experiments which utilize aqueous solvent, the polystyrene is not a problem. Other more tolerant plastics such as polypropylene are available and are ideal for the kit. Large size 24-well microtiter plates which allow 3 ml of sample to be assayed (allowing enough sample for multiple TLC or HPLC analysis) have been developed. Other formats may also be useful for different applications.

Each kit is prepared by addition of a stir bar, buffer (0.1M Na phosphate pH 7.0) and 1 U of each enzyme to each well of a 24 well polypropylene tray (Tomtec). Enzymes are aliquotted into each well or vial in set amounts so that it can be assured that an equal amount of activity is provided for comparison. The entire kit is then lyophilized, sealed with heat seal foil (3M) and labeled. Separate experiments found that there was no significant loss in enzyme activity when proteins were lyophilized in the kit trays as suggested by earlier experiments comparing glass to plastic. In addition to enzymes, each kit contains four control wells that are composed of buffers at pH's from 6–9 since it was found that some of the substrates tested tend to be unstable in buffered solutions which can confuse positive results with autohydrolysis. The rest of the kit is composed of an instruction manual, a data sheet, a sample preparation vial a glass eye dropper and a plastic eye dropper. The kit is formulated in such a way that only solvent and substrate need be added to each well. The rapid-screen indicator dye method described in Example 12 can also be included in each well or vial. This makes a preliminary qualitative determination of enzyme effectiveness simple and fast.

EXAMPLE 20

Cloning and Characterization of Recombinant Proteins

Figure 12:
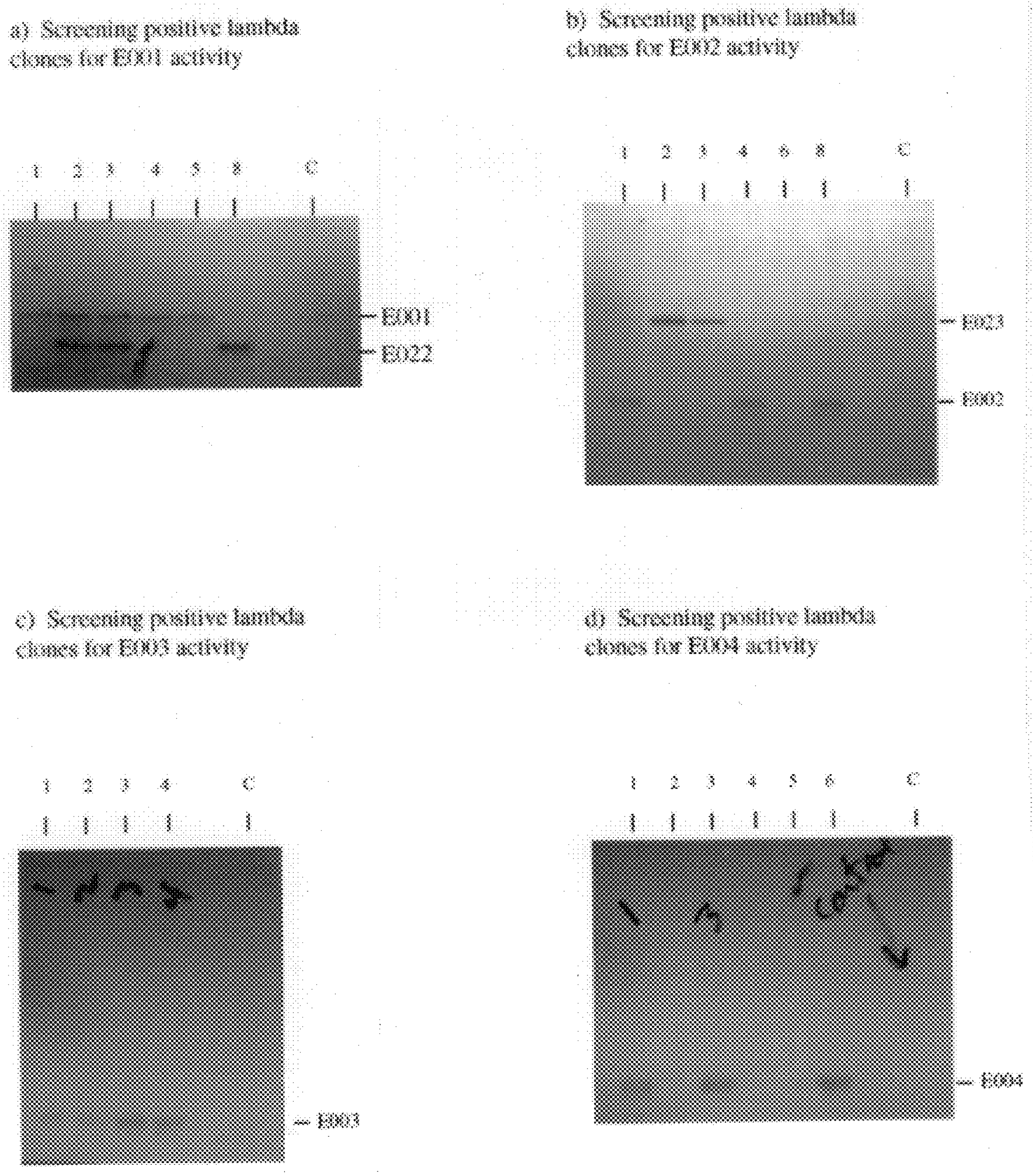
FIGS. 12*a–r*. Examples of screening technique using esterase activity stain of recombinant protein from phage lysates. Once esterase-positive candidiates are identified, phage lysates are screened for the correct ester hydrolysis activity on a native 4–15% gradient BioRad ReadyGel. After electrophoresis, the gels are equilibrated in pH 7.6 Trizrna buffer and then stained for activity by using a 0.15% X-acetate overlay. The gels are then incubated at room temperature for up to 30 minutes. The figures shows a typical examples of how the tequnique is used to identify proteins with the same mobility characteristics as the native protein. a) Screening positive clones from a bank made from strain isolate S1 to identify E001. Lanes indicate lambdaTGE1 isolates 1, 2, 3, 4, 5, 8 and native control protein (C); b) Screening positive clones from a bank made from strain isolate 54 to identify E002. Lanes indicate lambdaTGE2 isolates 1, 2, 3, 4, 6, 8 and native control protein (C); c) Screening positive clones from a bank made from strain isolate 50 to identify E003. Lanes indicate lambda TGE3 isolates 1, 2, 3, 4 and native control protein (C); d) Screening positive clones from a bank made from strain isolate GP1 to identify E004. Lanes indicate lambda TGE4 isolates 1, 2, 3, 4, 5, 6 and native control protein (C); e) Screening positive clones from a bank made from strain isolate C-1 to identify E005. Lanes indicate lambda TGE5 isolates 1, 2, 3, 4, 5, 6 and native control protein (C); f) Screening positive clones from a bank made from strain isolate 55 to identify E006. Lanes indicate lambda TGE6 isolates 1, 2, 3, 4, 5, 6 and native control protein (C); g) Screening positive clones from a bank made from strain isolate 30 to identify E008. Lanes indicate lambda TGE8 isolates 1, 2, 3, 4, 5, 6 and native control protein (C); h) Screening positive clones from a bank made from strain isolate 28 to identify E009. Lanes indicate lambda TGE9 isolates 1, 2, 3, 4, 5, 6, 7 and native control protein (C); i) Screening positive clones from a bank made from strain isolate 29 to identify E010. Lanes indicate lambda TGE10 isolates 1, 2, 3, 4, 5, 6, 7, 8, 9, 10, 11, 12 and native control protein (C); j) Screening positive clones from a bank made from strain isolate 31 to identify E011. Lanes indicate lambda TGE11 isolates 1, 2, 3, 4, 7, 8 and native control protein (C) on the first gel and lambda TGE11 isolates 7, 8, 9, 10 and native control protein (C) on the second gel; k) Screening positive clones from a bank made from strain isolate 26b to identify E012. Lanes indicate lambda TGE12 isolates 1, 2, 3, 4, 5, 6 and native control protein (C); l) Screening positive clones from a bank made from strain isolate 27 to identify E013. Lanes indicate lambda TGE13 isolates 1, 2, 3, 4, 7, 8 and native control protein (C); m) Screening positive clones from a bank made from strain isolate 34 to identify E014. Lanes indicate lambda TGE14 isolates 3, 5, 6, 8, 9 and native control protein (C); n) Screening positive clones from a bank made from strain isolate 62 to identify E015. Lanes indicate lambda TGE15 isolates 1, 2, 3, 4, 5, 6, 7, 8 and native control protein (C); o) Screening positive clones from a bank made from strain isolate 47 to identify E016. Lanes indicate lambda TGE16 isolates 1, 2, 3, 4, 5, 6, 7 and native control protein (C); p) Screening positive clones from a bank made from strain isolate 4 to identify E019. Lanes indicate lambda TGE19 isolates 1, 2, 3, 4, 5, 6 and native control protein (C); q) Screening positive clones from a bank made from strain isolate 7 to identify E020. Lanes indicate lambda TGE20 isolates 3, 4, 6, and native control protein (C); r) Screening positive clones from a bank made from strain isolate 32 to identify E021 (E017b). Lanes indicate lambda TGE21 isolates 6, 8, 9 and native control protein (C)

The cloning and characterization of recombinant proteins from strain isolates which produced the native isolated protein (as listed in Table 1) was carried out as described in Example 37. Lambda expression vectors were isolated as described above (specific named isolates are shown in Table 7). *E. coli* clones harboring the excised hybrid phage-plasmids were derived as summarized in Table 7, and were finally selected for esterase activity by subsequent screening, which after 3 rounds of stabilizing procedure was calculated to approximate units of activity per mg of total cell protein obtained. Esterase activity stain gel used to screen positive phage library candidates for the recombinant proteins are shown in FIG. 12, which allowed the identification of alternative recombinant proteins as well. Production of the recombinant protein is carried out as described in Example 38, using TB for the media and purifying the enzyme as described for the native (nonrecombinant) protein in Example 4.

EXAMPLE 21

Sequencing of Recombinant Proteins

The isolation and cloning of the genes encoding for the enzymes of the instant invention results in DNA segments in which an open reading frame (ORF) may be found which corresponds to translated protein amino acid sequence. Sequencing of the DNA inserts which contain the corresponding nucleic acid sequence which encode for the protein enzymes can be conducted by the usual methods, either manually or using automated apparatus.

Once obtained, analysis of the nucleic acid sequence can reveal the presence of alternative start codons, a phenomenon recognized in the art, however the encoded protein enzyme will comprise at minimum a core protein ORF. FIG. 16A is an isolated nucleic acid sequence, and translated amino acid sequence which correspond to E001 enzyme ORF, alternative start codons are underlined. FIG. 16B is the cloned isolated nucelic acid sequence which contains the E001 ORF. FIG. 16C is an isolated nucleic acid sequence, and translated amino acid sequence which correspond to E009 enzyme ORF, alternative start codons are underlined. FIG. 16D is the cloned isolated nucleic acid sequence which contains the E009 ORF. FIG. 16E is an isolated nucleic acid sequence, and translated amino acid sequence which correspond to E011 enzyme ORF, alternative start codons are underlined. FIG. 16F is the cloned isolated nucleic acid sequence which contains the E011 ORF. FIG. 16G is an isolated nucleic acid sequence, and translated amino acid sequence which corresponds to E101 enzyme ORF, alternative start codons are underlined. FIG. 16H is the cloned isolated nucleic acid sequence which contains the E101 ORF.

FIG. 17A is an isolated nucleic acid sequence, and translated amino acid sequence which corresponds to E019 enzyme ORF. FIG. 17B is the cloned isolated nucleic acid sequence which contains the E019 ORF. FIG. 17C is an isolated nucleic acid sequence, and translated amino acid sequence which corresponds to E005 enzyme. FIG. 17D is the cloned isolated nucleic acid sequence which contains the E005 ORF.

6. Sigurgisladottir, S., M. Konraosdottir, A. Jonsson, J. K. Kristjansson and E. Matthiasson. (1993) Lipase Activity of Thermophilic Bacteria from Icelandic Hot Springs. *Biotechnol Lett.* 15:361–366.
7. Margolin, A. L. (1993) Enzymes in the Synthesis of Chiral Drugs—Review. *Enzyme Microb Technol.* 15:266–280.
8. Hodgson, 1. (1992) Controlling chirality in enzymatic sysnthesis. *Biotechnology*. 10:1093–1097.
9. Klunder, A., F. Gastel and B. Zwanenburg. (1988) Structural requirements in the enzymatic optical resolution of bicyclic esters using pig liver esterase. *Tetrahedron Letters.* 29:2697–2700.
10. Rao, Y. K., C. K. Chen and J. Fried. (1993) Enantiospecific and Regiospecific Partial Hydrolysis of Racemic Diol Diacetates by Pig Liver Esterase. *J Org Chem.* 58:1882–1886.
11. Faulds, C. B. and G. Williamson. (1993) Ferulic Acid Esterase from Aspergillus niger—Purification and Partial Characterization of 2 Forms from a Commercial Source of Pectinase. *Biotechnol Appl Biochem.* 17:349–359.
12. Chattopadhyay, S. and V. R. Mamdapur. (1993) Enzymatic Esterification of 3-Hydroxybutyric Acid. *Biotechnol Left.* 15:245–250.
13. Frykman, H., N. Ohrner, T. Norin and K. Hult. (1993) S-Ethyl Thiooctanoate as Acyl Donor in Lipase Catalysed Resolution of Secondary Alcohols. *Tetrahedron Lett.* 34:1367–1370.

TABLE 10

ThermoCat ™ E001–E020 Spec comparison

| Biocatalyst | Specific Activity | MW | Temperature Opt. | Temperature Useful Range | pH Opt. | pH 50% Range | Half life (hours) 40° C. | Half life (hours) 60° C. |
|---|---|---|---|---|---|---|---|---|
| E001 | 0.5 u/mg | 22 kDal | 45° C. | RT-55° C. | 7.5 | broad | +++ | 34 |
| E002 | 1.0 u/mg | 28 kDal | 45° C. | RT-60° C. | 7.0 | broad | +++ | 30 |
| E003 | 0.5 u/mg | 28 kDal | 45° C. | RT-60° C. | 7.0 | broad | +++ | 60 |
| E004 | 0.6 u/mg | 36 kDal | 45° C. | RT-60° C. | 6.5 | <6.0–8.0 | +++ | 10 |
| E005 | 6.7 u/mg | 28 kDal | 45° C. | RT-60° C. | 7.0 | broad | +++ | 15 |
| E006 | 3.6 u/mg | 36 kDal | 45° C. | RT-60° C. | 6.5–7.0 | broad | +++ | 30 |
| E007 | 2.7 u/mg | 28 kDal | 35° C. | RT-60° C. | 7.0 | <6.0–8.0 | >480 | 90 |
| E008 | 1.5 u/mg | 28 kDal | 40° C. | RT-55° C. | 6.5–7.0 | <6.0–8.0 | 50 | <1 |
| E009 | 1.3 u/mg | 36 kDal | 45° C. | RT-50° C. | 6.5–7.0 | <6.0–8.0 | +++ | <1 |
| E010 | 4.9 u/mg | 46 kDal | 45° C. | RT-55° C. | 6.5 | <6.0–8.0 | +++ | <1 |
| E011 | 6.2 u/mg | 36 kDal | 45° C. | RT-60° C. | 6.5–7.0 | <6.0–8.0 | +++ | 4 |
| E012 | 10.7 u/mg | 28 kDal | 45° C. | RT-60° C. | <=6.0 | <6.0–7.5 | +++ | 240 |
| E013 | 5.3 u/mg | 36 kDal | 45° C. | RT-60° C. | 7.0 | <6.0–8.0 | >480 | 6 |
| E014 | 0.9 u/mg | 36 kDal | 45° C. | RT-50° C. | 7.0 | <6.0–8.0 | +++ | <1 |
| E015 | 3.0 u/mg | 36 kDal | 45° C. | RT-60° C. | >9.0 | 7.5 -> 9.0 | +++ | 6 |
| E016 | 1.2 u/mg | 28 kDal | 45° C. | RT-60° C. | nd | nd | +++ | 240 |
| E017b | 0.4 u/mg | 36 kDal | 40° C. | RT-50° C. | >9.0 | 7.5 -> 9.0 | +++ | 4 |
| E018 | 0.2 u/mg | nd | nd | nd | nd | nd | 120 | 30 |
| E019 | 0.9 u/mg | 30 kDal | 45° C. | RT-60° C. | >9.0 | broad | nd | 25 |
| E020 | 3.9 u/mg | 28 kDal | 45° C. | RT-60° C. | broad | broad | +++ | 12 |

*broad pH range refers to > 50% activity through all pH tested (6.0–8.5)

REFERENCES

1. Barman, T. E. *Enzyme Handbook*, Springer-Verlag, Berlin-Heidelberg. 1969.
2. Dixon, M., E. C. Webb, C. J. R. Thorne and K. F. Tipton. *Enzymes*, Academic Press, New York. 1979.
3. Santaniello, E., P. Ferraboschi, P. Grisenti and A. Manzocchi. (1992) The biocatalytic approach to the preparation of enantiomerically pure chiral building blocks. *Chem. Rev.* 92:1071–1140.
4. Klibanov, A. (1989) Enzymatic catalysis in anhydrous organic solvents. *TIBS*. 14:141–144.
5. Fitzpatrick, P. and A. Klibanov. (1991) How can the solvent affect enzyme enantioselectivity. *J Am Chem Soc.* 113:3166–3171.
14. Hedstrom, G., M. Backlund and J. Slotte. (1993) Enantioselective synthesis of ibuprofen esters in aot/isooctane microemulsions by *Candida cylindracea* lipase. *Biotech and Bioeng.* 42:618–624.
15. Pozo, M. and V. Gotor. (1993) Chiral carbamates through an enzymatic alkoxycarbonylauion reaction. *Tetrahedron.* 49:43214326.
16. Puertas, S., R. Brieva, F. Rebolledo and V. Gotor. (1993) Lipase Catalyzed Aminolysis of Ethyl Propiolate and Acrylic Esters—Synthesis of Chiral Acrylamides. *Tetrahedron.* 49:4007–4014.
17. Bonini, C., R. Racioppi, G. Righi and L. Viggiani. (1993) Polyhydroxylated Chiral Building Block by Enzymatic Desymmetrization of Meso 1,3 Syn Diols. *J Org Chem.* 58:802–803.

18. Chenevert, R. and R. Gagnon. (1993) Lipase-Catalyzed Enantioselective Esterification or Hydrolysis of 1-O-Alkyl-3-O-Tosylglycerol Derivatives—Practical Synthesis of (S)-(+)-1-O-Hexadecyl-2,3-di-O-Hexadecanoylglycerol, a Marine Natural Product. *J Org Chem*. 58:1054–1057.

19. Henly, R., C. J. J. Elie, H. P. Buser, G. Ramos and H. E. Moser. (1993) The Influence of Protecting Groups on Lipase Catalyzed Transesterifications—Enzymatic Resolution of Racemic cis-1,3-Cyclopentanediol Derivatives. *Tetrahedron Lett*. 34:2923–2926.

20. Paul, P., A. Chauopadhyay, S. Udupa and A. Banerji. (1993) Biotransformation with Rhizopus arrhizus: preparation of enantiomers of sulcatol. *Biotechnol Lett*. 15:367–372.

21. Ng, T. K. and W. F. Kenealy. Industrial Applications of Thermostable Enzymes. In *Thermophiles; General. Molecular, and Applied Microbiology*. Ed. by T. D. Brock, Wiley-Interscience, p. 197–215. 1986.

22. Wiegel, J. and L. G. Ljungdahl. (1986) The Importance of Thermophilic Bacteria in Biotechnology. *Crc Crit. Rev. of Biotech*. 3:39–108.

23. Saiki, R. K., D. H. Gelfand, S. Stoffel, S. J. Scharf, R. Higuchi, G. T. Horn, K. B. Mullis and H. A. Erlich. (1988) Primer-Directed Enzymatic Amplification of DNA with a Thermostable DNA Polymerase. *Science*. 239:487–491.

24. Stoflet, E. S., D. D. Koeberl, G. Sarkar and S. S. Sommer. (1988) Genomic Amplification with Transcript Sequencing. *Science*. 239:487–491.

25. Brumm, P., R. Hebeda and M. Teague. (1988) Purification and properties of a new, commercial, thernostable *Bacillis stearothermophilus* alpha-amylase. *Food Biotech*. 2:67–80.

26. Cowan, D. A. (1992) Enzymes from thermophilic archaebacteria: current and future applications in biotechnology. *Biochem Soc Symp*.

27. Mozhaev, V. V., K. G. Poltevsky, V. I. Slepnev, G. A. Badun and A. V. Levashov. (1991) Homogeneous solutions of hydrophilic enzymes in nonpolar organic solvents. New systems for fundamental studies and biocatalytic transformations. *Febs Lett*. 292:159–61.

28. Puchegger, S., B. Redl and G. Stoffler. (1990) Purification and properties of a thermostable fumarate hydratase from the archaeobacterium Sulfolobus solfataricus. *J Gen Microbiol*.

29. Hanner, M., B. Redl and G. Stoffler. (1990) Isolation and characterization of an intracellular aminopeptidase from the extreme thermophilic archaebacterium Sulfolobus solfataricus. *Biochim Biophys Acta*. 1033:148–53.

30. Smith, L. D., N. Budgen, S. J. Bungard, M. J. Danson and D. W. Hough. (1989) Purification and characterization of glucose dehydrogenase from the thermoacidophilic archaebacterium Thermoplasma acidophilum. *Biochem J*. 261:973–7.

31. Veronese, F. M., E. Boccu, O. Schiavon, C. Grandi and A. Fontana. (1984) General stability of thermophilic enzymes: studies on 6-phosphogluconate dehydrogenase from *Bacillus stearothermophilus* and yeast. *J Appl Biochem*. 6:39–47.

32. Tulin, E. E., Y. Amaki, T. Nagasawa and T. Yamane. (1993) A *Bacillus stearothermophilus* Esterase Produced by a Recombinant *Bacillus brevis* Stabilized by Sulfhydryl Compounds. *Biosci Biotechnol Biochem*. 57:856–857.

33. Sugihara, A., M. Ueshima, Y. Shimada, S. Tsunasawa and Y. Tominaga. (1992) Purification and characterization of a novel thermostable lipase from *Pseudomonas cepacia*. *J Biochem*. 112:598–603.

34. Sugihara, A., T. Tani and Y. Tominaga. (1991) Purification and characterization of a novel thermostable lipase from Bacillus sp. *J Biochem*. 109:211–216.

35. Emanuilova, E., M. Kambourova, M. Dekovska and R. Manolov. (1993) Thermoalkalophilic Lipase-Producing Bacillus Selected by Continuous Cultivation. *FEMS Microbiol Lett*. 108:247–250.

36. Weber, J. M., S. Johnson, V. Vonstein, M. C. Casadaban and D. C. Demirjian. (1995) A chromosomal integration system for stable gene transfer into *Thermus flavus*. *Bio/Technology*. 13:271–275.

37. Sambrook, J., E. F. Fritsch and T. Maniatis. *Molecular Cloning, A Laboratory Manual*, Cold Spring Harbor Laboratory Press, NY. 1989.

38. Miller, J. H. *A short course in bacterial genetics*, Cold Spring Harbor Laboratory Press, Cold Spring Harbor. 1992.

39. Wu, S. H., Z. W. Guo and C. J. Sih. (1990) Enhancing the enantioselectivity of Candida lipase catalyzed ester hydrolysis via noncovalent enzyme modification. *J. Am. Chem. Soc*. 112:1990.

40. Kazlauskas, R. J., A. N. E. Weissfloch, A. T. Rappaport and L. A. Cuccia. (1991) A rule to predict which enantiomer of a secondary alcohol reacts faster in reactions catalyzed by cholesterol esterase, lipase from *Pseudomonas cepacia*, and lipase from *Candida rugosa*. *J. Org. Chem*. 56:2656.

41. Sugai, Y., H. Kakeya and H. Ohta. (1990) Enzymatic preparations of enantiomerically enriched tertiary α-benzyloxyacid esters. Application to the synthesis of (s) (−) frontalin. *J. Org. Chem*. 55:4643.

42. Whitesell, J. K., H. H. Chen and R. M. Lawrence. (1985) Trans-2-phenylcyclohexanol. A powerful and readily available chiral auxillary. *J. Org. Chem*. 50:4663.

43. Lin, J., T., T. Yamazki and T. Kitazume. (1987) A microbially based approach for the preparation of chiral molecules possessing the trifluoromethyl group. *J. Org. Chem*. 52:3211.

44. Hagan, D. and N. A. Zaidi. (1992) *J. Chem. Soc. Perkin Trans*. 947.

45. Kitazume, T., T. Sato, T. Kobayashi and J. T. Lin. (1986) Microbial approach to the practical monofluorinated chiral synthons. *J. Org. Chem*. 51:1003.

46. Cohen, S. G., A. Milovanovic, R. M. Shultz and S. Y. Weinstein. (1969) On the active site of alpha-chymotrypsin. Absolute configurations and kinetics of hydrolysis of cyclized and noncyclized substrates. *J. Biol. Chem*. 244:2664.

47. Crout, D. H., V. S. B. Gaundet, K. Lauman and M. Schneider. (1986) Enzymatic hydrolysis of (+/−)-trans-1, 2-diacetoxycycloalkanes. A facile route to optically active cycloalkane-1,2-diols. *Chem. Comm*. 808.

48. Sabbioni, G. and J. B. Jones. (1987) Enzymes in organic synthesis. 39. Preparations of chiral cyclic acid esters and bicyclic lactones via stereoselective pig liver esterase catalyzed hydrolyses of cyclic mesodiesters. *J. Org. Chem*. 52:4565.

49. Kobayashi, S., K. Kamijama, T. limori and M. Ohno. (1984) Creation of novel chiral synthons with enzymes and applications to natural products synthesis. 15. Efficient introduction of chiral centers into cyclohexane rings. *Tetrahedron Lett*. 25:2557.

50. Ladner, W. E. and G. M. Whitesides. (1984) Lipase catalyzed hydrolysis as a route to esters of chiral epoxyalcohols. *J. Am. Chem. Soc*. 106:7250.

51. Mohr, P., N. Wacspe-Saracevic, C. Tamm, K. Gawronska and J. K. Gawronski. (1983) A study of stereoselective hydrolysis of symmetrical diesters with pig liver esterase. *Helv. Chim. Acta*. 66:2501.

We claim:

1. An isolated recombinant DNA having the nucleic acid sequence of SEQ ID NO.: 1 or nucleic acids 1182–2690 of SEQ ID NO.: 1.

2. An isolated recombinant DNA having the nucleic acid sequence of SEQ ID NO.: 5 or nucleic acids 197–1699 of SEQ ID NO.: 5.

3. An isolated recombinant DNA having the nucleic acid sequence of SEQ ID NO.: 7 or nucleic acids 245–1231 of SEQ ID NO.: 7.

4. An isolated recombinant DNA having the nucleic acid sequence of SEQ ID NO.: 9 or nucleic acids 1397–2905 of SEQ ID NO.: 9.

5. An isolated recombinant DNA having the nucleic acid sequence of SEQ ID NO.: 11 or nucleic acids 1087–2595 of SEQ ID NO.: 11.

6. An isolated recombinant DNA having the nucleic acid sequence of SEQ ID NO.: 3 or nucleic acids 2214–3816 of SEQ ID NO.: 3.

7. An isolated recombinant DNA which encodes for a protein having the amino acid sequence of SEQ ID NO.: 2.

8. An isolated recombinant DNA which encodes for a protein having the amino acid sequence of SEQ ID NO.: 4.

9. An isolated recombinant DNA which encodes for a protein having the amino acid sequence of SEQ ID NO.: 6.

10. An isolated recombinant DNA which encodes for a protein having the amino acid sequence of SEQ ID NO.: 8.

11. An isolated recombinant DNA which encodes for a protein having the amino acid sequence of SEQ ID NO.: 10.

12. An isolated recombinant DNA which encodes for a protein having the amino acid sequence of SEQ ID NO.: 12.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
(A) LENGTH: 4315 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1182..2690
(D) OTHER INFORMATION: /note= "E001, longest open reading frame; other possible start codons at ATG/met5; GTG/val8; GTG/val10; TTG/leu17"

(ix) FEATURE:
(A) NAME/KEY: mat_peptide
(B) LOCATION: 1182..2690

(xi) SEQUENCE DESCRIPTION: SEQ ID NO:1:

```
GATCAAGTGG CGATCGACCG CGCGTTGATT GAACTTGACG GCACGGAAAA CAAAGGAAAG     60

CTTGGGGCGA ATGCTATTTT AGGCGTGTCG CTCGCGGTCG CTCGCGCTGC GGCTGATGAG    120

CTTGGCTTGC CGTTGTACCA ATACTTGGGC GGCTTTAACG CTAAAACGCT GCCTGTACCG    180

ATGATGAACA TTTTAAACGG CGGCGCGCAT GCGGACAACA ACGTTGACAT TCAAGAATTC    240

ATGATCATGC CGGTCGGTGC GGAAAGCTTC CGTGAAGCGC TGCGCATGGG TGCAGAAATT    300

TTCCATAGCT TAAAAGCTGT GTTAAAAGCG AAAGGCTACA ACACGGCTGT CGGTGACGAA    360

GGCGGATTTG CTCCGAACTT AAAATCGAAC GAAGAAGCGC TGCAAACGAT CATTGAAGCG    420

ATCGAAAAAG CCGGCTACAA ACCAGGCGAA CAAGTGATGC TCGCTATGGA CGTTGCTTCG    480

TCGGAGCTGT ACAACAAAGA AGATGGCAAA TATCATTTGG AAGGCGAAGG CGTCGTCAAA    540

ACATCAGAAG AAATGGTTGC TTGGTATGAA GAGCTTGTGT CGAAATATCC GATCATCTCG    600

ATCGAAGACG GACTTGACGA AAATGACTGG GAAGGCCATA AACTGCTTAC TGAGCGCCTT    660

GGCCACAAAG TGCAGCTCGT CGGTGACGAC TTGTTTGTAA CGAACACGAA AAAACTGGCC    720

GAAGGCATTG AAAAAGGCGT CGGCAACTCG ATTTTAATTA AAGTGAACCA AATCGGTACA    780

CTGACGGAAA CGTTCGATGC CATTGAGATG GCCAAACGCG CCGGCTACAC GGCGGTTGTG    840

TCGCACCGTT CCGGTGAAAC GGAAGACAGC ACGATTGCCG ATATCGCTGT CGCAACAAAC    900

GCTGGCCAAA TCAAAACGGG AGCACCGTCG CGTACGGACC GCGTCGCAAA ATACAACCAG    960

CTGCTCCGCA TTGAAGACGA ACTTGGCCAC ACGGCTATTT ACCAAGGCAT TCGTTCGTTT   1020

TACAATTTGA AAAAATAACG GGAATCAACA ACAAAGGGTG TCTCCAACGT TGCGAGACAC   1080

CCTCTTTAAT TACGGGAAAC AGAAATGATT TCCTATCGAT AGCAAAAAAT GGACGTGGGT   1140

AAACCATTCG TTTATAATAT CTTTTTGTAA TCGTTAGAAT A TTG AAA AAG GGG       1193
                                              Leu Lys Lys Gly
                                                1

ATG GGA ACC GTG ATC GTG GAA ACA AAG TAC GGT CGG TTG CGC GGG GGA     1241
Met Gly Thr Val Ile Val Glu Thr Lys Tyr Gly Arg Leu Arg Gly Gly
  5                  10                  15                  20

ACA AAT GAA GGG GTT TTC TAT TGG AAA GGG ATT CCG TAC GCG AAA GCG     1289
Thr Asn Glu Gly Val Phe Tyr Trp Lys Gly Ile Pro Tyr Ala Lys Ala
                 25                  30                  35
```

-continued

```
CCG GTC GGT GAA CGC CGT TTT TTG CCG CCG GAA CCG CCC GAT GCA TGG     1337
Pro Val Gly Glu Arg Arg Phe Leu Pro Pro Glu Pro Pro Asp Ala Trp
             40                  45                  50

GAC GGA GTG CGT GAG GCG ACA TCG TTT GGA CCG GTC GTC ATG CAG CCG     1385
Asp Gly Val Arg Glu Ala Thr Ser Phe Gly Pro Val Val Met Gln Pro
         55                  60                  65

TCC GAT TCG ATG TTC AGC CAG CTG CTC GGA CGG ATG AAT GAA CCA ATG     1433
Ser Asp Ser Met Phe Ser Gln Leu Leu Gly Arg Met Asn Glu Pro Met
     70                  75                  80

AGC GAG GAT GGG TTG TAT CTG AAC ATT TGG TCA CCG GCG GCG GAT GGG     1481
Ser Glu Asp Gly Leu Tyr Leu Asn Ile Trp Ser Pro Ala Ala Asp Gly
 85                  90                  95                 100

AAG AAG CGC CCG GTA TTG TTT TGG ATT CAT GGC GGC GCT TTT TTA TTC     1529
Lys Lys Arg Pro Val Leu Phe Trp Ile His Gly Gly Ala Phe Leu Phe
                105                 110                 115

GGC TCC GGT TCA TTT CCA TGG TAT GAT GGA ACG GCG TTT GCC AAA CAC     1577
Gly Ser Gly Ser Phe Pro Trp Tyr Asp Gly Thr Ala Phe Ala Lys His
            120                 125                 130

GGC GAT GTC GTT GTC GTG ACG ATC AAC TAC CGG ATG AGC GTG TTT GGC     1625
Gly Asp Val Val Val Val Thr Ile Asn Tyr Arg Met Ser Val Phe Gly
        135                 140                 145

TTT TTG TAT TTG GGA GAT GCG TTT GGC GAA ACG TAT GCC CAG GCG GGA     1673
Phe Leu Tyr Leu Gly Asp Ala Phe Gly Glu Thr Tyr Ala Gln Ala Gly
    150                 155                 160

AAT CTT GGC ATA TTG GAT CAA GTG GCG GCG CTG CGC TGG GTG AAA GAG     1721
Asn Leu Gly Ile Leu Asp Gln Val Ala Ala Leu Arg Trp Val Lys Glu
165                 170                 175                 180

AAC ATT GAG GCG TTC GGC GGT GAT CCG GAC AAC ATT ACG ATT TTT GGC     1769
Asn Ile Glu Ala Phe Gly Gly Asp Pro Asp Asn Ile Thr Ile Phe Gly
                185                 190                 195

GAA TCA GCC GGA GCG GCA AGC GTT GGC GTG CTG TTG TCG CTT CCG GAA     1817
Glu Ser Ala Gly Ala Ala Ser Val Gly Val Leu Leu Ser Leu Pro Glu
            200                 205                 210

GCA AGC GGG CTG TTT CGA CGC GCT ATA TTG CAA AGC GGA TCG GGT TCG     1865
Ala Ser Gly Leu Phe Arg Arg Ala Ile Leu Gln Ser Gly Ser Gly Ser
        215                 220                 225

CTT CTT CTT CGT TCT CCG GAG ACG GCG ATG GCT CTG ACT GAA CGC ATT     1913
Leu Leu Leu Arg Ser Pro Glu Thr Ala Met Ala Leu Thr Glu Arg Ile
    230                 235                 240

TTA GAA CGT GCC GGC ATC CGT CCG GGT GAC CGC GAT CGG CTG CTG TCG     1961
Leu Glu Arg Ala Gly Ile Arg Pro Gly Asp Arg Asp Arg Leu Leu Ser
245                 250                 255                 260

ATT CCA GCA GCA GAG CTA TTG CAG GCG GCG ATG TCG CTC GGC CCA GGA     2009
Ile Pro Ala Ala Glu Leu Leu Gln Ala Ala Met Ser Leu Gly Pro Gly
                265                 270                 275

ATC ACG TAC GGT CCG GTG GTT GAC GGA CAT GTG TTG CGA CGC CAT CCG     2057
Ile Thr Tyr Gly Pro Val Val Asp Gly His Val Leu Arg Arg His Pro
            280                 285                 290

ATC GAA GCG CTC CAC GAC GGG GCA GCA AGT GAT ATT CCA ATC CTA ATT     2105
Ile Glu Ala Leu His Asp Gly Ala Ala Ser Asp Ile Pro Ile Leu Ile
        295                 300                 305

GGC GTG ACG AAA GAC GAA TAC AAT TTG TTT TCA TTG ACT GAT CCG TCA     2153
Gly Val Thr Lys Asp Glu Tyr Asn Leu Phe Ser Leu Thr Asp Pro Ser
    310                 315                 320

TTG ACA AGA CTC GAA GAA AAA GAA CTG CTT GAC CGG ATG AAC CGT GAG     2201
Leu Thr Arg Leu Glu Glu Lys Glu Leu Leu Asp Arg Met Asn Arg Glu
325                 330                 335                 340

GTC GGG CCT ATT CCG GAG GAG GCG GTA CGC TAT TAC GCG GAA ACA GCG     2249
Val Gly Pro Ile Pro Glu Glu Ala Val Arg Tyr Tyr Ala Glu Thr Ala
                345                 350                 355
```

-continued

```
GAT CGG TCG GCA CCC GCG TGG CAA ACA TGG CTG CGC ATC ATG ACG TAC     2297
Asp Arg Ser Ala Pro Ala Trp Gln Thr Trp Leu Arg Ile Met Thr Tyr
            360                 365                 370

CTT GTT TTT GTC GAC GGA ATG TTG CGA ACG GCG GAT GCC CAA GCA GCG     2345
Leu Val Phe Val Asp Gly Met Leu Arg Thr Ala Asp Ala Gln Ala Ala
        375                 380                 385

CAA GGG GCG AAT GTG TAC ATG TAT CGG TTT GAT TAT GAA ACG CCG GCG     2393
Gln Gly Ala Asn Val Tyr Met Tyr Arg Phe Asp Tyr Glu Thr Pro Ala
    390                 395                 400

TTC GGT GGA CAA CTG AAA GCG TGC CAT ACG CTC GAG TTG CCG TTT GTG     2441
Phe Gly Gly Gln Leu Lys Ala Cys His Thr Leu Glu Leu Pro Phe Val
405                 410                 415                 420

TTT CAT AAC CTC CAT CAG CCT GGT GTC GAG AAT TTC GTC GGC AAC CGA     2489
Phe His Asn Leu His Gln Pro Gly Val Glu Asn Phe Val Gly Asn Arg
                425                 430                 435

CCA GAG CGT GAG GCG ATT GCC AGC GAA ATG CAT GGT GCC TGG CTT TCG     2537
Pro Glu Arg Glu Ala Ile Ala Ser Glu Met His Gly Ala Trp Leu Ser
            440                 445                 450

TTC GCC CGC ACC GGC AAC CCG AAC GGC GCT CAT TTA CCA GAG AAG TGG     2585
Phe Ala Arg Thr Gly Asn Pro Asn Gly Ala His Leu Pro Glu Lys Trp
        455                 460                 465

CCC GTA TAC ACA AAA GAG CAC AAA CCG GTG TTT GTC TTT TCG GCT GCG     2633
Pro Val Tyr Thr Lys Glu His Lys Pro Val Phe Val Phe Ser Ala Ala
    470                 475                 480

AGC CAT GTG GAA GAC GAT CCG TTC GGT CGC GAG CGG GAA GCG TGG CAA     2681
Ser His Val Glu Asp Asp Pro Phe Gly Arg Glu Arg Glu Ala Trp Gln
485                 490                 495                 500

GGA CGC CTT TGACGAAAAA ATCCATAAGC AACATGTGTT CTTTGTCTGA             2730
Gly Arg Leu

ACACGATCAA GGTACGCGCA TTTTCGCGGA AAAAGACCGT GGGCAAACGT TCGCCTTTAC   2790

CTCTAAAAGG AATGACGCAA CATGTCTGCA CTTCACAGGA AAGAGGACGA AACGGTTGGT   2850

TTTCAGAATA GGAAAAGGTG TCCCGTTTTT TGGGACACCT TCTTCTATGT ATCGCTCAAT   2910

CATTTGCTTC TGTGGCAGGA AGCCCGAATC GCTCGGCGAG TGCCGGATCA CGATCGATCG   2970

CCTCAATCAG TTTCCGCATG ACGTTCACAT CAAACGTAAA ATTCGAACCG ATTGGCGAGG   3030

TGACGAAAAT TTTCCCTTCT TTCGCCTCGC GTGCTCGTTT AAATTGATAG CCGTCAATCG   3090

CAATGACGAC TCGTTCGTCT GGCCTTGCCA TTAGGAATCC CTCCATCGCT GTTTTTTCTT   3150

TCATTGTACT TGATTTTGAG GATGAACACC AACGTTCATG ACACGCTCTT AAGGATAACG   3210

GATGGGAGAG CGTTAGAGGG CGGTGAATTT CATCAAGAAC GTAGCACAAA ACGACATTTT   3270

TTCATTATAG ACGTCTTGAT GTTTGGAATG ATCGGAAAAG GCGATTGTTA GGCGGGGATC   3330

ATGATCCACT AGCGGATGAA AGTGAAGAGC AACGAAATAG TCTCTTTGTT TCACAACAAA   3390

TGAATTGGTG CCATTCAGGG CGGAGACAGG TGAGACAGTT GCTGCAAACG ATAATGTATG   3450

GTATAGTAAA AATATTGCAA CGTAGGTCGT TGGAGGTGTC AGGCATGCAT GCCTTGCTTG   3510

TGACGTTGCT TGTCATTGTA TCGATTGCGC TGATTGCGAT TGTGTTGTTG CAGTCAGGCC   3570

GAAGCGCAGG GCTGTCGGGG GCGATTACCG GCGGTGCCGA GCAGCTGTTT GGCAAACAGA   3630

AAGCGCGCGG GCTTGATGCA GTGTTTCAGC GCGTGACGGT CGTGTTGGCC ATTTTGTTTT   3690

TTGTGTTGAC GATTCTCGTC GCATATGTCC AACCATCATA AGCGAAAAGC GGGGGGCGGT   3750

CCTAACAAAA ACGGGCTGCC TTTTCTATTT CATCTAGAGA GGAAGGAGAA CGATGATGAA   3810

AATTGTTCCG CCAAAACCGT TTTTCTTTGA AGCCGGGGAG CGTGCCGTTT TGCTTTTGCA   3870

CGGATTTACC GGAAACTCCG CTGATGTTCG GATGCTCGGA CGCTTTCTCG AATCAAAAGG   3930
```

-continued

CTACACGTGC CATGCGCCGA TTTACAAAGG GCATGGCGTG CCGCCGGAAG AGCTCGTCCA 3990

TACCGGTCCG GACGATTGGT GGCAAGATGT GATGAACGGT TATCAGTTTT TGAAAAACAA 4050

AGGATATGAA AAAATCGCGG TTGCTGGGTT GTCGCTTGGA GGCGTATTTT CCTTAAAATT 4110

AGGTTACACT GTACCTATAG AAGGAATTGT GACCATGTGC GCACCGATGT ACATCAAAAG 4170

CGAAGAAACG ATGTATGAAG GTGTGCTTGA GTATGCGCGC GAATATAAAA AACGGGAAGG 4230

AAAATCGGCA GAACAAATCG AACAGGAAAT GGAACGGTTC AAACAAACGC CGATGAAAAC 4290

ATTAAAAGCG CTGCAAGCGT TGATC 4315

(2) INFORMATION FOR SEQ ID NO:2:

(i) SEQUENCE CHARACTERISTICS:
(A) LENGTH: 503 amino acids
(B) TYPE: amino acid
(D) TOPOLOGY: linear (ii) MOLECULE TYPE: protein (xi) SEQUENCE DESCRIPTION: SEQ ID NO:2:

Leu Lys Lys Gly Met Gly Thr Val Ile Val Glu Thr Lys Tyr Gly Arg
1 5 10 15

Leu Arg Gly Gly Thr Asn Glu Gly Val Phe Tyr Trp Lys Gly Ile Pro
20 25 30

Tyr Ala Lys Ala Pro Val Gly Glu Arg Arg Phe Leu Pro Pro Glu Pro
35 40 45

Pro Asp Ala Trp Asp Gly Val Arg Glu Ala Thr Ser Phe Gly Pro Val
50 55 60

Val Met Gln Pro Ser Asp Ser Met Phe Ser Gln Leu Leu Gly Arg Met
65 70 75 80

Asn Glu Pro Met Ser Glu Asp Gly Leu Tyr Leu Asn Ile Trp Ser Pro
85 90 95

Ala Ala Asp Gly Lys Lys Arg Pro Val Leu Phe Trp Ile His Gly Gly
100 105 110

Ala Phe Leu Phe Gly Ser Gly Ser Phe Pro Trp Tyr Asp Gly Thr Ala
115 120 125

Phe Ala Lys His Gly Asp Val Val Val Val Thr Ile Asn Tyr Arg Met
130 135 140

Ser Val Phe Gly Phe Leu Tyr Leu Gly Asp Ala Phe Gly Glu Thr Tyr
145 150 155 160

Ala Gln Ala Gly Asn Leu Gly Ile Leu Asp Gln Val Ala Ala Leu Arg
165 170 175

Trp Val Lys Glu Asn Ile Glu Ala Phe Gly Gly Asp Pro Asp Asn Ile
180 185 190

Thr Ile Phe Gly Glu Ser Ala Gly Ala Ala Ser Val Gly Val Leu Leu
195 200 205

Ser Leu Pro Glu Ala Ser Gly Leu Phe Arg Arg Ala Ile Leu Gln Ser
210 215 220

Gly Ser Gly Ser Leu Leu Leu Arg Ser Pro Glu Thr Ala Met Ala Leu
225 230 235 240

Thr Glu Arg Ile Leu Glu Arg Ala Gly Ile Arg Pro Gly Asp Arg Asp
245 250 255

Arg Leu Leu Ser Ile Pro Ala Ala Glu Leu Leu Gln Ala Ala Met Ser
260 265 270

Leu Gly Pro Gly Ile Thr Tyr Gly Pro Val Val Asp Gly His Val Leu
275 280 285

-continued

```
Arg Arg His Pro Ile Glu Ala Leu His Asp Gly Ala Ala Ser Asp Ile
    290                 295                 300

Pro Ile Leu Ile Gly Val Thr Lys Asp Glu Tyr Asn Leu Phe Ser Leu
305                 310                 315                 320

Thr Asp Pro Ser Leu Thr Arg Leu Glu Glu Lys Glu Leu Leu Asp Arg
                325                 330                 335

Met Asn Arg Glu Val Gly Pro Ile Pro Glu Glu Ala Val Arg Tyr Tyr
            340                 345                 350

Ala Glu Thr Ala Asp Arg Ser Ala Pro Ala Trp Gln Thr Trp Leu Arg
        355                 360                 365

Ile Met Thr Tyr Leu Val Phe Val Asp Gly Met Leu Arg Thr Ala Asp
    370                 375                 380

Ala Gln Ala Ala Gln Gly Ala Asn Val Tyr Met Tyr Arg Phe Asp Tyr
385                 390                 395                 400

Glu Thr Pro Ala Phe Gly Gly Gln Leu Lys Ala Cys His Thr Leu Glu
                405                 410                 415

Leu Pro Phe Val Phe His Asn Leu His Gln Pro Gly Val Glu Asn Phe
            420                 425                 430

Val Gly Asn Arg Pro Glu Arg Glu Ala Ile Ala Ser Glu Met His Gly
        435                 440                 445

Ala Trp Leu Ser Phe Ala Arg Thr Gly Asn Pro Asn Gly Ala His Leu
    450                 455                 460

Pro Glu Lys Trp Pro Val Tyr Thr Lys Glu His Lys Pro Val Phe Val
465                 470                 475                 480

Phe Ser Ala Ala Ser His Val Glu Asp Asp Pro Phe Gly Arg Glu Arg
                485                 490                 495

Glu Ala Trp Gln Gly Arg Leu
            500
```

(2) INFORMATION FOR SEQ ID NO:3:

(i) SEQUENCE CHARACTERISTICS:
(A) LENGTH: 6263 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 2314..3816
(D) OTHER INFORMATION: /note= "E009 sequence with longest open reading frame; possible other start codons are ATG/met4; TTG/leu7; GTG/val8; GTG/val15; GTG/val36"

(ix) FEATURE:
(A) NAME/KEY: mat_peptide
(B) LOCATION: 2314..3816

(xi) SEQUENCE DESCRIPTION: SEQ ID NO:3:

```
GATCCAAAAA CGAAAAAAGG CTTTTGTGGA TGAATTTGTC GTCCCTTTGG TGCAAGAAGC     60

CCACAAACTG GGGATTACGG AAAGTGAAGT GTTTGCGCTG ATCAAAAAAG AAAGGAAAGG    120

GATTGAGGAT GAATTATAAA GTGGAATTCG ACAATGTATC GTTGCGATAC AAAGACTTTG    180

AGGCGCTCAA AAATGTTTCC TTCCAACTGG AAAGCGGAAA GATTTACGGT TTGCTCGGCC    240

GGAACGGAGC CGGAAAGACC TCCCTCCTTT CTCTCTTGTC ATCTTTTCGC CTGCCGACGG    300

AAGGATCAAT CTTGATCAGC GGGGAACCGC CGTTTGAAAA CCCGAAGATC ATGCCTCATG    360

TTGTGTTGGT TTACGAAAAA GATTACAAGG AAGAGCGGAA TAAAGTCTCC ACCTTCATTC    420
```

-continued

```
AGGATGCAGC CAAGTTCCGC CCGTTCTTTG ACATGAATTA TGCACTTCGG CTGGCTGAGA    480

AATTCAAGCT TCCTTTAAAC AAAGAAGTGA GAAAACTGTC AAGAGGAATG AAGTCGGCGA    540

TGAATGTGAC CATCGGACTG GCCAGCCGGG CGCCCGTGAC CATTTTTGAC GAGGCTTATC    600

TTGGCATGGA TGCTCCGACC CGGGAAATGT TTTATAAAGA ATTGTTGAGA GACCAAGCCA    660

AACATCCCCG GACCATGATT TTATCCACCC ACTTGGTGTC TGAAATGGAT TATTTGTTTG    720

AAGAAGTGCT GATTCTCGAT CGCGGAAAGC TGTTGCTCCA TGAAGACTAT GAAACCTTGA    780

TTTCCAAGGG ACTCATCATC ACAGGAGATG CCGGGGCGGT TGATGATTTC ACCAAAGGTC    840

GGAAGATCCT GAACGAAGAG CAGCTCGGAA ATACAAAATC GGTAATTGTG TTCGGGGATT    900

TCAATGAAGA TCTCCGGTTG GAAGCCGAAG AACAAGGATT GGAAACCGGG ACCTGCTCTT    960

TGCAAGATCT GTTTATTCAT TTAACAGGCA AGGAGGATGC ATATGAAACC AACAGCCGTA   1020

TTTCCTAAAG TGGCCAAAGA CATGTACTTG GAACAAATGA AATGGACGGT TTGGTTTCTG   1080

GTTTTTGTGT TGGTTACCCA AATCGTACAT CTTTATTCCA GTTATTTTAC AATCGATGAT   1140

AACACCGCGG TGAAAGGGAT TTTGGTGCAT CTTTTTCCAT CGGCAAAGGT TTATATGATC   1200

GTGATCGCAA TTATTTCCGT CAACGGATTC CTGTCTTATT ATGTCGGGCA GGGAGTCACC   1260

CGGAGAGATT TTTGGGCCGG CTCGATGCTT GCCGCGCTCG GGCTGACGGC CACGATCACT   1320

TTCTCCGCTG TGATTCTCAC TTATTTGGAA TACGGGATTT TGGAGATGTT CCAGCTATCT   1380

CATTTGCTGT CTGACGAATT TTTGAACGGA AACGGGTGGC TGGTGATTCA ATATCTGCTT   1440

AATATCTTTT TCTATTACTT GGCAGGTTAC CTGATCGGAG TCGGTTTTTA CCGGTTCCAC   1500

TGGATCGTCG GAATCGGATT TGTTGCCTTT TTCCTTCTTT CTGTTTCAGC GCTGGAATGG   1560

AGCGAAAAAT ATTCGCTCGG GCTGAATATA TTGAGTTCTG CGGCGGCCAT TGTCCTCTTT   1620

CTCACCTTAT TGCGCCAGTT AACAAAGAAT ATCGCCGTGA AGTTGTAAAT GGATCCGGGA   1680

GACTCAGGTC CGCATGTTGC CTGAGTCTCT TTGCCTTTTC ATGGCGTCTG GGATTCATCC   1740

CTTTTTTGCT TTGCCAAGCG TTTTTTTTGA ATCCAGACCA GCAATTTAAG GATCAGGAAC   1800

AACAGAAAGA TGGCTCCTGA TACAAGAATA ATGGCTCCTG ATATGATGGA CACAACCTTC   1860

CAAAAACCAA AAAGTTCGC  GGCCCGCAAA ATGATGAGCA GGATGGCAAA AGGAATGAGA   1920

AAGCCGATGA CATCCTTCCC TTTCACTAAC CCCTCTTCCT CCTTTTTTGT TGGAATATCG   1980

TTCAGGTTAA CGGGCTTGTC CCTCAGTGTC AATAAGGTGT AAGTGACAAC ATCCCAAACA   2040

AAATTCAGTG CGAAAAAACA AAGCGGGACG GATTGGCCGG AGGTTGATCA AAAGGGCACC   2100

CCCTCTAATT CACGCTGGAT CTTTCCTTTG TGTTTTAAAA CTTAAAGCAC CGGATTGCCG   2160

GCTGTATGGT CCGGTTGGAT ATTGTCATCA CATCGTGGAT ATCAGTGGAT CCGGTGCGAT   2220

GGATTGCTTC AGGGGAACTT TTAAACACTT GAGTTTGACA ACCACTCCTT AATCATTTAA   2280

GATTTAAATG AAAATTAAAA TAAATCAAAA AGA TTG ATT CAA ATG AAT ACG TTG   2334
                                     Leu Ile Gln Met Asn Thr Leu
                                       1               5

GTG GAA ACC CGT TTT GGG AAA GTG CAA GGC GGT ACA GAC GGA GAG GTT      2382
Val Glu Thr Arg Phe Gly Lys Val Gln Gly Gly Thr Asp Gly Glu Val
         10                  15                  20

TGT TTT TGG AAA GGG ATT CCT TAT GCG AAA CCT CCG GTG GGA AAA CGC      2430
Cys Phe Trp Lys Gly Ile Pro Tyr Ala Lys Pro Pro Val Gly Lys Arg
     25                  30                  35

CGC TTT CAA AAA CCG GAA CCG CCG GAG AAA TGG GAT GGC GTT TGG GAG      2478
Arg Phe Gln Lys Pro Glu Pro Pro Glu Lys Trp Asp Gly Val Trp Glu
 40                  45                  50                  55

GCC ACC CGG TTC CGG TCC ATG GTG ATG CAG CCG TCC GGC ACC ACC TTC      2526
Ala Thr Arg Phe Arg Ser Met Val Met Gln Pro Ser Gly Thr Thr Phe
```

-continued

```
                 60                  65                  70

AGC ACC GTG CTC GGG GAA GCG GAT CTT CCT GTG AGC GAA GAC GGT CTT      2574
Ser Thr Val Leu Gly Glu Ala Asp Leu Pro Val Ser Glu Asp Gly Leu
             75                  80                  85

TAT CTG AAT ATC TGG TCG CCG GCA GCC GAC GGA AAA AAG CGG CCG GTG      2622
Tyr Leu Asn Ile Trp Ser Pro Ala Ala Asp Gly Lys Lys Arg Pro Val
         90                  95                 100

CTC TTC TGG ATC CAT GGC GGC GCC TAC CAG TTT GGG TCC GGC GCT TCC      2670
Leu Phe Trp Ile His Gly Gly Ala Tyr Gln Phe Gly Ser Gly Ala Ser
    105                 110                 115

CCC TGG TAT GAC GGG ACG GAG TTT GCC AAA AAC GGA GAT GTG GTG GTT      2718
Pro Trp Tyr Asp Gly Thr Glu Phe Ala Lys Asn Gly Asp Val Val Val
120                 125                 130                 135

GTC ACG ATC AAC TAC CGG TTG AAC GCG TTT GGA TTT TTG TAC TTG GCA      2766
Val Thr Ile Asn Tyr Arg Leu Asn Ala Phe Gly Phe Leu Tyr Leu Ala
                140                 145                 150

GAT TGG TTC GGC GAC GAA TTT TCA GCG TCG GGC AAC CTG GGA ATT TTG      2814
Asp Trp Phe Gly Asp Glu Phe Ser Ala Ser Gly Asn Leu Gly Ile Leu
            155                 160                 165

GAC CAA GTC GCT GCA CTG CGC TGG GTG AAA GAA AAC ATT TCG GCA TTC      2862
Asp Gln Val Ala Ala Leu Arg Trp Val Lys Glu Asn Ile Ser Ala Phe
        170                 175                 180

GGC GGC GAC CCG GAG CAA ATC ACC ATC TTC GGG GAG TCG GCC GGA GCC      2910
Gly Gly Asp Pro Glu Gln Ile Thr Ile Phe Gly Glu Ser Ala Gly Ala
    185                 190                 195

GGA AGC GTC GGG GTT CTG CTT TCC CTC CCG GAA ACC AAA GGG CTG TTT      2958
Gly Ser Val Gly Val Leu Leu Ser Leu Pro Glu Thr Lys Gly Leu Phe
200                 205                 210                 215

CAA CGG GCG ATC TTG CAA AGC GGA TCG GGT GCC ATT TTG CTC CGT TCC      3006
Gln Arg Ala Ile Leu Gln Ser Gly Ser Gly Ala Ile Leu Leu Arg Ser
                220                 225                 230

TCT CAG ACA GCC TCG GGC ATC GCG GAA CAA ATT CTT ACG AAA GCC GGC      3054
Ser Gln Thr Ala Ser Gly Ile Ala Glu Gln Ile Leu Thr Lys Ala Gly
            235                 240                 245

ATT CGA AAA GGA GAC CGC GAC CGG TTG TTA TCC ATC CCG GCC GGT GAA      3102
Ile Arg Lys Gly Asp Arg Asp Arg Leu Leu Ser Ile Pro Ala Gly Glu
        250                 255                 260

CTC CTT GAA GCC GCA CAA TCC GTG AAT CCG GGA ATG GTT TTT GGT CCC      3150
Leu Leu Glu Ala Ala Gln Ser Val Asn Pro Gly Met Val Phe Gly Pro
    265                 270                 275

GTT GTG GAC GGC ACC GTA TTG AAA ACC CAT CCG ATT GAA GCG TTG GAA      3198
Val Val Asp Gly Thr Val Leu Lys Thr His Pro Ile Glu Ala Leu Glu
280                 285                 290                 295

ACC GGA GCC GCC GGC GAT ATC CCG ATC ATC ATC GGG GTG ACA AAG GAT      3246
Thr Gly Ala Ala Gly Asp Ile Pro Ile Ile Ile Gly Val Thr Lys Asp
                300                 305                 310

GAG TAC AAT TTA TTT ACA CTG ACT GAC CCT TCC TGG ACG ACA GCG GGA      3294
Glu Tyr Asn Leu Phe Thr Leu Thr Asp Pro Ser Trp Thr Thr Ala Gly
            315                 320                 325

AAA GAA GAA CTG ATG GAC CGG ATC GAA CAG GAA ATC GGG CCG GTT CCG      3342
Lys Glu Glu Leu Met Asp Arg Ile Glu Gln Glu Ile Gly Pro Val Pro
        330                 335                 340

GAA AAA GTT TTT CCA TAT TAC TTA TCT TTT GGG GAT CCA TCG CAA CCG      3390
Glu Lys Val Phe Pro Tyr Tyr Leu Ser Phe Gly Asp Pro Ser Gln Pro
    345                 350                 355

GTA TGG CAA AAG CTG TTG CGC GCC ATG ACC TAC CAC ATC TTT ACC CGG      3438
Val Trp Gln Lys Leu Leu Arg Ala Met Thr Tyr His Ile Phe Thr Arg
360                 365                 370                 375

GGC ATG TTA AAA ACG GCT GAC GCC CAA ATC AAG CAA GGC GGG AAG GTT      3486
Gly Met Leu Lys Thr Ala Asp Ala Gln Ile Lys Gln Gly Gly Lys Val
```

-continued

```
            380                 385                 390

TGG GTT TAC CGG TTT GAT TAC GAA ACC CCG CTC TTT GAC GGT CGG TTG     3534
Trp Val Tyr Arg Phe Asp Tyr Glu Thr Pro Leu Phe Asp Gly Arg Leu
            395                 400                 405

AAA GCA TGT CAC GCA CTG GAA ATC CCC TTT GTC TTT CAC AAC CTG CAT     3582
Lys Ala Cys His Ala Leu Glu Ile Pro Phe Val Phe His Asn Leu His
        410                 415                 420

CAA CCG GGG GTC GAT GTG TTC ACC GGC ACA CAT CCG AAG CGG GAG CTA     3630
Gln Pro Gly Val Asp Val Phe Thr Gly Thr His Pro Lys Arg Glu Leu
    425                 430                 435

ATT TCC CGG CAA ATG CAT GAA GCA TGG ATT GCC TTT GCC CGG ACA GGG     3678
Ile Ser Arg Gln Met His Glu Ala Trp Ile Ala Phe Ala Arg Thr Gly
440                 445                 450                 455

GAT CCG AAC GGC GAC CAT CTC CCC GAT GCG TGG TTG CCC TTT GCA CAA     3726
Asp Pro Asn Gly Asp His Leu Pro Asp Ala Trp Leu Pro Phe Ala Gln
            460                 465                 470

AAA GAC CGG CCG GCC ATG GTC TTT GAC ACC GAA ACC AGA GCG GAA AAG     3774
Lys Asp Arg Pro Ala Met Val Phe Asp Thr Glu Thr Arg Ala Glu Lys
            475                 480                 485

CAT CTG TTT GAC CGC GAG CAG GAA CTG TGG GAA TCA AAG GCT             3816
His Leu Phe Asp Arg Glu Gln Glu Leu Trp Glu Ser Lys Ala
        490                 495                 500

TGAGTGATTT GCTCAAGCCT TTTTTGCATT TCACGTATGT ATTCGGATTT GGAATTAAAC   3876

AATGGTGCTT TTATCGAAAT GGGGAGTGTT TGCTTATAAT GAACGGGTTT ACAAAGCTTG   3936

TTTTGGTACC GGATTACTGA AATGATCCGT GTTTATCATT TGGATGCTTT CTATTGGAAA   3996

CCGGGCTGGG TGGAGTCTTC CCCGGAGGAG TTCGTTGCAG CTCAGCAAGA AATTGTGAAC   4056

CAATGCCAAT GGATTGTGGA AGGGAATTAC AGTAGAGAGA AATAAATAAG AACGCCGAAG   4116

AAAGGTCGAA CCGTTATTAT AAGAAAACAT GAGATTTTGG GGATTAGTTC CAGCGAATAA   4176

GTGGGGGGTA TTATGAAATG GAGAAAAAGC AAGGTACCTG CTGATAAGCA ATCAATTGAT   4236

CAGGTAAAAA ATTTTGGGAT TCAATTTCCT TCCGATTTCC GACAAATTGC AATTACTTCT   4296

CATGGAACCC AACCAAGTCC TGATACGATT GACTTTGGAG TTCTAAAAAA TCATCTTCTT   4356

CAAACCAAAC AGAAAAACGA ACCTCACGAA TCGTTTTATT CAAAATTTCT CACTCTGTTA   4416

AAGTGGGATG TCAGTAAACG TTATAAAAAT ATCTTTTGAT GATTGTATCA TCAGCAATGA   4476

AAGAAAGACA AAAGAGGACT ATGAGATATT TCTTTACAAC AAAAGATGGA TTATCCTGAG   4536

GATAGTATAT ATATTCCTAA TCCTTTGAAT ATCATCCGGA TTGGATAGAG GGGTCGTTAT   4596

GCAATGGTAT CATCATGTTA GTGAAGATGC AAAGGCGGCT TTTTATTTAT CTTTAACAGA   4656

AAAAGTATTG GATAAAATCA GTCATTATGA ATGGTTTCCT CATGTAAAAG AAACCATGAA   4716

CATGTGTTGG GATTGGATTG AGGAAAAAGG ATGGAGTGGA CATGATCTTT ATGAAAGGCT   4776

TGATGATGAA GAATCAGAAA CAGGGTTATT TTCAATTCAC ATGAATGAAG TCGATGCTGG   4836

TTTAGATGAC GATGAAGATG AACTTGCTTT TTTCTGTGTA ATTGATGCAG TGGCCTACAC   4896

GGTTTGGCAA GCCTGTAAGT ATGAAGAGAA AGGCTATGTT CCGCAAGCAA TTGAAGTTGT   4956

AAATGATGAA TTTACAGACG GCGAATTTAT GAGAAAAATT TGCCAGATTC ATGATTACCA   5016

AGAAGAATGG ATTGAGCGAT TAAAACAACA CCTGATAAAA AACCACCCGG CAGGCAGTGA   5076

CAAGAAGATC CAAAGAGAAG AATTGTTGAG CTTGATTGCG TAAAAATTGG TTTCATGGAT   5136

TTCTTTGAAA GCCCGCCGGT CAAAAGGTGC GGGTTTTGTT TTTGTTAAAG GTGAAAGAAA   5196

AGTAACGTGT TTCCATAGGT TATCATTGAA TGATTCGATT TCATATTTTG GGAGGTGATC   5256

AGAGCAATGA GCGACTTTTC TTTTTTGAAA AATATGTCC TTCCATCCGT AAACGTTCAA   5316
```

-continued

```
GCACCACCAG AGTATAAACA TGTATTTTAT CCGCTGGATA TATGTGAAGT GGAAGAAGCG   5376

GAACATAGAC TCAATCGAAC GTTTCCAAAA GAGTTAAGGG AATTTTATTT GCAAATTGGA   5436

TATGGCTTTA TGTGTATTCA TCAGAAGACT TTTGATAACC GTATCATGGA TCCCGATTCC   5496

CTTGCAGATT TGATCTTGGG TGAAGACATT TGGGAAGATT ATGATCTGAT GGAAGAGATC   5556

GGAGAACCAC ATTTATTCCC GTTTTTTTTC TTGGGTAATG ATGACTTGAT TTTTTTCGAT   5616

TTGAGTCAAG AGACAAGAGA AGGAATTCAT CCGGTTGACT ATGGAAGGGT GATCATTGCG   5676

GAATCCCTTG AAGATTTTTT ACGTAAGTTA GATGCTAAAG AAAATTATTA TATCAATGTT   5736

GTTGATGATA AATCGGGTTT TTGAAAGATT TTCCCCCATT ATAAAAAATA TAGTGGCACC   5796

TGATTGAACG ATAGAATATC AAATGCTGAA AAGTTGATTC CGATTTTGCG GCCGATATTA   5856

TGGAACAATG TAACGAACTT GGGAGGCAAT AGAGTGTGGA GTGGTACAAA AAGGTAAATA   5916

TGGATGCGAG AGCGGCTTAT TTTTTAGCTT TATCTGAGAA AGTTTTAGAT AAATTAACTA   5976

AATTTGATTG GTTTCCGGCA ATAAGAAAGT CCATGGATTT GTGTTGGAAA TGGATCACGG   6036

CGACGCAAAT GCTGGATTCC ATGCAACGCA ATCCAAGGCC CACCCGGGCG GAAGCCAGCG   6096

ACGTGGCCAA TGCGATTTTG GACGGAACTG ATGCCATCAT GTTGTCCGGG GAAACGGCGG   6156

CCGGGAAATA TCCGGTGGAA TCCGTCAGTA CCATGGCGCG GATTGCCATT CGCACGGAAT   6216

CATCGCTTCG GTATCAGGAA CGTTTTCAAC AAAAAATCAG AGAGATC                 6263
```

(2) INFORMATION FOR SEQ ID NO:4:

(i) SEQUENCE CHARACTERISTICS:
(A) LENGTH: 501 amino acids
(B) TYPE: amino acid
(D) TOPOLOGY: linear (ii) MOLECULE TYPE: protein (xi) SEQUENCE DESCRIPTION: SEQ ID NO:4:

```
Leu Ile Gln Met Asn Thr Leu Val Glu Thr Arg Phe Gly Lys Val Gln
  1               5                  10                  15

Gly Gly Thr Asp Gly Glu Val Cys Phe Trp Lys Gly Ile Pro Tyr Ala
             20                  25                  30

Lys Pro Pro Val Gly Lys Arg Arg Phe Gln Lys Pro Glu Pro Pro Glu
         35                  40                  45

Lys Trp Asp Gly Val Trp Glu Ala Thr Arg Phe Arg Ser Met Val Met
     50                  55                  60

Gln Pro Ser Gly Thr Thr Phe Ser Thr Val Leu Gly Glu Ala Asp Leu
 65                  70                  75                  80

Pro Val Ser Glu Asp Gly Leu Tyr Leu Asn Ile Trp Ser Pro Ala Ala
                 85                  90                  95

Asp Gly Lys Lys Arg Pro Val Leu Phe Trp Ile His Gly Gly Ala Tyr
            100                 105                 110

Gln Phe Gly Ser Gly Ala Ser Pro Trp Tyr Asp Gly Thr Glu Phe Ala
        115                 120                 125

Lys Asn Gly Asp Val Val Val Val Thr Ile Asn Tyr Arg Leu Asn Ala
    130                 135                 140

Phe Gly Phe Leu Tyr Leu Ala Asp Trp Phe Gly Asp Glu Phe Ser Ala
145                 150                 155                 160

Ser Gly Asn Leu Gly Ile Leu Asp Gln Val Ala Ala Leu Arg Trp Val
                165                 170                 175

Lys Glu Asn Ile Ser Ala Phe Gly Gly Asp Pro Glu Gln Ile Thr Ile
            180                 185                 190
```

```
Phe Gly Glu Ser Ala Gly Ala Gly Ser Val Gly Val Leu Leu Ser Leu
        195                 200                 205

Pro Glu Thr Lys Gly Leu Phe Gln Arg Ala Ile Leu Gln Ser Gly Ser
    210                 215                 220

Gly Ala Ile Leu Leu Arg Ser Ser Gln Thr Ala Ser Gly Ile Ala Glu
225                 230                 235                 240

Gln Ile Leu Thr Lys Ala Gly Ile Arg Lys Gly Asp Arg Asp Arg Leu
                245                 250                 255

Leu Ser Ile Pro Ala Gly Glu Leu Leu Glu Ala Ala Gln Ser Val Asn
            260                 265                 270

Pro Gly Met Val Phe Gly Pro Val Val Asp Gly Thr Val Leu Lys Thr
        275                 280                 285

His Pro Ile Glu Ala Leu Glu Thr Gly Ala Ala Gly Asp Ile Pro Ile
    290                 295                 300

Ile Ile Gly Val Thr Lys Asp Glu Tyr Asn Leu Phe Thr Leu Thr Asp
305                 310                 315                 320

Pro Ser Trp Thr Thr Ala Gly Lys Glu Glu Leu Met Asp Arg Ile Glu
                325                 330                 335

Gln Glu Ile Gly Pro Val Pro Glu Lys Val Phe Pro Tyr Tyr Leu Ser
            340                 345                 350

Phe Gly Asp Pro Ser Gln Pro Val Trp Gln Lys Leu Leu Arg Ala Met
        355                 360                 365

Thr Tyr His Ile Phe Thr Arg Gly Met Leu Lys Thr Ala Asp Ala Gln
    370                 375                 380

Ile Lys Gln Gly Gly Lys Val Trp Val Tyr Arg Phe Asp Tyr Glu Thr
385                 390                 395                 400

Pro Leu Phe Asp Gly Arg Leu Lys Ala Cys His Ala Leu Glu Ile Pro
                405                 410                 415

Phe Val Phe His Asn Leu His Gln Pro Gly Val Asp Val Phe Thr Gly
            420                 425                 430

Thr His Pro Lys Arg Glu Leu Ile Ser Arg Gln Met His Glu Ala Trp
        435                 440                 445

Ile Ala Phe Ala Arg Thr Gly Asp Pro Asn Gly Asp His Leu Pro Asp
    450                 455                 460

Ala Trp Leu Pro Phe Ala Gln Lys Asp Arg Pro Ala Met Val Phe Asp
465                 470                 475                 480

Thr Glu Thr Arg Ala Glu Lys His Leu Phe Asp Arg Glu Gln Glu Leu
                485                 490                 495

Trp Glu Ser Lys Ala
            500
```

(2) INFORMATION FOR SEQ ID NO:5:

(i) SEQUENCE CHARACTERISTICS:
(A) LENGTH: 4090 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 197..1699
(D) OTHER INFORMATION: /note= "E011 sequence of longest open reading frame; other possible start codons ATG/met4; TTG/leu7; GTG/val8; GTG/val15; GTG/val36; ATG/met62"

(ix) FEATURE:
(A) NAME/KEY: mat_peptide (B) LOCATION: 197..1699

(xi) SEQUENCE DESCRIPTION: SEQ ID NO:5:

```
GATCTTTCCT TTGTGTTTTA AAACTTAAAG CACCGGATTG CCGGCTGTAT GGTCCGGTTG     60

GATATTGTCA TCACATCGTG GATATCAGTG GATCCGGTGC GATGGATTGC TTCAGGGGAA    120

CTTTTAAACA CTTGAGTTTG ACAACCACTC CTTAATCATT TAAGATTTAA ATGAAAATTA    180

AAATAAATCA AAAAGA GTG ATT CAA ATG AAT ACG TTG GTG GAA ACC CGT        229
                  Val Ile Gln Met Asn Thr Leu Val Glu Thr Arg
                    1               5                  10

TTT GGG AAA GTG CAA GGC GGT ACA GAC GGA GAG GTT TGT TTT TGG AAA      277
Phe Gly Lys Val Gln Gly Gly Thr Asp Gly Glu Val Cys Phe Trp Lys
             15                  20                  25

GGG ATT CCT TAT GCG AAA CCT CCG GTG GGA AAA CGC CGC TTT CAA AAA      325
Gly Ile Pro Tyr Ala Lys Pro Pro Val Gly Lys Arg Arg Phe Gln Lys
         30                  35                  40

CCG GAA CCG CCG GAG AAA TGG GAT GGC GTT TGG GAG GCC ACC CGG TTC      373
Pro Glu Pro Pro Glu Lys Trp Asp Gly Val Trp Glu Ala Thr Arg Phe
     45                  50                  55

CGG TCC ATG GTG ATG CAG CCG TCC GGC ACC ACC TTC AGC ACC GTG CTC      421
Arg Ser Met Val Met Gln Pro Ser Gly Thr Thr Phe Ser Thr Val Leu
 60                  65                  70                  75

GGG GAA GCG GAT CTT CCT GTG AGC GAA GAC GGT CTT TAT CTG AAT ATC      469
Gly Glu Ala Asp Leu Pro Val Ser Glu Asp Gly Leu Tyr Leu Asn Ile
                 80                  85                  90

TGG TCG CCG GCA GCC GAC GGA AAA AAG CGG CCG GTG CTC TTC TGG ATC      517
Trp Ser Pro Ala Ala Asp Gly Lys Lys Arg Pro Val Leu Phe Trp Ile
             95                 100                 105

CAT GGC GGC GCC TAC CAG TTT GGG TCC GGC GCT TCC CCC TGG TAT GAC      565
His Gly Gly Ala Tyr Gln Phe Gly Ser Gly Ala Ser Pro Trp Tyr Asp
        110                 115                 120

GGG ACG GAG TTT GCC AAA AAC GGA GAT GTG GTG GTT GTC ACG ATC AAC      613
Gly Thr Glu Phe Ala Lys Asn Gly Asp Val Val Val Val Thr Ile Asn
    125                 130                 135

TAC CGG TTG AAC GCG TTT GGA TTT TTG TAC TTG GCA GAT TGG TTC GGC      661
Tyr Arg Leu Asn Ala Phe Gly Phe Leu Tyr Leu Ala Asp Trp Phe Gly
140                 145                 150                 155

GAC GAA TTT TCA GCG TCG GGC AAC CTG GGA ATT TTG GAC CAA GTC GCT      709
Asp Glu Phe Ser Ala Ser Gly Asn Leu Gly Ile Leu Asp Gln Val Ala
                160                 165                 170

GCA CTG CGC TGG GTG AAA GAA AAC ATT TCG GCA TTC GGC GGC GAC CCG      757
Ala Leu Arg Trp Val Lys Glu Asn Ile Ser Ala Phe Gly Gly Asp Pro
            175                 180                 185

GAG CAA ATC ACC ATC TTC GGG GAG TCG GCC GGA GCC GGA AGC GTC GGG      805
Glu Gln Ile Thr Ile Phe Gly Glu Ser Ala Gly Ala Gly Ser Val Gly
        190                 195                 200

GTT CTG CTT TCC CTC CCG GAA ACC AAA GGG CTG TTT CAA CGG GCG ATC      853
Val Leu Leu Ser Leu Pro Glu Thr Lys Gly Leu Phe Gln Arg Ala Ile
    205                 210                 215

TTG CAA AGC GGA TCG GGT GCC ATT TTG CTC CGT TCC TCT CAG ACA GCC      901
Leu Gln Ser Gly Ser Gly Ala Ile Leu Leu Arg Ser Ser Gln Thr Ala
220                 225                 230                 235

TCG GGC ATC GCG GAA CAA ATT CTT ACG AAA GCC GGC ATT CGA AAA GGA      949
Ser Gly Ile Ala Glu Gln Ile Leu Thr Lys Ala Gly Ile Arg Lys Gly
                240                 245                 250

GAC CGC GAC CGG TTG TTA TCC ATC CCG GCC GGT GAA CTC CTT GAA GCC      997
Asp Arg Asp Arg Leu Leu Ser Ile Pro Ala Gly Glu Leu Leu Glu Ala
            255                 260                 265

GCA CAA TCC GTG AAT CCG GGA ATG GTT TTT GGT CCC GTT GTG GAC GGC     1045
Ala Gln Ser Val Asn Pro Gly Met Val Phe Gly Pro Val Val Asp Gly
```

-continued

```
        270                 275                 280

ACC GTA TTG AAA ACC CAT CCG ATT GAA GCG TTG GAA ACC GGA GCC GCC      1093
Thr Val Leu Lys Thr His Pro Ile Glu Ala Leu Glu Thr Gly Ala Ala
    285                 290                 295

GGC GAT ATC CCG ATC ATC ATC GGG GTG ACA AAG GAT GAG TAC AAT TTA      1141
Gly Asp Ile Pro Ile Ile Ile Gly Val Thr Lys Asp Glu Tyr Asn Leu
300                 305                 310                 315

TTT ACA CTG ACT GAC CCT TCC TGG ACG ACA GCG GGA AAA GAA GAA CTG      1189
Phe Thr Leu Thr Asp Pro Ser Trp Thr Thr Ala Gly Lys Glu Glu Leu
                320                 325                 330

ATG GAC CGG ATC GAA CAG GAA ATC GGG CCG GTT CCG GAA AAA GTT TTT      1237
Met Asp Arg Ile Glu Gln Glu Ile Gly Pro Val Pro Glu Lys Val Phe
            335                 340                 345

CCA TAT TAC TTA TCT TTT GGG GAT CCA TCG CAA CCG GTA TGG CAA AAG      1285
Pro Tyr Tyr Leu Ser Phe Gly Asp Pro Ser Gln Pro Val Trp Gln Lys
        350                 355                 360

CTG TTG CGC GCC ATG ACC TAC CAC ATC TTT ACC CGG GGC ATG TTA AAA      1333
Leu Leu Arg Ala Met Thr Tyr His Ile Phe Thr Arg Gly Met Leu Lys
    365                 370                 375

ACG GCT GAC GCC CAA ATC AAG CAA GGC GGG AAG GTT TGG GTT TAC CGG      1381
Thr Ala Asp Ala Gln Ile Lys Gln Gly Gly Lys Val Trp Val Tyr Arg
380                 385                 390                 395

TTT GAT TAC GAA ACC CCG CTC TTT GAC GGT CGG TTG AAA GCA TGT CAC      1429
Phe Asp Tyr Glu Thr Pro Leu Phe Asp Gly Arg Leu Lys Ala Cys His
                400                 405                 410

GCA CTG GAA ATC CCC TTT GTC TTT CAC AAC CTG CAT CAA CCG GGG GTC      1477
Ala Leu Glu Ile Pro Phe Val Phe His Asn Leu His Gln Pro Gly Val
            415                 420                 425

GAT GTG TTC ACC GGC ACA CAT CCG AAG CGG GAG CTA ATT TCC CGG CAA      1525
Asp Val Phe Thr Gly Thr His Pro Lys Arg Glu Leu Ile Ser Arg Gln
        430                 435                 440

ATG CAT GAA GCA TGG ATT GCC TTT GCC CGG ACA GGG GAT CCG AAC GGC      1573
Met His Glu Ala Trp Ile Ala Phe Ala Arg Thr Gly Asp Pro Asn Gly
    445                 450                 455

GAC CAT CTC CCC GAT GCG TGG TTG CCC TTT GCA CAA AAA GAC CGG CCG      1621
Asp His Leu Pro Asp Ala Trp Leu Pro Phe Ala Gln Lys Asp Arg Pro
460                 465                 470                 475

GCC ATG GTC TTT GAC ACC GAA ACC AGA GCG GAA AAG CAT CTG TTT GAC      1669
Ala Met Val Phe Asp Thr Glu Thr Arg Ala Glu Lys His Leu Phe Asp
                480                 485                 490

CGC GAG CAG GAA CTG TGG GAA TCA AAG GCT TGAGTGATTT GCTCAAGCCT       1719
Arg Glu Gln Glu Leu Trp Glu Ser Lys Ala
            495                 500

TTTTTGCATT TCACGTATGT ATTCGGATTT GGAATTAAAC AATGGTGCTT TTATCGAAAT   1779

GGGGAGTGTT TGCTTATAAT GAACGGGTTT ACAAAGCTTG TTTTGGTACC GGATTACTGA   1839

AATGATCAGA AGGAAATATC ATGACGTAAT AATCAGGGGA TCTTGAGAAA GAAATACATG   1899

GAGTGTTATG TCCCTTGAAA AACAGAGACG CCGGTGGCAT CACCATCACA GGGTCTTTCT   1959

TTTCAAATCA TGGTTTGTAG TTTATAATGC AAACTAGTTA ATCATACATA TGGAGTGTGG   2019

TTCCATTGAT GCCCTTTAAG GAAATGGCAA AACTGAATAA ATTGATTCAC GAACCGGCCC   2079

GACTTGCCAT TATGAGCGCG CTGGACGCCT GCACGATGGC TGAATTTTTG TTTTTGCAAG   2139

AATTGACAGG CTTGACGAAA GGAAACCTTT CTTCCCATTT ATCCAAATTA GAAAAGGCGG   2199

AATATATCCA AATCCAGAAA CAATTCGTAC GCAAAAAAAT CCCGCATACC ACCATACGAA   2259

TCACACATGA AGGCCGGGCT GCGCTTCACA ATTATTGGGA ACAACTGGAT CGCATCCGCG   2319

AGGTAACCAA AAAATGGAAT AATAGTTAGG AAGCGGATTC TCTCAACCTC TTCCCCTCTG   2379
```

-continued

```
TTTTTCAGAG GGTTTTTCTT CCTTAAAATC CCAACACAAA GAGAGCGATT CCAAGGCCCC   2439

TTACATCTTT TCACCCCCTT TTTCGACCTG TTCCTCTCAA AAAGAAATAA ACCGCCCTTA   2499

AATCGAAAAT CAGAAGGCCG TTTTTTCTGA AACGAAATTT TTGATTCCAT TTATTGGAAT   2559

GTATTTTTCT CCATCCGGCT GCTTATCTCT TGATTATTTT GTTTGTTCTG ATTAACAAGA   2619

ATATTTGTGG CGCGAAACAG CCGCGGGTTT CCTTCTCCTC CCTCTTGATC CACTCTATTT   2679

ATGCCCTCTA CAGGGTTACA AAACAATTCT TTTGTAACTA TATAAAGATA AAATGCCGAA   2739

ACCCCTTTAT TTACAAGGGG TTTGGCGATC GGATATTTCC CACACATTTT TCCATCTGTC   2799

TGAGAGTCAA ATGGTCGTCT CACCAAGTTA ACTTGTTAAT GAGATATCAA TCTGCTGCTA   2859

TTTTCTTCAC CATATGGACG TTATTCAAAA ACATGTGAAA TCCTTCCTCC TCCAGCAAGC   2919

CCGTCACCAT TTTCTTCTTT GCGGGGCAGT ATAAAAACTG GTATCGGGAT GCTTCCGCGG   2979

AAGCCATCAC ATGTCGCAAC AACTGACGGG CCAGTTCTTC CGCTTCAGGA TGCTCCGGGG   3039

CTGTCTCCAA TTGCAACAAA GTCAAATCTT GCACTCGTCC TAGGTCATCG GTTGTCCGCC   3099

TCACCAACGC ATATCCGGCT TCCTTTCCGG AAGAATCGGA AATGATCCAT GCTTCATCTC   3159

CTTGAAACCA ATGGGTTTGC CACGGAGCCG GATCGGGATA AAAAGAAAAA GCGGCAACGG   3219

TTACCGGATG GGCGCTGCGG ATGTTGTATC CGGGAGCCGC TGGTTGTTTC CGGCTGAAGT   3279

TTTCTGTCTG GTAAATGAAC AAGGAATCAT CGATGTCATA CCCGTATTGC TGATATAACC   3339

GGATGGCCGG CTTGTTTTCG GCGATCGCTT CCAGTGTTGC CAGTTGCACA TGTTCCCGTT   3399

GATACATCTC CACCAATGCT TCCATCAGCC GGCTCCCAAC CCCTTTTCGT CTCCATCCGG   3459

GAAGAACGGC TGTCCCTCCG TTCCAAGCGA CTTTTTTTCC TTTGATCTCC CCGATAGCCG   3519

TGAACACAAA ACCGACCGGC CGGCCATCGG CCCAAGCCAC CAGGGAATGG GCCGGCGAAA   3579

TTTTTTCCCG GACCATCCTG TTCATTAACC GGTCAAAAGT GAAATTCATG TTCACAAAGT   3639

AATCCGCAAA GGCTTCGTTC CACAATTGCA ACGTTTGTTC CCACGTGCAC CTGCTCAATG   3699

GATGAATCGT AACCATGGCG CTTCCTTTCT TTTTGTTTGA TATAATATCG GTGTAAAACG   3759

TTTGTGGGGA TTAAAACGCG GATTCCTGAA GGACTTCCTC TTCTTCGGAA ATGCCTTGTT   3819

TTTTAAATTG CAACCGGCAC CAAAAAGCCG ACTTGGCATA ATCCCAAAGA TACCGGCTGA   3879

ATTCCCCGTT TGGATGTAAA TAGTTCCACA CCTCAGGGAA ATATTTCTTT ATATCAGATA   3939

AAATCTCCTT TTCCTTCTGA CTCATCACAT GCAAGTTATG CCGGTATTTC AAACCCAGGG   3999

TTGTCAGGCA GTCCGTCACC TCCACCGGGA CTTTCCGCCA GATTTGTTTC CACTCTTCAT   4059

AAGGTTCCAT CAAATAATGA ACATTCAGAT C                                  4090
```

(2) INFORMATION FOR SEQ ID NO:6:

(i) SEQUENCE CHARACTERISTICS:
(A) LENGTH: 501 amino acids
(B) TYPE: amino acid
(D) TOPOLOGY: linear (ii) MOLECULE TYPE: protein (xi) SEQUENCE DESCRIPTION: SEQ ID NO:6:

```
Val Ile Gln Met Asn Thr Leu Val Glu Thr Arg Phe Gly Lys Val Gln
  1               5                  10                  15

Gly Gly Thr Asp Gly Glu Val Cys Phe Trp Lys Gly Ile Pro Tyr Ala
             20                  25                  30

Lys Pro Pro Val Gly Lys Arg Arg Phe Gln Lys Pro Glu Pro Pro Glu
         35                  40                  45

Lys Trp Asp Gly Val Trp Glu Ala Thr Arg Phe Arg Ser Met Val Met
```

-continued

```
    50                  55                  60

Gln Pro Ser Gly Thr Thr Phe Ser Thr Val Leu Gly Glu Ala Asp Leu
 65                  70                  75                  80

Pro Val Ser Glu Asp Gly Leu Tyr Leu Asn Ile Trp Ser Pro Ala Ala
                 85                  90                  95

Asp Gly Lys Lys Arg Pro Val Leu Phe Trp Ile His Gly Gly Ala Tyr
            100                 105                 110

Gln Phe Gly Ser Gly Ala Ser Pro Trp Tyr Asp Gly Thr Glu Phe Ala
        115                 120                 125

Lys Asn Gly Asp Val Val Val Val Thr Ile Asn Tyr Arg Leu Asn Ala
    130                 135                 140

Phe Gly Phe Leu Tyr Leu Ala Asp Trp Phe Gly Asp Glu Phe Ser Ala
145                 150                 155                 160

Ser Gly Asn Leu Gly Ile Leu Asp Gln Val Ala Ala Leu Arg Trp Val
                165                 170                 175

Lys Glu Asn Ile Ser Ala Phe Gly Gly Asp Pro Glu Gln Ile Thr Ile
            180                 185                 190

Phe Gly Glu Ser Ala Gly Ala Gly Ser Val Gly Val Leu Leu Ser Leu
        195                 200                 205

Pro Glu Thr Lys Gly Leu Phe Gln Arg Ala Ile Leu Gln Ser Gly Ser
    210                 215                 220

Gly Ala Ile Leu Leu Arg Ser Ser Gln Thr Ala Ser Gly Ile Ala Glu
225                 230                 235                 240

Gln Ile Leu Thr Lys Ala Gly Ile Arg Lys Gly Asp Arg Asp Arg Leu
                245                 250                 255

Leu Ser Ile Pro Ala Gly Glu Leu Leu Glu Ala Ala Gln Ser Val Asn
            260                 265                 270

Pro Gly Met Val Phe Gly Pro Val Val Asp Gly Thr Val Leu Lys Thr
        275                 280                 285

His Pro Ile Glu Ala Leu Glu Thr Gly Ala Ala Gly Asp Ile Pro Ile
    290                 295                 300

Ile Ile Gly Val Thr Lys Asp Glu Tyr Asn Leu Phe Thr Leu Thr Asp
305                 310                 315                 320

Pro Ser Trp Thr Thr Ala Gly Lys Glu Glu Leu Met Asp Arg Ile Glu
                325                 330                 335

Gln Glu Ile Gly Pro Val Pro Glu Lys Val Phe Pro Tyr Tyr Leu Ser
            340                 345                 350

Phe Gly Asp Pro Ser Gln Pro Val Trp Gln Lys Leu Leu Arg Ala Met
        355                 360                 365

Thr Tyr His Ile Phe Thr Arg Gly Met Leu Lys Thr Ala Asp Ala Gln
    370                 375                 380

Ile Lys Gln Gly Gly Lys Val Trp Val Tyr Arg Phe Asp Tyr Glu Thr
385                 390                 395                 400

Pro Leu Phe Asp Gly Arg Leu Lys Ala Cys His Ala Leu Glu Ile Pro
                405                 410                 415

Phe Val Phe His Asn Leu His Gln Pro Gly Val Asp Val Phe Thr Gly
            420                 425                 430

Thr His Pro Lys Arg Glu Leu Ile Ser Arg Gln Met His Glu Ala Trp
        435                 440                 445

Ile Ala Phe Ala Arg Thr Gly Asp Pro Asn Gly Asp His Leu Pro Asp
    450                 455                 460

Ala Trp Leu Pro Phe Ala Gln Lys Asp Arg Pro Ala Met Val Phe Asp
465                 470                 475                 480
```

```
Thr Glu Thr Arg Ala Glu Lys His Leu Phe Asp Arg Glu Gln Glu Leu
            485                 490                 495

Trp Glu Ser Lys Ala
            500
```

(2) INFORMATION FOR SEQ ID NO:7:

(i) SEQUENCE CHARACTERISTICS:
(A) LENGTH: 3147 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 245..1231
(D) OTHER INFORMATION: /note= "TspA E101 sequence longest open reading frame; other possible start codons are TTG/leu9; TTG/leu13; TTG/leu15; GTG/val43"

(ix) FEATURE:
(A) NAME/KEY: mat_peptide
(B) LOCATION: 245..1231

(xi) SEQUENCE DESCRIPTION: SEQ ID NO:7:

```
GATCCGCTTC ATCCAGCAGG TCCTGGAGCA GCGGGAGCGG GAGGACACCT TCCGCCTCAA     60

GCGCATCAAG GGCAAGATCG AGGCCCGGGA AGCGGAGGAG GGGGGGCGGC CCAACCCCCA    120

CCTGGAGATC GGAGCGGGCC TCTAAGGCCG CCCCAGCTTG AGCCACCCCC CAGGCTTCCC    180

CTGGGGGGTT TACCCTTGAC CCGGTCCAAG GTTTTCGGGT AGGCTCCTCC TCGGAGGGAA    240

AACC ATG AGG CGG CTT TTG GGG CTC CTT TTG TTC CTG GCC TTG GCC TTG     289
     Met Arg Arg Leu Leu Gly Leu Leu Leu Phe Leu Ala Leu Ala Leu
       1               5                  10                  15

GCG CAA GGC CTT GGC CCT TAC TGG CAG GAG GTT CAG GCC CAG GGT ACG      337
Ala Gln Gly Leu Gly Pro Tyr Trp Gln Glu Val Gln Ala Gln Gly Thr
                20                  25                  30

GTC TGC TCG GAC GGC TCC CCC TGG CGG TTC TAC GTG AGC CCG GGG GAC      385
Val Cys Ser Asp Gly Ser Pro Trp Arg Phe Tyr Val Ser Pro Gly Asp
            35                  40                  45

CCC AAG AAG GTC CTT CTG GAC TTC CAG GGG GGC GGG GCC TGC TGG GAC      433
Pro Lys Lys Val Leu Leu Asp Phe Gln Gly Gly Gly Ala Cys Trp Asp
        50                  55                  60

GCC CAG ACC TGC GGT CCC CAG AGC CAG ACC TAC CGG AAG CGG GTG GAC      481
Ala Gln Thr Cys Gly Pro Gln Ser Gln Thr Tyr Arg Lys Arg Val Asp
    65                  70                  75

GTG CAG GAA CTC CTC CTG GCC CAG GGG ATC TAC AAC CGG GCG AGC ATC      529
Val Gln Glu Leu Leu Leu Ala Gln Gly Ile Tyr Asn Arg Ala Ser Ile
 80                  85                  90                  95

GCC AAC CCC TTC TTC GGC TGG ACC CAC GTC TTC ATC CCC TAC TGC ACG      577
Ala Asn Pro Phe Phe Gly Trp Thr His Val Phe Ile Pro Tyr Cys Thr
                100                 105                 110

GGG GAC CTG CAC GTG GGC CGG GCC ACG GTG GAC TAC GGC GGC TTT AAG      625
Gly Asp Leu His Val Gly Arg Ala Thr Val Asp Tyr Gly Gly Phe Lys
            115                 120                 125

GTC CAC CAC CAG GGG GCG CGA AAC GCC CTG GCC GCC TTG GAG TAC GTC      673
Val His His Gln Gly Ala Arg Asn Ala Leu Ala Ala Leu Glu Tyr Val
        130                 135                 140

TTC AAG AAC TAC CCC AAG GCA GAG CGG GTC TTC GTC ACC GGG TGC AGC      721
Phe Lys Asn Tyr Pro Lys Ala Glu Arg Val Phe Val Thr Gly Cys Ser
    145                 150                 155

GCC GGG GGG TAC GGG GCG GTC TTC TGG GCG GAC AAG GTC CTT GCC ACC      769
Ala Gly Gly Tyr Gly Ala Val Phe Trp Ala Asp Lys Val Leu Ala Thr
```

-continued

```
160                 165                 170                 175

TAC AAA AGC GCC CAG ATC GCC GTT TGC GGG GAC GCC GCC TTG GGC GTG      817
Tyr Lys Ser Ala Gln Ile Ala Val Cys Gly Asp Ala Ala Leu Gly Val
                180                 185                 190

AGC ACA TCG GAC TTC CCC GGG AGC CGG GTT TGG AAC GCC CGC CTG CCC      865
Ser Thr Ser Asp Phe Pro Gly Ser Arg Val Trp Asn Ala Arg Leu Pro
            195                 200                 205

GAG CTT CCC GGC CTG GGC CCG AAC CCC AGC GTG GAG GAG ATC TAC CGG      913
Glu Leu Pro Gly Leu Gly Pro Asn Pro Ser Val Glu Glu Ile Tyr Arg
        210                 215                 220

GCC CTG GCC CGG GCC TAC CCC GGC GCG GCC TTC GCC CAG TAC ACC ACC      961
Ala Leu Ala Arg Ala Tyr Pro Gly Ala Ala Phe Ala Gln Tyr Thr Thr
    225                 230                 235

CAG CTG GAC GGG ACC CAG ATC TAC TTC TAC GCC CTC ATG AAG AAG GAG     1009
Gln Leu Asp Gly Thr Gln Ile Tyr Phe Tyr Ala Leu Met Lys Lys Glu
240                 245                 250                 255

GTA CCC CCC TCC GAG GCC ACC GCC CGG GAG TGG GCC GTC CGG GCC CAG     1057
Val Pro Pro Ser Glu Ala Thr Ala Arg Glu Trp Ala Val Arg Ala Gln
                260                 265                 270

ACC AGC CTC CAG AGC CTG GCC CAG GAG TCC AAC TTC ACC TAC TAC CTG     1105
Thr Ser Leu Gln Ser Leu Ala Gln Glu Ser Asn Phe Thr Tyr Tyr Leu
            275                 280                 285

GCC CCG GGG AGC CAA CAC TGC ATC CTG CCC CGG CCC GAG CTC TAC ACC     1153
Ala Pro Gly Ser Gln His Cys Ile Leu Pro Arg Pro Glu Leu Tyr Thr
        290                 295                 300

CTG AAG GTG GGG GAG GTG AGC GTT CTG GAC TGG CTC AGG AGC CTG GCG     1201
Leu Lys Val Gly Glu Val Ser Val Leu Asp Trp Leu Arg Ser Leu Ala
    305                 310                 315

GAG AAG GGG CAG GCC CCC CGC GTA GGT CCG TGAGGTCGGG GAGGGCCTCG       1251
Glu Lys Gly Gln Ala Pro Arg Val Gly Pro
320                 325

AGGAGGACCC GGTACGCCTC CTTGGGGGAG GGGGCCTGGA GGAGGGCCCG GAGGACCCCC   1311

TCCCCTTTCG CCACCAGGAC GTCCGCCTTC AGGGCGAAGA CCCCTTGGAA GTAGAGGGCG   1371

TCCGCCAGGC TGGTGCGGAG CCGGTCATAG GCGCTGAGGC GGGGGTTGGG GGGTCTTAGC   1431

CGGGCGAGGA GGCGCGCCCA GGCCAGGTAA AGGGGGTACC GCTCAGGGTA GGCCCCCTTC   1491

AGGGCGAAGA GGAAGAGGTA GTTGGCCAGG AACTCGTCCA GCCAGCGGCG GCCGGTCCTG   1551

AGCCGCCAGG CCACCTGGAC CGCGTGGGCG TGCTCGTGCC CCAGGGTGAG GTCCAAGAAC   1611

TCCTCCAGCG CCCCGGGGAG ACCCTCCTCC GCCACAGGCA GGAGGACCTG GCGCAGGCGG   1671

TGGAGGAGGC GCTCGGGGTA GACCAGAGGG ACGAAGAGGT AAAGCCGGGT CCGGCTCGTC   1731

CTCTGGAAGG GGAGGCCGTA GGGCACCCGG GTCCTCTCCC GCCAGTCCCT CTCCGAGAGG   1791

ACGAAGAGGG TCACGGGGGG AAGGGGGCGG TAGCGGGCCA GGAGGCGGTG GAGCCCCTCC   1851

AGGTAGGCCT GGACCTGGGC GGTGCGGGCC TTTCCCCCCG GGCTGTAGAA GGCGGGGAGG   1911

TCGGGGTGGG GGAGGGCGTT CATATCACCT CCCGGAACCC GATGCGCTCC GCCTGGGCCT   1971

GGAGCTCCCG CCGCAGGAGG GGGTGGGCCT CGAGGCGGGG GTCCTTCTCC AGGATCTCCT   2031

ACAACGTGGA CTTCTAAAGC CCGCCGGGCC CTCCCCCCGC CCCCCGGGGC GGGGGGTTGG   2091

CCTTTTTCCG GCCCAGGCCA GGGAGCCTTG CGCGTTCGGC GTTTGGCGTT CAGCCTTCGG   2151

CGTTTGGCCC ATAATCGGGA CCAGGCGAAA CGGGTATCAT GGAGGTATGC GCTGGCTGGG   2211

GGTGCTCCTC CTGGGCCTGG CCCTGGCCCA GGGGCTGGAC CTGGCCCAGT CCCTCCTGCG   2271

CCAGGGCCAG TACGAGCAGG CCCTGGCCCG GCTGGAGCGG GAGCCCCCCG GCCCGGAGGT   2331

CCTGGCCCTG AAGGGCCGGG CCTACCTGCT CCTGGGCCGG CCGGAGGCGG CCCGGGAGGC   2391
```

-continued

```
CCTGGAGGGG GCGGCCCGCC TGGGCCGGGG GGCGGAGGTG GAGCGGCTCA AGGGGTGGCT   2451

GGCCCTGGAG GCGGGAAAGG CCGAGGAGGC CCGGCGGGCC TTCCAGGCCG CGGCCATCTA   2511

CTCGGGCCTT CCCCAAGACG CCCTCCTCTG GGCCCTGGCG GCTTGGGAGG CGGGCCGCTC   2571

TTCCGAGGAG GCCCTGGCCC GGGCGGAGCG GGCGGGAGGC GGGGCGGAGG CGGCCCTCCT   2631

TAAGGGGCTC TTCCTCCTGG CCCAGGACCC GGCGGAGGCC CTGGCCGCCT TCCGCCGGGC   2691

GGGGGACGGC CCCTTCAAGG CCCAGGCCCT CTACCTGCAG GGCCTGGCCC TCGAGGCCCT   2751

GGGCCGGGAC CCGGAGGCCC GGGAGGCCTA CCGCCAGGCC CTGAAGGCCT CCCCGGACTA   2811

CCTCCCCGCC CGCCGGGCTT TAGGGCTCTA GTACCACCCC ATCCTGGCGT ACGCCAGGAT   2871

GGGGGCCCCG GTAAAGCCTT AGCCTTCCGA CGAAGCGGGG AATGAGGGGA AGCCTGAATG   2931

ACGGAAAAGA GGATGGAAAA ATCGGTCTTC CGCTACCAAG GCCCCGAGCC CAAGGGGGAC   2991

CAGCCCAAGG CCATCCGGGA GCTGGTGGAG GCCCTGGAGG CGGGGGAGCG GTTCGTCACC   3051

CTTTTGGGGG CCACCGGCAC GGGGAAGACG GTCACCATGG CCAAGGTGAT CGAGGCCCTG   3111

GGCAGGCCCA CCCTGGTCCT CGCCCCCAAC AAGATC                              3147
```

(2) INFORMATION FOR SEQ ID NO:8:

(i) SEQUENCE CHARACTERISTICS:
(A) LENGTH: 329 amino acids
(B) TYPE: amino acid
(D) TOPOLOGY: linear (ii) MOLECULE TYPE: protein (xi) SEQUENCE DESCRIPTION: SEQ ID NO:8:

```
Met Arg Arg Leu Leu Gly Leu Leu Leu Phe Leu Ala Leu Ala Leu Ala
  1               5                  10                  15

Gln Gly Leu Gly Pro Tyr Trp Gln Glu Val Gln Ala Gln Gly Thr Val
             20                  25                  30

Cys Ser Asp Gly Ser Pro Trp Arg Phe Tyr Val Ser Pro Gly Asp Pro
         35                  40                  45

Lys Lys Val Leu Leu Asp Phe Gln Gly Gly Gly Ala Cys Trp Asp Ala
     50                  55                  60

Gln Thr Cys Gly Pro Gln Ser Gln Thr Tyr Arg Lys Arg Val Asp Val
 65                  70                  75                  80

Gln Glu Leu Leu Leu Ala Gln Gly Ile Tyr Asn Arg Ala Ser Ile Ala
                 85                  90                  95

Asn Pro Phe Phe Gly Trp Thr His Val Phe Ile Pro Tyr Cys Thr Gly
            100                 105                 110

Asp Leu His Val Gly Arg Ala Thr Val Asp Tyr Gly Gly Phe Lys Val
        115                 120                 125

His His Gln Gly Ala Arg Asn Ala Leu Ala Ala Leu Glu Tyr Val Phe
    130                 135                 140

Lys Asn Tyr Pro Lys Ala Glu Arg Val Phe Val Thr Gly Cys Ser Ala
145                 150                 155                 160

Gly Gly Tyr Gly Ala Val Phe Trp Ala Asp Lys Val Leu Ala Thr Tyr
                165                 170                 175

Lys Ser Ala Gln Ile Ala Val Cys Gly Asp Ala Ala Leu Gly Val Ser
            180                 185                 190

Thr Ser Asp Phe Pro Gly Ser Arg Val Trp Asn Ala Arg Leu Pro Glu
        195                 200                 205

Leu Pro Gly Leu Gly Pro Asn Pro Ser Val Glu Glu Ile Tyr Arg Ala
    210                 215                 220
```

-continued

```
Leu Ala Arg Ala Tyr Pro Gly Ala Ala Phe Ala Gln Tyr Thr Thr Gln
225                 230                 235                 240

Leu Asp Gly Thr Gln Ile Tyr Phe Tyr Ala Leu Met Lys Lys Glu Val
                245                 250                 255

Pro Pro Ser Glu Ala Thr Ala Arg Glu Trp Ala Val Arg Ala Gln Thr
            260                 265                 270

Ser Leu Gln Ser Leu Ala Gln Glu Ser Asn Phe Thr Tyr Tyr Leu Ala
        275                 280                 285

Pro Gly Ser Gln His Cys Ile Leu Pro Arg Pro Glu Leu Tyr Thr Leu
    290                 295                 300

Lys Val Gly Glu Val Ser Val Leu Asp Trp Leu Arg Ser Leu Ala Glu
305                 310                 315                 320

Lys Gly Gln Ala Pro Arg Val Gly Pro
                325
```

(2) INFORMATION FOR SEQ ID NO:9:

(i) SEQUENCE CHARACTERISTICS:
(A) LENGTH: 3545 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: NO (ix) FEATURE:
(A) NAME/KEY: CDS
(B) LOCATION: 1397..2905
(D) OTHER INFORMATION: /note= "E019 sequence of longest open reading frame; upstream untranslated region not exact"

(ix) FEATURE:
(A) NAME/KEY: mat_peptide
(B) LOCATION: 1397..2905

(xi) SEQUENCE DESCRIPTION: SEQ ID NO:9:

```
TCGGCGCGAC ATTCAACCCG TAGAAGTGGA AGTAAACACG GGAAGAAGGC GGTTTCGCCC     60

GTGCGTTAGT GCCAAGCGGC GTTTCGACGG GCGAATATGA AGCGGTTGAA TTGCGTGACG    120

GCGACAAAAA CCGCTACCTC GGCAAAGGGG TGCTCAAAGC GGTTGAGAAC GTCAACGAAG    180

TGATTGCTCC GGAAATCATC GGCTTAGAAG TGACTGATCA AGTGGCGATC GACCGCGCGT    240

TGATTGAACT TGACGGCACG GAAAACAAAG GAAAGCTTGG GGCGAATGCT ATTTTAGGCG    300

TGTCGCTCGC GGTCGCTCGC GCTGCGGCTG ATGAGCTTGG CTTGCCGTTG TACCAATACT    360

TGGGCGGCTT TAACGCTAAA ACGCTGCCTG TACCGATGAT GAACATTTTA AACGGCGGCG    420

CGCATGCGGA CAACAACGTT GACATTCAAG AATTCATGAT CATGCCGGTC GGTGCGGAAA    480

GCTTCCGTGA AGCGCTGCGC ATGGGTGCAG AAATTTTCCA TAGCTTAAAA GCTGTGTTAA    540

AAGCGAAAGG CTACAACACG GCTGTCGGTG ACGAAGGCGG ATTTGCTCCG AACTTAAAAT    600

CGAACGAAGA AGCGCTGCAA ACGATCATTG AAGCGATCGA AAAAGCCGGC TACAAACCAG    660

GCGAACAAGT GATGCTCGCT ATGGACGTTG CTTCGTCGGA GCTGTACAAC AAAGAAGATG    720

GCAAATATCA TTTGGAAGGC GAAGGCGTCG TCAAAACATC AGAAGAAATG GTTGCTTGGT    780

ATGAAGAGCT TGTGTCGAAA TATCCGATCA TCTCGATCGA AGACGGACTT GACGAAAATG    840

ACTGGGAAGG CCATAAACTG CTTACTGAGC GCCTTGGCCA CAAAGTGCAG CTCGTCGGTG    900

ACGACTTGTT TGTAACGAAC ACGAAAAAAC TGGCCGAAGG CATTGAAAAA GGCGTCGGCA    960
```

-continued

```
ACTCGATTTT AATTAAAGTG AACCAAATCG GTACACTGAC GGAAACGTTC GATGCCATTG   1020

AGATGGCCAA ACGCGCCGGC TACACGGCGG TTGTGTCGCA CCGTTCCGGT GAAACGGAAG   1080

ACAGCACGAT TGCCGATATC GCTGTCGCAA CAAACGCTGG CCAAATCAAA ACGGGAGCAC   1140

CGTCGCGTAC GGACCGCGTC GCAAAATACA ACCAGTTGCT CCGCATTGAA GACGAACTTG   1200

GCCACACGGC TATTTACCAA GGCATTCGTT CGTTTTACAA TTTGAAAAAA TAACGGGAAT   1260

CAACAACAAA GGGTGTCTCC AACGTTGCGA GACACCCTCT TTAATTACGG GAAACAGAAA   1320

TGATTTCCTA TCGATAGCAA AAAATGGACG TGGGTAAACC ATTCGTTTAT AATATCTTTT   1380

TGTAATCGTT AGAATA TTG AAA AAG GGG ATG GGA ACC GTG ATC GTG GAA       1429
                  Leu Lys Lys Gly Met Gly Thr Val Ile Val Glu
                    1               5                  10

ACA AAG TAC GGT CGG TTG CGC GGG GGA ACA AAT GAA GGG GTT TTC TAT     1477
Thr Lys Tyr Gly Arg Leu Arg Gly Gly Thr Asn Glu Gly Val Phe Tyr
            15                  20                  25

TGG AAA GGG ATT CCG TAC GCG AAA GCG CCG GTC GGT GAA CGC CGT TTT     1525
Trp Lys Gly Ile Pro Tyr Ala Lys Ala Pro Val Gly Glu Arg Arg Phe
        30                  35                  40

TTG CCG CCG GAA CCG CCC GAT GCA TGG GAC GGA GTG CGT GAG GCG ACA     1573
Leu Pro Pro Glu Pro Pro Asp Ala Trp Asp Gly Val Arg Glu Ala Thr
    45                  50                  55

TCG TTT GGA CCG GTC GTC ATG CAG CCG TCC GAT TCG ATG TTC AGC CAG     1621
Ser Phe Gly Pro Val Val Met Gln Pro Ser Asp Ser Met Phe Ser Gln
 60                  65                  70                  75

CTG CTC GGA CGG ATG AAT GAA CCA ATG AGC GAG GAT GGG TTG TAT CTG     1669
Leu Leu Gly Arg Met Asn Glu Pro Met Ser Glu Asp Gly Leu Tyr Leu
                80                  85                  90

AAC ATT TGG TCA CCG GCG GCG GAT GGG AAG AAG CGC CCG GTA TTG TTT     1717
Asn Ile Trp Ser Pro Ala Ala Asp Gly Lys Lys Arg Pro Val Leu Phe
            95                 100                 105

TGG ATT CAT GGC GGC GCT TTT TTA TTC GGC TCC GGT TCA TTT CCA TGG     1765
Trp Ile His Gly Gly Ala Phe Leu Phe Gly Ser Gly Ser Phe Pro Trp
        110                 115                 120

TAT GAT GGA ACG GCG TTT GCC AAA CAC GGC GAT GTC GTT GTC GTG ACG     1813
Tyr Asp Gly Thr Ala Phe Ala Lys His Gly Asp Val Val Val Val Thr
    125                 130                 135

ATC AAC TAC CGG ATG AGC GTG TTT GGC TTT TTG TAT TTG GGA GAT GCG     1861
Ile Asn Tyr Arg Met Ser Val Phe Gly Phe Leu Tyr Leu Gly Asp Ala
140                 145                 150                 155

TTT GGC GAA ACG TAT GCC CAG GCG GGA AAT CTT GGC ATA TTG GAT CAA     1909
Phe Gly Glu Thr Tyr Ala Gln Ala Gly Asn Leu Gly Ile Leu Asp Gln
                160                 165                 170

GTG GCG GCG CTG CGC TGG GTG AAA GAG AAC ATT GAG GCG TTC GGC GGT     1957
Val Ala Ala Leu Arg Trp Val Lys Glu Asn Ile Glu Ala Phe Gly Gly
            175                 180                 185

GAT CCG GAC AAC ATT ACG ATT TTT GGC GAA TCA GCC GGA GCG GCA AGC     2005
Asp Pro Asp Asn Ile Thr Ile Phe Gly Glu Ser Ala Gly Ala Ala Ser
        190                 195                 200

GTT GGC GTG CTG TTG TCG CTT CCG GAA GCA AGC GGG CTG TTT CGA CGC     2053
Val Gly Val Leu Leu Ser Leu Pro Glu Ala Ser Gly Leu Phe Arg Arg
    205                 210                 215

GCT ATA TTG CAA AGC GGA TCG GGT TCG CTT CTT CTT CGT TCT CCG GAG     2101
Ala Ile Leu Gln Ser Gly Ser Gly Ser Leu Leu Leu Arg Ser Pro Glu
220                 225                 230                 235

ACG GCG ATG GCT CTG ACT GAA CGC ATT TTA GAA CGT GCC GGC ATC CGT     2149
Thr Ala Met Ala Leu Thr Glu Arg Ile Leu Glu Arg Ala Gly Ile Arg
                240                 245                 250

CCG GGT GAC CGC GAT CGG CTG CTG TCG ATT CCA GCA GCA GAG CTA TTG     2197
```

-continued

```
Pro Gly Asp Arg Asp Arg Leu Leu Ser Ile Pro Ala Ala Glu Leu Leu
            255                 260                 265

CAG GCG GCG ATG TCG CTC GGC CCA GGA ATC ACG TAC GGT CCG GTG GTT     2245
Gln Ala Ala Met Ser Leu Gly Pro Gly Ile Thr Tyr Gly Pro Val Val
        270                 275                 280

GAC GGA CAT GTG TTG CGA CGC CAT CCG ATC GAA GCG CTC CAC GAC GGG     2293
Asp Gly His Val Leu Arg Arg His Pro Ile Glu Ala Leu His Asp Gly
    285                 290                 295

GCA GCA AGT GAT ATT CCA ATC CTA ATT GGC GTG ACG AAA GAC GAA TAC     2341
Ala Ala Ser Asp Ile Pro Ile Leu Ile Gly Val Thr Lys Asp Glu Tyr
300                 305                 310                 315

AAT TTG TTT TCA TTG ACT GAT CCG TCA TTG ACA AGA CTC GAA GAA AAA     2389
Asn Leu Phe Ser Leu Thr Asp Pro Ser Leu Thr Arg Leu Glu Glu Lys
                320                 325                 330

GAA CTG CTT GAC CGG ATG AAC CGT GAG GTC GGG CCT ATT CCG GAG GAG     2437
Glu Leu Leu Asp Arg Met Asn Arg Glu Val Gly Pro Ile Pro Glu Glu
            335                 340                 345

GCG GTA CGC TAT TAC GCG GAA ACA GCG GAT CGG TCG GCA CCC GCG TGG     2485
Ala Val Arg Tyr Tyr Ala Glu Thr Ala Asp Arg Ser Ala Pro Ala Trp
        350                 355                 360

CAA ACA TGG CTG CGC ATC ATG ACG TAC CTT GTT TTT GTC GAC GGA ATG     2533
Gln Thr Trp Leu Arg Ile Met Thr Tyr Leu Val Phe Val Asp Gly Met
    365                 370                 375

TTG CGA ACG GCG GAT GCC CAA GCA GCG CAA GGG GCG AAT GTG TAC ATG     2581
Leu Arg Thr Ala Asp Ala Gln Ala Ala Gln Gly Ala Asn Val Tyr Met
380                 385                 390                 395

TAT CGG TTT GAT TAT GAA ACG CCG GCG TTT GGT GGA CAA CTG AAA GCG     2629
Tyr Arg Phe Asp Tyr Glu Thr Pro Ala Phe Gly Gly Gln Leu Lys Ala
                400                 405                 410

TGC CAT ACG CTC GAG TTG CCG TTT GTG TTT CAT AAC CTC CAT CAG CCT     2677
Cys His Thr Leu Glu Leu Pro Phe Val Phe His Asn Leu His Gln Pro
            415                 420                 425

GGT GTC GAG AAT TTC GTC GGC AAC CGA CCA GAG CGT GAG GCG ATT GCC     2725
Gly Val Glu Asn Phe Val Gly Asn Arg Pro Glu Arg Glu Ala Ile Ala
        430                 435                 440

AGC GAA ATG CAT GGT GCC TGG CTT TCG TTC GCC CAC ACC GGC AAC CCG     2773
Ser Glu Met His Gly Ala Trp Leu Ser Phe Ala His Thr Gly Asn Pro
    445                 450                 455

AAC GGC GCT CAT TTA CCA GAG AAG TGG CCC GTA TAC ACA AAA GAG CAC     2821
Asn Gly Ala His Leu Pro Glu Lys Trp Pro Val Tyr Thr Lys Glu His
460                 465                 470                 475

AAA CCG GTG TTT GTC TTT TCG GCT GCG AGC CAT GTG GAA GAC GAT CCG     2869
Lys Pro Val Phe Val Phe Ser Ala Ala Ser His Val Glu Asp Asp Pro
                480                 485                 490

TTC GGT CGC GAG CGG GAA GCG TGG CAA GGA CGC CTT TGACGAAAAA         2915
Phe Gly Arg Glu Arg Glu Ala Trp Gln Gly Arg Leu
            495                 500

ATCCATAAGC AACATGTGTT CTTTGTCTGA ACACGATCAA GGTACGCGCA TTTTCGCGGA   2975

AAAAGACCGT GGGCAAACGT TCGCCTTTAC CTCTAAAAGG AATGACGCAA CATGTCTGCA   3035

CTTCACAGGA AAGAGGACGA AACGGTTGGT TTTCAGAATA GGAAAAGGTG TCCCGTTTTT   3095

TGGGACACCT TCTTCTATGT ATCGCTCAAT CATTTGCTTC TGTGGCAGGA AGCCCGAATC   3155

GCTCGGCGAG TGCCGGATCA CGATCGATCG CCTCAATCAG TTTCCGCATG ACGTTCACAT   3215

CAAACGTAAA ATTCGAACCG ATTGGCGAGG TGACGAAAAT TTTCCCTTCT TTCGCCTCGC   3275

GTGCTCGTTT AAATTGATAG CCGTCAATCG CAATGACGAC TCGTTCGTCT GGCCTTGCCA   3335

TTAGGAATCC CTCCATCGCT GTTTTTTCTT TCATTGTACT TGATTTTGAG GATGAACACC   3395

AACGTTCATG ACACGCTCTT AAGGATAACG GATGGGAGAG CGTTAGAGGG CGGTGAATTT   3455
```

CATCAAGAAC GTGGCACAAA ACGACATTTT TTCATTATAG ACGTCTTGAT GTTTGGAATG 3515

ATCGGAAAAG GCGATTGTTA GGCGGGGATC 3545

(2) INFORMATION FOR SEQ ID NO:10:

(i) SEQUENCE CHARACTERISTICS:
(A) LENGTH: 503 amino acids
(B) TYPE: amino acid
(D) TOPOLOGY: linear (ii) MOLECULE TYPE: protein (xi) SEQUENCE DESCRIPTION: SEQ ID NO:10:

```
Leu Lys Lys Gly Met Gly Thr Val Ile Val Glu Thr Lys Tyr Gly Arg
  1               5                  10                  15

Leu Arg Gly Gly Thr Asn Glu Gly Val Phe Tyr Trp Lys Gly Ile Pro
            20                  25                  30

Tyr Ala Lys Ala Pro Val Gly Glu Arg Arg Phe Leu Pro Pro Glu Pro
        35                  40                  45

Pro Asp Ala Trp Asp Gly Val Arg Glu Ala Thr Ser Phe Gly Pro Val
    50                  55                  60

Val Met Gln Pro Ser Asp Ser Met Phe Ser Gln Leu Leu Gly Arg Met
 65                  70                  75                  80

Asn Glu Pro Met Ser Glu Asp Gly Leu Tyr Leu Asn Ile Trp Ser Pro
                 85                  90                  95

Ala Ala Asp Gly Lys Lys Arg Pro Val Leu Phe Trp Ile His Gly Gly
            100                 105                 110

Ala Phe Leu Phe Gly Ser Gly Ser Phe Pro Trp Tyr Asp Gly Thr Ala
        115                 120                 125

Phe Ala Lys His Gly Asp Val Val Val Val Thr Ile Asn Tyr Arg Met
    130                 135                 140

Ser Val Phe Gly Phe Leu Tyr Leu Gly Asp Ala Phe Gly Glu Thr Tyr
145                 150                 155                 160

Ala Gln Ala Gly Asn Leu Gly Ile Leu Asp Gln Val Ala Ala Leu Arg
                165                 170                 175

Trp Val Lys Glu Asn Ile Glu Ala Phe Gly Gly Asp Pro Asp Asn Ile
            180                 185                 190

Thr Ile Phe Gly Glu Ser Ala Gly Ala Ala Ser Val Gly Val Leu Leu
        195                 200                 205

Ser Leu Pro Glu Ala Ser Gly Leu Phe Arg Arg Ala Ile Leu Gln Ser
    210                 215                 220

Gly Ser Gly Ser Leu Leu Leu Arg Ser Pro Glu Thr Ala Met Ala Leu
225                 230                 235                 240

Thr Glu Arg Ile Leu Glu Arg Ala Gly Ile Arg Pro Gly Asp Arg Asp
                245                 250                 255

Arg Leu Leu Ser Ile Pro Ala Ala Glu Leu Leu Gln Ala Ala Met Ser
            260                 265                 270

Leu Gly Pro Gly Ile Thr Tyr Gly Pro Val Val Asp Gly His Val Leu
        275                 280                 285

Arg Arg His Pro Ile Glu Ala Leu His Asp Gly Ala Ala Ser Asp Ile
    290                 295                 300

Pro Ile Leu Ile Gly Val Thr Lys Asp Glu Tyr Asn Leu Phe Ser Leu
305                 310                 315                 320

Thr Asp Pro Ser Leu Thr Arg Leu Glu Glu Lys Glu Leu Leu Asp Arg
                325                 330                 335
```

-continued

```
Met Asn Arg Glu Val Gly Pro Ile Pro Glu Glu Ala Val Arg Tyr Tyr
            340                 345                 350

Ala Glu Thr Ala Asp Arg Ser Ala Pro Ala Trp Gln Thr Trp Leu Arg
        355                 360                 365

Ile Met Thr Tyr Leu Val Phe Val Asp Gly Met Leu Arg Thr Ala Asp
    370                 375                 380

Ala Gln Ala Ala Gln Gly Ala Asn Val Tyr Met Tyr Arg Phe Asp Tyr
385                 390                 395                 400

Glu Thr Pro Ala Phe Gly Gly Gln Leu Lys Ala Cys His Thr Leu Glu
                405                 410                 415

Leu Pro Phe Val Phe His Asn Leu His Gln Pro Gly Val Glu Asn Phe
            420                 425                 430

Val Gly Asn Arg Pro Glu Arg Glu Ala Ile Ala Ser Glu Met His Gly
        435                 440                 445

Ala Trp Leu Ser Phe Ala His Thr Gly Asn Pro Asn Gly Ala His Leu
    450                 455                 460

Pro Glu Lys Trp Pro Val Tyr Thr Lys Glu His Lys Pro Val Phe Val
465                 470                 475                 480

Phe Ser Ala Ala Ser His Val Glu Asp Asp Pro Phe Gly Arg Glu Arg
                485                 490                 495

Glu Ala Trp Gln Gly Arg Leu
            500
```

(2) INFORMATION FOR SEQ ID NO:11:

(i) SEQUENCE CHARACTERISTICS:
(A) LENGTH: 2643 base pairs
(B) TYPE: nucleic acid
(C) STRANDEDNESS: single
(D) TOPOLOGY: Not Relevant (ii) MOLECULE TYPE: DNA (genomic)

(iii) HYPOTHETICAL: NO (iv) ANTI-SENSE: NO (ix) FEATURE:
(A) NAME/KEY: CDS
(B) LOCATION: 1087..2595
(D) OTHER INFORMATION: /note= "E005 sequence of longest open reading frame; upstream untranslated region not exact"

(ix) FEATURE:
(A) NAME/KEY: mat_peptide
(B) LOCATION: 1087..2595

(xi) SEQUENCE DESCRIPTION: SEQ ID NO:11:

```
TTGATTCCAA GCTCGAAATT AACCCTCACT AAAGGGAACA AAAGCTGGAG CTCGCGCGCC      60

TGCAGGTCGA CACTAGTGGA TCCCCTTTCA TTTATGATTT TGCAGCGGTC GAGCTGCTTT     120

TATGTTGTTG AATGAACTGT TCAATTTGAT CATGCCGGTC GGTGCGGAAA GCTTCCGTGA     180

AGCGCTGCGC ATGGGTGCAG AAATTTTCCA TAGCTTAAAA GCTGTGTTAA AAGCGAAAGG     240

CTACAACACG GCTGTCGGTG ACGAAGGCGG ATTTGCTCCG AACTTAAAAT CGAACGAAGA     300

AGCGCTGCAA ACGATCATTG AAGCGATCGA AAAAGCCGGC TACAAACCAG GCGAACAAGT     360

GATGCTCGCT ATGGACGTTG CTTCGTCGGA GCTGTACAAC AAAGAAGATG GCAAATATCA     420

TTTGGAAGGC GAAGGCGTCG TCAAAACATC AGAAGAAATG GTTGCTTGGT ATGAAGAGCT     480

TGTGTCGAAA TATCCGATCA TCTCGATCGA AGACGGACTT GACGAAAATG ACTGGGAAGG     540

CCATAAACTG CTTACTGAGC GCCTTGGCCA CAAAGTGCAG CTCGTCGGTG ACGACTTGTT     600
```

-continued

```
TGTAACGAAC ACGAAAAAAC TGGCCGAAGG CATTGAAAAA GGCGTCGGCA ACTCGATTTT    660

AATTAAAGTG AACCAAATCG GTACACTGAC GGAAACGTTC GATGCCATTG AGATGGCCAA    720

ACGCGCCGGC TACACGGCGG TTGTGTCGCA CCGTTCCGGT GAAACGGAAG ACAGCACGAT    780

TGCCGATATC GCTGTCGCAA CAAACGCTGG CCAAATCAAA ACGGGAGCAC CGTCGCGTAC    840

GGACCGCGTC GCAAAATACA ACCAGCTGCT CCGCATTGAA GACGAACTTG GCCACACGGC    900

TATTTACCAA GGCATTCGTT CGTTTTACAA TTTGAAAAAA TAACGGGAAT CAACAACAAA    960

GGGTGTCTCC AACGTTGCGA GACACCCTCT TTAATTACGG GAAACAGAAA TGATTTCCTA   1020

TCGATAGCAA AAAATGGACG TGGGTAAACC ATTCGTTTAT AATATCTTTT TGTAATCGTT   1080

AGAATA TTG AAA AAG GGG ATG GGA ACC GTG ATC GTG GAA ACA AAG TAC      1128
       Leu Lys Lys Gly Met Gly Thr Val Ile Val Glu Thr Lys Tyr
         1               5                  10

GGT CGG TTG CGC GGG GGA ACA AAT GAA GGG GTT TTC TAT TGG AAA GGG     1176
Gly Arg Leu Arg Gly Gly Thr Asn Glu Gly Val Phe Tyr Trp Lys Gly
 15                  20                  25                  30

ATT CCG TAC GCG AAA GCG CCG GTC GGT GAA CGC CGT TTT TTG CCG CCG     1224
Ile Pro Tyr Ala Lys Ala Pro Val Gly Glu Arg Arg Phe Leu Pro Pro
                 35                  40                  45

GAA CCG CCC GAT GCA TGG GAC GGA GTG CGT GAG GCG ACA TCG TTT GGA     1272
Glu Pro Pro Asp Ala Trp Asp Gly Val Arg Glu Ala Thr Ser Phe Gly
             50                  55                  60

CCG GTC GTC ATG CAG CCG TCC GAT TCG ATG TTC AGC CAG CTG CTC GGA     1320
Pro Val Val Met Gln Pro Ser Asp Ser Met Phe Ser Gln Leu Leu Gly
         65                  70                  75

CGG ATG AAT GAA CCA ATG AGC GAG GAT GGG TTG TAT CTG AAC ATT TGG     1368
Arg Met Asn Glu Pro Met Ser Glu Asp Gly Leu Tyr Leu Asn Ile Trp
     80                  85                  90

TCA CCG GCG GCG GAT GGG AAG AAG CGC CCG GTA TTG TTT TGG ATT CAT     1416
Ser Pro Ala Ala Asp Gly Lys Lys Arg Pro Val Leu Phe Trp Ile His
 95                 100                 105                 110

GGC GGC GCT TTT TTA TTC GGC TCC GGT TCA TTT CCA TGG TAT GAT GGA     1464
Gly Gly Ala Phe Leu Phe Gly Ser Gly Ser Phe Pro Trp Tyr Asp Gly
                115                 120                 125

ACG GCG TTT GCC AAA CAC GGC GAT GTC GTT GTC GTG ACG ATC AAC TAC     1512
Thr Ala Phe Ala Lys His Gly Asp Val Val Val Val Thr Ile Asn Tyr
            130                 135                 140

CGG ATG AGC GTG TTT GGC TTT TTG TAT TTG GGA GAT GCG TTT GGC GAA     1560
Arg Met Ser Val Phe Gly Phe Leu Tyr Leu Gly Asp Ala Phe Gly Glu
        145                 150                 155

ACG TAT GCC CAG GCG GGA AAT CTT GGC ATA TTG GAT CAA GTG GCG GCG     1608
Thr Tyr Ala Gln Ala Gly Asn Leu Gly Ile Leu Asp Gln Val Ala Ala
    160                 165                 170

CTG CGC TGG GTG AAA GAG AAC ATT GAG GCG TTC GGC GGT GAT CCG GAC     1656
Leu Arg Trp Val Lys Glu Asn Ile Glu Ala Phe Gly Gly Asp Pro Asp
175                 180                 185                 190

AAC ATT ACG ATT TTT GGC GAA TCA GCC GGA GCG GCA AGC GTT GGC GTG     1704
Asn Ile Thr Ile Phe Gly Glu Ser Ala Gly Ala Ala Ser Val Gly Val
                195                 200                 205

CTG TTG TCG CTT CCG GAA GCA AGC GGG CTG TTT CGA CGC GCT ATA TTG     1752
Leu Leu Ser Leu Pro Glu Ala Ser Gly Leu Phe Arg Arg Ala Ile Leu
            210                 215                 220

CAA AGC GGA TCG GGT TCG CTT CTT CTT CGT TCT CCG GAG ACG GCG ATG     1800
Gln Ser Gly Ser Gly Ser Leu Leu Leu Arg Ser Pro Glu Thr Ala Met
        225                 230                 235

GCT CTG ACT GAA CGC ATT TTA GAA CGT GCC GGC ATC CGT CCG GGT GAC     1848
Ala Leu Thr Glu Arg Ile Leu Glu Arg Ala Gly Ile Arg Pro Gly Asp
    240                 245                 250
```

```
CGC GAT CGG CTG CTG TCG ATT CCA GCA GCA GAG CTA TTG CAG GCG GCG     1896
Arg Asp Arg Leu Leu Ser Ile Pro Ala Ala Glu Leu Leu Gln Ala Ala
255                 260                 265                 270

ATG TCG CTC GGC CCA GGA ATC ACG TAC GGT CCG GTG GTT GAC GGA CAT     1944
Met Ser Leu Gly Pro Gly Ile Thr Tyr Gly Pro Val Val Asp Gly His
                275                 280                 285

GTG TTG CGA CGC CAT CCG ATC GAA GCG CTC CAC GAC GGG GCA GCA AGT     1992
Val Leu Arg Arg His Pro Ile Glu Ala Leu His Asp Gly Ala Ala Ser
            290                 295                 300

GAT ATT CCA ATC CTA ATT GGC GTG ACG AAA GAC GAA TAC AAT TTG TTT     2040
Asp Ile Pro Ile Leu Ile Gly Val Thr Lys Asp Glu Tyr Asn Leu Phe
        305                 310                 315

TCA TTG ACT GAT CCG TCA TTG ACA AGA CTC GAA GAA AAA GAA CTG CTT     2088
Ser Leu Thr Asp Pro Ser Leu Thr Arg Leu Glu Glu Lys Glu Leu Leu
    320                 325                 330

GAC CGG ATG AAC CGT GAG GTC GGG CCT ATT CCG GAG GAG GCG GTA CGC     2136
Asp Arg Met Asn Arg Glu Val Gly Pro Ile Pro Glu Glu Ala Val Arg
335                 340                 345                 350

TAT TAC GCG GAA ACA GCG GAT CGG TCG GCA CCC GCG TGG CAA ACA TGG     2184
Tyr Tyr Ala Glu Thr Ala Asp Arg Ser Ala Pro Ala Trp Gln Thr Trp
                355                 360                 365

CTG CGC ATC ATG ACG TAC CTT GTT TTT GTC GAC GGA ATG TTG CGA ACG     2232
Leu Arg Ile Met Thr Tyr Leu Val Phe Val Asp Gly Met Leu Arg Thr
            370                 375                 380

GCG GAT GCC CAA GCA GCG CAA GGG GCG AAT GTG TAC ATG TAT CGG TTT     2280
Ala Asp Ala Gln Ala Ala Gln Gly Ala Asn Val Tyr Met Tyr Arg Phe
        385                 390                 395

GAT TAT GAA ACG CCG GCG TTC GGT GGA CAA CTG AAA GCG TGC CAT ACG     2328
Asp Tyr Glu Thr Pro Ala Phe Gly Gly Gln Leu Lys Ala Cys His Thr
    400                 405                 410

CTC GAG TTG CCG TTT GTG TTT CAT AAC CTC CAT CAG CCT GGT GTC GAG     2376
Leu Glu Leu Pro Phe Val Phe His Asn Leu His Gln Pro Gly Val Glu
415                 420                 425                 430

AAT TTC GTC GGC AAC CGA CCA GAG CGT GAG GCG ATT GCC AGC GAA ATG     2424
Asn Phe Val Gly Asn Arg Pro Glu Arg Glu Ala Ile Ala Ser Glu Met
                435                 440                 445

CAT GGT GCC TGG CTT TCG TTC GCC CAC ACC GGC AAC CCG AAC GGC GCT     2472
His Gly Ala Trp Leu Ser Phe Ala His Thr Gly Asn Pro Asn Gly Ala
            450                 455                 460

CAT TTA CCA GAG AAG TGG CCC GTA TAC ACA AAA GAG CAC AAA CCG GTG     2520
His Leu Pro Glu Lys Trp Pro Val Tyr Thr Lys Glu His Lys Pro Val
        465                 470                 475

TTT GTC TTT TCG GCT GCG AGC CAT GTG GAA GAC GAT CCG TTC GGT CGC     2568
Phe Val Phe Ser Ala Ala Ser His Val Glu Asp Asp Pro Phe Gly Arg
    480                 485                 490

GAG CGG GAA GCG TGG CAA GGA CGC CTT TGACGAAAAA ATCCATAAGC           2615
Glu Arg Glu Ala Trp Gln Gly Arg Leu
495                 500

AACATGTGTT CTTTGTCTGA ACACGATC                                      2643
```

(2) INFORMATION FOR SEQ ID NO:12:

(i) SEQUENCE CHARACTERISTICS:
(A) LENGTH: 503 amino acids
(B) TYPE: amino acid
(D) TOPOLOGY: linear (ii) MOLECULE TYPE: protein (xi) SEQUENCE DESCRIPTION: SEQ ID NO:12:

```
Leu Lys Lys Gly Met Gly Thr Val Ile Val Glu Thr Lys Tyr Gly Arg
```

-continued

```
1               5                   10                  15

Leu Arg Gly Gly Thr Asn Glu Gly Val Phe Tyr Trp Lys Gly Ile Pro
            20                  25                  30

Tyr Ala Lys Ala Pro Val Gly Glu Arg Arg Phe Leu Pro Pro Glu Pro
        35                  40                  45

Pro Asp Ala Trp Asp Gly Val Arg Glu Ala Thr Ser Phe Gly Pro Val
    50                  55                  60

Val Met Gln Pro Ser Asp Ser Met Phe Ser Gln Leu Leu Gly Arg Met
 65                 70                  75                      80

Asn Glu Pro Met Ser Glu Asp Gly Leu Tyr Leu Asn Ile Trp Ser Pro
                85                  90                  95

Ala Ala Asp Gly Lys Lys Arg Pro Val Leu Phe Trp Ile His Gly Gly
            100                 105                 110

Ala Phe Leu Phe Gly Ser Gly Ser Phe Pro Trp Tyr Asp Gly Thr Ala
        115                 120                 125

Phe Ala Lys His Gly Asp Val Val Val Val Thr Ile Asn Tyr Arg Met
    130                 135                 140

Ser Val Phe Gly Phe Leu Tyr Leu Gly Asp Ala Phe Gly Glu Thr Tyr
145                 150                 155                 160

Ala Gln Ala Gly Asn Leu Gly Ile Leu Asp Gln Val Ala Ala Leu Arg
                165                 170                 175

Trp Val Lys Glu Asn Ile Glu Ala Phe Gly Gly Asp Pro Asp Asn Ile
            180                 185                 190

Thr Ile Phe Gly Glu Ser Ala Gly Ala Ala Ser Val Gly Val Leu Leu
        195                 200                 205

Ser Leu Pro Glu Ala Ser Gly Leu Phe Arg Arg Ala Ile Leu Gln Ser
    210                 215                 220

Gly Ser Gly Ser Leu Leu Leu Arg Ser Pro Glu Thr Ala Met Ala Leu
225                 230                 235                 240

Thr Glu Arg Ile Leu Glu Arg Ala Gly Ile Arg Pro Gly Asp Arg Asp
                245                 250                 255

Arg Leu Leu Ser Ile Pro Ala Ala Glu Leu Leu Gln Ala Ala Met Ser
            260                 265                 270

Leu Gly Pro Gly Ile Thr Tyr Gly Pro Val Val Asp Gly His Val Leu
        275                 280                 285

Arg Arg His Pro Ile Glu Ala Leu His Asp Gly Ala Ala Ser Asp Ile
    290                 295                 300

Pro Ile Leu Ile Gly Val Thr Lys Asp Glu Tyr Asn Leu Phe Ser Leu
305                 310                 315                 320

Thr Asp Pro Ser Leu Thr Arg Leu Glu Glu Lys Glu Leu Leu Asp Arg
                325                 330                 335

Met Asn Arg Glu Val Gly Pro Ile Pro Glu Glu Ala Val Arg Tyr Tyr
            340                 345                 350

Ala Glu Thr Ala Asp Arg Ser Ala Pro Ala Trp Gln Thr Trp Leu Arg
        355                 360                 365

Ile Met Thr Tyr Leu Val Phe Val Asp Gly Met Leu Arg Thr Ala Asp
    370                 375                 380

Ala Gln Ala Ala Gln Gly Ala Asn Val Tyr Met Tyr Arg Phe Asp Tyr
385                 390                 395                 400

Glu Thr Pro Ala Phe Gly Gly Gln Leu Lys Ala Cys His Thr Leu Glu
                405                 410                 415

Leu Pro Phe Val Phe His Asn Leu His Gln Pro Gly Val Glu Asn Phe
            420                 425                 430
```

-continued

```
Val Gly Asn Arg Pro Glu Arg Glu Ala Ile Ala Ser Glu Met His Gly
        435                 440                 445

Ala Trp Leu Ser Phe Ala His Thr Gly Asn Pro Asn Gly Ala His Leu
    450                 455                 460

Pro Glu Lys Trp Pro Val Tyr Thr Lys Glu His Lys Pro Val Phe Val
465                 470                 475                 480

Phe Ser Ala Ala Ser His Val Glu Asp Asp Pro Phe Gly Arg Glu Arg
                485                 490                 495

Glu Ala Trp Gln Gly Arg Leu
            500
```